United States Patent
Nel et al.

(10) Patent No.: US 12,171,884 B2
(45) Date of Patent: *Dec. 24, 2024

(54) MESOPOROUS SILICA NANOPARTICLES WITH LIPID BILAYER COATING FOR CARGO DELIVERY

(71) Applicant: The Regents of the University of California, Oakland, CA (US)

(72) Inventors: Andre E. Nel, Sherman Oaks, CA (US); Huan Meng, Los Angeles, CA (US); Xiangsheng Liu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 275 days.

This patent is subject to a terminal disclaimer.

(21) Appl. No.: 17/384,214

(22) Filed: Jul. 23, 2021

(65) Prior Publication Data
US 2022/0160644 A1 May 26, 2022

Related U.S. Application Data

(63) Continuation of application No. 16/947,539, filed on Aug. 5, 2020, now Pat. No. 11,096,900, which is a
(Continued)

(51) Int. Cl.
*A61K 9/51* (2006.01)
*A61K 9/127* (2006.01)
(Continued)

(52) U.S. Cl.
CPC .......... *A61K 9/5115* (2013.01); *A61K 9/127* (2013.01); *A61K 9/5123* (2013.01);
(Continued)

(58) Field of Classification Search
CPC .................................................. A61K 9/5115
See application file for complete search history.

(56) References Cited

U.S. PATENT DOCUMENTS

| 4,737,323 A | 4/1988 | Martin et al. |
| 5,670,631 A | 9/1997 | Bayerl et al. |
| (Continued) | | |

FOREIGN PATENT DOCUMENTS

| AU | 2017206077 B2 | 11/2021 |
| EP | 2964201 A1 | 1/2016 |
| (Continued) | | |

OTHER PUBLICATIONS

Dong Wang et al. "The eradication of breast cancer cells and stem cells by 8-hydroxyquinoline-loaded hyaluronan modified mesoporous silica nanoparticle-supported lipid bilayers containing docetaxel." Biomaterials, vol. 34 (2013) pp. 7662-7673. (Year: 2013).*
(Continued)

*Primary Examiner* — Isaac Shomer
(74) *Attorney, Agent, or Firm* — Mark S. Cohen; PEARL COHEN ZEDEK LATZER BARATZ LLP

(57) ABSTRACT

A nanocarrier including a silica body having a surface and defining a plurality of pores that are suitable to receive molecules therein is described. The nanocarrier also includes a lipid bilayer coating the surface, and a cargo-trapping agent within the phospholipid bilayer. The phospholipid bilayer stably seals the plurality of pores. The cargo-trapping reagent can be selected to interact with a desired cargo, such as a drug.

22 Claims, 49 Drawing Sheets

Specification includes a Sequence Listing.

Related U.S. Application Data continuation of application No. 16/164,030, filed on Oct. 18, 2018, now Pat. No. 10,765,636, which is a continuation of application No. 15/798,287, filed on Oct. 30, 2017, now Pat. No. 10,143,660, which is a continuation of application No. PCT/US2017/012625, filed on Jan. 6, 2017.

(60) Provisional application No. 62/276,634, filed on Jan. 8, 2016.

(51) Int. Cl.
| | |
|---|---|
| *A61K 31/4745* | (2006.01) |
| *A61K 45/06* | (2006.01) |
| *A61K 47/62* | (2017.01) |
| *A61K 47/69* | (2017.01) |
| *A61K 9/00* | (2006.01) |

(52) U.S. Cl.
CPC ........ *A61K 9/5192* (2013.01); *A61K 31/4745* (2013.01); *A61K 45/06* (2013.01); *A61K 47/62* (2017.08); *A61K 47/6923* (2017.08); *A61K 47/6929* (2017.08); *A61K 9/0019* (2013.01); *A61K 9/1278* (2013.01); *Y10S 977/773* (2013.01); *Y10S 977/906* (2013.01); *Y10S 977/907* (2013.01)

(56) References Cited

U.S. PATENT DOCUMENTS

| | | | |
|---|---|---|---|
| 6,296,870 B1 | 10/2001 | Needham et al. | |
| 6,868,343 B1 | 3/2005 | Bayerl et al. | |
| 8,734,816 B2 | 5/2014 | Liu et al. | |
| 8,758,811 B2 | 6/2014 | Ho et al. | |
| 8,992,984 B1 | 3/2015 | Brinker et al. | |
| 9,532,949 B2 | 1/2017 | Zeinelden et al. | |
| 9,579,283 B2 | 2/2017 | Brinker et al. | |
| 10,143,660 B2* | 12/2018 | Nel .............. | A61K 9/127 |
| 10,343,903 B2 | 7/2019 | Zink et al. | |
| 10,765,636 B2* | 9/2020 | Nel .............. | A61P 35/02 |
| 10,828,255 B2 | 11/2020 | Nel et al. | |
| 11,096,900 B2* | 8/2021 | Nel .............. | A61P 31/04 |
| 2003/0035842 A1 | 2/2003 | Kazakov et al. | |
| 2004/0005352 A1 | 1/2004 | Lopez et al. | |
| 2005/0249795 A1 | 11/2005 | Zhang et al. | |
| 2006/0154069 A1 | 7/2006 | Lin et al. | |
| 2007/0116753 A1* | 5/2007 | Hong ............ | A61K 9/1278 424/450 |
| 2008/0175992 A1 | 7/2008 | Plieth et al. | |
| 2010/0255103 A1 | 10/2010 | Liong et al. | |
| 2010/0284924 A1 | 11/2010 | Zink et al. | |
| 2010/0310465 A1 | 12/2010 | Zink et al. | |
| 2011/0104073 A1 | 5/2011 | Zeng et al. | |
| 2011/0123601 A1 | 5/2011 | Ho et al. | |
| 2011/0268791 A1* | 11/2011 | Liu .............. | A61K 33/242 435/375 |
| 2012/0021034 A1 | 1/2012 | Zink et al. | |
| 2012/0207795 A1 | 8/2012 | Zink et al. | |
| 2013/0046274 A1 | 2/2013 | Zink et al. | |
| 2013/0195963 A1 | 8/2013 | Serda et al. | |
| 2014/0079774 A1* | 3/2014 | Brinker .......... | A61K 9/1271 514/44 R |
| 2014/0138278 A1 | 5/2014 | Kennedy | |
| 2014/0301951 A1 | 10/2014 | Liu et al. | |
| 2015/0272885 A1* | 10/2015 | Ashley ........... | A61K 49/0423 514/21.3 |
| 2016/0008283 A1 | 1/2016 | Nel et al. | |
| 2017/0095418 A1 | 4/2017 | Zink et al. | |
| 2017/0173169 A1 | 6/2017 | Yantasee et al. | |
| 2018/0098945 A1 | 4/2018 | Nel et al. | |
| 2019/0160015 A1 | 5/2019 | Nel et al. | |
| 2019/0216736 A1 | 7/2019 | Nel et al. | |
| 2020/0383929 A1 | 12/2020 | Nel et al. | |
| 2021/0077397 A1 | 3/2021 | Nel et al. | |

FOREIGN PATENT DOCUMENTS

| | | | | |
|---|---|---|---|---|
| WO | WO 2006/015757 A1 | 2/2006 | | |
| WO | WO 2006/032136 A1 | 3/2006 | | |
| WO | WO 2010/078569 A2 | 7/2010 | | |
| WO | WO 2012/009448 A2 | 1/2012 | | |
| WO | WO 2012/149376 A2 | 11/2012 | | |
| WO | WO 2013/012891 A1 | 1/2013 | | |
| WO | WO-2014138278 A1 * | 9/2014 | ........... | A61K 31/337 |
| WO | WO 2017/013250 A1 | 1/2017 | | |
| WO | WO 2017/120537 A1 | 7/2017 | | |
| WO | WO 2019/133884 A1 | 7/2019 | | |

OTHER PUBLICATIONS

Kimberly S. Butler , Paul N. Durfee , Christophe Theron , Carlee E. Ashley , Eric C. Carnes , and C. Jeffrey Brinker. "Protocells: Modular Mesoporous Silica Nanoparticle-Supported Lipid Bilayers for Drug Delivery." Small, 2016, 12, No. 16, pp. 2173-2185. (Year: 2016).*
US Office Action (Restriction Requirement), dated Feb. 3, 2017, issued in U.S. Appl. No. 14/772,740.
US Office Action dated Jun. 2, 2017, issued in U.S. Appl. No. 14/772,740.
US Final Office Action dated Feb. 20, 2018, issued in U.S. Appl. No. 14/772,740.
US Advisory Action dated Jun. 1, 2018, issued in U.S. Appl. No. 14/772,740.
US Office Action dated Aug. 7, 2018, issued in U.S. Appl. No. 14/772,740.
US Final Office Action dated Apr. 1, 2019, issued in U.S. Appl. No. 14/772,740.
US Office Action dated Nov. 27, 2019, issued in U.S. Appl. No. 14/772,740.
US Notice of Allowance dated Jun. 22, 2020, issued in U.S. Appl. No. 14/772,740.
US Office Action dated Jan. 31, 2018, issued in U.S. Appl. No. 15/798,287.
US Office Action dated May 29, 2018, issued in U.S. Appl. No. 15/798,287.
US Notice of Allowance dated Jul. 19, 2018 issued in U.S. Appl. No. 15/798,287.
US Office Action dated Sep. 4, 2019 issued in U.S. Appl. No. 16/164,030.
US Miscellaneous Communication dated Apr. 22, 2020 issued in U.S. Appl. No. 16/164,030.
US Examiner Initiated Interview Summary dated Apr. 23, 2020 issued in U.S. Appl. No. 16/164,030.
US Notice of Allowance dated May 6, 2020 issued in U.S. Appl. No. 16/164,030.
US Office Action dated Sep. 9, 2020 issued in U.S. Appl. No. 16/947,539.
US Notice of Allowance dated Apr. 21, 2021 issued in U.S. Appl. No. 16/947,539.
US Office Action dated Jul. 9, 2020 issued in U.S. Appl. No. 16/235,950.
US Final Office Action dated Dec. 16, 2020 issued in U.S. Appl. No. 16/235,950.
US Office Action dated Nov. 19, 2021 issued in U.S. Appl. No. 16/235,950.
U.S. Appl. No. 14/253,030 Office Action dated Dec. 9, 2016.
U.S. Appl. No. 14/253,030 Response as filed on May 9, 2017.
PCT International Search Report and Written Opinion dated Jun. 24, 2014 issued in PCT/US2014/020857.
PCT International Report on Patentability and Written Opinion dated Sep. 17, 2015 issued in PCT/US2014/020857.
European Extended Search Report dated Jul. 27, 2016 issued in Application No. EP 14 760 467.2.

(56) References Cited

OTHER PUBLICATIONS

European Office Action dated Aug. 23, 2018 issued in Application No. EP 14 760 467.2.
European 2nd Office Action dated May 26, 2020 issued in Application No. EP 14 760 467.2.
European 3rd Office Action dated Sep. 2, 2021 issued in Application No. EP 14 760 467.2.
PCT International Search Report and Written Opinion dated Apr. 18, 2017 issued in PCT/US2017/012625.
PCT International Preliminary Report on Patentability and Written Opinion dated Jul. 10, 2018 issued in PCT/US2017/012625.
Australian Office Action dated Dec. 17, 2020 issued in AU 2017206077.
Chinese Office Action dated Aug. 14, 2020 issued in CN 201780010248.8.
Chinese 2nd Office Action dated May 17, 2021 issued in CN 201780010248.8.
European Extended Search Report dated Aug. 7, 2019 issued in Application No. EP 17736481.7.
Japanese Office Action dated Oct. 5, 2020 issued in JP 2018-535362.
Japanese 2nd Office Action dated Aug. 2, 2021 issued in JP 2018-535362.
Korean Office Action dated May 18, 2021 issued in KR 10-2018-7022622.
PCT International Search Report and Written Opinion dated Mar. 27, 2019 issued in PCT/US18/67970.
PCT International Preliminary Report on Patentability and Written Opinion dated Jul. 7, 2020 issued in PCT/US18/67970.
European Partial Supplementary Search Report dated Nov. 11, 2021 issued in EP Application No. EP 18897783.9.
Abigerges et al. (1995) "Phase I and pharmacologic studies of the camptothecin analog irinotecan administered every 3 weeks in cancer patients." *Clin Oncol* 13:210-221.
Al Shamsi et al. (2010) "Biocompatibility of calcined mesoporous silica particles with cellular bioenergetics in murine tissues." *Chem Res Toxicol* 23(11):1796-1805.
Angelos et al. (2007) "Mesostructured silica supports for functional materials and molecular machines." *Adv Funct Mater* 17:2261-2271.
Argyo, et al. (2013) "Multifunctional Mesoporous Silica Nanoparticles as a Universal Platform for Drug Delivery." *Chem. Mater.*, 26(1): 435-451.
Arruebo et al. (2006) "Development of Magnetic Nanostructured Silica-Based Materials as Potential Vectors for Drug-Delivery Applications." *Chem Mater* 18:1911-1919.
Arruebo et al. (Published Jul. 18, 2006) "Sustained release of doxorubicin from zeolite-magnetite nanocomposited prepared by mechanical activation." *Nanotechnology* 17:4057-4064.
Aryal, et al. (2011) "Polymeric Nanoparticles with Precise Ratiometric Control over Drug Loading for Combination Therapy." *Mol. Pharmaceutics* 8:1401-1407.
Ashley et al. (2011) "The targeted delivery of multicomponent cargos to cancer cells by nanoporous particle-supported lipid bilayers." *Nature Materials* 10(5):389-397.
Ashley et al. (2012) "Delivery of Small Interfering RNA by Peptide-Targeted Mesoporous Silica Nanoparticle-Supported Lipid Bilayers." *ACS Nano* 6:2174-2188.
Awasthi et al. (2013) "Comparative Benefits of Nab-Paclitaxel over Gemcitabine or Polysor- bate-Based Docetaxel in Experimental Pancreatic Cancer." *Carcinogenesis* 34: 2361-2369.
Bagwe et al. (Apr. 25, 2006) "Surface Modification of Silica Nanoparticles to Reduce Aggregation and Nonspecific Binding." *Langmuir* 22:4357-4362.
Baker et al. (2008) "Irinophore C, a Novel Nanoformulation of Irinotecan, Alters Tumor Vascular Function and Enhances the Distribution of 5-Fluorouracil and Doxorubicin." *Clin. Cancer Res.* 14:7260-7271.
Barbe et al. (2004) "Silica particles: A novel drug-delivery system." *Adv Mater* 16:1959-1966.

Bardelle (1993) "Membrane binding kinetics of factor VIII indicate a complex binding process." *J Biol Chem.* 268(12): 8815-24.
Bayerl, et al. (1990) "Physical Properties of Single Phospholipid Bilayers Adsorbed to Micro Glass Beads. A New Vesicular Model System Studied by 2H-Nuclear Magnetic Resonance." *Biophys. J.*, 58: 357-362.
Bourzac, K. (2012) "Nanotechnology: Carrying Drugs." *Nature*, 491: S58-S60.
Brigger et al. (2002) "Nanoparticles in cancer therapy and diagnosis." *Advanced Drug Delivery Reviews* 54:631-651.
Brumm et al. (1996) "The effect of increasing membrane curvature on the phase transition and mixing behavior of a dimyristoyl-sn-glycero-3-phosphatidylcholine/distearoyl-sn-glycero-3-phosphatidylcholine lipid mixture as studied by Fourier transform infrared spectroscopy and differential scanning calorimetry." *Biophys J.* 70: 1373-1379.
Buck et al. (2004) "Engineering Lipobeads: Properties of the Hydrogel Core and the Lipid Bilayer Shell" *Biomacromolecules*, 5: 2230-2237.
Buranda et al. (2003) "Biomimetic Molecular Assemblies on Glass and Mesoporous Silica Microbeads for Biotechnology" *Langmuir*, 19: 1654-1663.
Carmona-Ribeiro (2003) "Bilayer-forming synthetic lipids: drugs or carriers?" *Curr. Med. Chem.* 10: 2425-2446.
Cauda et al. (2010) "Colchicine-Loaded Lipid Bilayer-Coated 50 nm Mesoporous Nanoparticles Efficiently Induce Microtubule Depolymerization upon Cell Uptake" *Nano Letters* 10(7): 2484-2492.
Celano et al. (2004) "Cytotoxic effects of Gemcitabine-loaded liposomes in human anaplastic thyroid carcinoma cells," *BMC Cancer* 4(63):5 pages.
"CHEBI:53581—cetyttrimethylammonium chloride", Retrieved from the Internet: URL https://www.ebi.ac.uk/chebi/searchId.do?chebild-CHEBI:53581, Sep. 11, 2013 (Sep. 11, 2013), Section "Synonyms" (2 Pages).
Chemburu et al. (2010) "Biomimetic Silica Microspheres in Biosensing" *Molecules*, 15: 1932-1957.
Chen et al. (2009) "Co-delivery of Doxorubicin and Bcl-2 siRNA by Mesoporous Silica Nanoparticles Enhances the Efficacy of Chemotherapy in Multidrug Resistant Cancer Cells." *Small* 5(23):2673-2677.
Chen, et al. (2014) "Antitumor efficacy of irinotecan-loaded galactosyl modified lipid bilayer-coated mesoporous silica nanoparticles against hepatocellular carcinoma cells." *Acta Pharmaceutica Sinica*, 49(5): 718-725. [English Translation of Chinese Article—30 Pages].
Cho et al. (2008) "Therapeutic nanoparticles for drug delivery in cancer." *Clin. Cancer Res.* 14(5):1310-1316.
Chou et al. (2003) "Effect of Composition on the stability of liposomal irinotecan prepared by a pH gradient method." *J Biosci Bioeng* 95(4):405-408.
Cosco et al. (2009) "In vivo activity of gemcitabine-loaded PEGylated small unilamellar liposomes against pancreatic cancer" *Cancer Chemother Pharmacol*, 64(5):1009-1020.
Davis et al. (2008) "Nanoparticle therapeutics: an emerging treatment modality for cancer." *Nature Reviews Discovery* 7:771-782.
Davis, M. E., (2009) "The first targeted delivery of siRNA in humans via a self-assembling, cyclodextrin polymer-based nanoparticle: from concept to clinic." *Molecular Pharmacuetics* 6(3):659-668.
Dengler et al. (2013) "Mesoporous Silica-Supported Lipid Bilayers (Protocells) for DNA Cargo Delivery to the Spinal Cord." *J.Controlled Release* 168: 209-224.
Dolainsky et al. (1993) "Transverse relaxation in supported and nonsupported phospholipid model membranes and the influence of ultraslow motions: A 31P-NMR study" *J. Chem. Phys.* 98: 1712-1720.
Drummond et al. (2006) "Development of a highly active nanoliposomal irinotecan using a novel intraliposomal stabilization strategy." *Cancer Research* 66(6):3271-3277.
Duncan et al. (2005) "Polymer-drug conjugates: towards a novel approach for the treatment of endrocine-related cancer." *Endocrine-Related Cancer* 12: S189-S199.

(56) References Cited

OTHER PUBLICATIONS

Eschwege et al. (1996) "Detection of bilayer phospholipid-binding antibodies using flow cytometry" *Clin. Exp. Immunol.* 103: 171-175.
Federico et al. (2012) "Gemcitabine-Loaded Liposomes: Rationale, Potentialities and Future Perspectives." *Int. J. Nanomed.* 7: 5423-5436.
Ferrari, M. (2005) "Cancer Nanotechnology: Opportunities and Challenges." *Nat. Rev. Cancer* 5: 161-171.
Frese et al. (2012) "Nab-Paclitaxel Potentiates Gemcitabine Activity by Reducing Cytidine Deaminase Levels in a Mouse Model of Pancreatic Cancer." *Cancer Discovery* 2: 260-269.
Fritze et al. (2006) "Remote loading of doxorubicin into liposomes driven by transmembrane phosphate gradient," *Biochimica Et Biophysica Acta (BBA)—Biomembranes*, Elsevier, Amsterdam, NL, 1758(10):1633-1640.
Fuchs et al. (2006) "Irinotecan in the treatment of colorectal cancer." *Cancer Treat. Rev.* 32:491-503.
Gahlyan et al. (2014) "Oral Controlled Release Drug Delivery System—A Review" *PharmaTutor* 2(8): 170-178.
Gilbert et al. (1992) "Specificity of phosphatidylserine-containing membrane binding sites for factor VIII. Studies with model membranes supported by glass microspheres (liposheres)." *J. Biol. Chem.* 267: 15861-15868.
Gorelikov et al. (2008) "Single-step coating of mesoporous silica on cetyltrimethyl ammonium bromide-capped nanoparticles." *Nano Letters* 8(1):369-373.
Grün et al. (1997) "The Synthesis of Micrometer- and Submicrometer-Size Spheres of Ordered Mesoporous Oxide MCM-41." *Adv. Mater.* 9(3):254-257.
Guiotto et al. (2004) "Synthesis, Characterization, and Preliminary in Vivo Tests of New Poly(ethylene glycol) Conjugates of the Antitumor Agent 10-Amino-7-ethylcamptothecin." *J. Med. Chem.* 47(5): 1280-1289 [Abstract—2pages].
Haran et al. (1993) "Transmembrane ammonium sulfate gradients in liposomes produce efficient and stable entrapment of amphipathic weak bases." *Biochim Biophys Acta Biomembr* 1151:201-215.
He et al. (2011) "In vivo biodistribution and urinary excretion of mesoporous silica nanoparticles: effects of particle size and PEGylation." *Small* 7:271-280.
Hetzer et al. (1998) "Asymmetric Molecular Friction in Supported Phospholipid Bilayers Revealed by NMR Measurements of Lipid Diffusion" *Langmuir*, 14: 982-984.
Jabr-Milane et al. (2008) "Multi-functional nanocarriers to overcome tumor drug resistance." *Cancer Treat. Rev.* 34:592-602.
Jin et al. (1996) "Lipobeads: a hydrogen anchored lipid vesicle system" *FEBS Lett.* 397: 70-74.
Junglas et al. (2003) "Molecular Order Parameter Profiles and Diffusion Coefficients of Cationic Lipid Bilayers on a Solid Support" *Langmuir*, 19: 1914-1917.
Kasbauer et al. (1999) "Effect of cationic lipids in the formation of asymmetries in supported bilayers." *Biophys. J.* 76: 2600-2605.
Katiyar et al. (2006) "Synthesis of ordered large pore SBA-15 spherical particles for adsorption of biomolecules." *J Chromatog* 1122(1-2):13-20.
Kiser et al. (1998) "A synthetic mimic of the secretory granule for drug delivery" *Nature*, 394: 459-62.
Kiser et al. (2000) "Lipid-coated microgels for the triggered release of doxorubicin" *J. Control Release*, 68: 9-22.
Kneuer et al. (2000) "A nonviral DNA delivery system based on surface modified silica-nanoparticles can efficiently transfect cells in vitro." *Bioconjugate Chem.* 11:926-932.
Kochy & Bayerl (1993) "Lateral diffusion coefficients of phospholipids in spherical bilayers on a solid support measured by resonance relaxation" *Phys. Rev. E.* 47: 2109-16.
Lammers et al. (2010) "Nanomedicine Formulations for Combination Therapies." *Nano Rev.*, 1: 5705 (4 pages) DOI: 10.3402/nano.v1i0.5705.
Lee et al. (2008) "Synthesis and characterization of positive-charge functionalized mesoporous silica nanoparticles for oral drug delivery of an anti-inflammatory drug." *Advanced Functional Materials* 18:3283-3292.
Li et al. (2012) "Mesoporous silica nanoparticles in biomedical applications." *Chem Soc Rev* 41(7):2590-2605.
Li et al. (2013) "Preliminary study on pH-sensitive lipid bilayer-coated mesoporous silica nanoparticles as a novel drug carrier for antitumor drug." *Acta Pharmaceutica Sinica*, 48(2): 291-297. [English Translation of Chinese Article—27 Pages].
Li et al. (2015) "Multiple Layer-by-Layer Lipid-Polymer Hybrid Nanoparticles for Improved Folfirinox Chemotherapy in Pancreatic Tumor Models." *Adv Func Mat* 25(5):788-798.
Li et al. (2008) "Critical micelle concentrations of cetyltrimethylammonium chloride and their influence on the periodic structure of mesoporous silica." *Colloid Journal of The Russian Academy Of Sciences—Kolloidnyyie Zhurnal* 70(6): 747-752.
Lin et al. (2009) "Synthesis and Characterization of Biocompatible and Size-Tunable Multifunctional Porous Silica Nanoparticles." *Chem. Mater.* 21:3979-3986.
Linseisen et al. (1996) "2H-NMR and DSC study of DPPC-DODAB mixtures" *Chem. Phys. Lipids*, 83: 9-23.
Linseisen et al. (1997) "Differences in the Physical Properties of Lipid Monolayers and Bilayers on a Spherical Solid Support." *Biophys. J.* 72: 1659-1667.
Liong et al. (2008) "Multifunctional inorganic nanoparticles for imaging, targeting and drug delivery." *ACS Nano* 2(5):889-896 [and supporting information attached].
Liong et al. (2009) "Mesostructured Multifunctional Nanoparticles for Imaging and Drug Delivery." *J. Mater. Chem.* 19(35):6251-6257 15 pages.
Liu et al. (2009) "Electrostatically Mediated Liposome Fusion and Lipid Exchange with a Nanoparticle-Supported Bilayer for Control of Surface Charge, Drug Containment, and Delivery." *J. Am. Chem. Soc.* 131: 7567-7569.
Liu et al. (2009) "Porous Nanoparticle Supported Lipid Bilayers (Protocells) as Delivery Vehicles," *Journal of the American Chemical Society* 131(4):1354-1355.
Liu et al. (2012) "Delivering hydrophilic and hydrophobic chemotherapeutics simultaneously by magnetic mesoporous silica nanoparticles to inhibit cancer cells" *International Journal of Nanomedicine* 7: 999-1013.
Liu et al. (2016) "Irinotecan delivery by lipid-coated mesoporous silica nanoparticles shows improved efficacy and safety over liposomes for pancreatic cancer." *ACS Nano* 10:2702-2715 [24 pages—with Supplementary Materials].
Liu et al. (2016) "Irinotecan delivery by lipid-coated mesoporous silica nanoparticles shows improved efficacy and safety over liposomes for pancreatic cancer." *ACS Nano* 10:2702-2715.
Loidl-Stahlhofen et al. (2001) "Multilamellar liposomes and solid-supported lipid membranes (TRANSIL): screening of lipid-water partitioning toward a high-throughput scale" *Pharm. Res.* 18: 1782-1788.
Loidl-Stahlhofen et al. (2001) "Solid-Supported Biomolecules on Modified Silica Surfaces—A Tool for Fast Physicochemical Characterization and High-Throughput Screening" *Advanced Materials* 13: 1829-1834.
Loidl-Stahlhofen et al. (2001) "Solid-supported lipid membranes as a tool for determination of membrane affinity: High-throughput screening of a physicochemical parameter." *J. Pharm. Sci.* 90: 599-606.
Loidl-Stahlhofen et al. (1996) "The thermodynamic control of protein binding to lipid bilayers for protein chromatography" *Nat. Biotechnol.* 14: 999-1002.
Lu et al. (2007) "Mesoporous silica nanoparticles as a delivery system for hydrophobic anticancer drugs." *Small* 3:1341-1346.
Ma et al. (2013) "Nanoparticles for Combination Drug Therapy." *ACS Nano* 7: 9518-9525.
Mackowiak et al. (2013) "Targeted Drug Delivery in Cancer Cells with Red-Light Photoactivated Mesoporous Silica Nanoparticles." *Nano Lett.* 13: 2576-2583.
Mai et al. (2013) "Mesoporous Silica Nanoparticles: A Multifunctional Nano Therapeutic System." *Integr. Biol.* 5: 19-28.

(56) References Cited

OTHER PUBLICATIONS

Mayer et al. (2007) "Optimizing Combination Chemotherapy by Controlling Drug Ratios." *Mol. Interventions* 7: 216-223.
Meng et al. (2006) "A Family of Highly Ordered Mesoporous Polymer Resin and Carbon Structures from Organic-Organic Self-Assembly." *Chem Mat* 6(18):4447-4464.
Meng et al. (2010) "Autonomous in Vitro Anticancer Drug Release from Mesoporous Silica Nanoparticles by pH-Sensitive Nanovalves." *J. Am. Chem. Soc.* 132:12690-12697.
Meng et al. (2010) "Engineered Design of Mesoporous Silica Nanoparticles to Deliver Doxorubicin and P-Glycoprotein siRNA to Overcome Drug Resistance in a Cancer Cell Line," *ACS Nano* 4(8):4539-4550.
Meng et al. (2010) "Potent Angiogenesis Inhibition by the Particulate Form of Fullerene Derivatives." *American Chemical Society* 4(5):2773-2783.
Meng et al. (2011) "Aspect Ratio Determines the Quantity of Mesoporous Silica Nanoparticle Uptake by a Small GTPase-Dependent Macropinocytosis Mechanism," *ACS Nano*, 5(6):4434-4447.
Meng et al. (2011) "Use of Size and a Copolymer Design Feature to Improve the Biodistribution and the Enhanced Permeability and Retention Effect of Doxorubicin Loaded Mesoporous Silica Nanoparticles in a Murine Xenograft Tumor Model," *ACS Nano* 5(5):4131-4144.
Meng et al. (2012) "Development of Pharmaceutically Adapted Mesoporous Silica Nanoparticles Platform." *J. Phys. Chem. Lett.* 3: 358-359.
Meng et al. (2013) "Codelivery of an Optimal Drug/siRNA Combination Using Mesoporous Silica Nano-particles To Overcome Drug Resistance in Breast Cancer in Vitro and in Vivo." *ACS Nano* 7: 994-1005.
Meng et al. (2013) "Two-Wave Nanotherapy to Target the Stroma and Optimize Gemcitabine Delivery to a Human Pancreatic Cancer Model in Mice," *ACS Nano* 7(11):10048-10065.
Meng et al. (2015) "Use of a Lipid-Coated Mesoporous Silica Nanoparticle Platform for Synergistic Gemcitabine and Paclitaxel Delivery to Human Pancreatic Cancer in Mice" *ACS Nano* 9(4): 3540-3557.
Messerer et al. (2004) "Liposomal Irinotecan: Formulation Development and Therapeutic Assessment in Murine Xenograft Models of Colorectal Cancer." *Clin Cancer Res* 10(19):6638-6649.
Miao et al. (2014) "Nanoparticles with Precise Ratiometric Co-loading and Co-delivery of Gemcitabine Monophosphate and Cisplatin for Treatment of Bladder Cancer." *Adv. Funct. Mater.* 24(42): 6601-6611. [NIH Public Access; Author Manuscript—24 pages].
Moore et al. (2007) "Erlotinib Plus Gemcitabine Compared with Gemcitabine Alone in Patients with Advanced Pancreatic Cancer: A Phase III Trial of the National Cancer Institute of Canada Clinical Trials Group." *J. Clin. Oncol.* 25(15): 1960-1966.
Mornet, et al. (2005) "The Formation of Supported Lipid Bilayers on Silica Nanoparticles Revealed by Cryoelectron Microscopy." *Nano Lett.*, 5(2): 281-285.
Moura & Carmona-Ribeiro (2003) "Cationic Bilayer Fragments on Silica at Low Ionic Strength: Competitive Adsorption and Colloid Stability" *Langmuir* 19: 6664-6667.
Moura & Carmona-Ribeiro (2005) "Biomimetic Particles: Optimization of Phospholipid Bilayer Coverage on Silica and Colloid Stabilization" *Langmuir* 21: 10160-10164.
Naumann et al. (1992) "Phase transition behavior of single phosphatidylcholine bilayers on a solid spherical support studied by DSC, NMR and FT-IR" *Biophys J.* 63: 1314-1319.
Ng et al. (2001) "One-Step Synthesis of a Fluorescent Phospholipid-Hydrogel Conjugate for Driving Self-Assembly of Supported Lipid Membranes" *Macromolecules* 34: 5759-5765.
Ng et al. (2004) "Properties of a Self-Assembled Phospholipid Membrane Supported on Lipobeads" *Biophys J.* 87: 323-331.
Nordlund et al. (2009) "Formation of supported lipid bilayers on silica particles studied using flow cytometry." *Langmuir* 25, 4601-4606.

Obringer et al. (1995) Antiphospholipid antibody binding to bilayer-coated glass microspheres *J Immunol Meth.* 185: 81-93.
Onishi et al. (2003) "Antitumor Properties of Irinotecan-Containing Nanoparticles Prepared Using Poly(DL-lactic acid) and Poly(ethylene glycol)-block-poly(propylene glycol)-block-poly(ethylene glycol)." *Biol. Pharmaceut Bull.* 26(1):116-119.
Onivyde (irinotecan liposome injection)—Highlights of Prescribing Information—Reference ID: 3836766; 18 pages [accessed Oct. 23, 2015]. Retrieved from the Internet: URL: https://www.accessdata.fda.gov/drugsatfda_docs/label/Z015/207793lbl.pdf.
Park et al. (2004) "Characterization of radioligand binding to a transmembrane receptor reconstituted into Lipobeads" *FEBS Lett* 567: 344-348.
Pasqua et al. (Published online Feb. 3, 2007) "Preparation of bifunctional hybrid mesoporous silica potentially useful for drug targeting." *Microporous and Mesoporous Materials* 103:166-173.
Patil et al. (2010) "Use of nanoparticle mediated gene silencing and drug delivery to overcome tumor drug resistance." *Biomaterials* 31:358-365.
Pearse et al. (1987) "Structure and assembly of coated vesicles." *Annu. Rev. Biophys. Biophys. Chem.* 16:49-68.
Peer, et al. (2007) "Nanocarriers as an Emerging Platform for Cancer Therapy." *Nat. Nanotechnol.*, 2: 751-760.
Piyasena et al. (2008) "Biosensors based on release of compounds upon disruption of lipid bilayers supported on porous microspheres." *Biointerphases* 3: 38-49.
Ramsay et al. (2008) "A novel liposomal irinotecan formulation with significant anti-tumour activity: Use of the divalent cation ionophore A23187 and copper-containing liposomes to improve drug retention." *Eur J Pharm Biopharm* 68(3):607-617.
Rapuano & Carmona-Ribeiro (1997) "Physical Adsorption of Bilayer Membranes on Silica" *J. Colloid Interface Sci.* 193: 104-111.
Rapuano & Carmona-Ribeiro (2000) "Supported Bilayers on Silica" *J. Colloid Interface Sci.* 226: 299-307.
Reinl & Bayerl (1993) "Interaction of myelin basic protein with single bilayers on a solid support: an NMR, DSC and polarized infrared ATR study" *Biochim Biophys Acta.* 1151: 127-136.
Reinl & Bayerl (1994) "Lipid Transfer between Small Unilamellar Vesicles and Single Bilayers on a Solid Support: Self-Assembly of Supported Bilayers with Asymmetric Lipid Distribution" *Biochemistry* 33: 14091-14099.
Roggers et al. (2012) "Chemically Reducible Lipid Bilayer Coated Mesoporous Silica Nano-particles Demonstrating Controlled Release and HeLa and Normal Mouse Liver Cell Biocompatibility and Cellular Internalization." *Mol. Pharmaceutics* 9: 2770-2777.
Roiter et al. (2008) "Interaction of Nanoparticles with Liquid Membrane." *Nano Lett.* 8:941-944.
Saad et al. (2008) "Co-delivery of siRNA and an anticancer drug for treatment of multi-drug resistant cancer." *Nanomedicine* 3:761-776.
Sachse et al. (2017) "Surfactant-Templating of Zeolites: From Design to Application" *Chem. Mater.*, 29(9): 3827-3853, [Abstract only—2 pages].
Sackmann, E. (1996) "Supported Membranes: Scientific and Practical Applications." *Science*, 271(5245): 43-48.
Sadzuka et al. (1998) "Effect of liposomalization on the antitumor activity, side-effects and tissue distribution of CPT-11." *Cancer Lett.* 127(1):99-106.
Santos et al. (2009) "The Power of Ultrasound", *Ultrasound in Chemistry: Analytical Applications*, 16 pages.
Schmitt et al. (2001) "Polymer Cushions in Supported Phospholipid Bilayers Reduce Significantly the Frictional Drag between Bilayer and Solid Surface" *Langmuir* 17: 244-246.
Schmitz et al. (1999) "Interactions of Myristoylated Alanine-Rich C Kinase Substrate (MARCKS)-Related Protein with a Novel Solid-Supported Lipid Membrane System (TRANSIL)" *Anal. Biochem.* 268: 343-353.
Schuhmacher et al. (2004) "High-throughput determination of the free fraction of drugs strongly bound to plasma proteins." *J. Pharm. Sci.* 93: 816-830.
Sharma et al. (2004) "Bacteriorhodopsin conjugates as anchors for supported membranes." *Bioconjug. Chem.* 15: 942-947.
Shidhaye et al. (2008) "Nanogel Engineered Polymeric Micelles for Drug Delivery." *Current Drug Therapy* 3(3):209-217.

(56) References Cited

OTHER PUBLICATIONS

Singh et al. (2008) "Nanoengineering artificial lipid envelopes around adenovirus by self-assembly." *ACS Nano* 2: 1040-1050.
Slowing et al. (2008) "Mesoporous silica nanoparticles as controlled release drug delivery and gene transfection carriers." *Adv. Drug Deliv. Rev.* 60:1278-1288.
Sommerwerk et al. (2011) "Lipid Coated Chitosan Micro- particles as Protein Carriers." *Pulm. Pharmacol. Ther.* 8: 1978-1984.
Sugahara et al. (2010) "Coadministration of a tumor-penetrating peptiden enhances the efficacy fo cancer drugs." *Science* 328:1031-1035.
Szakacs et al. (2006) "Targeting multidrug resistance in cancer." *Nat. Rev. Drug Discov.* 5:219-234.
Tamanoi "Nanodelivery: Towards controlled release of anti-cancer drugs." Oral Presentation on Dec. 6, 2006 (see NanoBio—Tokyo 2006 Program), 7 pages. Abstract provided in Proceedings of UT Symposium on NanoBio Integration Program and Abstract provided.
Tang et al. (2012) "Mesoporous Silica Nanoparticles: Synthesis, Biocompatibility and Drug Delivery." *Adv Mat* 24(12):1504-1534.
Tardi et al. (2009) "In Vivo Maintenance of Synergistic Cytarabine:Daunorubicin Ratios Greatly Enhances Therapeutic Efficacy." *Leuk. Res.* 33: 129-139.
Tarn et al. (2013) "Mesoporous Silica Nanoparticle Nanocarriers: Biofunctionality and Biocompatibility." *Accounts of Chemical Research* 46(3):792-801.
Thorolfsson et al. (2002) "The binding of tyrosine hydroxylase to negatively charged lipid bilayers involves the N-terminal region of the enzyme." *FEBS Lett.* 519: 221-226.
Torney et al. (2007) "Mesoporous silica nanoparticles deliver DNA and chemicals into plants." *Nat. Nanotechnol.* 2:295-300.
Troutier & Ladaviere (2007) "An overview of lipid membrane supported by colloidal particles." *Adv. Colloid Interface Sci.* 133: 1-21.
Valencia et al. (2013) "Synergistic cytotoxicity of irinotecan and cisplatin in dual-drug targeted polymeric nanoparticles." *Nanomed* 8(5):687-698 [NIH Public Access—Author Manuscript—17pages].
Van Schooneveld et al. (2008) "Improved Biocompatibility and Pharmacokinetics of Silica Nanoparticles by Means of a Lipid Coating: A Multimodality Investigation." *Nano Lett.* 8(8): 2517-2525.
Van Vlerken et al. (2007) "Modulation of intracellular ceramide using polymeric nanoparticles to overcome multidrug resistance in cancer." *Cancer Res.* 67:4843-4850.
Von Hoff et al. (2011) "Gemcitabine Plus Nab-Paclitaxel Is an Active Regimen in Patients with Advanced Pancreatic Cancer: A Phase I/II Trial." *J. Clin. Oncol.* 29(34): 4548-4554.
Von Hoff et al. (2013) "Increased Survival in Pancreatic Cancer with Nab-Paclitaxel Plus Gemcitabine." *N. Engl. J. Med.* 369(18): 1691-1703.
Wu et al. (2007) "Reversal of multidrug resistance by transferrin-conjugated liposomes co-encapsulating doxorubicin and verapamil." *J Pharm. Pharmaceut. Sci.* 10:350-357.
Xia et al. (2009) "Polyethyleneimine Coating Enhances the Cellular Uptake of Mesoporous Silica Nanoparticles and Allows Safe Delivery of siRNA and DNA Constructs." *ACS Nano* 3(10):3273-3286.
Xu et al. (2013) "Biodistribution and Pharmacokinetics of EGFR-Targeted Thiolated Gelatin Nanoparticles Following Systemic Administration in Pancreatic Tumor-Bearing Mice." *Mol Pharmaceutics* 10:2031-2044.
Yang et al. (2010) "Lipid Coated Mesoporous Silica Nanoparticles as Photosensitive Drug Carriers." *Phys. Chem. Chem. Phys.* 12: 4418-4422.
Yezhelyev et al. (2008) "Proton-sponge coated quantum dots for siRNA delivery and intracellular imaging." *J. Am. Chem. Soc.* 130(28):9006-9012.
Zhang et al. (2011) "Synergistic Antitumor Activity of Gemcitabine and ABT-737 in Vitro and in Vivo through Disrupting the Interaction of USP9X and Mcl-1." *Mol. Cancer Ther.* 10: 1264-1275.
Zhang et al. (2013) "Facile Large-Scale Synthesis of Monodisperse Mesoporous Silica Nanospheres with Tunable Pore Structure" *J. Am. Chem. Soc.*, 135(7): 2427-2430.
Zhang et al. (2014) "Biofunctionalized polymer-lipid supported mesoporous silica nanoparticles for release of chemotherapeutics in multidrug resistant cancer cells." *Biomaterials* 35:3650-3665.
Zhu et al. (2004) "Poly(L-lysine)-modified silican nanoparticles for the delivery of anitsense oligonucleotides." *Biotechnol. Appl. Biochem.* 39:179-187.
Zucker et al. (2009) "Liposome drugs' loading efficiency: A working model based on loading conditions and drug's physicochemical properties." *J Control Release* 139(1):73-80.
AU Office action dated May 22, 2023, in AU Application No. AU2022200881.
CA Office Action dated Feb. 3, 2023, in Application No. CA3010711.
CA Office Action dated Oct. 24, 2023, in Application No. CA3010711.
CN Office Action dated Jan. 30, 2022, in Application No. CN201780010248.8 with English translation.
EP Extended European Search Report dated Jul. 11, 2023, in Application No. 23158990.4.
Extended European Search Report dated Mar. 15, 2022, in Application No. 18897783.9.
JP Office Action dated Apr. 17, 2023 in Application No. JP2022-72344 with English translation.
JP Office Action dated Oct. 16, 2023 in Application No. JP2022-72344 with English translation.
KR Office Action dated Mar. 22, 2023 in Application No. KR10-2022-7019372 with English translation.
KR Office Action dated Sep. 25, 2023 in Application No. KR10-2022-7019372 with English translation.
U.S. Advisory Action dated Feb. 7, 2023 in U.S. Appl. No. 16/235,950.
U.S. Final Office Action dated Oct. 26, 2023 in U.S. Appl. No. 16/235,950.
U.S. Final office Action dated Sep. 28, 2022 in U.S. Appl. No. 16/235,950.
U.S. Non-Final Office Action dated Apr. 13, 2023 in U.S. Appl. No. 16/235,950.
U.S. Non-Final Office Action dated Aug. 22, 2023, in U.S. Appl. No. 16/948,498.
U.S. Notice of Allowance dated Nov. 17, 2023 in U.S. Appl. No. 16/948,498.

\* cited by examiner

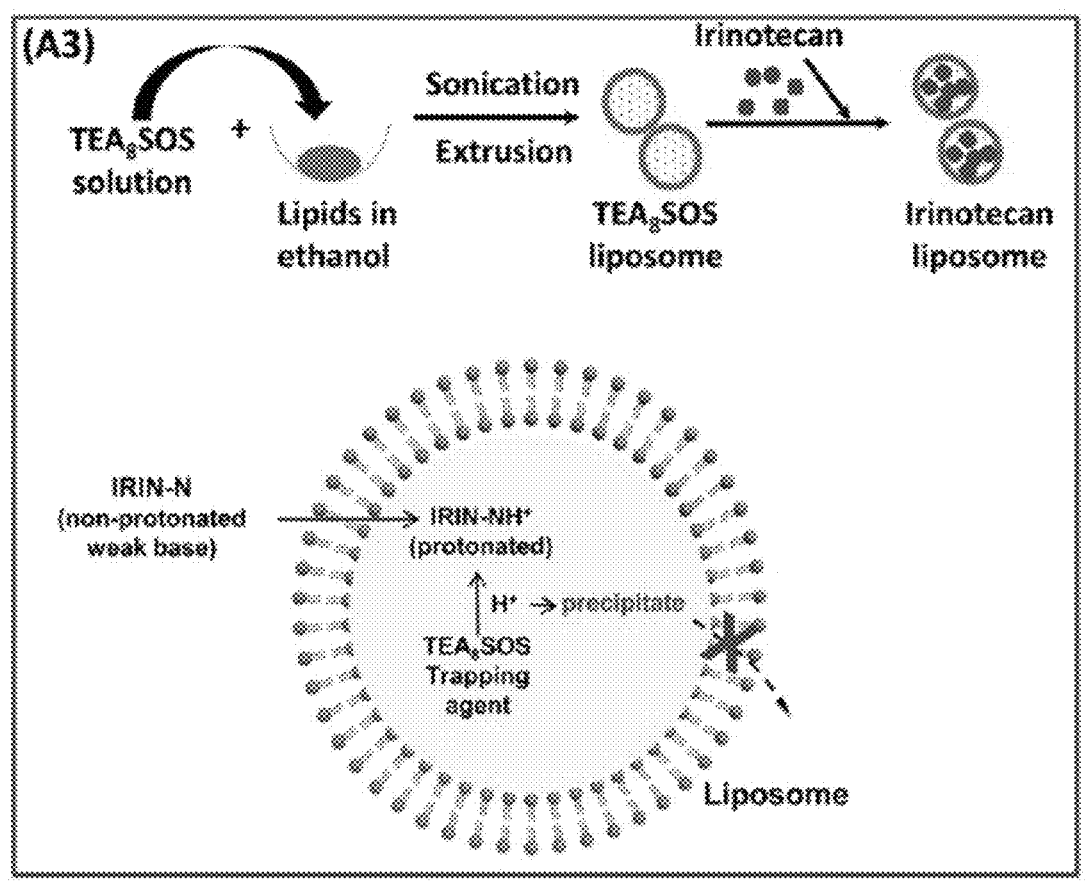
Fig. 1A, cont'd.

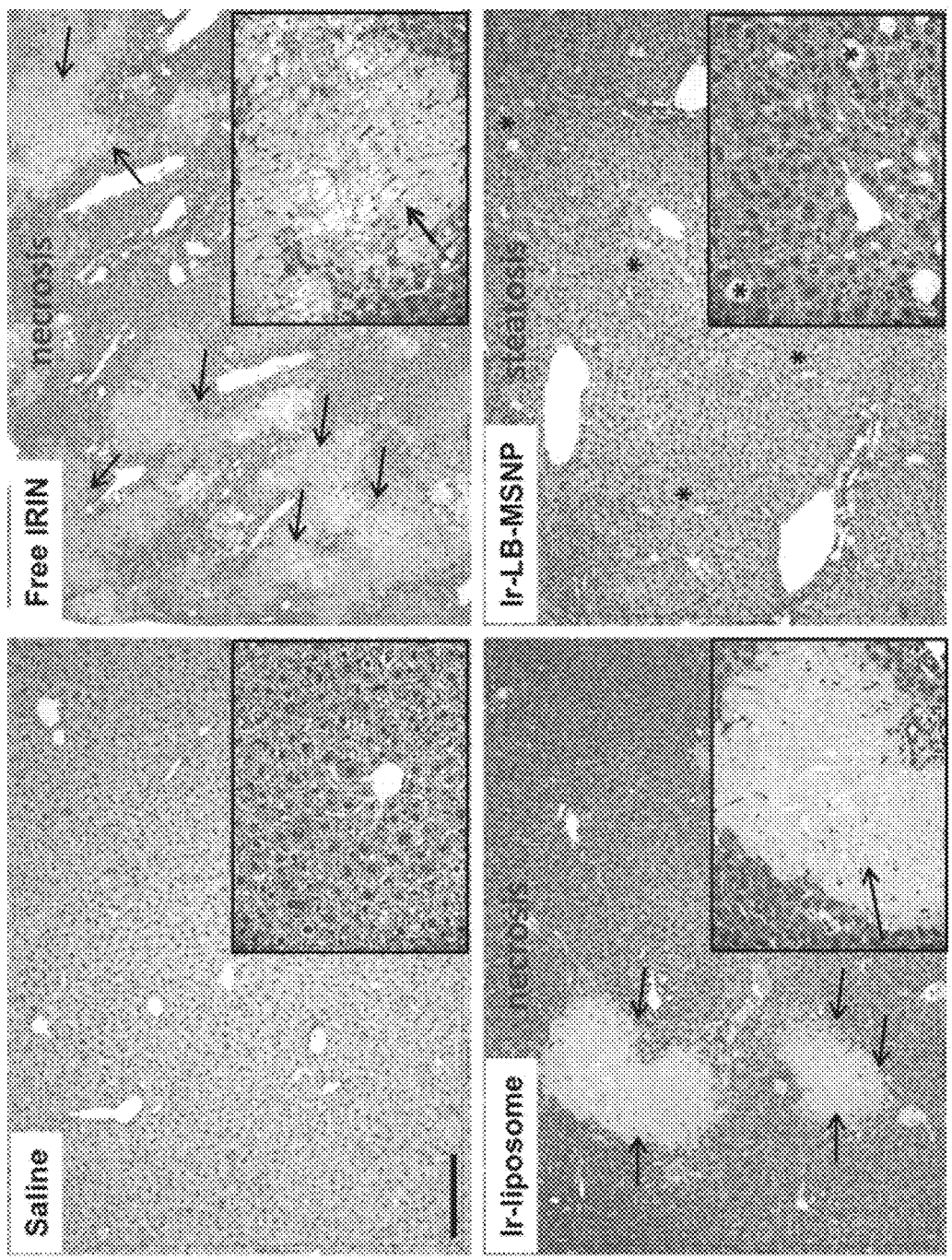

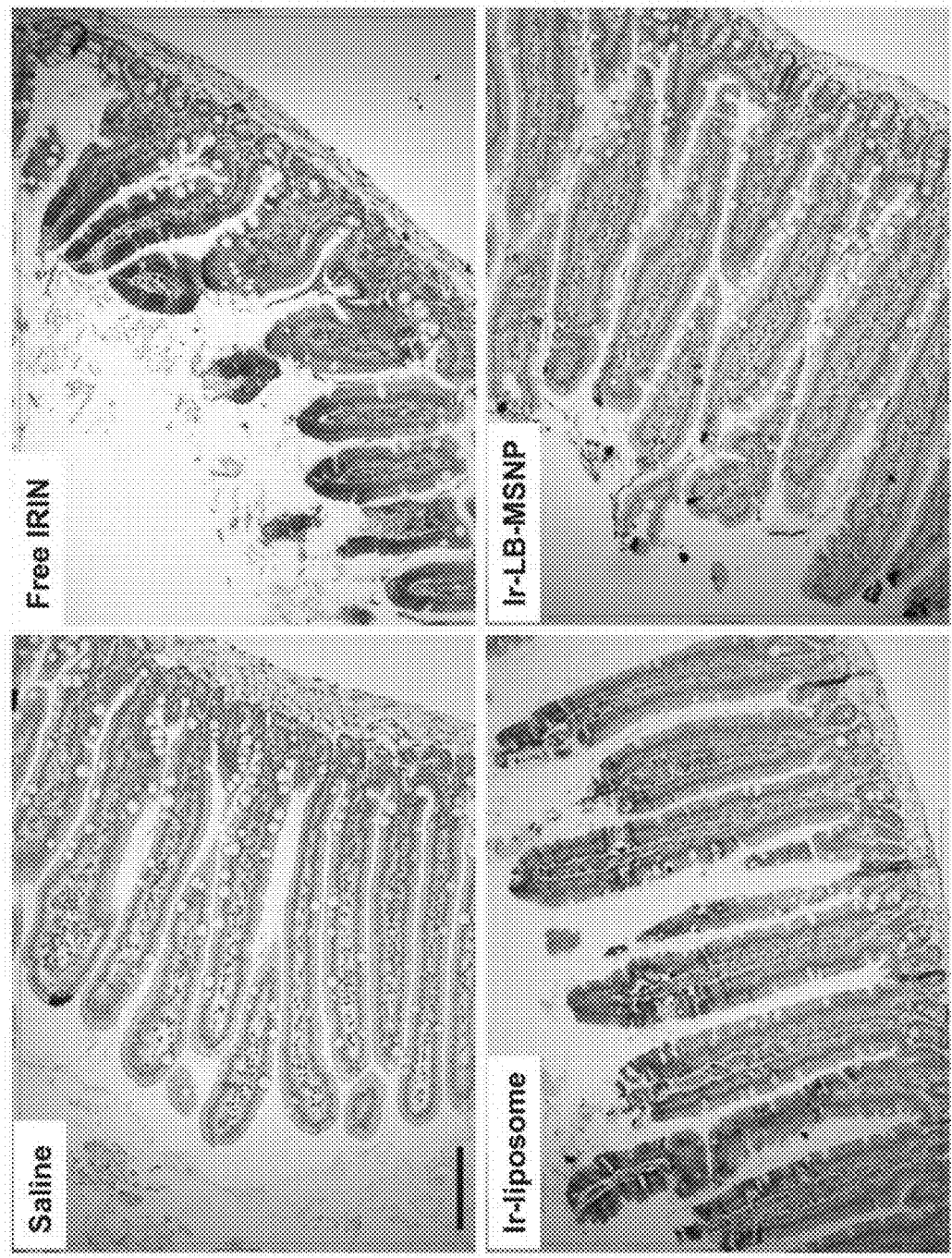

MESOPOROUS SILICA NANOPARTICLES WITH LIPID BILAYER COATING FOR CARGO DELIVERY

CROSS-REFERENCE TO RELATED APPLICATIONS

This application is a continuation of U.S. Ser. No. 16/947,539, filed Aug. 5, 2020, which is a continuation of U.S. Ser. No. 16/164,030, filed Oct. 18, 2018, U.S. Pat. No. 10,765,636, which is a continuation of U.S. Ser. No. 15/798,287, filed Oct. 30, 2017, U.S. Pat. No. 10,143,660, which is a continuation of International Application PCT/US2017/012625, with an international filing date of Jan. 6, 2017, which claims benefit of and priority to U.S. Ser. No. 62/276,634, filed on Jan. 8, 2016, all of which are incorporated herein by reference in their entirety for all purposes.

STATEMENT OF GOVERNMENTAL SUPPORT

This invention was made with government support under Grant Numbers CA133697 and CA198846, awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "UCLA-P166C4US_ST25.txt" created on Feb. 10, 2022 and having a size of 3,168 bytes. The contents of the text file are incorporated by reference herein in their entirety.

BACKGROUND

Pancreatic ductal adenocarcinoma (PDAC) is a fatal disease with a 5-year survival rate of less than 6% (Siegel et al. (2014) *CA Cancer J. Clin.* 64(1): 9-29). Currently, the major treatment regimens for chemotherapy include either a single reagent, gemcitabine (GEM), or a four-drug regimen). While FOLFIRINOX has a better response rate than GEM (31.6% versus 9.4%), with improved survival (11 months versus 6.8 months), the former combination is significantly more toxic and restricted to a minority of PDAC patients with good performance status (Conroy et al. (2011) *N. Engl. J. Med.* 364(19): 1817-1825). Irinotecan contributes significantly to this toxicity, including a severe impact on the bone marrow (e.g. neutropenia), liver (e.g. necrosis and steatosis) and the gastrointestinal (GI) tract (e.g. vomiting, diarrhea) (Conroy et al. (2011) *N. Engl. J. Med.* 364(19): 1817-1825; Ueno et al. (2007) *Cancer Chemother. Pharmacol.* 59(4): 447-454; Loupakis et al. (2013) *Br. J. Cancer,* 108(12): 2549-2556). Thus, there is a great demand for a treatment regimen that improves irinotecan toxicity, with a view to improving the available drugs for first-line therapy in PDAC.

One approach to reducing irinotecan toxicity, with maintenance of efficacy, is high-dose drug encapsulation in a nanocarrier with protected delivery to the cancer site while reducing systemic drug release. Different carrier types, including polymeric particles and liposomes, have been employed with some success for irinotecan delivery (Chou et al. (2003) *J. Biosci. Bioeng.,* 95(4): 405-408; Onishi et al. (2003) *Biol. Pharmaceut. Bull.* 26(1): 116-119; Messerer et al. (2004) *Clin. Cancer Res,* 10(19): 6638-6649; Drummond et al. (2006) *Cancer Res.,* 66(6): 3271-3277; Valencia et al. (2013) *Nanomed.* 8(5): 687-698; Sadzuka et al. (1998) *Cancer Lett.,* 127(1): 99-106; Ramsay et al. (2008) *Eur. J. Pharm. Biopharm.* 68(3): 607-617; Li et al. (2015) *Adv. Func. Mat.* 25(5): 788-798). However, while polymeric nanoparticles showed promising in vitro results, the limited capacity to load irinotecan (<1%, w/w) plus premature drug release (e.g., 40% in 5 hours), the nanoparticles did not achieve the required toxicity reduction while improving intratumoral drug delivery (Valencia et al. (2013) *Nanomed.* 8(5): 687-698). While liposomes could achieve high irinotecan loading capacity through the use of ammonium sulfate or proton entrapment agents (Chou et al. (2003) *J. Biosci. Bioeng.,* 95(4): 405-408; Messerer et al. (2004) *Clin. Cancer Res,* 10(19): 6638-6649; Drummond et al. (2006) *Cancer Res.,* 66(6): 3271-3277; Sadzuka et al. (1998) *Cancer Lett.,* 127(1): 99-106; Ramsay et al. (2008) *Eur. J. Pharm. Biopharm.* 68(3): 607-617), carrier instability under shear and osmotic stress, as well as bilayer disruption by serum proteins, resulted in premature drug release and toxicity (Liu et al. (2000) In: *Colloids and Surfaces A: Physicochemical and Engineering Aspects,* 172(1-3): 57-67; Heurtault et al. (2003) *Biomaterials,* 24(23): 4283-4300; Sabin et al. (2006) *Eur. Phys. J. E.* 20(4): 401-408).

As noted above, many attempts to deliver cancer drugs in clinical trials or in a therapeutic setting have been based on liposomal (Messerer et al. (2004) *Clin. Cancer Res,* 10(19): 6638-6649; *Cancer Res.* 2006, 66, 3271) or polymer-based systems (Onishi et al. (2003) *Biol. Pharm. Bull.* 26(1): 116-119). Most of these carriers are spherical particles or supramolecular assemblies in the size range of 80-200 nm, often containing PEG coating on the surface to prolong circulatory half-life, and typically exhibiting loading capacities from ~5 w/w % (e.g., polymer-based nanoparticles) to ~50 w/w % (e.g., liposomal carrier). At a pre-clinical level, the potential benefits of these nanocarriers in animal studies, including murine PDAC models, have been shown to include a reduction in in vivo toxicity, enhanced antitumor efficacy, and improved survival rate.

However, only a small number of nanocarriers have advanced to clinical trials for PDAC patients. Nanocarriers including an ionophore (A23187, also known as calimycin) enabled irinotecan delivery liposomal formulation (Irinophore C) and a protonating agent irinotecan delivering liposomal formulation (MM-398) (Baker et al. (2008) *Clin. Cancer Res.* 14: 7260-7271; Drummond et al. (2006) *Cancer Res.* 15(66): 3271-3277. The Irinophore C formulation (Champions Biotechnology) is a liposomal carrier that makes use of active irinotecan loading through the generation of transmembrane proton gradients, using the ionophore, A23187, or ammonium sulfate (Ramsay et al. (2008) *Eur. J. Pharm. Biopharm.* 68: 607-617). The Irinophore C formulation was used in a clinical study that commenced in 2011, but there have been no updated information about the outcome of the study or the results.

While in a recent phase 3 clinical trial, the development of a liposomal carrier (MM-398) for irinotecan by Merrimack showed an improved survival benefit in PDAC as a $2^{nd}$-line treatment option, the relatively high rate of GI tract and bone marrow toxicity has resulted in a black box warning for severe and life-threatening diarrhea and neutropenia (Von Hoff et al. (2013) *Br. J. Cancer,* 109(4): 920-925; www.fda.gov/newsevents/newsroom/pressannouncements/ucm468654.htm). Human subjects participating in MM-398 clinical trials also showed significant elevations of liver enzymes, including alanine aminotransferase (ALT) (see, e.g., www.accessdata.fda.gov/drugsatfda_docs/label/2015/207793LB.pdf). Nonetheless, MM-398 received FDA approval for use in PDAC for patients failing to respond to GEM therapy, and is marketed as Onivyde® (see, e.g., www.fda.gov/newsevents/newsroom/pressannouncements/ucm468654.htm).

The MM-398 liposomal formulation (Merrimack Pharmaceuticals) incorporates irinotecan hydrochloride with the assistance of a polyanionic trapping agent (ESMO G12014, www.merrimackpharma.com). More specifically, irinotecan loading into the MM-398 liposome was achieved by intraliposomal drug encapsulation of a multivalent anionic trapping agent, triethylammonium sucrose octasulfate ($TEA_8SOS$). This chemical leads to irinotecan protonation and entrapment at more than 10 times the loading that can be achieved through passive drug encapsulation (Drummond et al. (2006) *Cancer Res.* 66(6): 3271-3277). IV administration of MM-398 liposome has been shown to induce complete tumor regression in various PDAC tumor models in mice, including inhibition of metastatic tumor foci (Paz et al. (2102) *Cancer Res.* 72(12 Suppl): Abstract A63). MM-398 is currently in a Phase 3 clinical trial and lays claim to providing improved tumor inhibition, pharmacokinetics and efficacy compared to free irinotecan in animal and human studies (Kalra (2012) *AACR meeting*, Abstract #5622). This includes experimental data claiming complete PDAC regression using a dose of 20 mg/kg MM-398 (human equivalent dose 60-120 mg/m2) in murine xenograft studies (Paz et al. (2102) *Cancer Res.* 72(12 Suppl): Abstract A63). MM-398 also increases the maximum tolerated dose (MTD) of free irinotecan from 80 to 324 mg/kg in mice (Drummond et al. (2006) *Cancer Res.* 66(6): 3271-3277). Additionally, in the Phase 3 clinical trial by Merrimack Pharmaceuticals (Hoff et al. ESMO GI 2014, www.merrimackpharma.com) involving 417 PDAC patients, the combination of MM-398, 5-FU and leucovorin resulted in an overall survival (OS) of 6.1 months, which is 1.9 months longer than the control arm receiving 5-FU and leucovorin. However, while the active loading of irinotecan into the MM-398 liposomal formulation enhances drug loading capacity over a passive encapsulation procedure, the synthesis technique requires multiple steps and liposomal carriers do not provide the same colloidal stability or the same amount of intracellular release compared to the LB-MSNP platform provided herein. Nonetheless, MM-398 received FDA approval for use in PDAC for patients failing to respond to GEM therapy, and is marketed as ONIVYDE®. The use of polyanionic polymers to increase drug entrapment in liposomes leads to ~80 nm drug precipitation (Zhu et al. (1996) 39(1): 138-142; Colbern et al. (1998) *Clin. Cancer Res.* 4(12): 3077-3082), which constitutes one of the reasons for slow irinotecan release from the liposomal carrier compared to LB-MSNP pores.

Thus, there is still an unmet need for nanocarriers and delivery methods that enable efficient drug delivery, including chemotherapy such as irinotecan chemotherapy, with an improved margin of safety and reduced toxicity.

SUMMARY

Urgent intervention is required to improve the 5-year survival rate of pancreatic ductal adenocarcinoma (PDAC). While the 4-drug regimen, FOLFIRINOX (comprised of irinotecan (IRIN), 5-fluorouracil (5-FU), oxaliplatin (OX), and leucovorin (LV)), has a better survival outcome than the more frequently used gemcitabine (GEM), the former treatment regimen is highly toxic and restricted for use in a patient with good performance status. Since irinotecan contributes significantly to FOLFIRINOX toxicity (bone marrow and gastrointestinal tract), one specific aim of the present invention is to reduce the toxicity of the former drug with a custom-designed mesoporous silica nanoparticle (MSNP) platform, which uses a proton gradient for high-dose irinotecan loading across a coated lipid bilayer (LB). The improved stability of the LB-coated MSNP (LB-MSNP) carrier allows for better protected irinotecan delivery and increased tumor drug concentrations when compared, for example, to a liposomal equivalent in a Kras-derived orthotopic PDAC model in immunocompetent mice. The LB-MSNP nanocarrier is also more efficient for treating tumor metastases. Equally important, the reduced leakage and slower rate of drug release by the LB-MSNP carrier dramatically reduces the rate of bone marrow, gastrointestinal and liver toxicity compared to a liposomal carrier. The combination of high efficacy and reduced toxicity by the LB-MSNP carrier facilitates the use of irinotecan as a first-line therapeutic to improve PDAC survival.

Generally, in one aspect of the present invention, a nanocarrier is provided comprising a silica body having a surface and defining a plurality of pores that are suitable to receive molecules therein, a lipid bilayer (e.g., a phospholipid bilayer) coating the surface, and a cargo-trapping agent contained in the pores by the coated lipid bilayer, where the submicron structure has a maximum dimension of less than one micron, and wherein the phospholipid bilayer stably seals the plurality of pores and can serve as a basis for additional packaging, targeting, imaging and functionalization.

One significant aspect of the present invention includes new methods for making improved cargo/agent (e.g. irinotecan or other molecule(s) with the chemical structures described herein) nanocarriers. These methods generally include providing an unloaded nanocarrier comprising a silica body having a surface with a plurality of pores that are suitable to receive molecules therein, and encapsulating a cargo-trapping, targeting or imaging agent within the pores by a lipid bilayer (e.g., a phospholipid bilayer). As discussed in detail below, working examples include, but are not limited to new methods of making concentrated irinotecan nanocarriers. In certain embodiments these methods include selecting a nanocarrier comprising a silica body having a surface including a plurality of pores suitable to receive irinotecan therein. In these methods, an agent having an ability to specifically influence the diffusion of and/or trap the irinotecan molecule (e.g. triethylammonium sucrose octasulfate) is also selected and disposed within the plurality of pores. The nanocarrier and pores are completely coated with a lipid bilayer (for example using a sonication process). Typically the silica body nanocarrier is not dried and/or washed immediately prior to this coating step. Optionally, in certain embodiments, this lipid bilayer can comprise one or more bioactive molecules selected to facilitate the nanocarrier function (such as polyethylene glycol, and/or targeting ligands, and/or paclitaxel and/or activated irinotecan, SN38). Following this coating step, irinotecan is then allowed to migrate across the lipid bilayer into the pores where it is entrapped. This is also known as "remote drug loading". In this way, irinotecan nanocarriers with surprisingly high loading capacities (e.g. 40 wt % or greater than 40% drug/MSNP) can be formed. In addition to these high drug loading capacities, irinotecan nanocarriers formed using these methods have a constellation of other desirable properties, for example exhibiting <5% irinotecan leakage over 24 hours in a biological buffer with pH of 7.4 at 37° C.

Various embodiments contemplated herein may include, but need not be limited to, one or more of the following:

Embodiment 1: A nanoparticle drug carrier comprising:
a silica nanoparticle having a surface and defining a plurality of pores that are suitable to receive molecules therein;
a lipid bilayer coating the surface;
a cargo-trapping agent within pores comprising said plurality of pores; and
a cargo comprising a drug, where said cargo is associated with said cargo-trapping agent in said pores;
wherein the submicron structure has a maximum dimension of less than one micron, and wherein the lipid bilayer stably seals the plurality of pores.

Embodiment 2: The nanoparticle drug carrier of embodiment 1, wherein said lipid bilayer comprises a phospholipid, cholesterol (CHOL), and an mPEG phospholipid.

Embodiment 3: The nanoparticle drug carrier according to any one of embodiments 1-2, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 4: The nanoparticle drug carrier of embodiment 3, wherein said phospholipid comprises a saturated fatty acid selected from the group consisting of phosphatidylcholine (DPPC), dimyristoylphosphatidylcholine (DMPC), distearoylphosphatidylcholine (DSPC), and diactylphosphatidylcholine (DAPC).

Embodiment 5: The nanoparticle drug carrier of embodiment 3, wherein said phospholipid comprises a natural lipid selected from the group consisting of egg phosphatidylcholine (egg PC), and soy phosphatidylcholine (soy PC).

Embodiment 6: The nanoparticle drug carrier of embodiment 3, wherein said phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine.

Embodiment 7: The nanoparticle drug carrier according to any one of embodiments 1-6, wherein said lipid bilayer comprises an mPEG phospholipid with a phospholipid C14-C18 carbon chain, and a PEG molecular weight ranging from about 350 Da to 5000 Da.

Embodiment 8: The nanoparticle drug carrier of embodiment 7, wherein said lipid bilayer comprises 1,2-distearoyl-sn-glycero-3-phosphoethanolamine-PEG (DSPE-PEG).

Embodiment 9: The nanoparticle drug carrier of embodiment 2, wherein said lipid bilayer comprises DPPC/Chol/DSPE-PEG or DSPC/Chol/DSPE-PEG.

Embodiment 10: The nanoparticle drug carrier of embodiment 9, wherein said lipid bilayer comprises DSPC/Chol/DSPE-PEG.

Embodiment 11: The nanoparticle drug carrier of embodiment 10, wherein wherein said lipid bilayer comprises DSPC/Chol/DSPE-PEG2000.

Embodiment 12: The nanoparticle drug carrier according to any one of embodiments 1-11, wherein said lipid bilayer comprises a phospholipid, cholesterol, and mPEG phospholipid at a ratio of 50-90 mol % phospholipid:10-50 mol % CHOL:1-10 mol % mPEG phospholipid.

Embodiment 13: The nanoparticle drug carrier of embodiment 10, wherein said lipid bilayer comprises DSPC/Chol/DSPE-PEG in a molar ratio of about 3:2:0.15.

Embodiment 14: The nanoparticle drug carrier according to any one of embodiments 1-13, wherein said lipid bilayer forms a substantially continuous bilayer encompassing the entire nanoparticle.

Embodiment 15: The nanoparticle drug carrier according to any one of embodiments 1-14, wherein said lipid bilayer forms a substantially uniform and intact bilayer encompassing the entire nanoparticle.

Embodiment 16: The nanoparticle drug carrier according to any one of embodiments 1-15, wherein said silica nanoparticle is a mesoporous silica nanoparticle.

Embodiment 17: The nanoparticle drug carrier of embodiment 16, wherein said silica nanoparticle comprises a sol-gel synthesized mesoporous silica nanoparticle.

Embodiment 18: The nanoparticle drug carrier according to any one of embodiments 16-17, wherein said mesoporous silica nanoparticle is size-controlled.

Embodiment 19: The nanoparticle drug carrier according to any one of embodiments 16-18, wherein said mesoporous silica nanoparticle is is colloidally stable.

Embodiment 20: The nanoparticle drug carrier according to any one of embodiments 16-19, wherein said mesoporous silica has an average pore size that ranges from about 1 to about 20 nm, or from about 1 to about 10 nm, or from about 2 to about 8 nm.

Embodiment 21: The nanoparticle drug carrier according to any one of embodiments 1-20, wherein said mesoporous silica nanoparticles has an average size ranging from about 50 nm up to about 300 nm, or from about 50 up to about 200 nm, or from about 50 up to about 150 nm, or from about 50 up to about 100 nm, or from about 50 up to about 80 nm, or from about 50 up to about 70 nm, or from about 60 up to about 70 nm.

Embodiment 22: The nanoparticle drug carrier according to any one of embodiments 1-21, wherein cargo-trapping agent before reaction with said drug is selected from the group consisting of triethylammonium sucrose octasulfate (TEA$_8$SOS), (NH$_4$)$_2$SO$_4$, an ammonium salt, a trimethylammonium salt, and a triethylammonium salt.

Embodiment 23: The nanoparticle drug carrier of embodiment 22, wherein said cargo trapping agent comprises (NH$_4$)$_2$SO$_4$.

Embodiment 24: The nanoparticle drug carrier of embodiment 22, wherein said cargo trapping agent comprises an ammonium salt selected from the group consisting of ammonium sulfate; ammonium sucrose octasulfate, ammonium α-cyclodextrin sulfate, ammonium β-cyclodextrin sulfate, ammonium γ-cyclodextrin sulfate, ammonium phosphate; ammonium α-cyclodextrin phosphate, ammonium β-cyclodextrin phosphate, ammonium γ-cyclodextrin phosphate, ammonium citrate, and ammonium acetate.

Embodiment 25: The nanoparticle drug carrier of embodiment 22, wherein said cargo trapping agent comprises a trimethylammonium salt selected from the group consisting of trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, and trimethylammonium acetate.

Embodiment 26: The nanoparticle drug carrier of embodiment 22, wherein said cargo trapping agent comprises a triethylammonium salt selected from the group consisting of triethylammonium sulfate, triethylammonium sucrose octasulfate, triethylammonium α-Cyclodextrin sulfate, triethylammonium β-Cyclodextrin sulfate, triethylammonium γ-Cyclodextrin sulfate, triethylammonium phosphate, triethylammonium α-Cyclodextrin phosphate, triethylammonium β-Cyclodextrin phosphate, triethylammonium γ-Cyclodextrin phosphate, triethylammonium citrate, and triethylammonium acetate.

Embodiment 27: The nanoparticle drug carrier of embodiment 22, wherein cargo-trapping agent before reaction with said drug is triethylammonium sucrose octasulfate (TEA$_8$SOS).

Embodiment 28: The nanoparticle drug carrier of embodiment 27, wherein said drug is protonated and trapped in said pores as a gel-like precipitate in association of SOS$^{8-}$.

Embodiment 29: The nanoparticle drug carrier according to any one of embodiments 1-28, wherein said drug comprises at least one weakly basic group capable of being protonated, and the cargo-trapping agent comprises at least one anionic group.

Embodiment 30: The nanoparticle drug carrier according to any one of embodiments 1-29, wherein said drug is selected to have a pKa greater than 7 and less than 11.

Embodiment 31: The nanoparticle drug carrier according to any one of embodiments 1-30, said drug comprises a primary, secondary, and tertiary amine.

Embodiment 32: The nanoparticle drug carrier according to any one of embodiments 1-31, wherein said drug is selected to have a water solubility index of about 5 to about 25 mg/mL.

Embodiment 33: The nanoparticle drug carrier according to any one of embodiments 1-32, wherein the cargo is selected to have an octanol/water partition coefficient or log P value of about −3.0 to about 3.0.

Embodiment 34: The nanoparticle drug carrier according to any one of embodiments 1-33, wherein the cargo is selected to be 2-8 nm and less than the average or median size of the pores of the silica nanoparticle.

Embodiment 35: The nanoparticle drug carrier according to any one of embodiments 29-34, wherein said cargo comprises an anti-cancer drug.

Embodiment 36: The nanoparticle drug carrier of embodiment 35, wherein said cargo comprises irinotecan.

Embodiment 37: The nanoparticle drug carrier of embodiment 35, wherein said cargo comprises one or more drugs independently selected from the group consisting of a topoisomerase inhibitor, an antitumor anthracycline antibiotic, a mitotic inhibitor, an alkaloid, an alkaline alkylating agent, a purine or pyrimidine derivative, and a protein kinase inhibitor.

Embodiment 38: The nanoparticle drug carrier of embodiment 37, wherein said carrier comprises a topoisomerase inhibitor comprising topotecan.

Embodiment 39: The nanoparticle drug carrier of embodiment 37, wherein said carrier comprises an alkaloid selected from the group consisting of topotecan, 10-hydroxycamptothecin, belotecan, rubitecan, vinorelbine, and LAQ824.

Embodiment 40: The nanoparticle drug carrier of embodiment 37, wherein said carrier comprises an antitumor anthracycline antibiotic selected from the group consisting of doxorubicin, and mitoxantrone.

Embodiment 41: The nanoparticle drug carrier of embodiment 37, wherein said carrier comprises a mitotic inhibitor selected from the group consisting of vinblastine, and vinorelbine.

Embodiment 42: The nanoparticle drug carrier of embodiment 37, wherein said carrier comprises an alkaline alkylating agent selected from the group consisting of cyclophosphamide, mechlorethamine, and temozolomide.

Embodiment 43: The nanoparticle drug carrier of embodiment 37, wherein said carrier comprises a purine or pyrimidine derivative selected from the group consisting of 5-fluorouracil, 5'-deoxy-5-fluorouridine, and gemcitabine.

Embodiment 44: The nanoparticle drug carrier of embodiment 37, wherein said carrier comprises a protein kinase inhibitor selected from the group consisting of imatinib, osimertinib and sunitinib pazopanib, enzastaurin, vandetanib, erlotinib, dasatinib, and nilotinib.

Embodiment 45: The nanoparticle drug carrier according to any one of embodiments 1-44, wherein said drug carrier is conjugated to a moiety selected from the group consisting of a targeting moiety, a fusogenic peptide, and a transport peptide.

Embodiment 46: The nanoparticle drug carrier of embodiment 45, wherein said drug carrier is conjugated to a peptide that binds a receptor on a cancer cell or tumor blood vessel.

Embodiment 47: The nanoparticle drug carrier of embodiment 46, wherein said drug carrier is conjugated to an iRGD peptide.

Embodiment 48: The nanoparticle drug carrier of embodiment 46, wherein said drug carrier is conjugated to a targeting peptide shown in Table 2.

Embodiment 49: The nanoparticle drug carrier according to any one of embodiments 45-48, wherein said drug carrier is conjugated to transferrin, and/or ApoE, and/or folate.

Embodiment 50: The nanoparticle drug carrier according to any one of embodiments 45-49, wherein said drug carrier is conjugated to a targeting moiety that comprises an antibody that binds to a cancer marker.

Embodiment 51: The nanoparticle drug carrier of embodiment 50, wherein said drug carrier is conjugated to a targeting moiety that comprises an antibody that binds a cancer marker shown in Table 1.

Embodiment 52: The nanoparticle drug carrier according to any one of embodiments 29-34, wherein said cargo comprises an antibiotic, an antiviral agent, or an antifungal agent.

Embodiment 53: The nanoparticle drug carrier of embodiment 52, wherein said cargo comprises an antibiotic selected from the group consisting of ciprofloxacin, and levofloxacin.

Embodiment 54: The nanoparticle drug carrier of embodiment 52, wherein said cargo comprises an HIV antiviral.

Embodiment 55: The nanoparticle drug carrier of embodiment 54, wherein said cargo comprises an antiviral selected from the group consisting of tenofovir, disoproxil, and fumarate.

Embodiment 56: The nanoparticle drug carrier of embodiment 52, wherein said cargo comprises an antifungal agent selected from the group consisting of Amphotericin B, Anidulafungin, Caspofungin, Fluconazole, Flucytosine, Isavuconazole, Itraconazole, Micafungin, Posaconazole, and Voriconazole.

Embodiment 57: The nanoparticle drug carrier according to any one of embodiments 1-56, wherein said drug carrier has less than about 20%, or less than about 15%, or less than about 10%, or less than about 5% leakage of the cargo over 24 hours in a biological buffer with pH of 7.4 at 37° C.

Embodiment 58: The nanoparticle drug carrier according to any one of embodiments 1-57, wherein said drug carrier has a drug loading capacity of at least about 8% w/w, or at least about 10% w/w, or at least about 20% w/w, or at least about 30% w/w, or greater than about 40% w/w, or greater than about 50% w/w, or greater than about 60% w/w, or greater than about 70% w/w, or greater than about 80% w/w.

Embodiment 59: The nanoparticle drug carrier according to any one of embodiments 1-57, wherein said drug carrier has a drug loading capacity of at least 80% w/w.

Embodiment 60: The nanoparticle drug carrier according to any one of embodiments 1-59, wherein the lipid bilayer comprises a hydrophobic drug.

Embodiment 61: The nanoparticle drug carrier of embodiment 60, wherein the lipid bilayer comprises a hydrophobic drug selected from the group consisting of paclitaxel, ellipticine, camptothecin, SN-38, and a lipid prodrug (e.g., acyclovir diphosphate dimyristoylglycerol, doxorubicin conjugated phospholipid prodrug, phospholipid derivatives of nucleoside analogs, phospholipid linked chlorambucil, and the like).

Embodiment 62: The nanoparticle drug carrier of embodiment 60, wherein the lipid bilayer comprises paclitaxel.

Embodiment 63: The nanoparticle drug carrier according to any one of embodiments 1-61, wherein said drug carriers in suspension are stable for at least 1 month, or at least 2 months, or at least 3 months, or at least 4 months, or at least 5 months, or at least 6 months when stored at 4° C.

Embodiment 64: The nanoparticle drug carrier according to any one of embodiments 1-63, wherein a population of said drug carriers in suspension shows a size distribution ranging in width (full width half maximum) of less than about 30 nm, or less than about 20 nm, or less than about 10 nm, or less than about 5 nm, or less than about 3 nm, or less than about 2 nm.

Embodiment 65: The nanoparticle drug carrier according to any one of embodiments 1-64, wherein a population of said drug carriers in suspension shows a substantially unimodal size distribution.

Embodiment 66: The nanoparticle drug carrier according to any one of embodiments 1-65, wherein a population of said drug carriers in suspension shows PDI less than about 0.2, or less than about 0.1.

Embodiment 67: The nanoparticle drug carrier according to any one of embodiments 1-66, wherein a population of said drug carriers in suspension shows a coefficient of variation in size less than about 0.1 or less than about 0.05, or less than about 1.7/120.

Embodiment 68: The nanoparticle drug carrier according to any one of embodiments 1-67, wherein ~3% or more of said nanoparticle drug carriers distribute to developing tumor sites on IV injection.

Embodiment 69: The nanoparticle drug carrier according to any one of embodiments 1-68, wherein said nanoparticle drug carrier forms a stable suspension on rehydration after lyophilization.

Embodiment 70: The nanoparticle drug carrier according to any one of embodiments 1-69, wherein said nanoparticle drug carriers, when loaded with an anti-cancer drug, provide more effective cancer cell killing than free drug, or liposomes containing said drug, in an orthotopic PDAC model.

Embodiment 71: The nanoparticle drug carrier according to any one of embodiments 1-70, wherein said nanoparticle drug carriers, when loaded with an anti-cancer drug, show reduced drug toxicity as compared to free drug and/or drug in liposomes.

Embodiment 72: The nanoparticle drug carrier according to any one of embodiments 1-71, wherein said nanoparticle drug carrier has colloidal stability in physiological fluids with pH 7.4 and remains monodisperse to allow systemic biodistribution and is capable of entering a disease site by vascular leakage (EPR effect) or transcytosis.

Embodiment 73: A pharmaceutical formulation said formulation comprising:

a plurality of nanoparticle drug carriers according to any one of embodiments 1-72; and a pharmaceutically acceptable carrier.

Embodiment 74: The formulation of embodiment 73, wherein said formulation is an emulsion, dispersion, or suspension.

Embodiment 75: The formulation of embodiment 74, wherein said suspension, emulsion, or dispersion is stable for at least 1 month, or at least 2 months, or at least 3 months, or at least 4 months, or at least 5 months, or at least 6 months when stored at 4° C.

Embodiment 76: The formulation according to any one of embodiments 73-75, wherein the nanoscale drug carriers in said formulation show a substantially unimodal size distribution.

Embodiment 77: The formulation according to any one of embodiments 73-76, wherein the drug carriers in said suspension, emulsion, or dispersion shows a PDI less than about 0.2, or less than about 0.1.

Embodiment 78: The formulation according to any one of embodiments 73-77, wherein said formulation is formulated for administration via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 79: The formulation according to any one of embodiments 73-77, wherein said formulation is a sterile injectable.

Embodiment 80: The formulation according to any one of embodiments 73-79, wherein said formulation is a unit dosage formulation.

Embodiment 81: A method of treating a cancer, said method comprising:

administering to a subject in need thereof an effective amount of a nanoparticle drug carrier according to any one of embodiments 1-51 or 57-72, or a pharmaceutical formulation according to any one of embodiments 73-80, where the drug in said nanoparticle drug carrier and/or said pharmaceutical formulation comprises an anti-cancer drug.

Embodiment 82: The method of embodiment 81, wherein said nanoparticle drug carrier and/or said pharmaceutical formulation is a primary therapy in a chemotherapeutic regimen.

Embodiment 83: The method of embodiment 81, wherein said nanoparticle drug carrier and/or said pharmaceutical formulation is a component in a multi-drug chemotherapeutic regimen.

Embodiment 84: The method of embodiment 83, wherein said multi-drug chemotherapeutic regimen comprises at least two drugs selected from the group consisting of irinotecan (IRIN), oxaliplatin (OX), 5-fluorouracil (5-FU), and leucovorin (LV).

Embodiment 85: The method of embodiment 83, wherein said multi-drug chemotherapeutic regimen comprises at least three drugs selected from the group consisting of irinotecan (IRIN), oxaliplatin (OX), 5-fluorouracil (5-FU), and leucovorin (LV).

Embodiment 86: The method of embodiment 83, wherein said multi-drug chemotherapeutic regimen comprises at least irinotecan (IRIN), oxaliplatin (OX), 5-fluorouracil (5-FU), and leucovorin (LV).

Embodiment 87: The method according to any one of embodiments 81-86, wherein said cancer is pancreatic ductal adenocarcinoma (PDAC).

Embodiment 88: The method according to any one of embodiments 81-86, wherein said cancer is a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sézary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 89: The method according to any one of embodiments 81-88, wherein said nanoparticle drug carrier is not conjugated to an iRGD peptide and the nanoparticle drug carrier is administered in conjunction with an iRGD peptide.

Embodiment 90: A method of treating an infection, said method comprising:
administering to a subject in need thereof an effective amount of a nanoparticle drug carrier according to any one of embodiments 1-34 or 52-56, or a pharmaceutical formulation according to any one of embodiments 73-80, where the drug in said nanoparticle drug carrier and/or said pharmaceutical formulation comprises an antimicrobial drug.

Embodiment 91: The method of embodiment 81, wherein said infection comprises an infection by a drug-resistant bacterium, virus, or fungus.

Embodiment 92: The method according to any one of embodiments 81-91, where the nanoparticle drug carrier and/or pharmaceutical formulation is administered via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 93: The method according to any one of embodiments 81-91, where the nanoparticle drug carrier and/or pharmaceutical formulation is administered as an injection, from an IV drip bag, or via a drug-delivery cannula.

Embodiment 94: The method according to any one of embodiments 81-93, wherein said subject is a human.

Embodiment 95: The method according to any one of embodiments 81-93, wherein said subject is a non-human mammal.

Embodiment 96: A method of making a nanoparticle drug carrier, said method comprising: providing a nanoparticle comprising a silica having a surface and defining a plurality of pores that are suitable to receive drug molecules therein; disposing a trapping agent in pores comprising said plurality of pores where said trapping agent is selected for its ability to trap said drugs within said pores; coating the pores of the nanoparticle with a lipid bilayer; and contacting or bathing said nanoparticle coated with a lipid bilayer with a drug that can pass through said bilayer where said drug enters said pores, reacts with said trapping agent and is retained within the bilayer.

Embodiment 97: The method of embodiment 96, wherein said lipid bilayer comprises a phospholipid, cholesterol (CHOL), and an mPEG phospholipid.

Embodiment 98: The method according to any one of embodiments 96-97, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 99: The method of embodiment 98, wherein said phospholipid comprises a saturated fatty acid selected from the group consisting of phosphatidylcholine (DPPC), dimyristoylphosphatidylcholine (DMPC), distearoylphosphatidylcholine (DSPC), and diactylphosphatidylcholine (DAPC).

Embodiment 100: The method of embodiment 98, wherein said phospholipid comprises a natural lipid selected from the group consisting of egg phosphatidylcholine (egg PC), and soy phosphatidylcholine (soy PC).

Embodiment 101: The method of embodiment 98, wherein said phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine.

Embodiment 102: The method according to any one of embodiments 96-101, wherein said lipid bilayer comprises an mPEG phospholipid with a phospholipid C14-C18 carbon chain, and a PEG molecular weight ranging from about 350 Da to 5000 Da.

Embodiment 103: The nanoparticle drug carrier of embodiment 102, wherein said lipid bilayer comprises 1,2-distearoyl-sn-glycero-3-phosphoethanolamine-PEG (DSPE-PEG).

Embodiment 104: The method of embodiment 97, wherein said lipid bilayer comprises DPPC/Chol/DSPE-PEG or DSPC/Chol/DSPE-PEG.

Embodiment 105: The method of embodiment 104, wherein said lipid bilayer comprises DSPC/Chol/DSPE-PEG.

Embodiment 106: The method of embodiment 105, wherein wherein said lipid bilayer comprises DSPC/Chol/DSPE-PEG2000.

Embodiment 107: The method according to any one of embodiments 96-106, wherein said lipid bilayer comprises a phospholipid, cholesterol, and mPEG phospholipid at a ratio of 50-90 mol % phospholipid:10-50 mol % CHOL:1-10 mol % mPEG phospholipid.

Embodiment 108: The method of embodiment 105, wherein said lipid bilayer comprises DSPC/Chol/DSPE-PEG in a molar ratio of about 3:2:0.15.

Embodiment 109: The method according to any one of embodiments 96-108, wherein the lipids comprising said lipid bilayer are combined with said nanoparticles in a ratio sufficient to form a continuous bilayer over the entire nanoparticle.

Embodiment 110: The method according to any one of embodiments 96-109, wherein the lipids comprising said lipid bilayer are combined with said nanoparticles in particle:lipid ratio ranging from about 1.0:3.0.

Embodiment 111: The method according to any one of embodiments 96-109, wherein the lipids comprising said lipid bilayer are combined with said nanoparticles in particle:lipid ratio of about 1.0:1.1.

Embodiment 112: The method according to any one of embodiments 96-111, wherein said lipid bilayer forms a substantially continuous bilayer encompassing the entire nanoparticle.

Embodiment 113: The method according to any one of embodiments 96-112, wherein said lipid bilayer forms a substantially uniform and intact bilayer encompassing the entire nanoparticle.

Embodiment 114: The method according to any one of embodiments 96-113, wherein said silica nanoparticle is a mesoporous silica nanoparticle.

Embodiment 115: The method of embodiment 114, wherein said silica nanoparticle comprises a sol-gel synthesized mesoporous silica nanoparticle.

Embodiment 116: The method according to any one of embodiments 96-115, wherein said mesoporous silica nanoparticle is size-controlled.

Embodiment 117: The method according to any one of embodiments 96-116, wherein said mesoporous silica nanoparticle is colloidally stable.

Embodiment 118: The method according to any one of embodiments 96-117, wherein said mesoporous silica has an average pore size that ranges from about 1 to about 20 nm, or from about 1 to about 10 nm, or from about 2 to about 8 nm.

Embodiment 119: The method according to any one of embodiments 96-118, wherein said mesoporous silica nanoparticles has an average size ranging from about 50 nm up to about 300 nm, or from about 50 up to about 200 nm, or from about 50 up to about 150 nm, or from about 50 up to about 100 nm, or from about 50 up to about 80 nm, or from about 50 up to about 70 nm, or from about 60 up to about 70 nm.

Embodiment 120: The method according to any one of embodiments 96-119, wherein cargo-trapping agent before reaction with said drug is selected from the group consisting of triethylammonium sucrose octasulfate (TEA$_8$SOS), (NH$_4$)$_2$SO$_4$, an ammonium salt, a trimethylammonium salt, and a triethylammonium salt.

Embodiment 121: The method of embodiment 120, wherein said cargo trapping agent comprises (NH$_4$)$_2$SO$_4$.

Embodiment 122: The method of embodiment 120, wherein said cargo trapping agent comprises an ammonium salt selected from the group consisting of ammonium sulfate; ammonium sucrose octasulfate, ammonium α-cyclodextrin sulfate, ammonium β-cyclodextrin sulfate, ammonium γ-cyclodextrin sulfate, ammonium phosphate; ammonium α-cyclodextrin phosphate, ammonium β-cyclodextrin phosphate, ammonium γ-cyclodextrin phosphate, ammonium citrate, and ammonium acetate.

Embodiment 123: The method of embodiment 120, wherein said cargo trapping agent comprises a trimethylammonium salt selected from the group consisting of trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, and trimethylammonium acetate.

Embodiment 124: The method of embodiment 120, wherein said cargo trapping agent comprises a triethylammonium salt selected from the group consisting of triethylammonium sulfate, triethylammonium sucrose octasulfate, triethylammonium α-Cyclodextrin sulfate, triethylammonium β-Cyclodextrin sulfate, triethylammonium γ-Cyclodextrin sulfate, triethylammonium phosphate, triethylammonium α-Cyclodextrin phosphate, triethylammonium β-Cyclodextrin phosphate, triethylammonium γ-Cyclodextrin phosphate, triethylammonium citrate, and triethylammonium acetate.

Embodiment 125: The method of embodiment 120, wherein cargo-trapping agent before reaction with said drug is triethylammonium sucrose octasulfate (TEA$_8$SOS).

Embodiment 126: The method of embodiment 125, wherein said drug is protonated and trapped in said pores as a gel-like precipitate in association of $SOS^{8-}$.

Embodiment 127: The method according to any one of embodiments 96-126, wherein said drug comprises at least one weakly basic group capable of being protonated, and the cargo-trapping agent comprises at least one anionic group.

Embodiment 128: The method according to any one of embodiments 96-127, wherein said drug is selected to have a pKa greater than 7 and less than 11.

Embodiment 129: The method according to any one of embodiments 96-128, said drug comprises a primary, secondary, tertiary or quaternary amine.

Embodiment 130: The method according to any one of embodiments 96-129, wherein said drug is selected to have a water solubility index of about 5 to about 25 mg/mL.

Embodiment 131: The method according to any one of embodiments 96-130, wherein the cargo is selected to have an octanol/water partition coefficient or log P value of about −3.0 to about 3.0.

Embodiment 132: The method according to any one of embodiments 96-131, wherein the cargo is selected to be 2-8 nm and less than the average or median size of the pores of the silica nanoparticle.

Embodiment 133: The method according to any one of embodiments 127-132, wherein said cargo comprises an anti-cancer drug.

Embodiment 134: The method of embodiment 133, wherein said cargo comprises irinotecan.

Embodiment 135: The method of embodiment 133, wherein said cargo comprises one or more drugs independently selected from the group consisting of a topoisomerase inhibitor, an antitumor anthracycline antibiotic, a mitotic inhibitor, an alkaloid, an alkaline alkylating agent, a purine or pyrimidine derivative, a protein kinase inhibitor.

Embodiment 136: The method of embodiment 135, wherein said carrier comprises a topoisomerase inhibitor comprising topotecan.

Embodiment 137: The method of embodiment 135, wherein said carrier comprises an alkaloid selected from the group consisting of topotecan, 10-hydroxycamptothecin, belotecan, rubitecan, vinorelbine, and LAQ824.

Embodiment 138: The method of embodiment 135, wherein said carrier comprises a antitumor anthracycline antibiotic selected from the group consisting of doxorubicin, and mitoxantrone.

Embodiment 139: The method of embodiment 135, wherein said carrier comprises a mitotic inhibitor selected from the group consisting of vinblastine, and vinorelbine.

Embodiment 140: The method of embodiment 135, wherein said carrier comprises a alkaline alkylating agent selected from the group consisting of cyclophosphamide, mechlorethamine, and temozolomide.

Embodiment 141: The method of embodiment 135, wherein said carrier comprises a purine or pyrimidine derivative selected from the group consisting of 5-fluorouracil, 5'-deoxy-5-fluorouridine, and gemcitabine.

Embodiment 142: The method of embodiment 135, wherein said carrier comprises a protein kinase inhibitor selected from the group consisting of imatinib, osimertinib and sunitinib pazopanib, enzastaurin, vandetanib, erlotinib, dasatinib, and nilotinib.

Embodiment 143: The method according to any one of embodiments 96-142, wherein said drug carrier is conjugated to a moiety selected from the group consisting of a targeting moiety, a fusogenic peptide, and a transport peptide.

Embodiment 144: The method according to any one of embodiments 96-143, wherein said method produces a nanoparticle drug carrier according to any one of embodiments 1-72.

Embodiment 145: The method of embodiment 143, wherein said drug carrier is conjugated to a peptide that binds a receptor on a cancer cell.

Embodiment 146: The method of embodiment 145, wherein said drug carrier is conjugated to an iRGD peptide.

Embodiment 147: The method of embodiment 145, wherein said drug carrier is conjugated to a targeting peptide shown in Table 2.

Embodiment 148: The method according to any one of embodiments 143-147, wherein said drug carrier is conjugated to transferrin, and/or ApoE, and/or folate.

Embodiment 149: The method according to any one of embodiments 143-148, wherein said drug carrier is conjugated to a targeting moiety that comprises an antibody that binds to a cancer marker.

Embodiment 150: The method of embodiment 149, wherein said drug carrier is conjugated to a targeting moiety that comprises an antibody that binds a cancer marker shown in Table 1.

Embodiment 151: The method according to any one of embodiments 127-132, wherein said cargo comprises an antibiotic.

Embodiment 152: The method of embodiment 151, wherein said cargo comprises an antibiotic selected from the group consisting of ciprofloxacin, levofloxacin, and an HIV antiretroviral (e.g., tenofovir disoproxil fumarate, etc.).

Embodiment 153: The method according to any one of embodiments 96-152, wherein said drug carrier is loaded to a capacity of at least 30% w/w, or greater than about 40% w/w, or greater than about 50% w/w, or greater than about 60% w/w, or greater than about 70% w/w, or greater than about 80% w/w.

Embodiment 154: The method according to any one of embodiments 96-152, wherein said drug carrier is loaded to a capacity of at least 80% w/w.

Embodiment 155: The method according to any one of embodiments 96-154, wherein the lipid bilayer comprises a hydrophobic drug.

Embodiment 156: The method of embodiment 155, wherein the lipid bilayer comprises a hydrophobic drug selected from the group consisting of paclitaxel, ellipticine, camptothecan, SN-38, and a lipid prodrug (e.g., acyclovir diphosphate dimyristoylglycerol, doxorubicin conjugated phospholipid prodrug, phospholipid derivatives of nucleoside analogs, phospholipid linked chlorambucil, and the like).

Embodiment 157: The method of embodiment 155, wherein the lipid bilayer comprises paclitaxel.

Embodiment 158: A method of making an irinotecan nanocarrier, comprising: providing a nanocarrier comprising a silica body having a surface including a plurality of pores suitable to receive irinotecan therein, disposing an agent selected for its ability to trap irinotecan within the plurality of pores; coating the pores of the nanocarrier with a phospholipid bilayer (optionally using a sonication process); and introducing irinotecan into the phospholipid bilayer coated pores, so that a phospholipid bilayer coated irinotecan nanocarrier is made.

Embodiment 159: The method of embodiment 158, wherein said silica body comprises a sol-gel synthesized, size-controlled and colloidally stable silica body.

Embodiment 160: The method of embodiment 158, wherein the irinotecan trapping agent is triethylammonium sucrose octasulfate (TEA$_8$SOS).

Embodiment 161: The method of embodiment 160, wherein the nanocarrier:

(a) has an irinotecan loading capacity of at least 20% (or 30% or 40%) w/w; and/or (b) show <5% (or <10%) irinotecan leakage over 24 hours in a biological buffer with pH of 7.4 at 37° C.

Embodiment 162: The method of embodiment 161, wherein the nanocarrier has colloidal stability in physiological fluids with pH 7.4 and remains monodisperse to allow systemic biodistribution and is capable of entering the disease site by vascular leakage (EPR effect) or transcytosis.

Embodiment 163: The method of embodiment 161, wherein the phospholipid bilayer comprises cholesterol and/or paclitaxel.

Embodiment 164: A method of making a nanocarrier, comprising: providing an unloaded nanocarrier including a silica body having a surface and defining a plurality of pores that are suitable to receive molecules therein, and a phospholipid bilayer coating the surface; encapsulating a cargo-trapping agent within the phospholipid bilayer.

Embodiment 165: The method of embodiment 164, further comprising exposing the nanocarrier to a cargo selected to interact with the cargo-trapping agent.

Embodiment 166: The method of embodiment 165, wherein the cargo is selected to have a pKa greater than 7 and less than 11 and capable of being protonated, and the cargo-trapping agent includes at least one anionic group.

Embodiment 167: The method of embodiment 165, wherein the cargo is irinotecan and the cargo-trapping agent is triethylammonium sucrose octasulfate (TEA$_8$SOS).

Embodiment 168: The method of embodiment 165, wherein the cargo is a topoisomerase I inhibitor, topotecan; one or more antitumor anthracycline antibiotics, doxorubicin and mitoxantrone; one or more mitotic inhibitors, vinblastine and vinorelbine; or one or more tyrosine-kinase inhibitors imatinib, osimertinib and sunitinib.

Embodiment 169: The method of embodiment 165, wherein the nanocarrier has a drug loading capacity of at least 30% w/w.

Embodiment 170: A nanocarrier, comprising: a silica body having a surface and defining a plurality of pores that are suitable to receive molecules therein; a phospholipid bilayer coating the surface; and a cargo-trapping agent within the phospholipid bilayer; wherein the submicron structure has a maximum dimension of less than one micron, and wherein the phospholipid bilayer stably seals the plurality of pores.

Embodiment 171: The nanocarrier of embodiment 170, further comprising a cargo within the phospholipid bilayer.

Embodiment 172: The nanocarrier of embodiment 171, wherein the cargo is associated with the cargo-trapping agent.

Embodiment 173: The nanocarrier of embodiment 172, wherein the cargo includes at least one weakly basic group capable of being protonated, and the cargo-trapping agent includes at least one anionic group.

Embodiment 174: The nanocarrier of embodiment 171, wherein the cargo is selected to have a pKa greater than 7 and less than 11.

Embodiment 175: The nanocarrier of embodiment 171, wherein the cargo comprises a primary, secondary, tertiary or quaternary amine.

Embodiment 176: The nanocarrier of embodiment 171, wherein the cargo is selected to have a water solubility index of 5-25 mg/mL.

Embodiment 177: The nanocarrier of embodiment 171, wherein the cargo is selected to have an octanol/water partition coefficient or log P value of −3.0 to 3.0.

Embodiment 178: The nanocarrier of embodiment 171, wherein the cargo is selected to be 2-8 nm and less than the size of the pores of the nanocarrier.

Embodiment 179: The nanocarrier of embodiment 171, wherein the cargo is irinotecan and the cargo-trapping agent is triethylammonium sucrose octasulfate (TEA$_8$SOS).

Embodiment 180: The nanocarrier of embodiment 171, wherein the cargo is a topoisomerase I inhibitor, topotecan; one or more antitumor anthracycline antibiotics, doxorubicin and mitoxantrone; one or more mitotic inhibitors, vinblastine and vinorelbine; or one or more tyrosine-kinase inhibitors imatinib, osimertinib and sunitinib.

Embodiment 181: The nanocarrier of embodiment 171, wherein the nanocarrier has a less than 5% leakage of the cargo over 24 hours in a biological buffer with pH of 7.4 at 37° C.

Embodiment 182: The nanocarrier of embodiment 171, wherein the nanocarrier has a drug loading capacity of at least 30% w/w.

Embodiment 183: The nanocarrier of embodiment 171, wherein the nanocarrier has a drug loading capacity of at least 80% w/w.

Embodiment 184: The nanocarrier of embodiment 170, wherein the phospholipid bilayer comprises paclitaxel.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

Definitions

The terms "subject," "individual," and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for a pathology to which the nanoparticle drug carriers described herein (silicasomes) are directed. Thus, for example, in certain embodiments the subject is a subject with a cancer (e.g., pancreatic ductal adenocarcinoma (PDAC), breast cancer (e.g., drug-resistant breast cancer), colon cancer, brain cancer, and the like). In certain embodiments the subject is a subject with a microbial infection including, but not limited to drug-resistant microbial infections.

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment which includes a delay in the onset or the prevention of the onset of a pathology or disease.

The terms "coadministration" or "administration in conjunction with" or "cotreatment" when used in reference to the coadministration of a first compound (e.g., a silicasome containing irinotecan) and a second compound (e.g., an iRGD peptide) indicates that the first compound and the second compound are administered so that there is at least some chronological overlap in the biological activity of first compound and the second compound in the organism to which they are administered. Coadministration can include simultaneous administration or sequential administration. In sequential administration there may even be some substantial delay (e.g., minutes or even hours) between administration of the first compound and the second compound as long as their biological activities overlap. In certain embodiments the coadministration is over a time frame that permits the first compound and second compound to produce an enhanced therapeutic or prophylactic effect on the organism. In certain embodiments the enhanced effect is a synergistic effect.

The terms "nanocarrier" and "nanoparticle drug carrier" and "silicasome" are used interchangeably and refer to a nanostructure having a porous particle core, which is interchangeable with the term "porous nanoparticle" as used herein, and a lipid bilayer encasing (or surrounding or enveloping) the porous particle core. In certain embodiments the silica nanoparticle is a porous silica nanoparticle (e.g., mesoporous silica nanoparticle (MSNP)).

As used herein, the term "lipid" refers to conventional lipids, phospholipids, cholesterol, chemically functionalized lipids for attachment of PEG and ligands, etc.

As used herein, the terms "lipid bilayer" or "LB" refers to any double layer of oriented amphipathic lipid molecules in which the hydrocarbon tails face inward to form a continuous non-polar phase.

As used herein, the term "liposome" refers to an aqueous compartment enclosed by a lipid bilayer, as being conventionally defined (see, e.g., Stryer (1981) Biochemistry, 2d Edition, W. H. Freeman & Co., p. 213).

Compared with the lipid bilayer defined in a silicasome, the lipid bilayer in a liposome can be referred to as an "unsupported lipid bilayer" and the liposome itself (when unloaded) can be referred to as an "empty liposome". The lipid bilayer in a silicasome can be referred to as a "supported lipid bilayer" because the lipid bilayer in a silicasome is located on the surface and supported by a porous particle core. In certain embodiments, the lipid bilayer can have a thickness ranging form about 6 nm to about 7 nm which includes a 3-4 nm thickness of the hydrophobic core, plus the hydrated hydrophilic head group layers (each about 0.9 nm) plus two partially hydrated regions of about 0.3 nm each.

As used herein, the term "selective targeting" or "specific binding" refers to use of targeting ligands on the surface of silicasomes (empty or loaded), in particular, on the surface of the lipid bilayer of the silicasomes, wherein the ligands interact specifically/selectively with receptors or other biomolecular components expressed on the target, e.g., a cell surface of interest. The targeting ligands can include such molecules and/or materials as peptides, antibodies, aptamers, targeting peptides, polysaccharides, and the like.

A silicasome having targeting ligands can be referred to as a "targeted silicasome".

The term "silicasome" refers to a drug containing (drug delivery) silica nanoparticle in which the silica nanoparticle is fully covered with a lipid bilayer (e.g., a phospholipid bilayer). In certain embodiments the silica nanoparticle is a porous silica nanoparticle (e.g., mesoporous silica nanoparticle).

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "drug" as used herein refers to a chemical entity of varying molecular size, small and large, naturally occurring or synthetic, that exhibits a therapeutic effect in animals and humans. A drug may include, but is not limited to, an organic molecule (e.g., a small organic molecule), a therapeutic protein, peptide, antigen, or other biomolecule, an oligonucleotide, an siRNA, a construct encoding CRISPR cas9 components and, optionally one or more guide RNAs, and the like.

A "pharmaceutically acceptable carrier" as used herein is defined as any of the standard pharmaceutically acceptable carriers. The pharmaceutical compositions of the subject invention can be formulated according to known methods for preparing pharmaceutically useful compositions. The pharmaceutically acceptable carrier can include diluents, adjuvants, and vehicles, as well as carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W [1995] Easton Pa., Mack Publishing Company, 19th ed.) describes formulations which can be used in connection with the silicasomes described herein.

As used herein, an "antibody" refers to a protein consisting of one or more polypeptides substantially encoded by immunoglobulin genes or fragments of immunoglobulin genes or derived therefrom that is capable of binding (e.g., specifically binding) to a target (e.g., to a target polypeptide). The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on a phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In certain embodiments antibodies should include all that have been displayed on phage (e.g., scFv, Fv, Fab and disulfide linked Fv (see, e.g, Reiter et al. (1995) *Protein Eng*. 8: 1323-1331) as well as affibodies, unibodies, and the like.

The term "specifically binds", as used herein, when referring to a biomolecule (e.g., protein, nucleic acid, antibody, etc.), refers to a binding reaction that is determinative of the presence of a biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

BRIEF DESCRIPTION OF THE DRAWINGS

Referring now to the drawings in which like reference numbers represent corresponding parts throughout:

FIG. 1A shows schematics depicting the synthesis method and loading of irinotecan by LB-MSNPs and liposomes (FIG. 1A, panel A1). After soaking TEA$_8$SOS into the MSNP particles, the pores are sealed by a LB, derived from sonication of a lipid biofilm (Lu et al. (2007) *Small*, 3: 1341-1346). FIG. 1A, panel A2: TEA$_8$SOS-soaked particles are incubated in an irinotecan solution, allowing the amphipathic drug to diffuse across the lipid bilayer for protonation by TEA$_8$SOS (TEA$_8$SOS↔8TEA+20 8H$^+$+SOS$^{8-}$). The lipid-soluble TEA exits the particle, while the H$^+$ converts irinotecan to a hydrophilic derivative that cannot cross the LB. The protonated drug interacts with SOS$^{8-}$ to form a gel-like precipitate, that is retained in the pores. FIG. 1A, panel A3: The same technique was used to produce a liposomal equivalent for irinotecan entrapment (Drummond et al. (2006) *Cancer Res.*, 66(6): 3271-3277). FIG. 1B: Assessment of the drug loading capacity (DLC) of the Ir-MSNP and Ir-liposome carriers. DLO [the total amount of irinotecan (m$_0$)–non-encapsulated irinotecan (m$_1$)]/[the total amount of particle (m$_{MSNP}$ or m$_{lipid}$)×100%. The inclusion of TEA$_8$SOS had a negligible effect on hydrodynamic size and zeta potential of the particles. Hydrodynamic size and zeta potential data are shown in Table 3 (Example 2). FIG. 1C: CryoEM images of the empty, non-coated MSNP, Ir-MSNP and Ir-liposome carriers. The technique is sensitive enough to visualize irinotecan precipitation in the liposome. FIG. 1D: Carrier stability was assessed by incubation in 100% serum at 37° C. for 24 hrs, and determining drug leakage by HPLC. FIG. 1E) Carrier stability, as determined by the change in hydrodynamic diameter and % drug leakage, following lyophilization and water resuspension.

FIG. 2A: Interval IVIS imaging over 48 hrs to compare the biodistribution of IV injected NIR-labeled carriers to the KPC-derived orthotopic tumor site (n=3). NIR fluorescence images in representative animals after IV injection of 100 mg/kg NIR-labeled LB-MSNPs or liposomes are shown. FIG. 2B: Ex vivo imaging of explanted organs in the same experiment; animals were sacrificed after 24 hrs. Confocal microscopy confirmed a higher abundance of NIR-labeled LB-MSNP compared to liposomes at the tumor site. FIG. 2C: Irinotecan tumor content was determined in an orthotopic KPC-derived xenograft model (n=3). Animals received IV injection of an irinotecan dose equivalent of 60 mg/kg for the different drug formulations. Following animal sacrifice after 24 hrs, tumor tissues were collected for the measurement of irinotecan content by HPLC. Irinotecan content was expressed as % total injected dose per gram of tumor tissue (% ID/g). Data represent mean±SD, *p<0.05. FIG. 2D: HPLC measurement of plasma irinotecan concentration in the same experiment. Data represent mean±SD, *p<0.05.

FIG. 3A: Assessment of the MTD in an acute dose finding study, using a NCI protocol. FIG. 3B: Growth inhibition of KPC-derived orthotopic tumors in B6/129 mice, following IV administration of 40 mg/kg free drug or encapsulated irinotecan every 4 days for up to 8 administrations. Interval IVIS imaging was used for monitoring tumor growth, which was quantitatively expressed according to the image intensity at the operator-defined ROI. FIG. 3C: Quantitative analysis of apoptosis (using IHC staining for cleaved caspase-3) at the primary tumor site of the animals after treatment (sacrificed on day 40-47). FIG. 3D: Representative autopsy results and ex vivo imaging of bioluminescence intensity in the moribund animals (sacrificed on day 40-47), to show treatment impact on surrounding metastases. Visible metastatic spread could be seen in the stomach, intestines, liver, spleen, kidneys, diaphragm, and abdominal wall. There was no infiltration of the heart or lung. FIG. 3E: Heat map display to summarize the comparative analysis of tumor spread determined by quantitative ex vivo imaging in (FIG. 3D). Data represent mean±SEM, *p<0.05.

FIGS. 4A-4E illustrate a comparative analysis of toxicity reduction by Ir-LB-MSNP vs. Ir-liposomes, in accordance with one or more embodiments described herein. FIG. 4A: Liver histology obtained from representative moribund animals (sacrificed on day 40-47), using tissue from the experiment shown in FIG. 3B. The arrows in the H&E stained sections point to necrotic liver tissue, while sites marked with an asterisk denote steatosis. Bar is 200 µm. FIG. 4B: Dual IHC staining of cleaved caspase-3 (apoptosis marker, red) and F4/80 (KC marker, green) in the livers of animal receiving different irinotecan formulations at a dose equivalent of 60 mg/kg, followed by sacrifice at 24 hrs. The nucleus was stained with Hoechst 33342 (blue). Bar=100 µm. FIG. 4C: IHC staining for cleaved caspase-3, with H&E counter staining to reveal the spread of apoptosis and blunting of the intestinal villi in the same treated animal groups studied in FIG. 3B. The bar represents 100 µm. FIG. 4D: Separate experiment, in which a 40 mg/kg dose-equivalent of irinotecan, injected IV every $2^{nd}$ day, 3 times, were used to study the impact on sternal bone marrow. The sternums were collected on day 7 for embedding, decalcification and H&E staining. The bar represents 200 µm. FIG. 4E: Schematic to explain the differential hepatotoxicity of Ir-LB-MSNP and Ir-liposome formulations in the liver. Without being bound to a specific theory, it is contemplated that the injected nanocarriers are initially taken up by KCs, where carrier disintegration leads to the irinotecan release to bystander hepatocytes. The subsequent rate of carrier disintegration and drug release to the hepatocytes could determine whether the extent to which the irinotecan is metabolized and rendered inactive. It is further hypothesized that the higher instability of the liposomal carrier leads to more rapid drug release than the more stable Ir-LB-MSNP, which explains the differences in apoptosis and necrosis.

FIG. 6A: CryoEM images (TF20, FET) of Ir-LB-MSNP(+SOS) (upper panel) and Ir-Lipo(+SOS) (bottom). The coated lipid bilayer on the MSNP surface can be clearly seen. The upper zoom-in image shows a MSNP with intact lipid coating on the particle surface, while the porous interior shows the presence of the high density complex between $TEO_8SOS$ and irinotecan. Similarly, in the liposome images (lower panel), the irinotecan-trapping agent complex can be seen as high density precipitates on the inside (red arrows marked). FIG. 6B: Drug release profiles of Ir-LB-MSNP(+SOS) and Ir-Lipo(+SOS) in PBS (pH=7.4) and phagolysosomal simulant fluid (PSF, pH 4.5). For drug release measurement, the NPs were prepared in PBS or PSF (1 mL, irinotecan 0.1 mg/mL), followed by shaking at 37° C. At the indicated time points, the released irinotecan was separated from NPs by a centrifugal filter unit with size cut off of 30 kD. The irinotecan concentration in the filtrate was determined by a microplate reader at OD of 360 nm. The experiments were repeated at least twice.

FIG. 8, panels A-C: The cell viability of PANC-1 cells was determined by a MTS assay, following treatment with free IRIN, Ir-LB-MSNP(+SOS) and Ir-Lipo (+SOS) at the concentrations shown. Experiments were also carried out over different time intervals (24 hours, 48 hours and 72 hours). FIG. 8, panels D-F: The cell viability of BxPC-3 cells after treatment with free IRIN, Ir-LB-MSNP (+SOS) and Ir-LB-MSNP(+SOS) at different drug concentrations and time points as described for PANC-1 cells.

FIG. 21A: The top panel provides a schematic that shows the synthesis steps for constructing silicasomes and remote drug loading (see Example 1 and Liu et al. (2016) *ACS Nano.* 10(2): 2702-2715). Briefly, MSNP cores were synthesized by sol-gel chemistry and soaked in a solution containing the protonating agent, TEA$_8$SOS. These particles were coated with a LB, using a sonication procedure in the presence of a lipid biofilm (Id.). This was followed by remote irinotecan loading across the proton gradient provided by TEA$_8$SOS. Box 1: Schematic of the different silicasome components. Box 2: iRGD peptide conjugation to the LB, using a thiol-maleimide reaction to link the cysteine-modified iRGD peptide to DSPE-PEG$_{2000}$-maleimide. Box 3: Cryo-EM images to show the bare particles and the silicasomes, with and without the embedding of ~10 nm Au cores (for TEM visualization). The synthesis procedures are described in Example 3 Supplemental Materials and Methods. Bars=50 nm. FIG. 21B: Autopsy and IVIS images of the KPC-derived orthotopic PDAC model in immunocompetent B6/129 mice. The orthotopic implantation involves minor surgery to inject of 2×10$^6$ KPC-luc cells in the tail of the pancreas (left panel). The autopsy and bioluminescence imaging reveal primary tumor growth after 1-2 weeks, followed by tumor metastases by 3-5 weeks. Macrometastases are marked by arrows.

FIG. 22A: The tumor-bearing mice received (i) IV 50 mg/kg of the NIR-labeled silicasome IV with co-administration of 8 μmol/kg free iRGD (n=3, referred to as "silicasome+iRGD"), (ii) 50 mg/kg of the NIR-labeled, iRGD-conjugated silicasome (n=3, referred to as "silicasome-iRGD"), or (iii) 50 mg/kg NIR labeled silicasome without iRGD. Animals were sacrificed 24 h post injection, followed by ex vivo NIR imaging, using IVIS. FIG. 22B: NIR fluorescence intensity and Si content were used to quantify the nanoparticle content in the orthotopic tumors. Data represent mean±SD, *p<0.05.

FIG. 23A: Schedule of the efficacy study in the luciferase expressing KPC-derived orthotopic tumor model (n=6). The chosen Ir-silicasome dose (40 mg/kg irinotecan; 80 mg/kg MSNP) is based on a previous efficacy study (Liu et al. (2016) *ACS Nano.* 10(2): 2702-2715). This dose of the Ir-silicasome was IV injected, with or without co-administration of 8 μmol/kg iRGD. The injections were repeated every 3 days, for a total of 4 administrations. The controls involved animal groups receiving identical doses of free iRGD or the Ir-silicasome alone. FIG. 23B: Representative ex vivo imaging of the bioluminescence intensity in the mice prior to sacrifice to show the primary tumor burden and metastases. The images show that iRGD co-administration could enhance the silicasome efficacy. FIG. 23C: Heat map summarizing the impact on tumor and tumor metastasis inhibition in FIG. 23B. FIG. 23D: iRGD co-administration improved the survival impact of the Ir-silicasome, as shown by the Kaplan-Meier analysis. The effect of the silicasome alone is highly significant compared to PBS and free iRGD (p=0.001). iRGD co-administration further enhances survival (p=0.027). FIG. 23E: HPLC analysis of the irinotecan content in the tumor, 24 h after a one-time dose of the Ir-silicasome (40 mg/kg drug), was injected, with or without the co-administration of 8 μmol/kg iRGD. Data represent mean±SD (n=3), *p<0.05.

FIG. 24A: Schematic to demonstrate the mechanism by which iRGD initiates nanoparticle transcytosis. FIG. 24C: Interference of an anti-NRP-1 antibody on iRGD-mediated silicasome biodistribution. Fifty μg of the blocking antibody or a control IgG was IV injected 15 mins before IV injection of 50 mg/kg of the NIR-silicasome+8 μmol/kg free iRGD (n=3). Ex vivo NIR images showing nanoparticle biodistribution after 24 h. The NIR intensity as well as Si content was used to quantify the nanoparticle uptake at the orthotopic tumor site. Data represent mean±SD, *p<0.05.

FIG. 25A: Mice bearing orthotopic tumors were injected with 50 mg/kg Au-silicasomes, with or without co-administration of 8 μmol/kg iRGD. Tumors were harvested at 24 h and immediated fixed for TEM analysis. At least 10 regions of interest in each group were viewed to quantitatively express the abundance of grouped, interconnected vesicles (yellow arrows) in the blood vessel endothelial cells. We calculated the number of vesicles per 1 μm$^2$ of the intracellular surface area (left panel). Data represent mean±SD, *p<0.05. Representative TEM pictures with high and low magnification are shown. L=lumen; R=red blood cell. FIG. 25B: TEM visualization of silicasome transcytosis in tumor-bearing mice that received 50 mg/kg Au-silicasome and then sacrificed 24 h later. The electron micrograph shows silicasomes in: (i) the lumen of a tumor blood vessel (red arrow), (ii) transport in the endothelial vesicles (pink arrow), and a deposition in the tumor interstitium (blue arrow). High magnification images of regions "1"-"3" are provided in the panels on the right. E=endothelial cell; L=lumen; P=pericyte; R=red blood cell. FIG. 25C: TEM image showing the presence of silicasomes in a perinuclear distribution inside a cancer cell. N=nucleus; M=mitochondrion.

FIG. 26A: A pair of tumors (XWR #8 and XWR #187), with matched stromal abundance but differing levels of NRP-1 expression, was selected for a biodistribution study in the absence and presence of iRGD co-administration. Masson's trichrome staining shows equivalent levels of collagen expression in both tumors. Multi-color IHC staining (green fluorescent antibody for NRP-1, red fluorescent antibody for CD31) was used to determine the relative abundance of NRP-1 expression, and the extent of overlap with endothelial cells, using image J software. Data represent mean±SD, *p<0.05. FIG. 26B: The tumor-bearing animals received IV injection 50 mg/kg NIR-labeled silicasome with or without the co-administration of 8 μmol/kg iRGD. Animals were sacrificed after 24 h (n=3). Ex vivo assessment of the uptake of silicasomes as determined by NIR fluorescence intensity and Si content. Data represent mean±SD, *p<0.05.

DETAILED DESCRIPTION

Figure 1A:
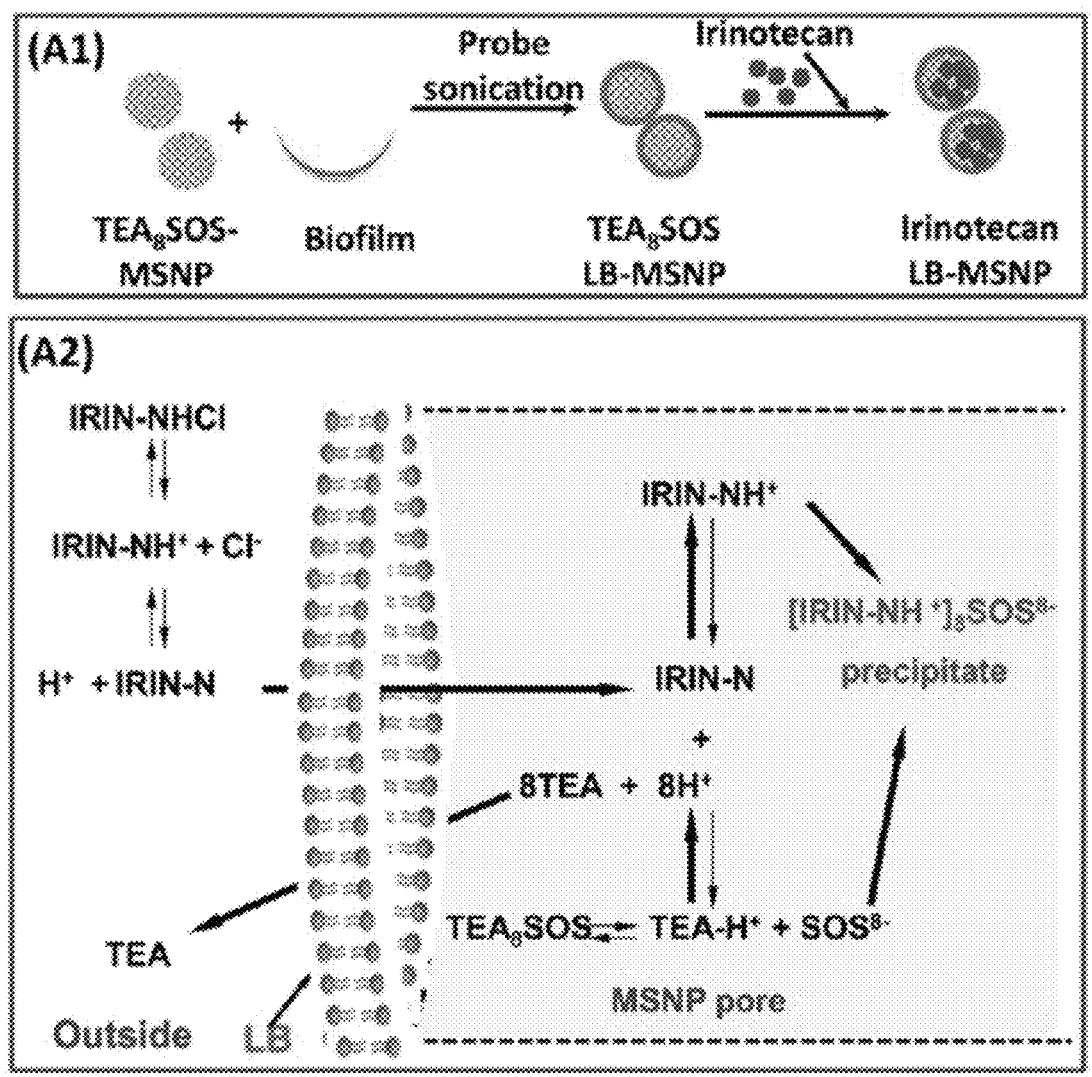
FIGS. 1A-1E illustrate the preparation of LB-MSNP and liposomal irinotecan carriers that use a protonating agent for drug loading, in accordance with one or more embodiments described herein.

In order to address the high rate of toxicity while maintaining or increasing therapeutic efficacy, drug delivering nanocarriers are provided to enhance drug delivery (e.g., chemotherapy drugs, antimicrobial drugs, etc.) at a target site (e.g. a tumor site, a site of infection, etc.) while limiting the amount of free drug that can cause systemic toxicity. It is desirable that the carrier itself maintains stable drug loading in order to prevent toxicity and improve efficacy. The use of nanocarriers to deliver chemotherapeutic agents in animal tumor models established from various cancer cells has demonstrated an ability of such nanocarriers to prolong the drug circulatory half-life, deliver high drug concentrations to the tumor site with improved cytotoxic killing, as well as reduce systemic toxicity compared to free drug equivalents (see, e.g., Messerer et al. (2004) *Clin. Cancer Res.* 10(19): 6638-6649; Drummond et al. (2006) *Cancer Res.* 66(6): 3271-3277; Ramsay et al. (2008) *Clin. Cancer Res.* 14(4): 1208-1217).

In view of the failure of many liposomal carriers to improve the safety of highly toxic drugs such as irinotecan, novel nanoparticle drug carriers are provided herein that use a lipid bilayer (LB) applied to silica nanoparticles (e.g., mesoporous silica nanoparticles (MSNPs)), thereby providing a supported lipid bilayer. These lipid bilayer coated porous silica nanoparticles (also known as silicasomes) provide a drug carrier that is significantly less leaky than liposomes (Meng et al. (2013) *ACS Nano*, 7(2): 994-1005; Meng et al. (2011) *ACS Nano*, 5(5): 4131-4144; Meng et al. (2013) *ACS Nano*, 7(11): 10048-10065; Meng et al. (2015) *ACS Nano*, 9(4): 3540-3557). Due to a large internal surface area that can be used for drug packaging, tunable pore sizes, carrier stability, and controlled drug release abilities, MSNPs have been demonstrated to constitute a versatile and multifunctional nanocarrier platform for cancer therapy (Meng et al. (2013) *ACS Nano*, 7(2): 994-1005; Meng et al. (2011) *ACS Nano*, 5(5): 4131-4144; Meng et al. (2013) *ACS Nano*, 7(11): 10048-10065; Meng et al. (2015) *ACS Nano*, 9(4): 3540-3557; Meng et al. (2010) *J. Am. Chem. Soc.* 132(36): 12690-12697; Li et al. (2012) *Chem. Soc. Rev.* 41(7): 2590-2605; Tang et al. (2012) *Adv. Mat.* 24(12): 1504-1534; Tarn et al. (2013) *Acc. Chem. Res.* 46(3): 792-801). However methods of effectively loading lipid-bilayer coated silica particles have been limited, typically providing loading ranging from about 10 wt % up to 40 wt %.

In various embodiments new loading methods are provided herein that achieve significantly greater loading of lipid-bilayer coated nanoparticle drug carriers. In general the new loading method utilizes a cargo trapping reagent, to retain the cargo (e.g., drug or drugs of interest) within the pores of the nanoparticle inside the lipid bilayer. More specifically, in certain embodiments, the method can involve:

providing a nanocarrier comprising a porous silica body comprising a plurality of pores capable of receiving the cargo (e.g., drug) of interest);

disposing a trapping agent (a cargo trapping agent) within the plurality of pores where the agent is selected for its ability to trap the cargo within the pores;

coating the surface pores of the nanocarrier with a lipid bilayer;

and introducing the cargo into the pores coated by the lipid bilayer, where the cargo reacts with the trapping agent and is retained within the pores.

In certain embodiments the trapping agent comprises a protonating agent and the methods involve providing a drug or drugs that can pass through the lipid bilayer into the bilayer-coated porous nanoparticle. The protonating agent in the porous nanoparticle converts the drug into a hydrophilic derivative that is incapable of back diffusion across the lipid bilayer.

In the illustrative, but non-limiting embodiment shown in Example 1, MSNP cores were synthesized by sol-gel chemistry and soaked in a solution containing the protonating agent, TEA$_8$SOS. These particles were coated with a LB, using a sonication procedure in the presence of a lipid biofilm of optimal composition for bilayer stability. This was followed by remote irinotecan loading by the proton gradient provided by TEA$_8$SOS. Irinotecan is a weak basic and amphipathic molecule that can diffuse across the LB into the MSNP interior packaging space, where proton release by prior entrapped triethylammonium sucrose octasulfate (TEA$_8$SOS) converts the drug into a hydrophilic derivative, incapable of back-diffusion across the LB. Using this method high loading capacities (e.g., greater than 40 wt %, or greater than 45 wt %, or greater than 50 wt %, or greater than 60 wt %, or greater than 70 wt %, %, or greater than 80 wt %, etc.) are achieved.

The lipid bilayer nanoparticle drug carriers (LB-MSNPs or "silicasomes") produced using the methods described herein offer numerous advantages. Combining an existing biofilm coating method to synthesize LB-MSNPs with a protonating agent, such as TEA$_8$SOS, provides active and high dose loading of drugs such as irinotecan in a particulate carrier that shows numerous advantages over liposomes. Such advantages include, but are not limited to ease of synthesis, improved drug loading and release profile, improved stability and improved biodistribution. In certain illustrative, but non-limiting embodiments, this method of remote loading leads to a 4-fold or greater increase in loading capacity of irinotecan compared to passive drug encapsulation behind the LB in MSNP. Using the methods described herein, non-encapsulated irinotecan gains entrance to MSNP pores by diffusing through the LB, whereupon protonation renders the irinotecan hydrophilic and incapable of escape.

Furthermore, the increased loading capacity of the nanocarrier leads to increased drug delivery at the cancer site, with less of the free drug becoming available at sites such as the bone marrow and gastrointestinal tract (GIT), where irinotecan causes toxicity. In one instance, the LB-MSNP has an improved loading capacity (83.5 weight % irinotecan loading) versus an in-house liposomal equivalent of MM-398 (42.5 weight % loading capacity). After optimization of loading time, trapping agent concentration, and amount of irinotecan offered for loading, embodiments of the LB-MSNP formulation have demonstrated 3-5 times higher release capacity at an acidic pH (4.5) compared to the liposomal formulation. The accompanying dose adjustment allows administration of less drug dose to obtain the same efficacy, leading to further reduction in systemic drug toxicity. In one instance, in the calculation of maximum tolerated dose (MTD), embodiments of the LB-MSNP showed a 5-fold improvement in the tolerated dose compared to the free drug. The increased MTD was similar to the liposomal formulation. Analysis of bone marrow histology showed that the irinotecan toxicity was greatly reduced by the LB-MSNP.

Additionally, the synthesis/loading methods described herein are easier to perform than either making conventional liposomes or the polymer-lipid technology used by Zhang et al. (2104) *Biomaterials*, 35(11): 3560-3665). This is advantageous for scale-up to GMP manufacturing, including cost savings by reducing the quantity of non-encapsulated drug.

While the methods and nanoparticle drug carriers (silicasomes) produced thereby described herein with respect to irinotecan, it will be understood that, as explained below, the method can be applied to a number of other cargos (e.g., cargos comprising one or more drugs). Moreover, in view of the teachings provided herein, it is believed the improvements in drug delivery (on target), and/or reduced toxicity, and/or improved biodistribution, and/or improved release profile will be achieved using the methods and compositions described herein with numerous other drugs.

According, in certain embodiments, a LB-MSNP-based nanocarrier delivery system is described, that allows for stable and protected loading of cargo at high loading levels, with the assistance of a cargo-trapping agent. In some embodiments, the cargo can be a drug. Drug delivery by the modified LB-MSNP encapsulation and trapping allows for more frequent use of drug encapsulation, e.g., chemotherapy drugs, because of enhanced efficacy, high drug loading capacity and reduced systemic toxicity. From a nanocarrier design perspective, various embodiments of this system, for example a polyanionic cargo-trapping agent within LB-MSNP, are employed as an effective design principle for delivering a range of additional weakly basic molecules and drugs, for the treatment of several different types of cancer and other disease processes.

In one instance, with respect to irinotecan, delivery by the modified LB-MSNP encapsulation and trapping procedure allows for more frequent use of irinotecan and FOLFIRINOX in human PDAC patients because of enhanced efficacy, high drug loading capacity and reduced systemic toxicity of irinotecan. This also allows more PDAC patients to be treated with a more potent therapeutic regimen than gemcitabine, with promise of increased survival. Ultimately, an IV injectable, efficient, biocompatible, and translationally competitive irinotecan formulation (versus MM398 liposome) for PDAC treatment is provided. Particularly in view of the methods and resulting nanoparticle drug carriers described herein, irinotecan and FOLFIRINOX therapy may also be available for the treatment of other cancers including, but not limited to colon, rectal, lung, and ovarian cancer.

The silicasome delivery system disclosed herein is a multifunctional platform. Mesoporous silica drug carriers have been demonstrated to be able to deliver a wide range of cargoes to cancer cells as well as a variety of human cancer models in animals. These include gemcitabine and paclitaxil co-delivery to xenograft and orthotopic PDAC tumors in mice. Moreover, MSNPs are biodegradable and proven to be safe in extensive animal testing (Meng et al. (2013) *ACS Nano*, 7(2): 994-1005; Meng et al. (2011) *ACS Nano*, 5(5): 4131-4144; Meng et al. (2013) *ACS Nano*, 7(11): 10048-10065; Meng et al. (2015) *ACS Nano*, 9(4): 3540-3557; Tang et al. (2012) *Adv. Mat.* 24(12): 1504-1534; Tarn et al. (2013) *Acc. Chem. Res.* 46(3): 792-801; Zhang et al. (2012) *J. Am. Chem. Soc.* 134(38): 15790-15804; Lu et al. (2010) *Small*, 6(16): 1794-1805).

In view of the improved loading, the resulting pharmacokinetic profiles described herein, and the like, it is believed the loading methods, lipid bilayer composition and stability of the resulting nanoparticle drug carriers described herein provide significant improvements and advantages over previous nanoparticle drug carriers.

Methods of Loading Lipid-Bilayer Coated Porous Nanoparticles.

In various embodiments, improved methods of loading lipid bilayer-coated porous nanoparticles (e.g., mesoporous silica particles) are provided along with the drug delivery nanoparticles produced by such methods. In certain embodiments the methods described herein achieve extremely high levels of drug loading e.g., greater than 40 wt %, or greater than 45 wt %, or greater than 50 wt %, or greater than 60 wt %, or greater than 70 wt %, %, or greater than 80 wt %, etc.).

As noted above, in certain embodiments, the methods can involve:

providing a nanocarrier comprising a porous silica body comprising a plurality of pores capable of receiving the cargo (e.g., drug) of interest;

disposing a trapping agent (a cargo trapping agent) within the plurality of pores where the agent is selected for its ability to trap the cargo within the pores;

coating the surface pores of the nanocarrier with a lipid bilayer; and introducing the cargo into the pores coated by the lipid bilayer, where the cargo reacts with the trapping agent and is retained within the pores.

While it has never been used in a MSNP platform previously, the polyanionic compound, TEA$_8$SOS, was used in MM-398 to entrap irinotecan (Drummond et al. (2006) *Cancer Res.*, 66(6): 3271-3277). Prior to the studies described herein, however, it was unknown whether or not TEA$_8$SOS could be used to effectively perform remote loading of porous nanoparticles at significantly greater levels than other loading or soak-in methods.

Figure 1B:
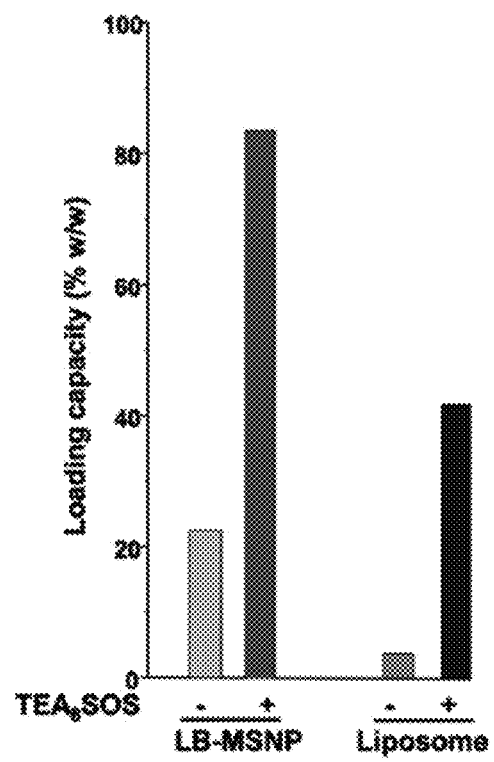

As described in the Examples, TEA$_8$SOS is a proton-generating agent that releases eight H+ ions and octavalent SOS$^{8-}$ upon hydrolysis (FIG. 1A, panel A2). Ion-exchange chromatography was used to generate TEA$_8$SOS, which was soaked into MSNP, as described below in the Methods section (Id.). The soaked particles were introduced to a round-bottom flask coated with a lipid biofilm, composed of DSPC/cholesterol/DSPE-PEG2000 at a molar ratio of 3:2:0.15. Sonication of the suspension yielded LB-coated particles, that contain the entrapment agent (FIG. 1A, panel A1). These particles were immediately incubated in an irinotecan solution, allowing the drug to be imported, protonated, and entrapped in the pores as a gel-like precipitate in association with SOS$^{8-}$ (FIG. 1A, panels A1 and A2, FIG. 1B). This allowed us to achieve an irinotecan loading capacity up to 80 wt % or greater (FIG. 1B), which approximates the theoretical maximum loading capacity (~100 wt %) of the porous carrier with a combined surface area of 850 m$^2$/g and a pore volume of ~0.7 cm$^3$/g, as previously demonstrated (Meng et al. (2015) *ACS Nano*, 9(4): 3540-3557).

While the methods are illustrated with respect to the use of drug irinotecan and TEA8SOS as the trapping agent, it will be recognized that, having demonstrated proof of principle, the same method can be used to incorporate numerous other drugs (especially weakly basic drugs) in a silica some and numerous other trapping agents can be similarly be utilized, e.g., as described herein.

Since drug loading capacity is an important manufacturing consideration that is also critical for therapeutic effectiveness and limitation of drug toxicity, much research has been devoted to optimizing the efficacy of drug encapsulation by MSNP, leading to increased loading capacity and the ability to co-deliver synergistic drug combinations. While it is possible to introduce drugs such as irinotecan into MSNPs by a traditional soaking method, this method of loading has proved to be relatively inefficient achieving loading levels of about 10 wt % (see, e.g., He et al. (2010) *Biomaterials*, 31(12): 3335-3346), and it is difficult to retain the drug in the pores (see, e.g., Meng et al. (2010) *J. Am. Chem. Soc.* 132(36): 12690-12697). Different from traditional drug loading approaches that depend on physical adsorption, electrostatic attachment, supramolecular assembly or use of entrapment methods (e.g., stoppers, nanovalves or blocking entities), the use of an intact lipid bilayer coating disposed on the porous nanoparticle provides rapid and instantaneous pore sealing for drug entrapment. This simplifies synthesis and provides stable and high drug loading capacity. The methods described herein are effective to load porous particle with cargos at high levels and are compatible with this rapid and instantaneous pore sealing with the lipid bilayer.

A biofilm technique has been developed for the LB-coated MSNP platform that can be used to rapidly encapsulate gemcitabine (GEM) (e.g. a water-soluble nucleoside) by a supported LB (Meng et al. (2015) *ACS Nano*, 9(4): 3540-3557). Not only has this allowed the LB-MSNPs to achieve a loading capacity of up to 40 wt % GEM, but also enabled co-delivery of hydrophobic paclitaxel (PTX) that could be incorporated in the lipid bilayer (LB) (Meng et al. (2015) *ACS Nano*, 9(4): 3540-3557). This has provided for a synergistic and ratiometric-designed carrier for PDAC treatment in an orthotopic human PDAC model in mice (Id.).

This supported LB coating method has also been demonstrated to be far superior to a comparable liposomal coating technique for MSNPs which involves several steps, including liposomal adhesion to the MSNP surface, rupture, partial covering of the MSNP surface by an incomplete coat that is secondarily sealed by the addition of additional liposome compositions (Liu et al. (2009) *J. Am. Chem. Soc.* 131: 7567-7569).

However, while the presence of the lipid bilayer (LB) provided an improvement on previous drug delivery nanoparticles, prior to the utilization of the remote loading methods described herein, the bilayer still provided an impediment to achieving even higher drug loading levels.

As noted above, in various embodiments drug loading by the LB-MSNP platform has been further improved by using the LB to encapsulate a protonating agent as the first step, followed by irinotecan loading, which is dependent on the drug's weak basic properties (pKa=8.1). As shown in the examples herein, comparisons were made between the MSNP carrier and a liposome equivalent, in which a non-supported LB was used for irinotecan loading subsequent to encapsulation of triethylammonium sucrose octasulfate (TEA$_8$SOS) (Drummond et al. (2006) *Cancer Res.*, 66(6): 3271-3277; Von Hoff et al. (2013) *Br. J. Cancer*, 109(4): 920-925). Not only did the MSNP carrier achieve higher loading capacity for irinotecan and tumor killing than the liposomal formulation in a robust orthotopic PDAC model, but it also prevented drug toxicity due to increased carrier stability and reduced leakage compared to liposomes. Thus, the LB-MSNP platform exhibits the properties desirable for a first-line irinotecan carrier for PDAC (or other cancer) treatment.

Recently, a polymer-lipid supported coating method has been described by Zhang et al. for irinotecan drug loading of MSNPs to treat drug-resistant breast cancer tumors in Balb/c nude mice (Zhang et al. (2014) *Biomaterials*, 35(11): 3650-3665). However, the methodology described in this reference is different, and does not achieve the same drug loading capacity compared to the methods and compositions described herein. First, Zhang et al. do not use a classical LB or a trapping agent, resulting in a carrier with only ⅕th the loading capacity (~15%, w/w) of the carrier provided herein (~83.5%, w/w).

A second major difference is in the drug loading procedure. The authors state that "CPT-11 @MSNs" were centrifuged and washed in PBS (pH 7.4), then dried under vacuum at room temperature. In contrast, the methods described herein do not require drying of the unprotected MSNPs. Drying of the MSNPs can be problematic because of the difficulty obtaining dispersion upon re-suspension in aqueous media which is a key requirement for systemic drug delivery. In addition, the present methods do not require washing of the drug (e.g. irinotecan)-loaded MSNP before pore sealing which minimizes drug loss, and facilitates a high loading capacity (e.g., ~83.5% (w/w)).

A third major difference is the composition of the LB formulation. In one or more embodiments, a mixture of commercially available lipids plus cholesterol (e.g., DSPC/cholesterol/DSPE-PEG) is used, while Zhang et al. use an in-house synthesized, pH-sensitive, Pluronic P123 grafted DOPE. The use of the Pluronic is apparently based on its ability to act as an inhibitor of drug efflux (see, e.g., Batrakova et al. (2004) *Pharm. Res.* 21(12): 2226-2233), hence the consideration to treat drug-resistant breast cancer. The absence of cholesterol in the coated bilayer decreases the fluidity and stability of the platform. In contrast, the presence of cholesterol in the silicasomes contributes to the excellent stability of the LB-MSNP disclosed herein (see Examples). Moreover, irinotecan encapsulation in the provided carrier shows <5% leakage over 24 hours in a biological buffer with pH of 7.4 at 37° C. This is 2.5× lower than the premature leakage (~16% leakage at pH 7.4 and 37° C. over 24 hours) described by Zhang et al. (2014) *Biomaterials*, 35: 3650-3665).

Another difference from the drug deliver platform described by Zhang et al. is that various embodiments of the present invention use probe sonication for biofilm rehydration and pore sealing, followed by centrifugation purification or size exclusion chromatography. On the other hand, Zhang et al. utilizes a membrane extrusion method, as for liposomes. Also, CTAC is used as a templating agent for MSNP synthesis, whereas Zhang et al. utilize CTAB. Finally, the present invention addresses the development of therapy for PDAC and other cancers and is not principally designed to overcome drug resistance, as are the drug delivery particles described by Zhang et al. for use in the breast cancer study. All considered, without being bound to a particular theory, it is believed the lipid bilayer coated nanoparticle drug carriers described herein (e.g., the irinotecan-delivering LB-MSNP) provide a unique design that outperforms the carriers of Zhang et al. based on drug loading capacity, colloidal stability, ease of production, and stable drug retention in the blood and body fluids.

Nanoparticles.

In various embodiments nanoparticle drug carriers described herein comprises a porous silica nanoparticle (e.g., a silica body having a surface and defining a plurality of pores that are suitable to receive molecules therein) coated with a lipid bilayer. For example, in certain embodiments the silica nanoparticle can be a mesoporous silica nanoparticle. The fact that the nanoparticle is referred to as a silica nanoparticle does not preclude materials other than silica from also being incorporated within the silica nanoparticle. In some embodiments, the silica nanoparticle may be substantially spherical with a plurality of pore openings through the surface providing access to the pores. However, in various embodiments the silica nanoparticle can have shapes other than substantially spherical shapes. Thus, for example, in certain embodiments the silica nanoparticle can be substantially ovoid, rod-shaped, a substantially regular polygon, an irregular polygon, and the like.

Generally, the silica nanoparticle comprises a silica body that defines an outer surface between the pore openings, as well as side walls within the pores. The pores can extend through the silica body to another pore opening, or a pore can extend only partially through the silica body such that that it has a bottom surface of defined by the silica body.

In some embodiments, the silica body is mesoporous. In other embodiments, the silica body is microporous. As used herein, "mesoporous" means having pores with a diameter between about 2 nm and about 50 nm, while "microporous" means having pores with a diameter smaller than about 2 nm. In general, the pores may be of any size, but in typical embodiments are large enough to contain one or more therapeutic compounds therein. In such embodiments, the pores allow small molecules, for example, therapeutic compounds such as anticancer compounds to adhere or bind to the inside surface of the pores, and to be released from the silica body when used for therapeutic purposes. In some embodiments, the pores are substantially cylindrical.

In certain embodiments the nanoparticles comprise pores having pore diameters between about 1 nm and about 10 nm in diameter or between about 2 nm and about 8 nm. In certain embodiments the nanoparticles comprise pores having pore diameters between about 1 nm and about 6 nm, or between about 2 nm and about 5 nm. Other embodiments include particles having pore diameters less than 2.5 nm. In other embodiments, the pore diameters are between 1.5 and 2.5 nm. Silica nanoparticles having other pore sizes may be prepared, for example, by using different surfactants or swelling agents during the preparation of the silica nanoparticles.

In various embodiments the nanoparticles can include particles as large (e.g., average or median diameter (or other characteristic dimension) as about 1000 nm. However in various embodiments the nanoparticles are typically less than 500 nm or less than about 300 nm as, in general, particles larger than 300 nm may be less effective in entering living cells or blood vessel fenestrations. In certain embodiments the nanoparticles range in size from about 40 nm, or from about 50 nm, or from about 60 nm up to about 100 nm, or up to about 90 nm, or up to about 80 nm, or up to about 70 nm. In certain embodiments the nanoparticle range in size from about 60 nm to about 70 nm. Some embodiments include nanoparticles having an average maximum dimension between about 50 nm and about 1000 nm. Other embodiments include nanoparticles having an average maximum dimension between about 50 nm and about 500 nm. Other embodiments include nanoparticles having an average maximum dimension between about 50 nm and about 200 nm. In some embodiments, the average maximum dimension is greater than about 20 nm, greater than about 30 nm, greater than 40 nm, or greater than about 50 nm. Other embodiments include nanoparticles having an average maximum dimension less than about 500 nm, less than about 300 nm, less than about 200 nm, less than about 100 nm or less than about 75 nm. As used herein, the size of the nanoparticle refers to the average or median size of the primary particles, as measured by transmission electron microscopy (TEM) or similar visualization technique.

Illustrative mesoporous silica nanoparticles include, but are not limited to MCM-41, MCM-48, and SBA-15 (see, e.g., Katiyar et al. (2006) *J. Chromatog.* 1122(1-2): 13-20).

Methods of making porous silica nanoparticles are well known to those of skill in the art. In certain embodiments mesoporous silica nanoparticle are synthesized by reacting tetraethyl orthosilicate (TEOS) with a template made of micellar rods. The result is a collection of nano-sized spheres or rods that are filled with a regular arrangement of pores. The template can then be removed by washing with a solvent adjusted to the proper pH (see, e.g., Trewyn et al. (2007) *Chem. Eng.* 1 137(1): 23-29. In certain embodiments mesoporous particles can also be synthesized using a simple sol-gel method (see, e.g., Nandiyanto, et al. (2009) *Microporous and Mesoporous Mat.* 120(3): 447-453, and the like). In certain embodiments tetraethyl orthosilicate can also be used with an additional polymer monomer (as a template). In certain embodiments 3-mercaptopropyl)trimethoxysilane (MPTMS) is used instead of TEOS.

In certain embodiments the mesoporous silica nanoparticles are cores were synthesized by a modification of the sol/gel procedure described by Meng et al. (2015) ACS Nano, 9(4): 3540-3557. To synthesize a batch of ~500 mg of MSNP, 50 mL of CTAC is mixed with 150 mL of $H_2O$ in a flask (e.g., a 500 mL conical flask), followed by stirring (e.g., at 350 rpm for 15 min at 85° C.). This us followed by the addition of 8 mL of 10% triethanolamine for 30 min at the same temperature. Then, 7.5 mL of the silica precursor, TEOS, is added dropwise at a rate of 1 mL/min using a peristaltic pump. The solution is stirred at 350 rpm at 85° C. for 20 min, leading to the formation particles with a primary size of ~65 nm. The surfactant can be removed by washing the particles with a mixture of methanol/HCl (500:19 v/v) at room temperature for 24 h. The particles can be centrifuged at 10 000 rpm for 60 min and washed three times in methanol.

While the loading methods described herein have been demonstrated with respect to the loading of porous silica nanoparticles (e.g., mesoporous silica), it will be recognized that similar loading methods can be used with other porous nanoparticles. Numerous other mesoporous materials that can be used in drug delivery nanoparticles are known to those of skill in the art. For example, in certain embodiments mesoporous carbon nanoparticles could be utilized. Mesoporous carbon nanoparticles are well known to those of skill in the art (see, e.g., Huang et al. (2016) Carbon, 101: 135-142; Zhu et al. (2014) Asian J. Pharm. Sci., 9(2): 82-91; and the like).

Similarly, in certain embodiments, mesoporous polymeric particle can be utilized. The syntheses of highly ordered mesoporous polymers and carbon frameworks from organic-organic assembly of triblock copolymers with soluble, low-molecular-weight phenolic resin precursors (resols) by an evaporation induced self-assembly strategy have been reported by Meng et al. (2006) Chem. Mat. 6(18): 4447-4464 and in the references cited therein.

The nanoparticles described herein are illustrative and non-limiting. Using the teachings provided herein numerous other lipid bilayer drug delivery nanoparticle will be available to one of skill in the art.

Lipid Bilayer.

The drug carrier nanoparticles described herein comprise a porous nanoparticle (e.g. a mesoporous silica nanoparticle (MSNP)) coated with a lipid bilayer. In certain embodiments the bilayer composition is optimized to provide a rapid and uniform particle coating, to provide colloidal and circulatory stability, and to provide effective cargo retention, while also permitting a desirable cargo release profile.

In certain embodiments the lipid bilayer comprises a combination of a phospholipid, cholesterol, and in certain embodiments, a pegylated lipid (e.g., $DSPE-PEG_{2000}$), or a factionalized pegylated lipid (e.g., $DSPE-PEG_{2000}$-maleimide) to facilitate conjugation with targeting or other moieties.

To attach a surface LB coating, a coated lipid film procedure was developed in which drug- or $TEO_8SOS$-soaked MSNP suspensions were added to a large lipid film surface, coated on, e.g., a round-bottom flask. Using different lipid bilayer compositions, a series of experiments can be performed to find a composition and optimal lipid/particle ratio that provides rapid and uniform particle wrapping, coating and effective cargo retention and/or release upon sonication. It is believed that this lipid composition and wrapping cannot be achieved by liposomal fusion to the particle surface under low energy vortexing conditions.

As described in Example 1, in certain embodiments, 500 mg MSNPs are soaked in a 20 mL $TEA_8SOS$ (80 mM solution), which is added on top of the lipid biofilm, comprised of a 550 mg mixture of $DSPC/Chol/DSPE-PEG_{2000}$ (molar ratio 3:2:0.15), coated at the bottom of a round bottom flask (see Example 1, and Liu et al. (2016) ACS Nano. 10(2): 2702-2715). The ratio of "3:2:0.15" equals to "58.3 mol %: 38.8 mol %: 3.9 mol %" if one uses mol % to present the ratio. This provides a lipid:particle ratio of ~1.1:1. After sonication to accomplish particle wrapping and coating with a LB, free $TEA_8SOS$ is removed by size exclusion chromatography over a Sepharose CL-4B column. The $TEA_8SOS$ loaded silicasomes are incubated in a 10 mg/mL irinotecan solution for drug loading in a water bath at 65° C. The loading is stopped after 30 min by quenching in and ice water bath, following which the drug-loaded silicasomes were washed 3 times by centrifugation and re-suspended in PBS.

The lipid bilayer formulation described above and in Example 1 is illustrative and non-limiting. Depending on the drug(s) being loaded into the silicasome and the desired release provide, in various embodiments different lipid bilayer formulations can be used and an optimal formulation can be determined.

Accordingly, in certain embodiments the lipid bilayer can comprise: 1) one or more saturated fatty acids with C14-C20 carbon chain, such as dimyristoylphosphatidylcholine (DMPC), dipalmitoylphosphatidylcholine (DPPC), distearoylphosphatidylcholine (DSPC), and diactylphosphatidylcholine (DAPC); and/or 2) One or more unsaturated fatty acids with a C14-C20 carbon chain, such as 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), 1,2-dieicosenoyl-sn-glycero-3-phosphocholine; and/or 3) Natural lipids comprising a mixture of fatty acids with C12-C20 carbon chain, such as Egg PC, and Soy PC, sphingomyelin, and the like. These lipids are illustrative but non-limiting and numerous other lipids are known and can be incorporated into a lipid bilayer for formation of a silicasome.

In certain embodiments the silicasome contains a lipid (e.g., a phospholipid), cholesterol, and a PEG functionalized lipid (e.g., a mPEG phospholipid). In certain embodiments the mPEG phospholipids comprises a C14-C18 phospholipid carbon chain from, and a PEG molecular weight from 350-5000 (e.g., MPEG 5000, MPEG 3000, MPEG 2000, MPEG 1000, MPEG 750, MPEG 550, MPEG 350, and the like). In certain embodiments the mPEG phospholipid comprises DSPE-PEG5000, DSPE-PEG3000, DSPE-PEG2000, DSPE-PEG1000, DSPE-PEG750, DSPE-PEG550, or DSPE-PEG350. MPEGs are commercially available (see, e.g., //avantilipids.com/product-category/products/polymers-polymerizable-lipids/mpeg-phospholipids/).

In certain embodiments the ratio of phospholipid:CHOL:PEG, is about phospholipid (50-90 mol %):CHOL (10-50 mol %):PEG (1-10 mol %).

This protocol provided above and in the Examples is illustrative. In certain embodiments the trapping agent can be altered, the lipid composition and molar ratios can be altered, and the drug or drugs can be altered to identify other silicasomes optimized for their particular cargo(s).

It is noted, for example, that an effective lipid formulation for a gemcitabine-containing silicasome comprises DPPC/cholesterol/DSPE-PEG at a molar ratio of 77.5:20:2.5, while an effective lipid formulation for an irinotecan containing silicasome comprises DSPC/Chol/DSPE-PEG$_{2000}$ (molar ratio 3:2:0.15, which equals 58.3 mol %:38.8 mol %:3.9 mol %).

In certain embodiments these methods can be varied to improve drug-loading capacity (weight of drug/total weight of carrier). In certain embodiments the drug loading capacity is at least about 30%, or at least about 40%, at least about 50%, at least about 60%, at least about 70%, or at least 80% w/w. In certain embodiments drug loading is greater than 40% w/w, or greater than 45% w/w, or greater than 50% w/w, or greater than 60% w/w, or greater than 70% w/w, %, or greater than 80% w/w.

The protocols described herein provide a nanoparticle drug carrier (nanocarrier) outperforms nanocarriers made by the liposomal method of coating by fusion with the MSNP surface, as illustrated by the descriptions of the ease of synthesis and improved loading capacity and release profile provided herein. In typical embodiments, the LB coating procedure is used to rapidly encapsulate the protonation agent, e.g., TEA$_8$SOS, which subsequently provides irinotecan loading and entrapment by protonating the incoming drug diffusing across the LB. This leads to high drug loading in the particles pores. The rapid and effective pore sealing to retain the trapping agent (e.g., TEA$_8$SOS), without leakage, contributes to the effectiveness and stability of the carrier.

Cargo Trapping Reagent.

The cargo-trapping reagent can be selected to interact with a desired cargo. In some embodiments, this interaction can be an ionic or protonation reaction, although other modes of interaction are contemplated. The cargo-trapping agent can have one or more ionic sites, i.e., can be mono-ionic or poly-ionic. The ionic moiety can be cationic, anionic, or in some cases, the cargo-trapping agent can include both cationic and anionic moieties. The ionic sites can be in equilibrium with corresponding uncharged forms; for example, an anionic carboxylate (—COO$^-$) can be in equilibrium with its corresponding carboxylic acid (—COOH); or in another example, an amine (—NH$_2$) can be in equilibrium with its corresponding protonated ammonium form (—NH$_3^+$). These equilibriums are influenced by the pH of the local environment.

Likewise, in certain embodiments, the cargo can include one or more ionic sites. The cargo-trapping agent and cargo can be selected to interact inside the nanoparticle (e.g., the mesoporous silica nanoparticle). This interaction can help retain the cargo within the nanoparticle until release of the cargo is desired. In some embodiments, the cargo can exist in a pH-dependent equilibrium between non-ionic and ionic forms. The non-ionic form can diffuse across the lipid bilayer and enter pores of the MSNP. There, the cargo-trapping agent (e.g., a polyionic cargo-trapping agent) can interact with the ionic form of the cargo and thereby retain the cargo within the nanocarrier, e.g., within pores of the MSNP (provided the ionic forms of the cargo and cargo-trapping agent have opposite charges). The interaction can be an ionic interaction, and can include formation of a precipitate. Trapping of cargo within the nanocarrier can provide higher levels of cargo loading compared to similar systems, e.g., nanocarriers that omit the cargo-trapping agent, or liposomes that do include a trapping agent. Release of the cargo can be achieved by an appropriate change in pH to disrupt the interaction between the cargo and cargo-trapping agent, for example, by returning the cargo to its non-ionic state which can more readily diffuse across the lipid bilayer. In one embodiment, the cargo is irinotecan and the cargo-trapping agent is TEA$_8$SOS.

The cargo trapping agent need not be limited to TEA8SOS. In certain embodiments the cargo trapping comprises small molecules like (NH$_4$)$_2$SO$_4$, and the like. Other trapping agents include, but are not limited to, ammonium salts (e.g., ammonium sulfate, ammonium sucrose octasulfate, ammonium α-cyclodextrin sulfate, ammonium β-cyclodextrin sulfate, ammonium γ-cyclodextrin sulfate, ammonium phosphate, ammonium α-cyclodextrin phosphate, ammonium β-cyclodextrin phosphate, ammonium γ-cyclodextrin phosphate, ammonium citrate, ammonium acetate, and the like), trimethylammonium salts (e.g., trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, trimethylammonium acetate, and the like), triethylammonium salts (e.g., triethylammonium sulfate, triethylammonium sucrose octasulfate, triethylammonium α-cyclodextrin sulfate, triethylammonium β-cyclodextrin sulfate, triethylammonium γ-cyclodextrin sulfate, triethylammonium phosphate, triethylammonium α-cyclodextrin phosphate, triethylammonium β-cyclodextrin phosphate, triethylammonium γ-cyclodextrin phosphate, triethylammonium citrate, triethylammonium acetate, and the like).

It is also worth pointing out that, in addition to TEA$_8$SOS, transmembrane pH gradients can also be generated by acidic buffers (e.g. citrate) (Chou et al. (2003) *J. Biosci. Bioengineer.*, 95(4): 405-408; Nichols et al. (1976) *Biochimica et Biophysica Acta (BBA)-Biomembranes*, 455(1): 269-271), proton-generating dissociable salts (e.g. (NH$_4$)$_2$SO$_4$) (Haran et al. (1993) *Biochimica et Biophysica Acta (BBA)-Biomembranes*, 1151(2): 201-215; Maurer-Spurej et al. (1999) *Biochimica et Biophysica Acta (BBA)-Biomembranes*, 1416 (1): 1-10; Fritze et al. (2006) *Biochimica et Biophysica Acta (BBA)-Biomembranes*, 1758(10): 1633-1640), or ionophore-mediated ion gradients from metal salts (e.g. A23187 and MnSO$_4$) (Messerer et al. (2004) *Clinical Cancer Res.* 10(19): 6638-6649; Ramsay et al. (2008) *Eur. J. Pharmaceut. Biopharmaceut.* 68(3): 607-617; Fenske et al. (1998) *Biochimica et Biophysica Acta (BBA)-Biomembranes*, 1414 (1)L 188-204). Moreover, it is possible to generate reverse pH gradients for drug loading, such as use a calcium acetate gradient to improve amphiphilic weak acid loading in LB-MSNP, a strategy that has been utilized in liposomes (Avnir et al. (2008) *Arthritis & Rheumatism*, 58(1): 119-129).

Cargo/Drug.

In one or more embodiments, the cargo comprises an organic compound that includes at least one primary amine group, or at least one secondary amine group, or at least one tertiary amine group, or at least one quaternary amine group, or any combination thereof, capable of being protonated. We have also identified a comprehensive list of weak basic drugs that can be loaded into LB-MSNPs through a proton gradient. The general characteristics of these cargo molecules include the following chemical properties:

(i) organic molecular compounds that include primary, secondary, tertiary or quaternary amine(s);
(ii) a pKa <11 to allow protonation and entrapment behind the LB (Zucker et al. (2009) *J. Control. Release*, 139(1): 73-80; Cern et al. (2012) *J. Control. Release*, 160(2): 147-157; Xu et al. (2014) *Pharmaceut. Res.* 31(10): 2583-2592);

(iii) a water solubility index of 5-25 mg/mL and amphipathic characteristics that allow diffusion across the LB;

(iv) an octanol/water partition coefficient or log P value of −3.0 to 3.0 (Zucker et al. (2009) *J. Control. Release*, 139(1): 73-80; Cern et al. (2012) *J. Control. Release*, 160(2): 147-157);

(v) suitable molecular weight with a geometric size less than MSNP pore size (2-8 nm), to allow entry into the MSNP pores (Li et al. (2012) *Chem. Soc. Rev.* 41(7): 2590-2605; Tang et al. (2012) *Adv. Mat.* 24(12): 1504-1534; Tarn et al. (2013) *Acc. Chem. Res.* 46(3): 792-801).

Without being all-inclusive, in various embodiments a list of potential chemotherapy agents can include irinotecan derivatives and metabolites such as SN38 together with other alkaloids (e.g. topotecan, 10-hydroxycamptothecin, belotecan, rubitecan, vinorelbine, LAQ824, vinblastine, vincristine, homoharringtonine, trabectedin), anthracyclines (e.g. doxorubicin, epirubicin, pirarubicin, daunorubicin, rubidomycin, valrubicin, amrubicin), alkaline anthracenediones (e.g. mitoxantrone), alkaline alkylating agents (e.g. cyclophosphamide, mechlorethamine, temozolomide), purine or pyrimidine derivatives (e.g. 5-fluorouracil, 5'-deoxy-5-fluorouridine, gemcitabine, capecitabine), and protein kinase inhibitors (e.g. pazopanib, enzastaurin, vandetanib erlotinib, dasatinib, nilotinib, sunitinib).

The ability to package and deliver one or a combination of the above agents will enhance the wider utility of the multifunctional LB-MSNP platform, including treatment consideration of additional cancer types such as colon, breast, lung, liver, glioma, melanoma, etc.

It is also possible to co-package drug combinations in the above list into a single carrier. For example, based on the success that we achieved with our GEM/PTX co-delivery platform (see, e.g. Meng et al. (2015) *ACS Nano*, 9(4): 3540-3557), it is possible to consider combining drugs in the FOLFIRINOX regimen (e.g., oxaliplatin with irinotecan) for synergistic and ratiometric delivery using the silicasomes described herein. Moreover, drug loading by our LB-MSNP can be used for non-cancerous applications, such as encapsulating antibiotics for infectious disease applications, e.g., ciprofloxacin, levofloxacin or HIV antiretrovirals (e.g., tenofovir disoproxil fumarate).

In addition to the above mentioned cancer drugs, as long as the drug molecules are basic as described above, the trapping reagent facilitated LB-MSNP platform is useful in efficient drug loading and delivery. For non-basic drug molecules, while the trapping reagent will provide limited help, the provided one-step biofilm technique for MSNP pore healing is still valid for an even larger spectrum of drug molecules, such as anticancer drugs, anti-viral drugs, anti-fungal drugs, and antibiotics.

For example, with the usage of LB biofilm for MSNP sealing, in certain embodiments efficient drug encapsulation includes, but is not limited to, everolimus, trabectedin, paclitaxel, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6,Azgly 10] (pyro-Glu-His-Trp-Ser-Tyr-D-Ser(Bu t)-Leu-Arg-Pro-Azgly-NH2 acetate [C59H84N18Oi4-(C2H4O2)X where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, and darbepoetin alfa, boceprevir, daclatasvir, asunaprevir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NSSA, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, ribavirin, pegylated interferon, PHX1766, SP-30, or a mixture thereof.

In certain embodiments the cargo comprise an antifungal agent. Illustrative antifungal agents include, but are not limited to Amphotericin B (e.g., for Most fungal infections except *Pseudallescheria* sp., and the like), Anidulafungin (e.g., for candidiasis, including candidemia, and the like), Caspofungin (e.g., for aspergillosis, candidiasis, including candidemia, and the like), Fluconazole (e.g., for mucosal and systemic candidiasis, cryptococcal meningitis, coccidioidal meningitis, and the like), Flucytosine (e.g., for Candidiasis (systemic), Cryptococcosis, and the like), Isavuconazole (e.g., for Aspergillosis, Mucormycosis, and the like), Itraconazole (e.g., for Dermatomycosis, Histoplasmosis, blastomycosis, coccidioidomycosis, sporotrichosis, and the like), Micafungin (e.g., for Candidiasis, including candidemia), Posaconazole (e.g., for prophylaxis for invasive aspergillosis and candidiasis, oral candidiasis, oral candidiasis refractory to itraconazole, and the like), Voriconazole (e.g., for Invasive aspergillosis, Fusariosis, Scedosporiosis, and the like), and so forth.

Dual Therapeutic Silicasomes.

It will be recognized that in certain embodiments, the nanoparticle drug carriers (silicasomes) described herein can comprise two or more therapeutic agents. Thus, for example, in certain embodiments the pores in the silicasome can be loaded with two, or with three, or with four, or more different therapeutic agents. This can, in certain embodiments, permit ratiometric delivery of these therapeutic agents. By way of non-limiting illustration, numerous multi-agent therapeutic regimen are known for the treatment of cancer. These include, but are not limited to COMP (methotrexate, prednisone), LSA$_2$-L$_2$ (cyclophosphamide, vincristine, prednisone, daunomycin, methotrexate, cytarabine, thioguanine, asparaginase, and carmustine), FOLFIRINOX (irinotecan, oxaliplatin, 5-fluorouracil, leucovorin), and the like. In certain embodiments two or more agents that meet the requirements described herein for drugs to be loaded into silicasomes using the methods described herein can be provided in the silicasomes. Where the multidrug regimen include agents that are not compatible with the loading methods described herein, some agents (e.g., irinotecan) can be provided in the silicasome to afford improved tolerance and other components of the treatment regimen can be administered by traditional modalities.

In certain embodiments hydrophobic (e.g., lipophilic) drugs, and other agents can be provided in the lipid bilayer component of the silicasome. Such hydrophobic drugs include, but are not limited to paclitaxel, ellipticine, camptothecan, L-asparaginase, doxorubicin, SN-38 and the like. In certain embodiments the lipid bilayer component of the silicasome can contain one or more phospholipid prodrugs (e.g., drugs conjugated to a lipid). Illustrative lipid prodrugs include, but are not limited to acyclovir diphosphate dimyristoylglycerol (see, e.g., Hostetler, et al. (1993) *Proc. Natl. Acad. Sci. USA*, 90(24): 11835-11839), doxorubicin conjugated phospholipid prodrugs (see, e.g., Wang et al. (2015) *J. Mater. Chem. B.*, 3: 3297-3305), Phospholipid Derivatives of Nucleoside Analogs (e.g., 5'-diphosphate-L-1,2-dipalmitin derivatives of 1-β-D-arabinofuranosylcytosine (ara-C), 9-β-D-arabinofuranosyladenine (ara-A), tubercidin, and the like (see, e.g., Matsushita et al. (1981) *Cancer Res.*, 41: 2707-2713)), phospholipid linked chlorambucil (see, e.g., Pederson et al. (2010) *J. Med. Chem.*, 53: 3782-3792), and the like.

The foregoing multi-agent silicasomes are illustrative and non-limiting. Using the teachings provided herein numerous combinations of therapeutic agents for incorporation in (or on) the silicasomes described herein will be available to one of skill in the art.

Targeting Ligands and Immunoconjugates.

In certain embodiments the LB-coated nanoparticle (silicasome) can be conjugated to one or more targeting ligands, e.g., to facilitate specific delivery in endothelial cells, to cancer cells, to fusogenic ligands, e.g., to facilitate endosomal escape, ligands to promote transport across the blood-brain barrier, and the like.

In one illustrative, but non-limiting embodiments, the silicasome is conjugated to a fusogenic peptides such as histidine-rich HSWYG (H$_2$N-GLFHAIAHFIHGGWHG-LIHGWYG-COOH, (SEQ ID NO:1)) (see, e.g., Midoux et al., (1998) *Bioconjug. Chem.* 9: 260-267).

In certain embodiments the silicasome is conjugated to targeting ligands which include antibodies as well as targeting peptides. Targeting antibodies include, but are not limited to intact immunoglobulins, immunoglobulin fragments (e.g., F(ab)'$_2$, Fab, etc.) single chain antibodies, diabodies, affibodies, unibodies, nanobodies, and the like. In certain embodiments antibodies will be used that specifically bind a cancer marker (e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention*, 22(2): 147-152). Other important targets for cancer immunotherapy are membrane bound complement regulatory glycoproteins CD46, CD55 and CD59, which have been found to be expressed on most tumor cells in vivo and in vitro. Human mucins (e.g. MUC1) are known tumor markers as are gp100, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, CD25. Hodgkin's disease has been characterized by the Leu-M1 marker. Various melanomas have been characterized by the HMB 45 marker. Non-hodgkins lymphomas have been characterized by the CD20, CD19, and Ia marker. And various prostate cancers have been characterized by the PSMA and SE10 markers.

In addition, many kinds of tumor cells display unusual antigens that are either inappropriate for the cell type and/or its environment, or are only normally present during the organisms' development (e.g., fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (ErbB2) HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table 1. Antibodies to these and other cancer markers are known to those of skill in the art and can be obtained commercially or readily produced, e.g. using phage-display technology. Such antibodies can readily be conjugated to the silicasomes described herein, e.g., in the same manner that iRGD peptide is conjugated in Example 3.

TABLE 1

Illustrative cancer markers and associated references, all of which are incorporated herein by reference for the purpose of identifying the referenced tumor markers.

| Marker | Reference |
| --- | --- |
| 5 alpha reductase | Délos et al. (1998) *Int J Cancer*, 75: 6 840-846 |
| α-fetoprotein | Esteban et al. (1996) *Tumour Biol.*, 17(5): 299-305 |
| AM-1 | Harada et al. (1996) *Tohoku J Exp Med.*, 180(3): 273-288 |
| APC | Dihlmann et al. (1997) *Oncol Res.*, 9(3) 119-127 |
| APRIL | Sordat et al. ('998) *J Exp Med.*, 188(6): 1185-1190 |
| BAGE | Böel et al. (1995) *Immunity*, 2: 167-175. |
| β-catenin | Hugh et al. (1999) *Int J Cancer*, 82(4): 504-11 |
| Bcl2 | Koty et al. (1999) *Lung Cancer*, 23(2): 115-127 |
| bcr-abl (b3a2) | Verfaillie et al. ('996) *Blood*, 87(11): 4770-4779 |
| CA-125 | Bast et al. ('998) *Int J Biol Markers*, 13(4): 179-187 |
| CASP-8/FLICE | Mandruzzato et al. (1997) *J Exp Med.*, 186(5): 785-793. |
| Cathepsins | Thomssen et al. (1995) *Clin Cancer Res.*, 1(7): 741-746 |
| CD19 | Scheuermann et al. (1995) *Leuk Lymphoma*, 18(5-6): 385-397 |
| CD20 | Knox et al. (1996) *Clin Cancer Res.*, 2(3): 457-470 |
| CD21, CD23 | Shubinsky et al. (1997) *Leuk Lymphoma*, 25(5-6): 521-530 |
| CD22, CD38 | French et al. (1995) *Br J Cancer*, 71(5): 986-994 |
| CD33 | Nakase et al. (1996) *Am J Clin Pathol.*, 105(6): 761-768 |
| CD35 | Yamakawa et al. *Cancer*, 73(11): 2808-2817 |
| CD44 | Naot et al. (1997) *Adv Cancer Res.*, 71: 241-319 |
| CD45 | Buzzi et al. (1992) *Cancer Res.*, 52(14): 4027-4035 |
| CD46 | Yamakawa et al. (1994) *Cancer*, 73(11): 2808-2817 |
| CD5 | Stein et al. (1991) *Clin Exp Immunol.*, 85(3): 418-423 |
| CD52 | Ginaldi et al. (1998) *Leuk Res.*, 22(2): 185-191 |
| CD55 | Spendlove et al. (1999) *Cancer Res.*, 59: 2282-2286. |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |

TABLE 1-continued

Illustrative cancer markers and associated references, all of which are incorporated herein by reference for the purpose of identifying the referenced tumor markers.

| Marker | Reference |
| --- | --- |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al. (1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al. (1996) *Melanoma Res.*, 6(1): 11-24 |
| gp75/TRP-1 | Lewis et al. (1995) *Semin Cancer Biol.*, 6(6): 321-327 |
| hCG | Hoermann et al. (1992) *Cancer Res.*, 52(6): 1520-1524 |
| Heparanase | Vlodaysky et al. (1999) *Nat Med.*, 5(7): 793-802 |
| Her2/neu | Lewis et al. (1995) *Semin Cancer Biol.*, 6(6): 321-327 |
| Her3 | |
| HMTV | Kahl et al. (1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/MART-1 | Lewis and Houghton (1995) *Semin Cancer Biol.*, 6(6): 321-327 |
| mesothelin | Chang et al. (1996) *Proc. Natl. Acad. Sci.*, USA, 93(1): 136-140 |
| MIC A/B | Groh et al. (1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci., USA*, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al. (1997) *Cancer Res.*, 57(12): 2321-2324 |
| RAGE-1 | Gaugler et al. (1996) *Immunogenetics*, 44(5): 323-330 |
| Rb | Dosaka-Akita et al. (1997) *Cancer*, 79(7): 1329-1337 |
| RCAS1 | Sonoda et al. (1996) *Cancer*, 77(8): 1501-1509. |
| SART-1 | Kikuchi et al. (1999( *Int J Cancer*, 81(3): 459-466 |
| SSX gene Family | Gure et al. (1997) *Int J Cancer*, 72(6): 965-971 |
| STAT3 | Bromberg et al. (1999) *Cell*, 98(3): 295-303 |
| STn (mucin assoc.) | Sandmaier et al. (1999) *J Immunother.*, 22(1): 54-66 |

TABLE 1-continued

Illustrative cancer markers and associated references, all of which are incorporated
herein by reference for the purpose of identifying the referenced tumor markers.

| Marker | Reference |
|---|---|
| TAG-72 | Kuroki et al. (1990) Cancer Res., 50(16): 4872-4879 |
| TGF-α | Imanishi et al. (1989) Br J Cancer, 59(5): 761-765 |
| TGF-β | Picon et al. (1998) Cancer Epidemiol Biomarkers Prey, 7(6): 497-504 |
| Thymosin β 15 | Bao et al. (1996) Nature Medicine. 2(12), 1322-1328 |
| IFN-α | Moradi et al. (1993) Cancer, 72(8): 2433-2440 |
| TPA | Maulard et al. (1994) Cancer, 73(2): 394-398 |
| TPI | Nishida et al. (1984) Cancer Res 44(8): 3324-9 |
| TRP-2 | Parkhurst et al. (1998) Cancer Res., 58(21) 4895-4901 |
| Tyrosinase | Kirkin et al. (1998) APMIS, 106(7): 665-679 |
| VEGF | Hyodo et al. (1998) Eur J Cancer, 34(13): 2041-2045 |
| ZAG | Sanchez et al. (1999) Science, 283(5409): 1914-1919 |
| p16INK4 | Quelle et al. (1995) Oncogene Aug. 17, 1995; 11(4): 635-645 |
| Glutathione S-transferase | Hengstler (1998) et al. Recent Results Cancer Res., 154: 47-85 |

Any of the foregoing markers can be used as targets for the targeting moieties comprising the silicasome constructs described herein. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, ligand to that receptor can function as targeting moieties. Similarly mimetics of such ligands can also be used as targeting moieties. Thus, in certain embodiments peptide ligands can be used in addition to or in place of various antibodies. An illustrative, but non-limiting list of suitable targeting peptides is shown in Table 2. In certain embodiments any one or more of these peptides can be conjugated to a silicasome described herein.

TABLE 2

Illustrative, but non-limiting peptides that
target membrane receptors expressed or
overexpressed by various cancer cells.

| Target Membrane Receptor | Targeting Peptide | SEQ ID NO |
|---|---|---|
| Integrin receptor A,β₃ | c(RGDfK) | 2 |
| | c(RGDfC) | 3 |
| | c(RGDyC) | 4 |
| | RGD | |
| GFR | GE11 (YHWYGYTPQNVI) | 5 |
| GFR | GSG-KCCYSL | 6 |
| SSTR2 | Ostreotide | |
| GRP | QWAVGHML | 7 |
| CCK | DYMGWMDF | 8 |

TABLE 2-continued

Illustrative, but non-limiting peptides that
target membrane receptors expressed or
overexpressed by various cancer cells.

| Target Membrane Receptor | Targeting Peptide | SEQ ID NO |
|---|---|---|
| NT | RRPYIL | 9 |
| | RRPYILQLYENKPRRPYIL | 10 |
| LHRH | Gondaorelin | |
| GPRC family members | Antagonist G | | c( ) indicates cyclopeptide.
Lower case indicates "D" amino acid.

In certain embodiments the silicasomes can be conjugated to moieties that facilitate stability in circulation and/or that hide the silicasome from the reticuloendothelial system (REC) and/or that facilitate transport across a barrier (e.g., a stromal barrier, the blood brain barrier, etc.), and/or into a tissue. In certain embodiments the silicasomes are conjugated to transferrin or ApoE to facilitate transport across the blood brain barrier. In certain embodiments the silicasomes are conjugated to folate.

Methods of coupling the silicasomes to targeting (or other) agents are well known to those of skill in the art. Examples include, but are not limited to the use of biotin and avidin or streptavidin (see, e.g., U.S. Pat. No. 4,885,172 A), by traditional chemical reactions using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. Appropriate reactions which may be applied to such couplings are described in Williams et al. Methods in Immunology and Immunochemistry Vol. 1, Academic Press, New York 1967. In one illustrative but non-limiting approach described in Example 3 a peptide (in this example iRGD) is coupled to the silicasome by substituting DSPE-PEG$_{2000}$ with DSPE-PEG$_{2000}$-maleimide (see methods section in Example 3), allowing thiol-maleimide coupling to the cysteine-modified peptide. It will also be recognized that in certain embodiments the targeting (and other) moieties can be conjugated to a lipid comprising the lipid bilayer.

The former conjugates and coupling methods are illustrative and non-limiting. Using the teachings provided herein, numerous other moieties can be conjugated to the silicasomes described herein by any of a variety of methods. Pharmaceutical Formulations, Administration and Therapy Pharmaceutical Formulations.

In some embodiments, the nanoparticle drug carriers described herein are administered alone or in a mixture with a physiologically-acceptable carrier (such as physiological saline or phosphate buffer) selected in accordance with the route of administration and standard pharmaceutical practice. For example, when used as an injectable, the silicasomes can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt-containing carriers, the carrier is preferably added following silicasome formation. Thus, after the silicasome is formed and loaded with suitable drug(s), the silicasome can be diluted into pharmaceutically acceptable carriers such as normal saline. These compositions may be sterilized by conventional, well-known sterilization techniques. The resulting aqueous solutions, suspensions, dispersions, emulsions, etc., may be packaged for use or filtered under aseptic conditions. In certain embodiments the silicasomes are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damages on storage. Lipophilic free-radical quenchers, such as alpha-tocopherol and water-soluble iron-specific chelators, such as ferrioxamine, are suitable.

The concentration of silicasomes in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, silicasomes composed of irritating lipids may be diluted to low concentrations to lessen inflammation at the site of administration. The amount of silicasomes administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

In some embodiments, e.g., it is desirable to include polyethylene glycol (PEG)-modified phospholipids in the silicasomes. Alternatively or additionally, in certain embodiments, PEG-ceramide, or ganglioside Gm-modified lipids can be incorporated in the silicasomes. Addition of such components helps prevent silicasome aggregation and provides for increasing circulation lifetime and increasing the delivery of the loaded silicasomes to the target tissues. In certain embodiments the concentration of the PEG-modified phospholipids, PEG-ceramide, or Gm-modified lipids in the silicasome will be approximately 1 to 15%.

In some embodiments, overall silicasome charge is an important determinant in silicasome clearance from the blood. It is believed that charged silicasomes will be typically taken up more rapidly by the reticuloendothelial system (see, e.g., Juliano (1975), *Biochem. Biophys. Res. Commun.* 63: 651-658 discussing liposome clearance by the RES) and thus have shorter half-lives in the bloodstream. Silicasomes with prolonged circulation half-lives are typically desirable for therapeutic uses. For instance, in certain embodiments, silicasomes that are maintained from 8 hrs, or 12 hrs, or 24 hrs, or greater are desirable.

In another example of their use, drug-loaded silicasomes can be incorporated into a broad range of topical dosage forms including but not limited to gels, oils, emulsions, and the like, e.g., for the treatment of a topical cancer. For instance, in some embodiments the suspension containing the drug-loaded silicasomes is formulated and administered as a topical cream, paste, ointment, gel, lotion, and the like.

In some embodiments, pharmaceutical formulations comprising silicasomes described herein additionally incorporate a buffering agent. The buffering agent may be any pharmaceutically acceptable buffering agent. Buffer systems include, but are not limited to citrate buffers, acetate buffers, borate buffers, and phosphate buffers. Examples of buffers include, but are not limited to citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate, benzoic acid, and the like.

In some embodiments, pharmaceutical formulations comprising silicasomes described herein additionally incorporate a chelating agent. The chelating agent may be any pharmaceutically acceptable chelating agent. Chelating agents include, but are not limited to ethylene diaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid (e.g., citric acid monohydrate) and derivatives thereof. Derivatives of citric acid include anhydrous citric acid, trisodiumcitrate-dihydrate, and the like. Still other chelating agents include, but are not limited to, niacinamide and derivatives thereof and sodium deoxycholate and derivatives thereof.

In some embodiments, pharmaceutical formulations comprising silicasomes described herein additionally incorporate a bioactive agent contain an antioxidant. The antioxidant may be any pharmaceutically acceptable antioxidant. Antioxidants are well known to those of ordinary skill in the art and include, but are not limited to, materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, sodium sulfite and N-acetyl cysteine. In certain embodiments such materials, when present, are typically added in ranges from 0.01 to 2.0%.

In some embodiments, pharmaceutical formulations comprising silicasomes described herein are formulated with a cryoprotectant. The cryoprotecting agent may be any pharmaceutically acceptable cryoprotecting agent. Common cryoprotecting agents include, but are not limited to, histidine, polyethylene glycol, polyvinyl pyrrolidine, lactose, sucrose, mannitol, polyols, and the like.

In some embodiments, pharmaceutical formulations comprising silicasomes described herein are formulated with an isotonic agent. The isotonic agent can be any pharmaceutically acceptable isotonic agent. This term is used in the art interchangeably with iso-osmotic agent, and is known as a compound that is added to the pharmaceutical preparation to increase the osmotic pressure, e.g., in some embodiments to that of 0.9% sodium chloride solution, which is iso-osmotic with human extracellular fluids, such as plasma. Illustrative isotonicity agents include, but are not limited to, sodium chloride, mannitol, sorbitol, lactose, dextrose and glycerol.

In certain embodiments pharmaceutical formulations of the silicasomes may optionally comprise a preservative. Common preservatives include, but are not limited to, those selected from the group consisting of chlorobutanol, parabens, thimerosol, benzyl alcohol, and phenol. Suitable preservatives include but are not limited to: chlorobutanol (e.g., 0.3-0.9% w/v), parabens (e.g., 0.01-5.0%), thimerosal (e.g., 0.004-0.2%), benzyl alcohol (e.g., 0.5-5%), phenol (e.g., 0.1-1.0%), and the like.

In some embodiments, pharmaceutical formulations comprising silicasomes are formulated with a humectant, e.g., to provide a pleasant mouth-feel in oral applications. Humectants known in the art include, but are not limited to, cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration and Therapy

The cargo (e.g., drug) loaded silicasomes can be administered to a subject (e.g., patient) by any of a variety of techniques.

In certain embodiments the pharmaceutical formulations are administered parenterally, e.g., intraarticularly, intravenously, intraperitoneally, subcutaneously, or intramuscularly. In some embodiments, the pharmaceutical compositions are administered intravenously, intraarteraly, or intraperitoneally by a bolus injection (see, e.g., U.S. Pat. Nos. 3,993,754; 4,145,410; 4,235,871; 4,224,179; 4,522,803; and 4,588,578 describing administration of liposomes). Particular pharmaceutical formulations suitable for this administration are found in Remington's Pharmaceutical Sciences, Mack Publishing Company, Philadelphia, Pa., 17th ed. (1985). Typically, the formulations comprise a solution of the silicasomes suspended in an acceptable carrier, preferably an aqueous carrier. As noted above, suitable aqueous solutions include, but are not limited to physiologically compatible buffers such as Hanks solution, Ringer's solution, or physiological (e.g., 0.9% isotonic) saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc., e.g., as described above.

In other methods, the pharmaceutical formulations containing silicsasomes described herein may be contacted with the target tissue by direct application of the preparation to the tissue. The application may be made by topical, "open" or "closed" procedures. By "topical" it is meant the direct application of the pharmaceutical preparation to a tissue exposed to the environment, such as the skin, oropharynx, external auditory canal, and the like. Open procedures are those procedures that include incising the skin of a patient and directly visualizing the underlying tissue to which the pharmaceutical formulations are applied. This is generally accomplished by a surgical procedure, such as a thoracotomy to access the lungs, abdominal laparotomy to access abdominal viscera, or other direct surgical approaches to the target tissue. Closed procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrizamide imaging of the spinal cord. Alternatively, the preparations may be administered through endoscopic devices. In certain embodiments the pharmaceutical formulations are introduced via a cannula.

In certain embodiments the pharmaceutical formulations comprising silicasomes described herein are administered via inhalation (e.g., as an aerosol). Inhalation can be a particularly effective delivery rout for administration to the lungs and/or to the brain. For administration by inhalation, the silicasomes are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In certain embodiments, the silicasomes described herein are formulated for oral administration. For oral administration, suitable formulations can be readily formulated by combining the silicasome(s) with pharmaceutically acceptable carriers suitable for oral delivery well known in the art. Such carriers enable the active agent(s) described herein to be formulated as tablets, pills, dragees, caplets, lozenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

In various embodiments the silicasome(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45), amphiphilic materials such as Suppocire AP and polyglycolized glyceride, and the like). The base is selected and compounded for a desired melting/delivery profile.

The route of delivery of silicasomes can also affect their distribution in the body. Passive delivery of silicasomes involves the use of various routes of administration e.g., parenterally, although other effective administration forms, such as intraarticular injection, inhalant mists, orally active formulations, transdermal iontophoresis, or suppositories are also envisioned. Each route produces differences in localization of the silicasomes.

Because dosage regimens for pharmaceutical agents are well known to medical practitioners, the amount of the liposomal pharmaceutical agent formulations that is effective or therapeutic for the treatment of a disease or condition in mammals and particularly in humans will be apparent to those skilled in the art. The optimal quantity and spacing of individual dosages of the formulations herein will be determined by the nature and extent of the condition being treated, the form, route and site of administration, and the particular patient being treated, and such optima can be determined by conventional techniques. It will also be appreciated by one of skill in the art that the optimal course of treatment, e.g., the number of doses given per day for a defined number of days, can be ascertained by those skilled in the art using conventional course of treatment determination tests.

In certain embodiments the silicasomes and/or pharmaceutical formations thereof can be used therapeutically in animals (including man) in the treatment of various cancers, or various infections, and the like including conditions that require: (1) repeated administrations, (2) the sustained delivery of the drug in its bioactive form, or (3) the decreased toxicity with suitable efficacy compared with the free drug in question. In various embodiments the silicasomes and/or pharmaceutical formations thereof are administered in a therapeutically effective dose. The term "therapeutically effective" as it pertains to the silicasomes described herein and formulations thereof means that a biologically active substance present or and/or in the silicasome provided/released in a manner sufficient to achieve a particular medical effect for which the biologically active substance (therapeutic agent) is intended. Examples, without limitation of desirable medical effects that can be attained are chemotherapy, antibiotic therapy, and regulation of metabolism. Thus, for example, a therapeutically effective dose for cancer chemotherapy may be a dose (and/or dosage regimen) effective to slow the growth and/or proliferation of cancer cells, and/or to slow, stop the growth of a solid tumor or shrink or eliminate a solid tumor, and/or slow, stop the proliferation of metastatic cells, and the like. A therapeutically effective dose for treating an infection can be a dose (and/or dosage regimen) sufficient to inhibit the growth and/or proliferation of a pathogen, and/or to kill a pathogen, and/or to mitigate one or more symptoms produced by the pathogen.

Exact dosages will vary depending upon such factors as the particular therapeutic agent and desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the silicasome(s) can be approximately equal to that employed for the free drug. However as noted above, the silicasomes described herein can significantly reduce the toxicity of the drug(s) administered thereby and significantly increase a therapeutic window. Accordingly, in some cases dosages in excess of those prescribed for the free drug will be utilized.

In certain embodiments, the dose of encapsulated drug administered at a particular time point will be in the range from about 1 to about 1,000 mg/m$^2$/day, or to about 800 mg/m$^2$/day, or to about 600 mg/m$^2$/day, or to about 400 mg/m$^2$/day. For example, in certain embodiments a dosage (dosage regimen) is utilized that provides a range from about 1 to about 350 mg/m$^2$/day, 1 to about 300 mg/m$^2$/day, 1 to about 250 mg/m$^2$/day, 1 to about 200 mg/m$^2$/day, 1 to about 150 mg/m$^2$/day, 1 to about 100 mg/m$^2$/day, from about 5 to about 80 mg/m$^2$/day, from about 5 to about 70 mg/m$^2$/day, from about 5 to about 60 mg/m$^2$/day, from about 5 to about 50 mg/m$^2$/day, from about 5 to about 40 mg/m$^2$/day, from about 5 to about 20 mg/m$^2$/day, from about 10 to about 80 mg/m$^2$/day, from about 10 to about 70 mg/m$^2$/day, from about 10 to about 60 mg/m$^2$/day, from about 10 to about 50 mg/m$^2$/day, from about 10 to about 40 mg/m$^2$/day, from about 10 to about 20 mg/m$^2$/day, from about 20 to about 40 mg/m$^2$/day, from about 20 to about 50 mg/m$^2$/day, from about 20 to about 90 mg/m$^2$/day, from about 30 to about 80 mg/m$^2$/day, from about 40 to about 90 mg/m$^2$/day, from about 40 to about 100 mg/m$^2$/day, from about 80 to about 150 mg/m$^2$/day, from about 80 to about 140 mg/m$^2$/day, from about 80 to about 135 mg/m$^2$/day, from about 80 to about 130 mg/m$^2$/day, from about 80 to about 120 mg/m$^2$/day, from about 85 to about 140 mg/m$^2$/day, from about 85 to about 135 mg/m$^2$/day, from about 85 to about 135 mg/m$^2$/day, from about 85 to about 130 mg/m$^2$/day, or from about 85 to about 120 mg/m²/day. In certain embodiments the does administered at a particular time point may also be about 130 mg/m²/day, about 120 mg/m²/day, about 100 mg/m²/day, about 90 mg/m²/day, about 85 mg/m²/day, about 80 mg/m²/day, about 70 mg/m²/day, about 60 mg/m²/day, about 50 mg/m²/day, about 40 mg/m²/day, about 30 mg/m²/day, about 20 mg/m²/day, about 15 mg/m²/day, or about 10 mg/m²/day.

Dosages may also be estimated using in vivo animal models, as will be appreciated by those skill in the art. In this regard, with respect to the irinotecan-loaded silicasomes described herein, it is noted that the effective therapeutic dose of the Ir-silicasome in a KPC-derived orthotopic animal model is about 40 mg/kg, which is equivalent to 120 mg/m² in a 70 Kg human subject (Liu, et al. (2016) *ACS Nano*, 10: 2702-2715). Fibonacci analysis indicates this dose can be achieved by starting and intermediary doses of 40 and 80 mg/m².

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician. Skilled artisans will be able to optimize effective local dosages without undue experimentation in view of the teaching provided herein.

Multiple doses (e.g., continuous or bolus) of the compositions as described herein may also be administered to individuals in need thereof of the course of hours, days, weeks, or months. For example, but not limited to, 1, 2, 3, 4, 5, or 6 times daily, every other day, every 10 days, weekly, monthly, twice weekly, three times a week, twice monthly, three times a month, four times a month, five times a month, every other month, every third month, every fourth month, etc.

Methods of Treatment.

In various embodiments methods of treatment using the nanoparticle drug carrier(s) and/or pharmaceutical formulation(s) comprising nanoparticle drug carriers described herein are provided. In certain embodiments the method(s) comprise a method of treating a cancer. In certain embodiments the method can comprise administering to a subject in need thereof an effective amount of a nanoparticle drug carrier, and/or a pharmaceutical formulation comprising a nanoparticle drug carrier as described herein, where the drug in said nanoparticle drug carrier and/or said pharmaceutical formulation comprises an anti-cancer drug. In certain embodiments the nanoparticle drug carrier and/or pharmaceutical formulation is a primary therapy in a chemotherapeutic regimen. In certain embodiments the nanoparticle drug carrier and/or pharmaceutical formulation is a component in a multi-drug chemotherapeutic regimen. In certain embodiments the multi-drug chemotherapeutic regimen comprises at least two drugs selected from the group consisting of irinotecan (IRIN), oxaliplatin (OX), 5-fluorouracil (5-FU), and leucovorin (LV). In certain embodiments the multi-drug chemotherapeutic regimen comprises at least three drugs selected from the group consisting of irinotecan (IRIN), oxaliplatin (OX), 5-fluorouracil (5-FU), and leucovorin (LV). In certain embodiments the multi-drug chemotherapeutic regimen comprises at least irinotecan (IRIN), oxaliplatin (OX), 5-fluorouracil (5-FU), and leucovorin (LV).

In various embodiments the nanoparticle drug carrier(s) and/or pharmaceutical formulation(s) comprising nanoparticle drug carriers described herein are effective for treating any of a variety of cancers. In certain embodiments the cancer is pancreatic ductal adenocarcinoma (PDAC). In certain embodiments the cancer is a cancer selected from the group consisting of acute lymphoblastic leukemia (ALL), acute myeloid leukemia (AML), adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, glioblastoma, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sezary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, chronic myeloid leukemia (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

In certain embodiments the nanoparticle drug carrier is not conjugated to an iRGD peptide and the nanoparticle drug carrier is administered in conjunction with an iRGD peptide (e.g., the nanoparticle drug carrier and the iRGD peptide are co-administered as separate formulations).

In certain embodiments the method(s) comprise a method of treating an infection. In certain embodiments the method can comprise administering to a subject in need thereof an effective amount of a nanoparticle drug carrier, and/or a pharmaceutical formulation comprising a nanoparticle drug carrier as described herein, where the drug in said nanoparticle drug carrier and/or said pharmaceutical formulation comprises an anti-microbial or anti-viral agent. In certain embodiments the infection comprises a nosocomial infection. In certain embodiments the infection is caused by viral, bacterial, or fungal pathogens. In certain embodiments the infection comprises a bloodstream infection (BSI), pneumonia (e.g., ventilator-associated pneumonia (VAP)), a gastrointestinal infection, a urinary tract infection (UTI), a surgical site infection (SSI), or a skin infection. In certain embodiments the infection is caused by a pathogen such as *Staphylococcus aureus* (e.g., blood infection), *Escherichia coli* (e.g., UTI), Enterococci (e.g., blood, UTI, wound), *Pseudomonas aeruginosa* (e.g., kidney or respiratory infection), *Mycobacterium tuberculosis* (e.g., lung), and the like. In certain embodiments the infection is a viral infection (e.g., HIV, hepatitis B, hepatitis C, etc.).

In certain embodiments the infection is caused by a drug-resistant pathogen. Illustrative drug-resistant pathogens include, but are not limited to methicillin-resistant *Staphylococcus aureus* (MRSA), vancomycin-resistant Enterococcus (VRE) and multi-drug-resistant *Mycobacterium tuberculosis* (MDR-TB), and *Klebsiella pneumoniae* carbapenemase-producing bacteria (KPC).

In various embodiments of these treatment methods, the nanoparticle drug carrier and/or pharmaceutical formulation is administered via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition. In certain embodiments the nanoparticle drug carrier and/or pharmaceutical formulation is administered as an injection, from an IV drip bag, or via a drug-delivery cannula. In various embodiments the subject is a human and in other embodiments the subject is a non-human mammal.

Kits.

In certain embodiments, kits are containing the lipid bilayer coated nanoparticle drug carriers described herein for the treatment of a pathology (e.g., a cancer, a microbial infection, a viral infection, etc.). The kits typically comprise a drug-loaded silicasome as described herein and/or an immunoconjugate comprising a drug-loaded silicasome described herein. In certain embodiments the silicasome contains irinotecan. In certain embodiments the silicasome has attached thereto an iRGD peptide while in other embodiments the kit contains a separate iRGD peptide formulated for co-administration with the drug (e.g., irinotecan) loaded silicasome or silicasome immunoconjugate.

Additionally, in certain embodiments, the kits can include instructional materials disclosing means of use of the drug-loaded silicasome or silicasome immunoconjugate (e.g. as a therapeutic for a pancreatic cancer, gastric cancer, cervical cancer, ovarian cancer, etc.).

In addition, the kits optionally include labeling and/or instructional materials providing directions (e.g., protocols) for the use of the nanoparticle drug carriers described herein, e.g., alone or in combination for the treatment of various cancers. Instructional materials can also include recommended dosages, description(s) of counterindications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Irinotecan Delivery by Lipid-Coated Mesoporous Silica Nanoparticles Shows Improved Efficacy and Safety Over Liposomes for Pancreatic Cancer Because of the concern that liposomal carriers may fail to improve the safety of highly toxic drugs such as irinotecan, we were interested in using a supported lipid bilayer (LB) that is applied to mesoporous silica nanoparticles (MSNPs) to see if this will result in a more stable carrier (than the liposome). Due to the large internal surface area that can be used for drug packaging, tunable pore sizes, carrier stability, and controlled drug release abilities, MSNPs have been demonstrated to constitute a versatile and multifunctional nanocarrier platform for cancer therapy (Lu et al. (2007) *Small*, 3: 1341-1346; Slowing et al. (2008) *Adv. Drug Deliv. Rev.* 60: 1278-1288; Meng et al. (2010) *J. Am. Chem. Soc.* 132(36): 12690-12697; Lee et al. (2010) *Angew. Chem.* 122: 8390-8395; Meng et al. (2011) *ACS Nano*, 5(5): 4131-4144; He and Shi (2011) *J. Mater. Chem* 21: 5845-5855; Gao et al. (2011) *ACS Nano*, 5: 9788-9798; Li et al. (2012) *Chem. Soc. Rev.* 41: 2590-2605; Tang et al. (2012) *Adv. Mat.* 24(12): 1504-1534; Meng et al. (2013) *ACS Nano*, 7(2): 994-1005; Tarn et al. (2013) *Acc. Chem. Res.* 46(3): 792-801; Meng et al. (2013) *ACS Nano*, 7(11): 10048-10065; Argyo et al. (2014) *Chem. Mater.* 26: 435-451; Meng et al. (2015) *ACS Nano*, 9(4): 3540-3557). Moreover, MSNPs are biodegradable and proven to be safe in extensive animal testing (Meng et al. (2011) *ACS Nano*, 5(5): 4131-4144; Tang et al. (2012) *Adv. Mat.* 24(12): 1504-1534; Meng et al. (2013) *ACS Nano*, 7(2): 994-1005; Tarn et al. (2013) *Acc. Chem. Res.* 46(3): 792-801; Meng et al. (2013) *ACS Nano*, 7(11): 10048-10065; Meng et al. (2015) *ACS Nano*, 9(4): 3540-3557; Lu et al. (2010) *Small*, 6(16): 1794-18050. While it is possible to introduce irinotecan or camptothecin into MSNPs by soaking-in, this method is relatively inefficient (loading capacity <10 wt %) (Lu et al. (2007) *Small*, 3: 1341-1346; He et al. (2010) *Biomaterials* 31: 3335-3346) and may result in poor drug retention (Meng et al. (2010) *J. Am. Chem. Soc.* 132(36): 12690-12697). However, we have developed a biofilm technique that can be used for rapid GEM encapsulation by a supported LB (Meng et al. (2015) *ACS Nano*, 9(4): 3540-3557). While a number of LB coating procedures have been published, including liposomal interaction and fusion with the particle surface (Liu, et al. (2009) *J. Am. Chem. Soc.*, 131(22): 7567-7569; Liu, et al. (2009) *J. Am. Chem. Soc.*, 131(4): 1354-1355) or solvent exchange utilizing EtOH-dispersed lipid solutions (Cauda et al. (2010) *Nano Lett.* 10: 2484-2492), the use of a biofilm technique provides more reproducible and complete coating, rapid encapsulation, and improved carrier stability (Meng et al. (2015) *ACS Nano*, 9(4): 3540-3557). Not only has this allowed LB-MSNPs to achieve a loading capacity of up to 40 wt % GEM, but it has also enabled co-delivery of paclitaxel (PTX), which could be incorporated in the LB (Id.). This allowed us to develop a synergistic and ratiometric-designed carrier for PDAC treatment in an orthotopic human PDAC model in mice (Id.). Recently, Zhang et al. reported a polymer-lipid-supported MSNP for delivery of irinotecan, but the drug loading was lower (i.e., ~16 wt %) (Zhang et al. (2014) *Biomaterials*, 35: 3650-3665).

In this example, we introduce, inter alia, a novel design feature for the LB-MSNP platform in which the LB is used to encapsulate a protonating agent; this allows remote loading of a high irinotecan drug load that utilizes the drug's weak basic properties (pKa=8.1). Moreover, the increased ability of the supported LB also allowed us to perform comparative analysis to a liposomal equivalent, where a nonsupported LB vesicle was used for remote loading of irinotecan by a trapping agent, triethylammonium sucrose octasulfate (TEA8SOS) (Drummond et al. (2006) *Cancer Res.*, 66(6): 3271-3277; Von Hoff et al. (2013) *Br. J. Cancer*, 109(4): 920-925). Not only did the MSNP carrier achieve higher loading capacity and tumor killing than the liposomal formulation in a robust orthotopic PDAC model, but it also prevented irinotecan toxicity due to improved carrier stability and reduced leakage. This provides an innovative approach for reducing the toxicity of highly toxic chemotherapeutic agents by a LB-coated carrier, which allows the use of irinotecan as a first-line treatment option for PDAC rather than being reserved for GEM treatment failure (current FDA-improved indication for the use of the liposomal carrier).

Results

High Irinotecan Loading in MSNP Through the Use of a Coated LB and a Proton Gradient.

Our first attempt was to produce a MSNP carrier that encapsulates irinotecan by a LB coat that provides rapid and uniform pore sealing (Meng et al. (2015) *ACS Nano*, 9(4): 3540-3557). This allowed passive entrapment of 22 wt % irinotecan (relative to MSNP weight). In order to further improve the loading capacity, we also determined whether entrapment of a protonating agent that converts amphipathic irinotecan, capable of diffusing across the LB, into a hydrophilic derivative that is retained in the pores (FIG. 1A, panel A1). We and others have used this entrapment procedure in liposomes for effective import and encapsulation of weak basic drugs, such as GEM and irinotecan (Chou et al. (2003) *J. Biosci. Bioeng.*, 95(4): 405-408; Meng et al. (2013) *ACS Nano*, 7(11): 10048-10065; Haran et al. (1993) *Biochim. Biophys. Acta, Biomembr.* 1151: 201-215). While it has never been used in a MSNP platform previously, the polyanionic compound, TEA$_8$SOS, was used in MM-398 to entrap irinotecan (Drummond et al. (2006) *Cancer Res.*, 66(6): 3271-3277). TEA$_8$SOS is a proton-generating agent that releases eight H+ ions and octavalent SOS$^{8-}$ upon hydrolysis (FIG. 1A, panel A2). Ion-exchange chromatography was used to generate TEA$_8$SOS, which was soaked into MSNP, as described below in the Methods section (Id.). The soaked particles were introduced to a round-bottom flask coated with a lipid biofilm, composed of DSPC/cholesterol/DSPE-PEG2000 at a molar ratio of 3:2:0.15. The optimal lipid:particle ratio was determined to be 1.1:1.0. Sonication of the suspension yielded LB-coated particles, which contain the entrapment agent (FIG. 1A, panel A1). These particles were immediately incubated in an irinotecan solution, allowing the drug to be imported, protonated, and entrapped in the pores as a gel-like precipitate in association with SOS$^{8-}$ (FIG. 1A, panels A1 and A2, FIG. 1B). This allowed us to achieve an irinotecan loading capacity up to 80 wt % (FIG. 1B), which approximates the theoretical maximum loading capacity (~100 wt %) of the porous carrier with a combined surface area of 850 m$^2$/g and a pore volume of ~0.7 cm$^3$/g, as previously demonstrated (Meng et al. (2015) *ACS Nano*, 9(4): 3540-3557). Subsequent studies were performed with particles containing 50 wt % irinotecan.

Figure 1C:
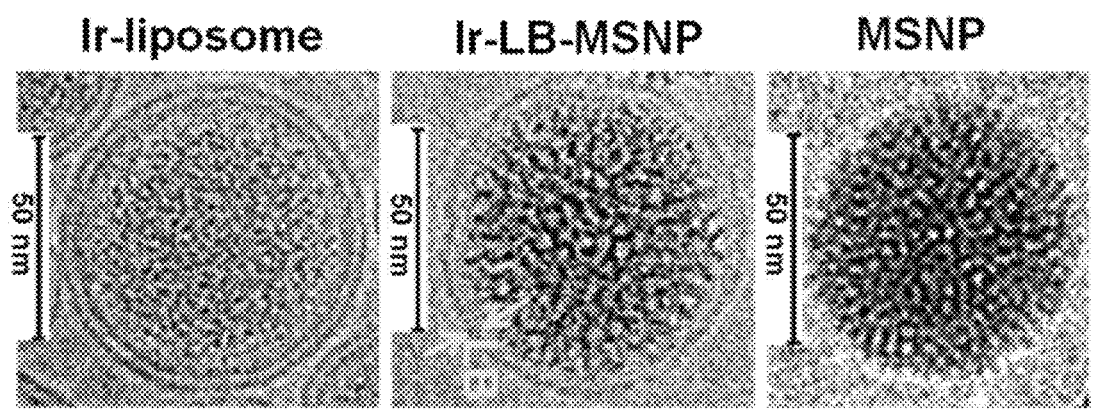
Figure 11:
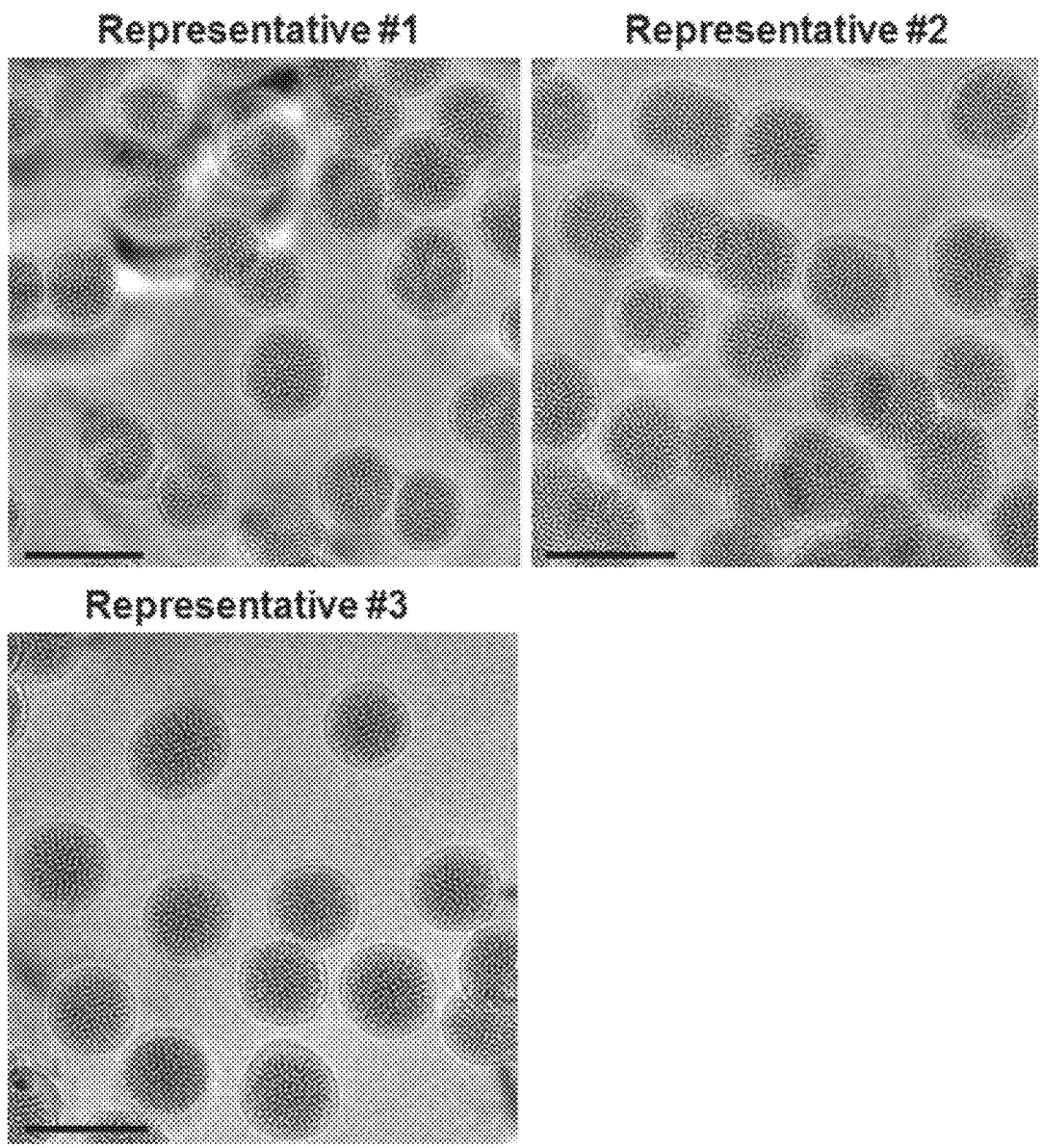
FIG. 11 shows low-resolution cyroEM images of representative irinotecan-loaded LB-MSNP, in accordance with one or more embodiments of the invention. Bars represent 100 nm. Visual examination of ~500 particles confirmed the structural integrity of the LB, with successful coating of >99% particles.

In order to compare the efficacy and safety of the irinotecan-loaded LB-MSNPs (Ir-LB-MSNP) with a liposomal carrier using TEA$_8$SOS, liposomes were constructed by a procedure analogous to that of MM-398 (FIG. 1A, panel A3) (Drummond et al. (2006) *Cancer Res.*, 66(6): 3271-3277). This yielded a liposome (designated "Ir-liposome") with ~40 wt % irinotecan loading capacity; that is considerably higher than producing a liposome without the entrapment agent (~5 wt %) (FIG. 1B). Cryo-electron microscopy (cryoEM) revealed particle sizes of ~75 and ~80 nm for liposomes and LB-MSNPs, respectively (FIG. 1C). High-magnification cryoEM images confirmed that there was uniform coating of Ir-LB-MSNPs by an intact ~7 nm thick bilayer. Low-magnification cyroEM images showed that the LB was intact in >99% of the particles (FIG. 11). This confirms the reproducibility of the one-step encapsulation protocol, which holds significant advances over other methods of MSNP bilayer coating (Meng et al. (2015) *ACS Nano*, 9(4): 3540-3557).

Figure 1D:
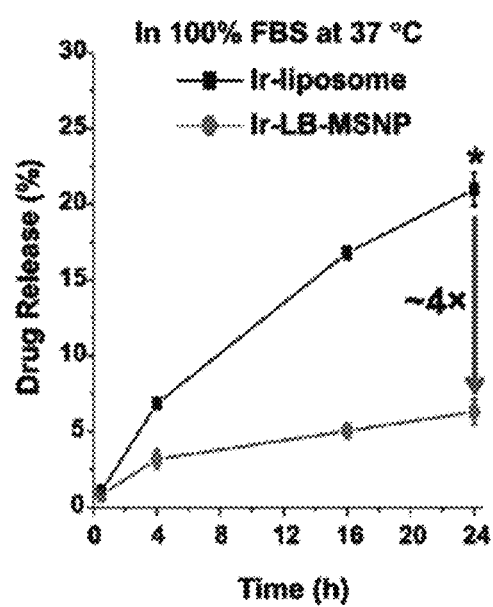
Figure 1E:
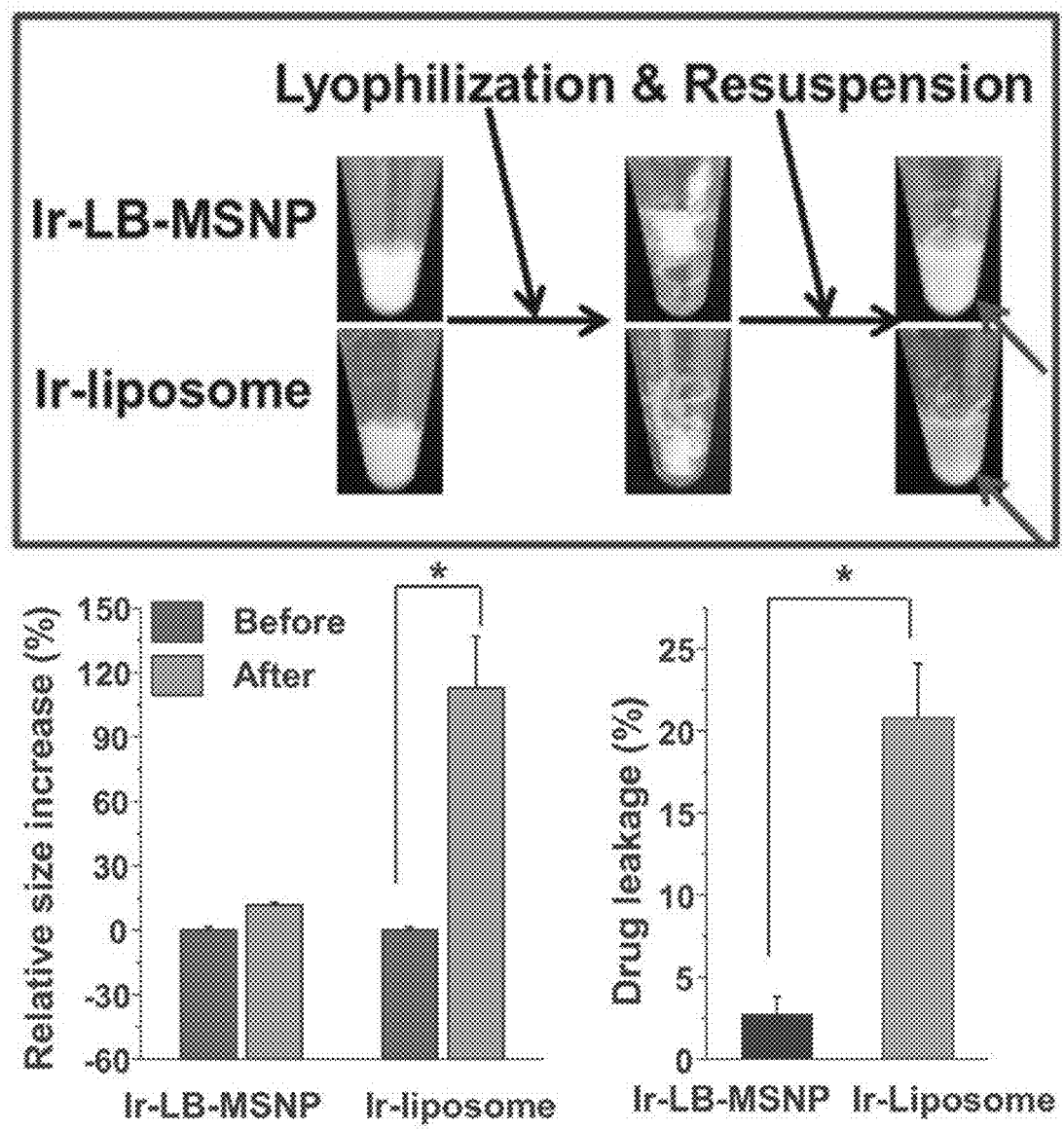

Since our major hypothesis is that LB-MSNP could improve the carrier stability compared to liposomes, both carriers were incubated in serum and lyophilized to determine their drug retention ability and irinotecan leakage. Both carriers were incubated for 24 h at 37° C. in 100% serum, with continuous and gentle shaking. Since adsorption of serum proteins interferes with cryoEM visualization, high-performance liquid chromatography (HPLC) analysis was used, instead, to determine drug release in the carrier suspensions; this showed <6% premature irinotecan release by LB-MSNPs, compared to ~22% from liposomes (FIG. 1D). However, particle storage in a serum-free suspension for 90 days at 4° C. showed that both carriers had high colloidal stability, with minor (<5%) premature drug release or change in hydrodynamic particle size (<5%). Conversely, particle lyophilization in a cryo-protective 5% dextrose solution40 showed significant differences in carrier stability upon resuspension in water (FIG. 1E). Thus, while Ir-LB-MSNPs did not change the hydrodynamic size and only led to 2.7% drug release, liposomes were visibly aggregated and released 20.8% of their irinotecan content. This confirms that although the LB-coated carriers look morphologically similar, LB-MSNPs are significantly more stable than liposomes.

Figure 2A:
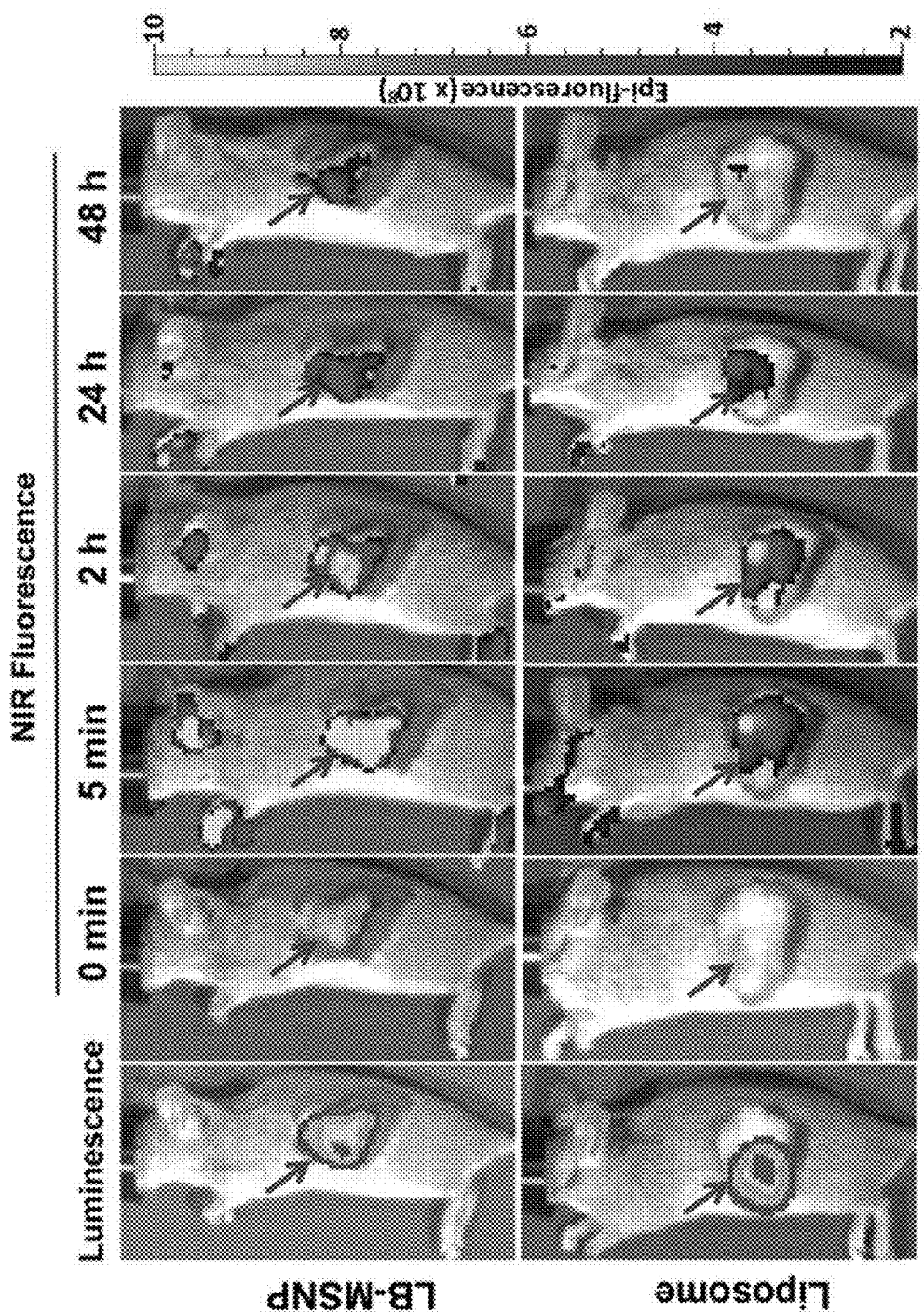
FIGS. 2A-2D illustrate the biodistribution of the Ir-LB-MSNP and Ir-liposomes, in accordance with one or more embodiments described herein.
Figure 2B:
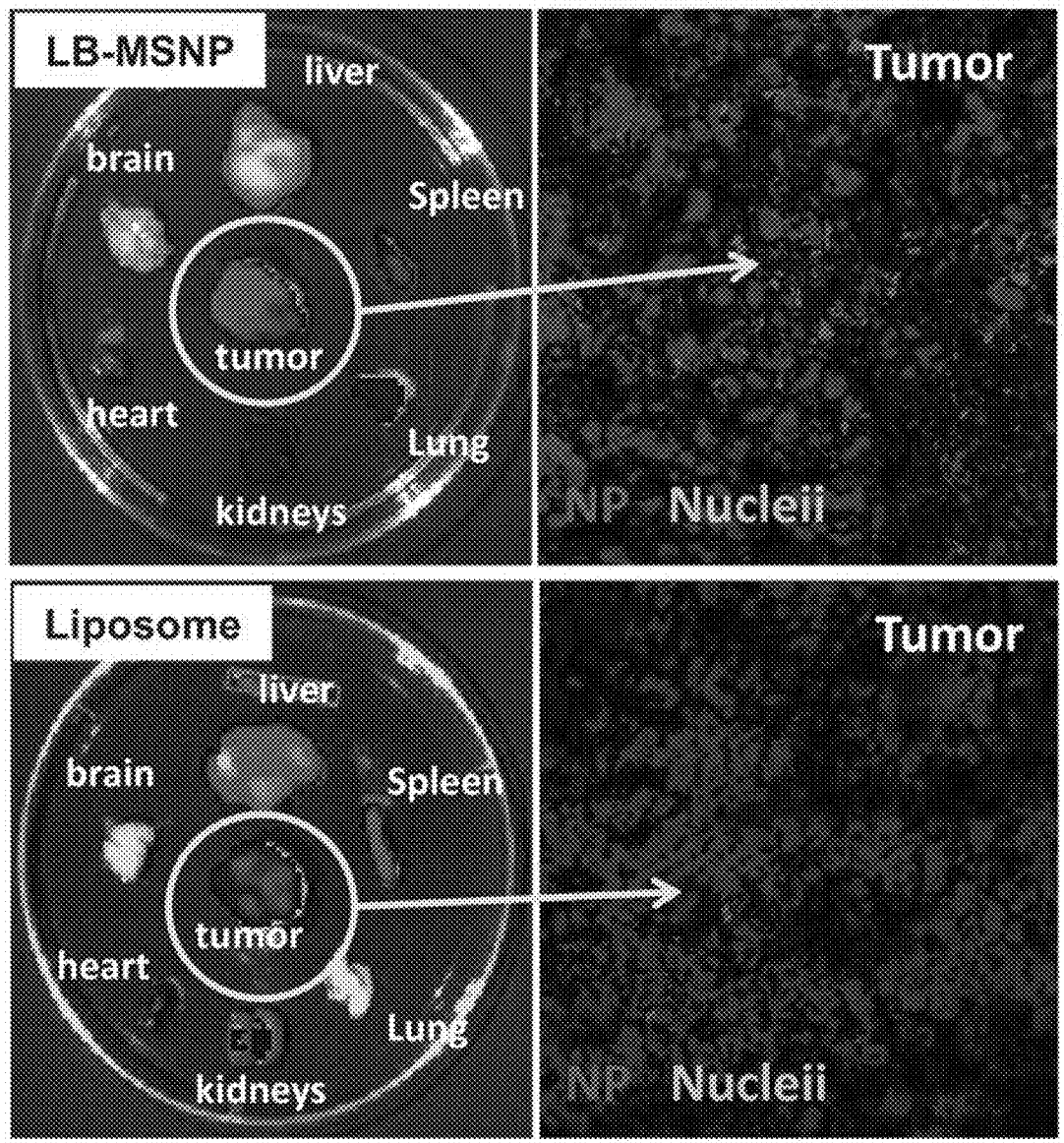
Figure 2C:
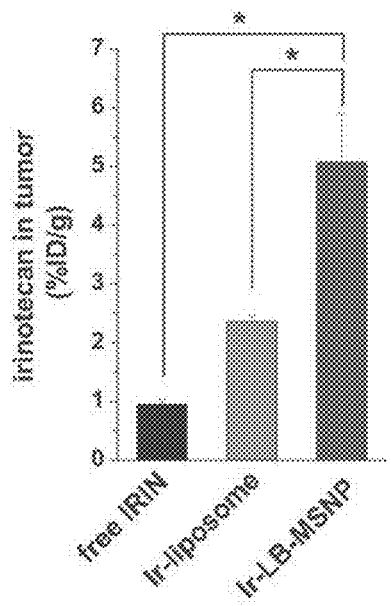
Figure 2D:
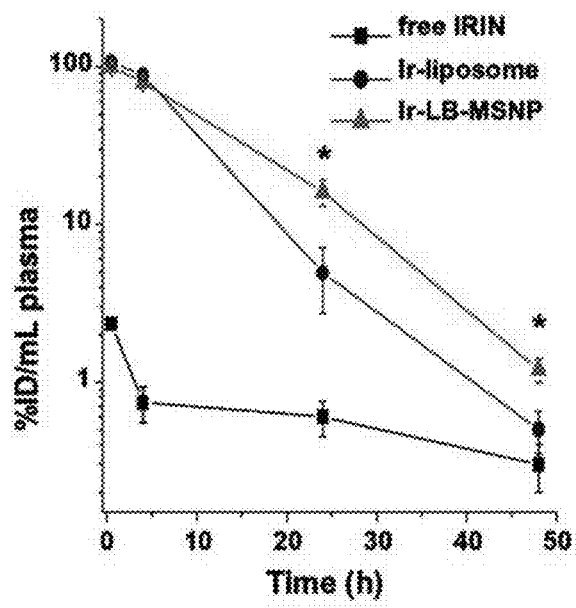
Figure 12:
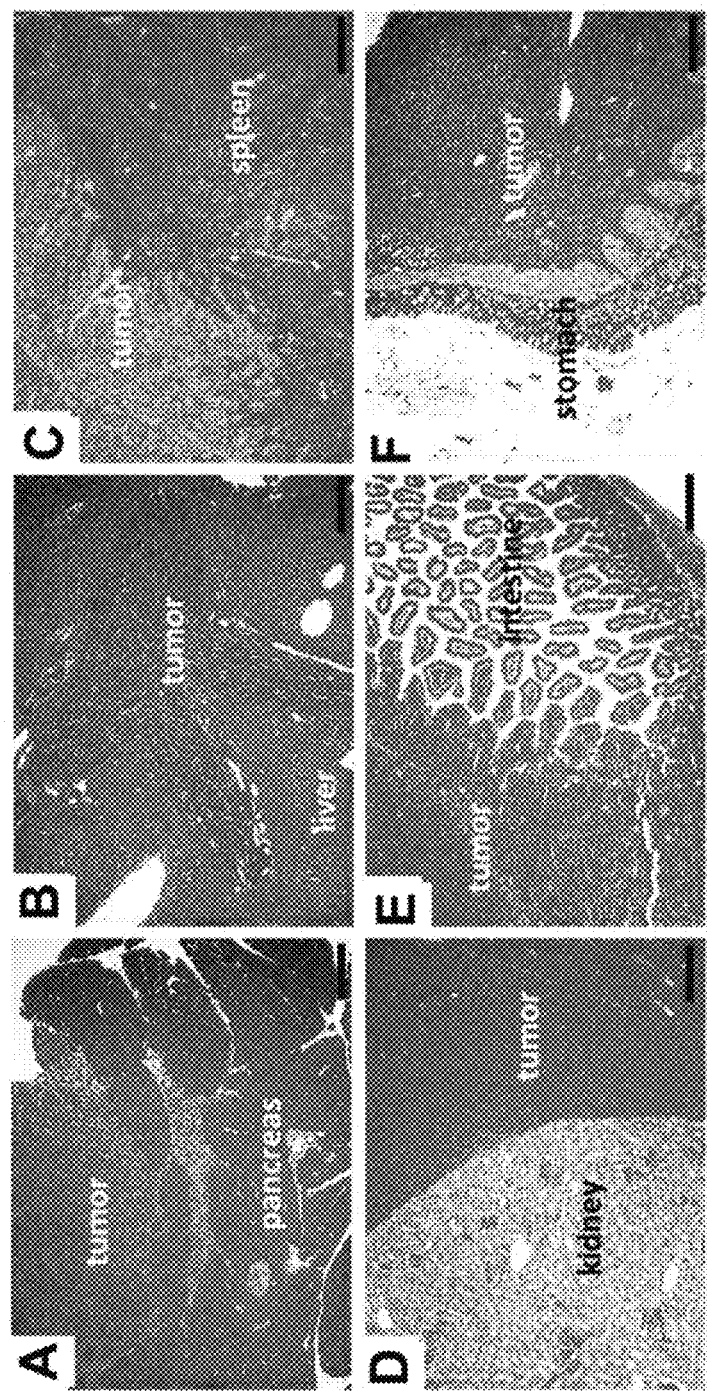
FIG. 12, panels A-F, shows H&E staining to show the infiltration of the KPC-derived tumor into surrounding organs, 5 weeks after implantation in B6/129 mice, in accordance with one or more embodiments of the invention. Representative images were captured to show infiltration of the pancreas (panel A), liver (panel B), spleen (panel C), kidney (panel D), intestine (panel E), and stomach (panel F). The bar size is 200 µm.
Figure 13:
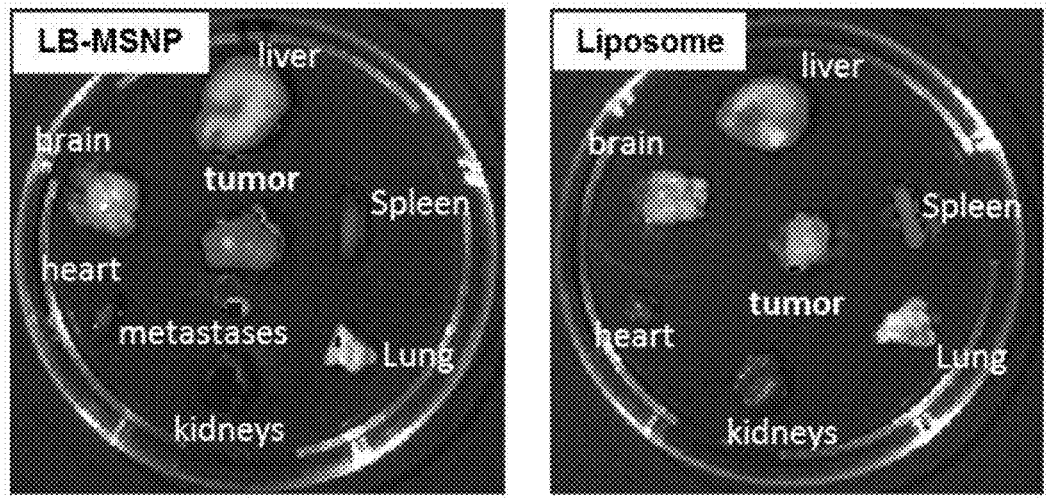
FIG. 13 shows an ex vivo IVIS image, captured 48 hrs post-IV injection of the NIR-labeled particles in the KPC-derived model in FIG. 2A, in accordance with one or more embodiments described herein. This demonstrates that for an equivalent particle dose, there is an increased abundance of LB-MSNPs at the tumor site compared to labeled liposomes.
Figure 14:
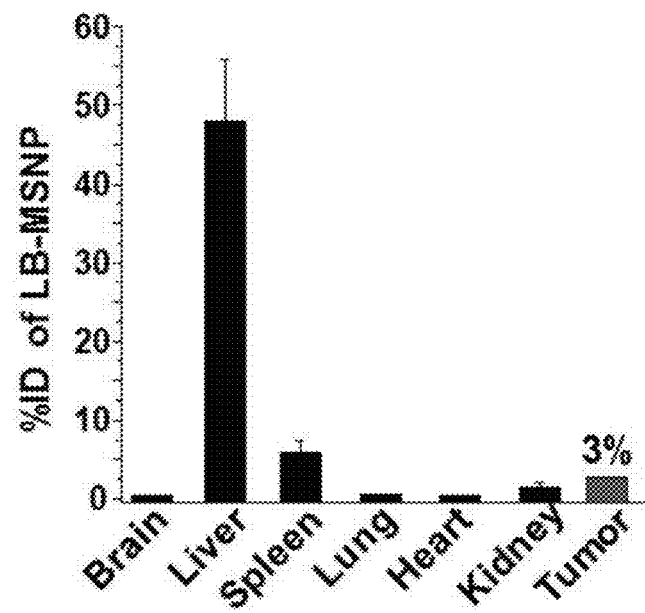
FIG. 14 shows the biodistribution of LB-MSNPs in the KPC-derived orthotopic tumor model in B6/129 mice (n=3), following IV injection of LB-MSNPs (100 mg/kg) and animal sacrifice at 24 hours, in accordance with one or more embodiments of the invention. Tumor tissues and major organs were collected for the measurement of the Si content using inductively coupled plasma optical emission spectroscopy. The particle biodistribution is expressed as % of total injected Si dose (% ID) for each location. Data represent mean±SD.
Figure 15A:
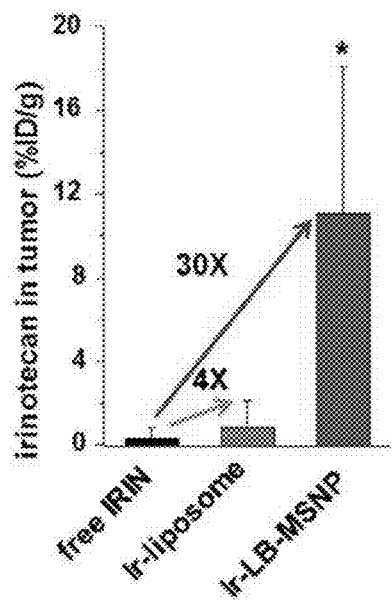
FIG. 15A shows irinotecan tumor content determined in a subcutaneous PANC-1 xenograft model in nude mice (n=3). Animals received IV injection of an irinotecan dose equivalent of 60 mg/kg for the different drug formulations. Following animal sacrifice after 24 hours, tumor tissues were collected for the measurement of irinotecan content by HPLC. Irinotecan content was expressed as % total injected dose per gram of tumor tissue (% ID/g). Data represent mean±SD, *p<0.05 for MSNP compared to other groups.
Figure 15B:
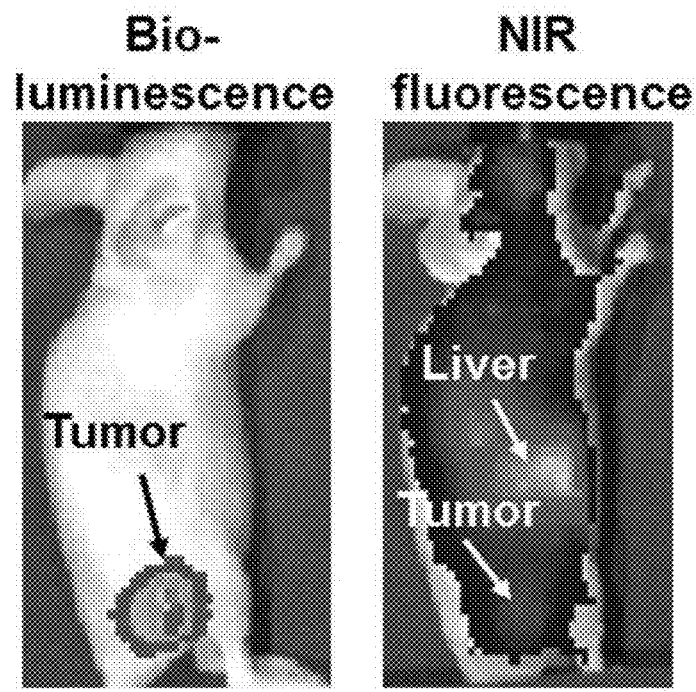
FIG. 15B shows NIR fluorescence images in a representative animal 24 hours after IV injection of 100 mg/kg NIR-labeled LB-MSNP.
Figure 16:
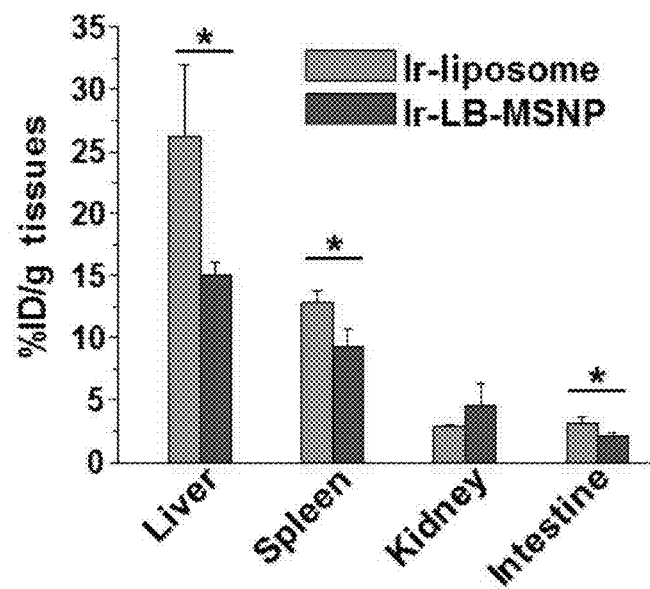
FIG. 16 shows HPLC quantification of irinotecan content in surrounding organs in B6/129 mice. Animals received IV injection of an irinotecan dose equivalent of 60 mg/kg for the different drug formulations (n=3). Following animal sacrifice after 24 hrs, tissues were collected for the measurement of irinotecan content by HPLC. Irinotecan content was expressed as % total injected dose per gram of tissue (% ID/g). Data represent mean±SD, *p<0.05.

Improved Biodistribution, Pharmacokinetics (PK), and Irinotecan Delivery by LB-MSNP Compared to Liposomes in a Kras-Derived Orthotopic PDAC Model Biodistribution and PK studies were performed in immuno-competent B6/129 mice, orthotopically implanted with a luciferase-expressing cell line derived from a spontaneous PDAC tumor in a transgenic KrasLSL-G12D/+; Trp53LSL-R172H/+; Pdx-1-Cre (KPC) animal (Hingorani et al. (2005) *Cancer Cell*, 7: 469-483). The KPC-derived orthotopic model mimics human PDAC in the Kras mutation, expression of a relatively abundant stroma, local tissue invasion, and development of metastases (Tseng et al. (2010) *Clin. Cancer Res.* 16: 3684-3695; Provenzano et al. (2013) *Br. J. Cancer*, 108: 1-8; Tones et al. (2013) *PLoS One*, 8: e80580). Primary tumors developed at the orthotopic implant site within 2-3 weeks, with appearance of metastases at ~5 weeks, agreeing with the literature (FIG. 12) (Id.). In order to follow the biodistribution of the irinotecan carriers to the tumor site, animals were IV injected with near-infrared (NIR)-labeled (Dylight 680) liposomes or LB-MSNPs, 3 weeks after orthotopic implantation (FIG. 2A). IVIS imaging was obtained prior to (column 2) and following IV injection of 100 mg/kg labeled LB-MSNPs or liposomes at the indicated time points (columns 3-6, FIG. 2A). This was coupled with bioluminescence IVIS imaging to detect luciferase expression in the developing tumors in animals receiving intraperitoneal (IP) injection of D-Luciferin (FIG. 2A, first column). Robust fluorescence intensity was observed at the tumor sites within 2 h of LB-MSNP injection, following which the signal was sustained for at least 48 h. In contrast, the NIR signal intensity was dimmer and disappeared more rapidly in mice injected with liposomes (with similar labeling efficiency). This was also confirmed by ex vivo imaging of the tumors and major organs collected from the animals, following sacrifice after 24 h postinjection (FIG. 2B). Ex vivo imaging was also carried out after 48 h, which confirmed stronger NIR signal intensity in the operator-defined region of interest (ROI) in LB-MSNP compared to liposome-treated animals (FIG. 13). In addition to abundant particle uptake at the tumor site, the liver and spleen were also major sites of particle distribution. Little signaling was obtained in the lung, heart, and kidney. Inductively coupled plasma optical emission spectrometry (ICP-OES) to quantify the silicon (Si) abundance in the tumor tissues and major organs demonstrated that ~3% of the total administered elemental Si dose could distribute to the developing tumor sites (FIG. 14). This represents exceptionally good biodistribution compared to liposomes, polymeric micelles, gelatin, or $MoS_2/Fe_3O_4$ nanoparticles, where the percentage of particles distributing to the PDAC site amounted to 0.2-2.4% (Yoshida et al. (2012) *PLoS One*, 7: e39545; Yu et al. (2015) *Theranostics*, 5: 931-945; Cabral et al. (2011) *Nat. Nanotechnol.* 6: 815-823; Guo et al. (2013) *Biomaterials* 34: 8323-8332; Xu et al. (2013) *Mol. Pharmaceutics*, 10: 2031-2044). We also obtained tumor sections for visualization of the intratumoral distribution of NIR-labeled particles by confocal microscopy; this demonstrated higher particle abundance at the tumor site after 24 h for LB-MSNPs compared to liposomes (FIG. 2B). In order to assess irinotecan content at the tumor site, the equivalent of 60 mg/kg drug was injected as a single dose in the form of free drug, Ir-LB-MSNP (60 mg/kg drug; 120 mg/kg particle dose) or Ir-liposomes (60 mg/kg drug; 150 mg/kg particle dose). Animals were sacrificed after 0.5, 4, 24, and 48 h for blood collection and tumor harvesting. These tissues were used for HPLC analysis to quantify the irinotecan tissue content, which was 5- and 2-fold higher for Ir-LB-MSNPs and Ir-liposomes than for free drug at 24 h (FIG. 2C). Circulatory half-life for irinotecan was calculated by using HPLC quantification of the plasma drug concentration and to 11, 8.7, and 1.0 h for LB-MSNPs, liposomes, and free drug, respectively (FIG. 2D). Logistical constraint of the volume of blood obtainable from mice precluded us from determining the blood residence time of the carriers. We also performed a biodistribution and PK study in a subcutaneous PANC-1 xenograft model, in which we observed 30- and 4-fold increases in tumor drug content for Ir-LB-MSNPs and Ir-liposomes, respectively, over free drug (FIG. 15). We also compared the drug content of individual organs (FIG. 16). This demonstrated a 0.8-, 0.2-, and 0.2-fold higher drug content in liver, spleen, and intestinal tissues, respectively, for the Ir-liposomes compared to the Ir-LB-MSNP at 24 h postinjection. No significant difference was seen for the kidney.

Ir-LB-MSNP Provides More Efficacious Killing than Free Drug or Ir-Liposomes in an Orthotopic PDAC Model.

Figure 3A:
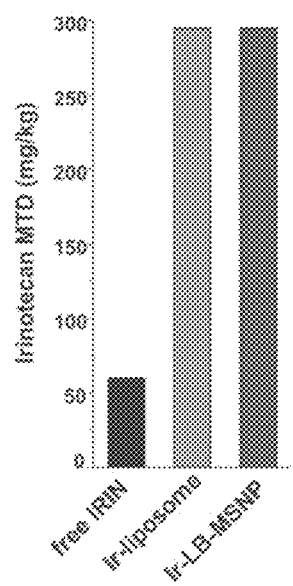
FIGS. 3A-3E show the differential tumor inhibitory effect of the free drug and encapsulated irinotecan carriers in the KPC-derived orthotopic tumor model, in accordance with one or more embodiments described herein.
Figure 3B:
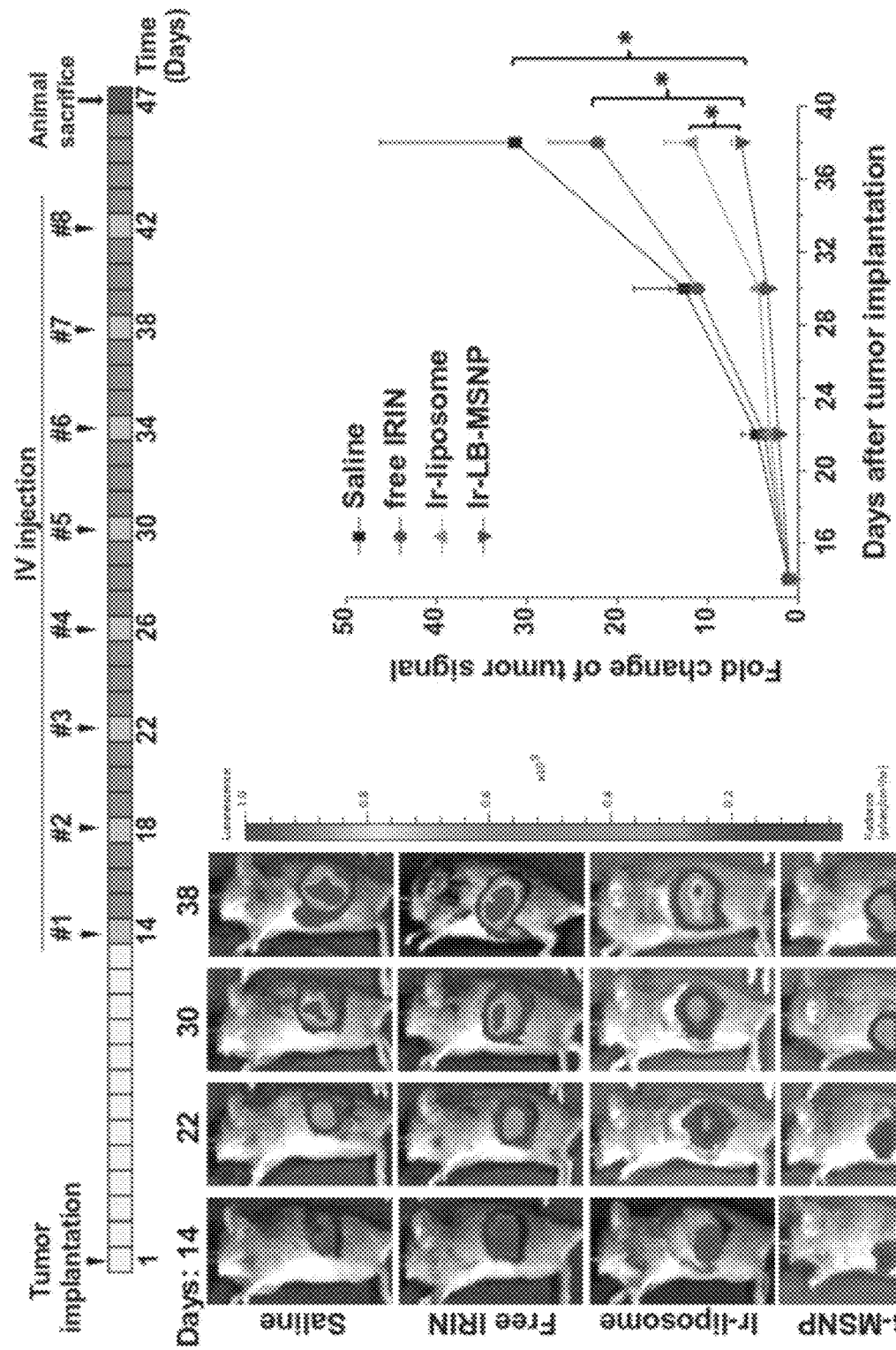
Figure 3C:
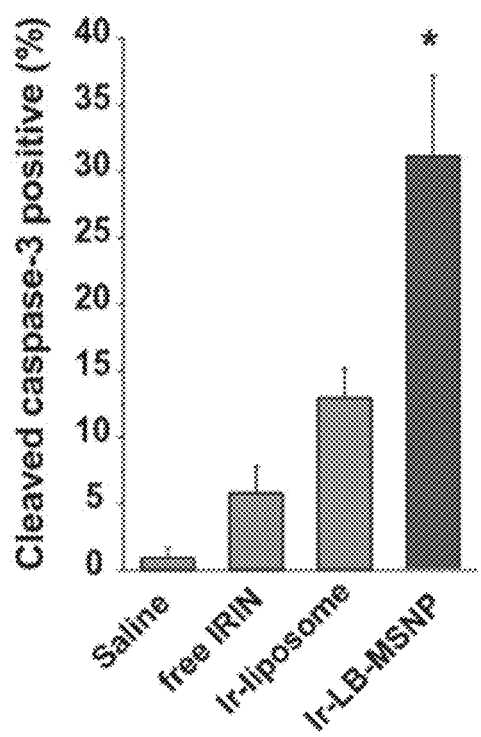

In order to develop a dose-seeking schedule for efficacy assessment, we used a protocol from the U.S. National Cancer Institute to determine the maximum tolerated dose (MTD) in healthy mice (Drummond et al. (2006) *Cancer Res.*, 66(6): 3271-3277). This assessment demonstrated a MTD of 60, 295, and 295 mg/kg for free irinotecan, Ir-liposomes, and Ir-LB-MSNPs, respectively (FIG. 3A). A drug dose of 40 mg/kg (equivalent to 66.7 or 13.3% of the MTD for free drug or encapsulated drug quantities) was chosen for subsequent experiments. These doses are equivalent to nanoparticle doses of 80 or 100 mg/kg for Ir-LB-MSNPs or Ir-liposomes, respectively. IV injection commenced on day 14 after orthotopic tumor implantation of $2\times10^6$ KPC cells; at this time, the mean primary tumor size was ~5 mm, without macro-metastases. IV injection was repeated every 4 days, for up to 8 repeat repetitions (FIG. 3B). The control group included animals receiving IV saline only. Orthotopic tumor growth was monitored at set time points by IVIS bioluminescence imaging (FIG. 3B). Quantitative expression of tumor growth by IVIS software to determine imaging intensity in the ROI, demonstrated significantly slower tumor growth by Ir-LB-MSNP treatment compared to saline, free drug, or Ir-liposomes (FIG. 3B). Antitumor efficacy was also measured according to the rates of apoptosis in tumor explants, collected from animals sacrificed on days 40-47. Utilizing an immunohistochemistry (IHC) staining protocol for the detection of activated (cleaved) caspase-3, we observed ~25% apoptotic cell death in Ir-LB-MSNP-treated mice, compared to ~6 and ~11% for free irinotecan or Ir-liposomes, respectively (FIG. 3C).

Figure 17:
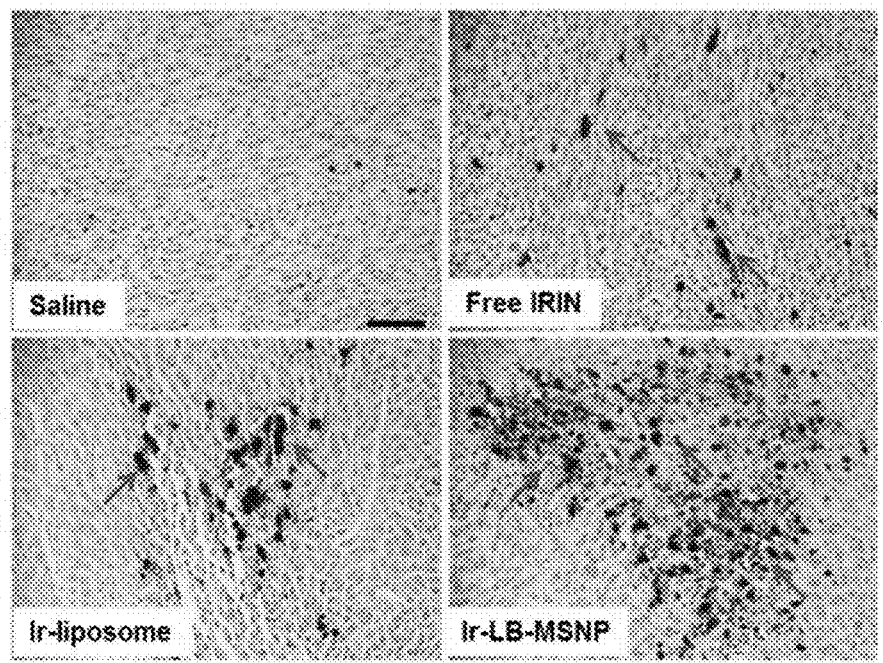
FIG. 17 shows representative images to show IHC staining for cleaved caspase-3 (apoptosis marker) at the primary tumor site, obtained from the primary tumor site in each animal group (sacrificed on day 40-47) in the experiment described in FIG. 3B. Apoptotic cells (brown color) are indicated by red arrows. Bar=50 µm.
Figure 18:
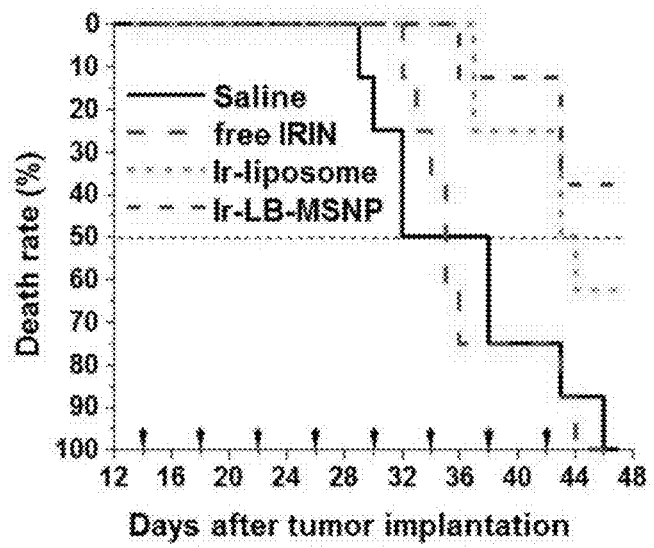
FIG. 18 shows death rate of the animals in each treatment group of the efficacy study described in FIG. 3B, in accordance with one or more embodiments of the invention. The arrows on the x-axis denote the injection days. The mice were monitored frequently and sacrificed based on "moribund criteria" (Zucker et al. (2009) *J. Control. Release*, 139(1): 73-80) instead of spontaneous death. Irinotecan loaded LB-MSNPs resulted in significant (p<0.01, compared by the log-rank test using SPSS 19.0, IBM SPSS Statistics, USA) survival improvement compared to saline and free irinotecan. A better survival outcome was observed for Ir-LB-MSNP compared to Ir-liposome.

Representative IHC images are shown in FIG. 17. Although we did not set out to perform an official survival study, it was possible to use a Kaplan-Meier data display after 47 days to compare the number of surviving animals at different stages of the investigation (FIG. 18). This demonstrated improved survival for both carriers over free drug, including better survival rate of Ir-LB-MSNP over the liposomal preparation (FIG. 18).

Figure 3D:
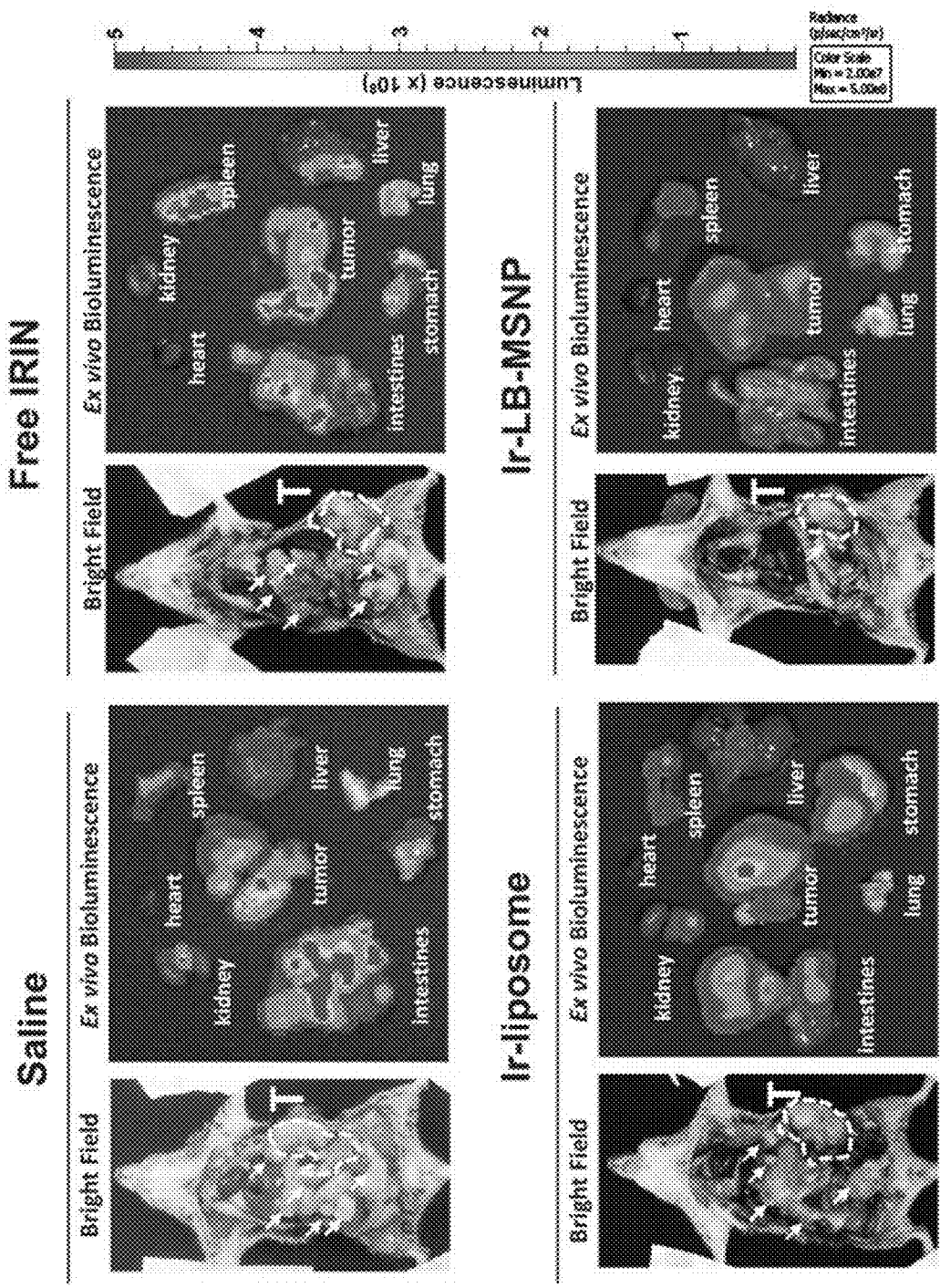
Figure 3E:
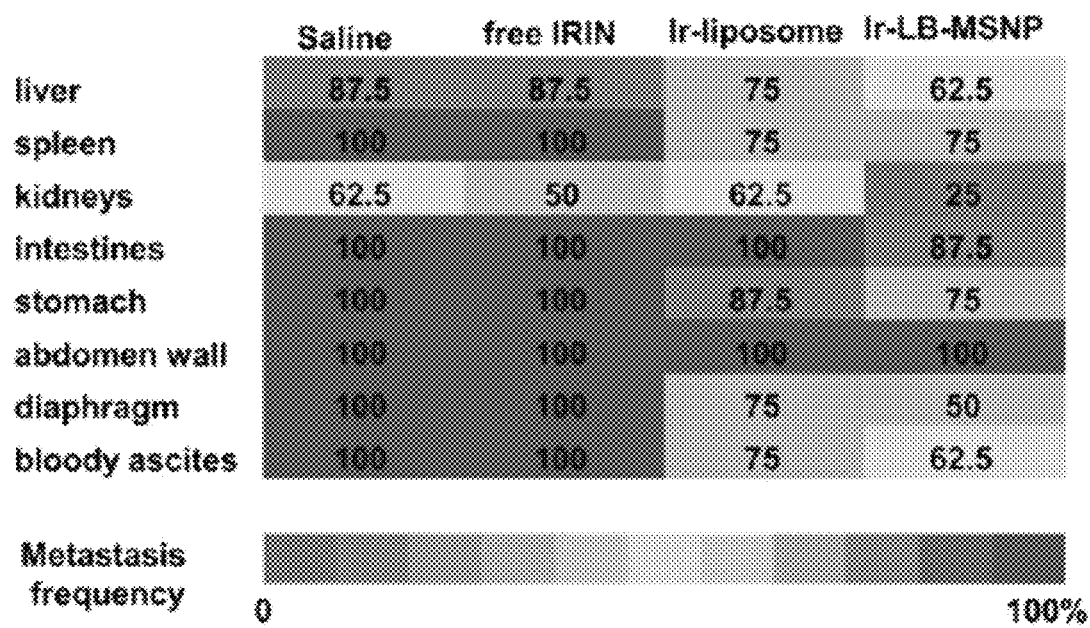

Animal autopsy was performed to assess local tumor spread and appearance of metastases (FIG. 3D). In addition to direct tumor invasion of the stomach, intestines, liver, spleen, kidneys, diaphragm, and abdominal wall, numerous macroscopic metastatic foci could be seen in saline-treated animals, which also developed hemorrhagic ascites. While free irinotecan failed to affect metastasis, Ir-liposomes provided a moderate reduction of bioluminescence intensity at the metastatic sites (FIG. 3D). In striking contrast, Ir-LB-MSNP treatment exerted a potent inhibitory effect, with evidence of dim bioluminescence outside the primary tumor region during IVIS imaging (FIG. 3D). This was especially prominent in the region of the kidney, which showed a higher but nonsignificant content of irinotecan during HPLC analysis (FIG. 16). The heat map in FIG. 3E provides a quantitative display of treatment impact on tumor metastasis.

LB-MSNPs but Not Liposomes Improve the Safety of Irinotecan Delivery in the Mouse Orthotopic Model.

Figure 4B:
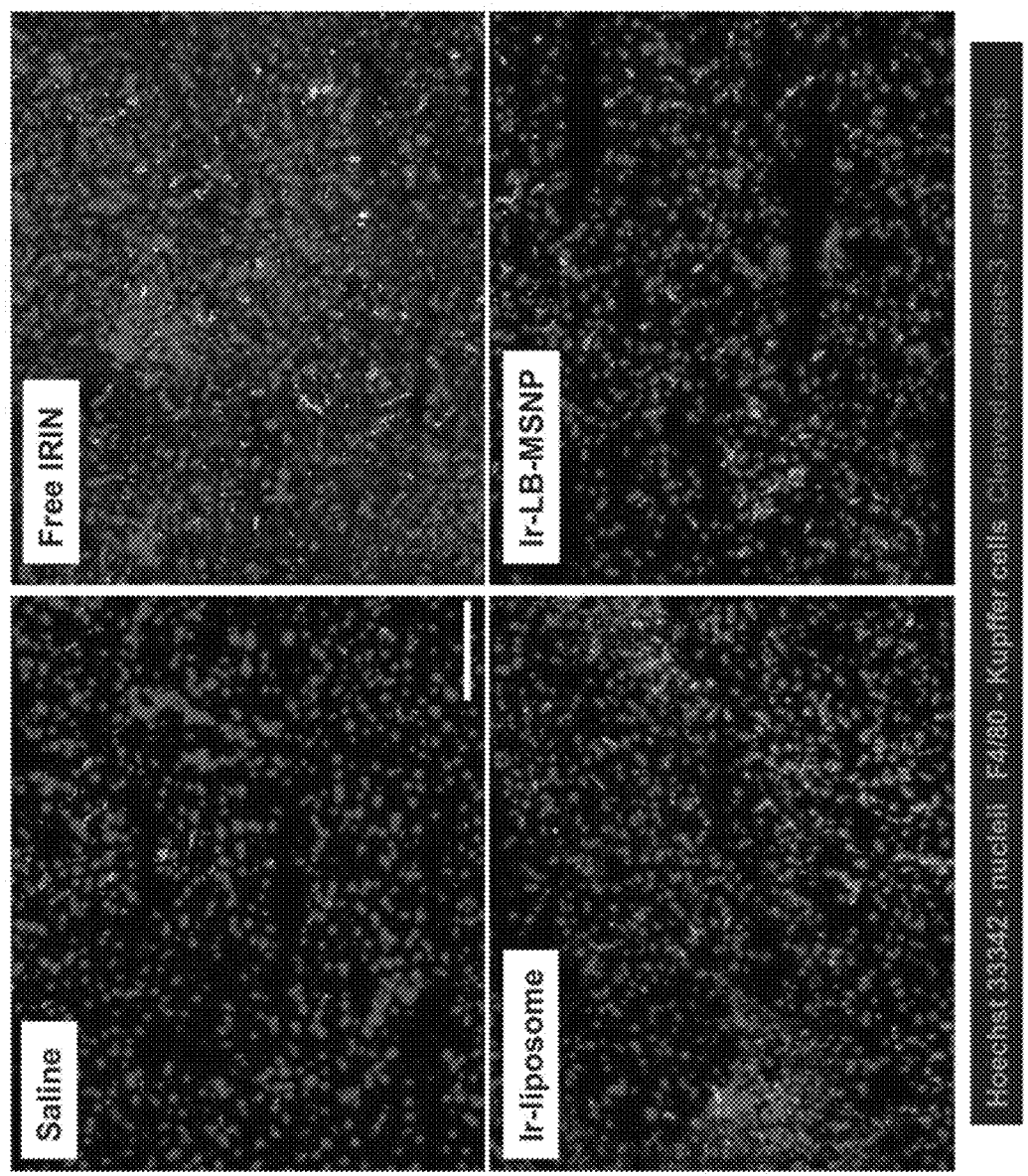

Since irinotecan contributes in a major way to FOL-FIRINOX toxicity, the possibility of reducing drug toxicity by encapsulated delivery is a major study objective. MTD assessment showed that both carriers are capable of increasing the acute lethal dose ~5-fold over free drug (FIG. 3A). In order to address irinotecan toxicity through encapsulated drug delivery (FIG. 3B), liver, sternal bone marrow, and intestinal tissues were collected from the sacrificed animals in the efficacy study. These are the major target organs for irinotecan toxicity in PDAC patients (Conroy et al. (2011) *N. Engl. J. Med.* 364(19): 1817-1825; Ueno et al. (2007) *Cancer Chemother. Pharmacol.* 59(4): 447-454; Loupakis et al. (2013) *Br. J. Cancer,* 108(12): 2549-2556). Histological examination of the liver demonstrated severe and extensive hepatocyte necrosis in animals treated with the free drug (FIG. 4A). This is reflected by the presence of pyknotic and fragmented nuclei in hepatic cells (Ziegler et al. (2004) *News Physiol. Sci.* 19: 124-128). While the severity of liver damage was somewhat reduced by Ir-liposomes, extensive hepatic necrosis was observed (FIG. 4A). In contrast, Ir-LB-MSNP-treated animals only exhibited minor steatosis, a reversible drug-induced stress response, without necrosis (FIG. 4A) (King and Perry (2001) *Oncologist,* 6: 162-176; Maor and Malnick (2013) *Int. J. Hepatol.* Art: 815105). The histological data were also confirmed by IHC analysis, in which liver tissue was used to stain Kuppfer cells (KC) (with a FITC-labeled anti-F4/80 antibody), apoptotic cells detected with a RITC-labeled antibody (recognizing cleaved caspase-3) and cellular nuclei with Hoechst 33342 (a blue dye) (FIG. 4B). Examination of the stained sections under a fluorescence microscope demonstrated extensive apoptosis throughout the liver of animals treated with the free drug. Animals receiving treatment with Ir-liposomes demonstrated less apoptosis, which frequently involved KC or adjacent hepatic tissue. In contrast, no apoptosis was seen in the livers of animals treated with Ir-LB-MSNP.

While H&E staining of the GI tract did not reveal microscopic evidence of toxicity in any of the treatment groups, IHC staining for cleaved caspase-3 demonstrated the presence of apoptotic cells and blunting of the intestinal villi by the free drug (FIG. 4C). While treatment with Ir-liposomes protected against blunting of the villi, IHC staining revealed the presence of apoptosis in apical enterocytes. This is in clear contrast to treatment with Ir-LB-MSNPs, which did not result in any apoptosis or damage to the villi (FIG. 4C).

Figure 4D:
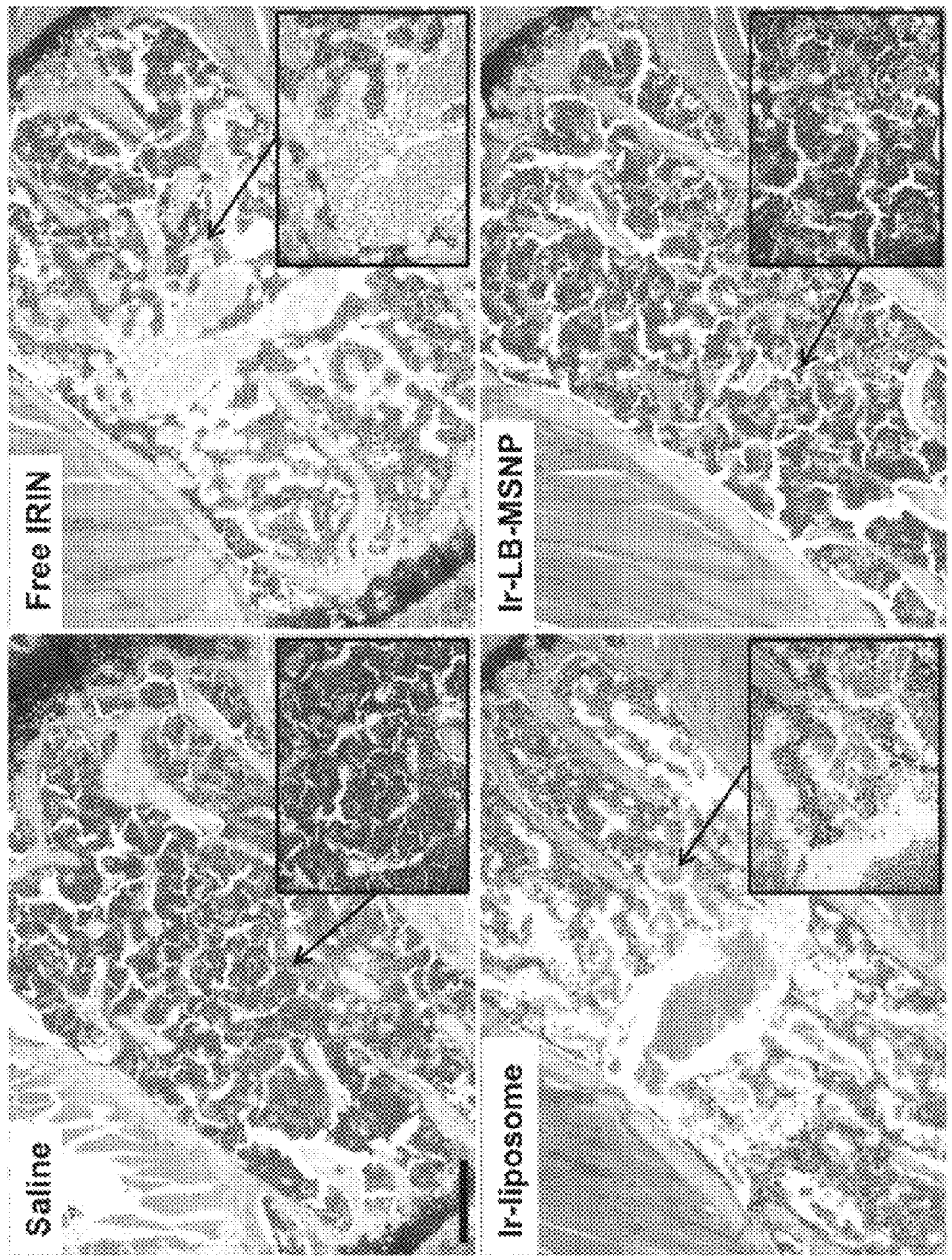
Figure 19:
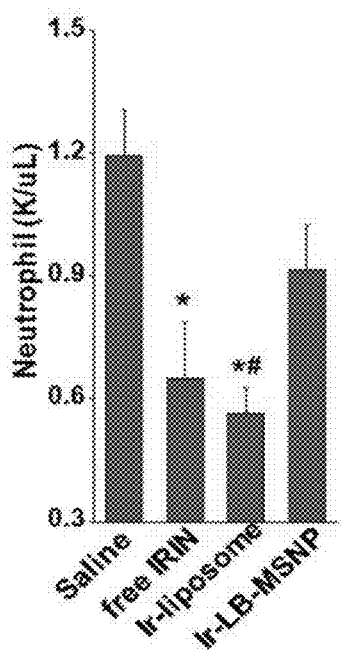
FIG. 19 shows full blood count analysis was performed on samples obtained from the experiment described in FIG. 4D, in accordance with one or more embodiments of the invention. The differential white cell count showed a significant decrease of the absolute neutrophil count performed for the free drug or Ir-liposome treated groups. In contrast, treatment with Ir-LB-MSNPs showed a small but non-significant drop in the neutrophil count. Data represent mean±SEM, *p<0.05 compared to control, #p<0.05 compared to LB-MSNP group.
Figure 20:
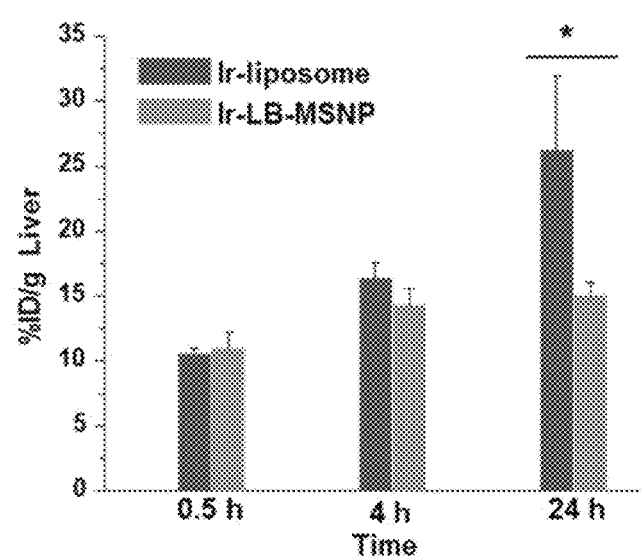
FIG. 20 shows HPLC quantification of irinotecan content in liver for the different drug carriers, in accordance with one or more embodiments described herein. Animals received IV injection of an irinotecan dose equivalent of 60 mg/kg for the different drug formulations (n=3). Following animal sacrifice after 0.5, 4, 24 hours, respectively, liver tissues were collected for the measurement of irinotecan content by HPLC. Irinotecan content was expressed as % total injected dose per gram of liver tissue (% ID/g). Data represent mean±SD, *p<0.05.

Bone marrow toxicity was studied in a separate experiment, in which animals received three injections of a 40 mg/kg irinotecan dose equivalent, as described above. After sacrifice, sternal bone marrow was collected to evaluate myelotoxicity by H&E staining (FIG. 4D) (Iusuf et al. (2014) *Mol. Cancer Ther.* 13: 492-503). While animals treated with free drug or Ir-liposomes showed extensive marrow damage, evidenced by <30% of the marrow space being filled by ematopoietic cells (Travlos (2006) *Toxicol. Pathol.* 34: 566-598), there was no change in marrow cellularity in Ir-LB-MSNP-treated animals (FIG. 4D). Moreover, damage to the bone marrow by the free drug or Ir-liposomes was accompanied by peripheral blood neutropenia, while Ir-LB-MSNP treatment showed a nonsignificant decline in neutrophil count (FIG. 19). All considered, these data demonstrate a significant reduction in systemic and target organ toxicity during treatment with Ir-LB-MSNP, while the liposomal carrier still exhibits substantial organ toxicity.

Discussion

We developed a custom-designed mesoporous silica nanoparticle platform, using a supported LB and a proton-generating entrapping agent, for high dose irinotecan loading and delivery and tested it in a KPC-derived pancreatic cancer model in immunocompetent mice. The improved stability and loading capacity of the carrier improved the biodistribution, circulatory half-life, and drug tumor content of irinotecan compared to an in-house synthesized MM-398 liposome equivalent, using the same loading procedure and trapping agent (TEA$_8$SOS). Not only was Ir-LB-MSNP more effective at inducing tumor killing at the primary tumor site, but it was also more active for treating metastases. Equally important, the LB-MSNP carrier did not induce pronounced systemic toxicity, which is in stark contrast to liposomes that had an adverse impact on the bone marrow, GI tract, and the liver. We ascribe the toxicity reduction with maintenance of treatment efficacy to the increased carrier ability of LB-MSNPs compared to that of liposomes. Thus, the LB-MSNP carrier provides an innovative approach for the introduction of irinotecan to the treatment of PDAC, with the possibility to promote the use of this drug, as a first-line consideration rather than being reserved for patients with failure of GEM treatment, as is currently the case for the recent FDA-improved liposomal carrier.

We have developed a robust MSNP carrier for irinotecan, with morphological resemblance to a liposomal equivalent. However, in addition to the superior drug encapsulation provided by an intact supported LB, the LB-MSNPs also allow dense drug packaging against the porous silica sidewalls as a result of bonding and/or electrostatic interactions (Tarn et al. (2013) *Acc. Chem. Res.* 46(3): 792-801; Meng et al. (2010) *ACS Nano,* 4: 4539-4550; Ashley et al. (2011) *Nat. Mater.,* 10: 389-397). This allowed us to achieve improved irinotecan loading capacity, which provides superior killing efficiency at the orthotopic tumor site, compared to liposomes. The improved loading capacity is further assisted by the supported LB stability, which improves cargo protection compared to the liposomal bilayer during blood circulation and biodistribution to the tumor site. We propose that the decreased fluctuation of the supported LB, presumably as a result of the robust electrostatic and van der Waals interactions with the particle surface, reduces the lipid loss due to serum protein interactions with a nonsupported lipid bilayer (liposome). A supported LB may also protect the carrier against complement-mediated lysis and the shear forces generated during blood flow (Liu et al. (2000) In: *Colloids and Surfaces A: Physicochemical and Engineering Aspects,* 172(1-3): 57-67; Heurtault et al. (2003) *Biomaterials,* 24(23): 4283-4300; Ashley et al. (2011) *Nat. Mater.,* 10: 389-397; Liang et al. (2004) *J. Colloid Interface Sci.* 278: 53-62; Anderson et al. (2009) *Langmuir,* 25: 6997-7005; Michel et al. (2012) *Int. J. Mol. Sci.* 13: 11610-11642; Wang et al. (2014) *Small* 10: 3927-3931). For instance, doxorubicin-loaded DOPC liposomes exhibit ~40% drug leakage within 24 h in a simulated serum-containing biofluid environment at 37° C. (Ashley et al. (2011) *Nat. Mater.*, 10: 389-397). This is in accordance with our finding that, while effective as a nanocarrier, Ir-liposomes are significantly less stable than Ir-LB-MSNPs in whole serum or following particle lyophilization and resuspension (FIGS. 1D and 1E). Premature release of the highly toxic topoisomerase inhibitor from Ir-liposomes was also accompanied by a high rate of toxicity in the bone marrow, liver, and intestines in animal studies, which is quite different from the protective effect of Ir-LB-MSNPs. Thus, despite the morphological resemblance to liposomes, the LB-MSNP carrier provides clear advantages over liposomal irinotecan delivery, from both efficacy and drug toxicity perspectives.

The bone marrow and the intestinal toxicity reduction by Ir-LB-MSNP is noteworthy from the perspective that the recently FDA-approved MM-398 liposomal formulation, Onivyde, is marketed with a black box warning of possible severe neutropenia and diarrhea during treatment of PDAC patients (see, e.g., www.fda.gov/newsevents/newsroom/pressannouncements/ucm468654.htm; www.accessdata.fda.gov/drugsatfda_docs/label/2015/207793LB.pdf). The warning states that fatal neutropenic sepsis was observed in 0.8% of patients, while severe or life-threatening neutropenic fever occurred in 3% (www.accessdata.fda.gov/drugsatfda_docs/label/2015/207793LB.pdf). Life-threatening neutropenia was observed in 20% of patients receiving Onivyde in combination with 5-fluorouracil and leucovorin (Id.). The same drug combination also caused severe diarrhea in 13% of treated subjects (Id.). Although we did not use Onivyde for comparison, an in-house liposomal formulation using $TEA_8SOS$ for irinotecan loading was associated with significant bone marrow and intestinal toxicity, similar to the free drug. Similar effects were not seen during treatment with the Ir-LB-MSNP platform.

Figure 4E:
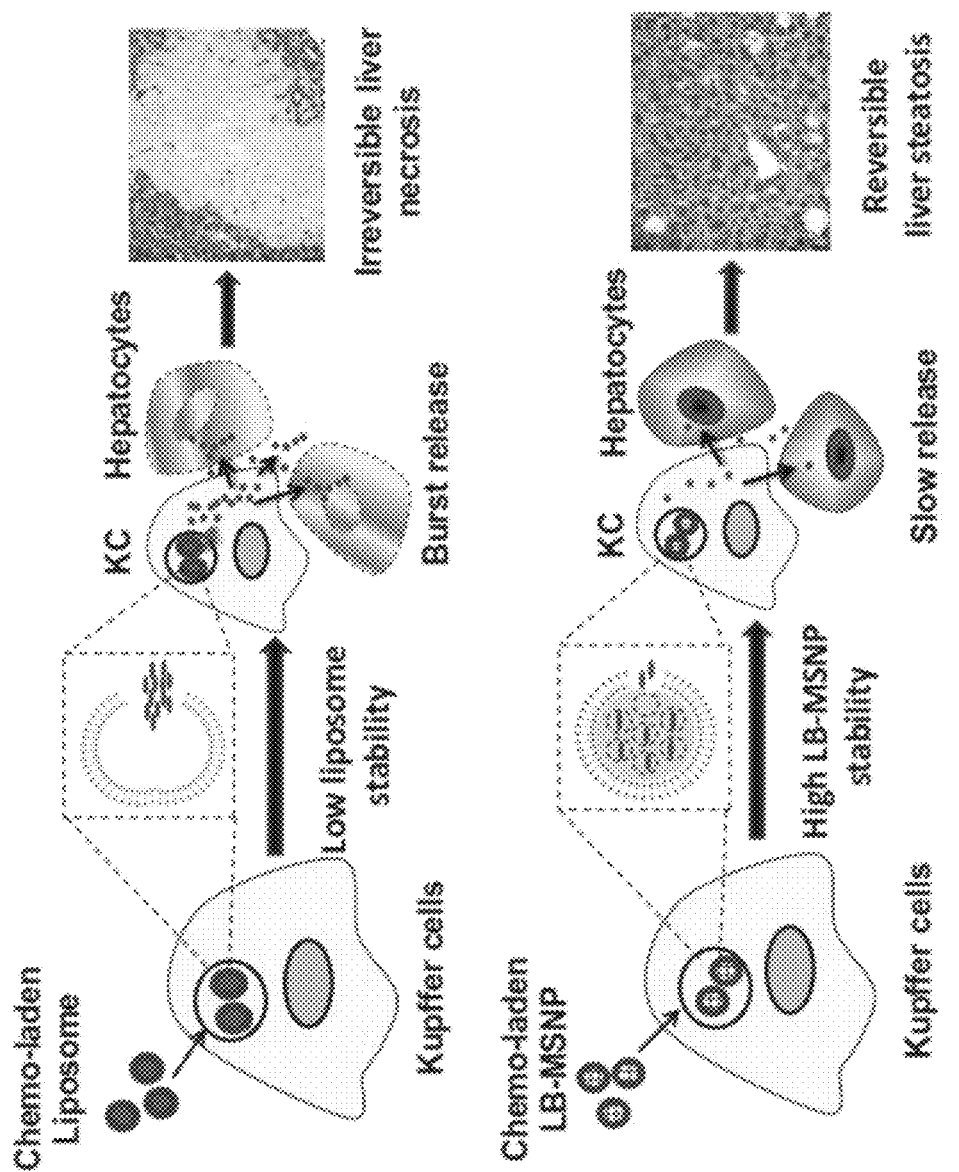

It is interesting that both the MSNP and liposomal carriers are sequestered by KCs in the liver, as demonstrated by confocal microscopy using NIR-labeled particles and FITC-labeled anti-F4/80 antibodies (not shown). While it is difficult to provide a direct in vivo demonstration, we propose that the disintegration of the LB and irinotecan release commence in acidic endo/lysosomal compartments in the KC (Hwang et al. (1980) *Proc. Natl. Acad. Sci. USA*, 77: 4030-4034; Derksen et al. (1988) *Biochim. Biophys. Acta, Bioenerg.* 971: 127-136; Kolter and Sandhoff (2010) *FEBS Lett.* 584: 1700-1712). The more rapid disintegration of the liposomes could explain why only sparse NIR-labeled particles are seen in animals injected with Ir-liposomes compared to the presence of abundant Ir-LB-MSNP (FIG. 2B). The rate of carrier disintegration could, in turn, determine the rate of drug release to bystander hepatocytes. This raises the possibility that irinotecan burst release from the liposomal carrier could overwhelm the hepatic metabolism of the drug, which is carried out by CYP 3A and uridine diphosphate-glucuronosyltransferase (UGT1A1) (Mathijssen et al. (2001) *Clin. Cancer Res.* 7: 2182-2194). Decreased metabolism could lead to higher retention of nonmetabolized drug, which leads to hepatocyte injury and necrosis, as shown in FIG. 4A. This could explain the significantly higher content of nonconjugated irinotecan in the liver tissue of animals treated with Ir-liposomes compared to Ir-LB-MSNP, that is, 26 vs 15% ID/g at 24 h post-IV injection (FIG. 16). These findings are also compatible with the IHC staining of KC and activated caspase-3, which demonstrates a high cell death rate in KC and adjacent hepatocytes during treatment with Ir-liposomes, compared to the absence of apoptosis in Ir-LB-MSNP-treated animals (FIG. 4B). The schematic in FIG. 4E outlines our hypothesis regarding the role of carrier stability and the rate of irinotecan release from KC in determining the extent of hepatocyte apoptosis and necrosis (Zhao et al. (2015) *In vivo. Sci. Bull.*, 60: 3-20). It was not possible to measure hepatic enzymes, due to the limited amount of blood that could be obtained from the animals in their moribund state.

GEM frequently serves as first-line therapy for PDAC, with a survival outcome of 6.8 months (Burris et al. (1997) *J. Clin. Oncol.*, 15: 2403-2413; Teague et al. (2014) *Ther. Adv. Med. Oncol.* 7: 68-84). While FOLFIRINOX can improve the survival to ~11 months, the frequent occurrence of serious drug toxicity (mostly due to irinotecan and oxaliplatin) precludes its use as first-line therapy. Thus, FOLFIRINOX is often reserved for patients with good performance status. Unfortunately, this position has not changed with the introduction of Onivyde, which is not approved as first-line therapy and includes black box warnings of severe diarrhea and neutropenia. Since approximately 80% of PDAC patients present at an advanced stage of disease, it would be advantageous to use drug in the FOLFIRINOX regimen as first-line treatment. Although we have not used Onivyde for comparative analysis, the Ir-LB-MSNP platform was more efficacious and biocompatible with lower systemic toxicity than our equivalent in-house Ir-liposomal formulation. We propose, therefore, that the Ir-LB-MSNP platform could be developed for first-line therapy in PDAC. We have recently demonstrated the feasibility of a dual delivery MSNP carrier for GEM and PTX in a PDAC model (Meng et al. (2015) *ACS Nano*, 9(4): 3540-3557). Each treatment approach should carefully consider the design complexity, cost, and impact on good manufacturing practice before implementation (Sugahara et al. (2010) *Science*, 328: 1031-1035).

Although the lipid-coated MSNPs have been shown to be efficacious for cargo delivery in vitro and/or in vivo (Meng et al. (2015) *ACS Nano*, 9(4): 3540-3557; Zhang et al. (2014) *Biomaterials*, 35: 3650-36651; Ashley et al. (2011) *Nat. Mater.*, 10: 389-397; Ashley et al. (2012) *ACS Nano*, 6: 2174-2188; Dengler et al. (2013) *J. Controlled Release*, 168: 209-224), this is the first demonstration of how a protonating agent can be used to increase the loading efficiency of this carrier platform. We have also identified a comprehensive list of weak basic drugs that can be loaded into LB-MSNPs through a proton gradient. The general characteristics of these cargo molecules include the following chemical properties:

(i) organic molecular compounds that include primary, secondary, tertiary, or quaternary amine(s);
(ii) a pKa <11 to allow protonation and entrapment behind the LB (Zucker et al. (2009) *J. Control. Release*, 139(1): 73-80; Cern Cern et al. (2012) *J. Control. Release*, 160(2): 147-157; Xu et al. (2014) *Pharmaceut. Res.* 31(10): 2583-2592);
(iii) a water solubility ranging from around 5 to 25 mg/mL and amphipathic characteristics that allow diffusion across the LB;
(iv) an octanol/water partition coefficient or log P value of −3.0 to 3.0; 71,72
(v) suitable molecular weight with a geometric size less than MSNP pore size (2-8 nm) to allow entry into the MSNP pores (Li et al. (2012) *Chem. Soc. Rev.* 41: 2590-2605; Tang et al. (2012) *Adv. Mat.* 24(12): 1504-1534; Tarn et al. (2013) *Acc. Chem. Res.* 46(3): 792-801).

Without being all-inclusive, the list of potential chemotherapy agents include the topoisomerase I inhibitor, topotecan; the antitumor anthracycline antibiotics, doxorubicin and mitoxantrone; the mitotic inhibitors, vinblastine and vinorelbine; the tyrosine kinase inhibitors, imatinib, osimerti-nib, and sunitinib, etc. The ability to package and deliver one or a combination of the above agents will enhance the wider utility of our multifunctional LB-MSNP platform, including treatment consideration of additional cancer types such as colon, breast, lung, liver, glioma, melanoma, etc. It is also possible to co-package drug combinations in the above list into a single carrier. For example, based on the success that we have achieved with our GEM/PTX co-delivery platform (Meng et al. (2015) *ACS Nano*, 9(4): 3540-3557), it is possible to consider combining drugs in the FOLFIRINOX regimen (e.g., oxaliplatin with irinotecan) for synergistic and ratiometric delivery. Moreover, drug loading by our LB-MSNP can be used for noncancerous applications, such as encapsulating antibiotics for infectious diseases, for example, ciprofloxacin, levofloxacin, or HIV anti-retrovirals (e.g., tenofovir disoproxil fumarate). It is also worth pointing out that, in addition to $TEA_8SOS$, transmembrane pH gradients can also be generated by acidic buffers (e.g., citrate) (Chou et al. (2003) *J. Biosci. Bioeng.*, 95(4): 405-408; Nichols et al. (1976) *Biochim. Biophys. Acta, Biomembr.* 455: 269-271), proton-generating dissociable salts (e.g., $(NH_4)_2SO_4$) (Haran et al. (1993) *Biochim. Biophys. Acta, Biomembr.* 1151: 201-215; Maurer-Spurej et al. (1999) *Biochim. Biophys. Acta, Biomembr.* 1416: 1-10; Fritze et al. (2006) *Biochim. Biophys. Acta, Biomembr.* 1758: 1633-1640), or ionophore-mediated ion gradients from metal salts (e.g., A23187 and $MnSO_4$) (Messerer et al. (2004) *Clin. Cancer Res,* 10(19): 6638-6649; Ramsay et al. (2008) *Eur. J. Pharm. Biopharm.* 68(3): 607-617; Fenske et al. (1998) *Biochim. Biophys. Acta, Biomembr.* 1414: 188-204). Moreover, it is OK possible to generate reverse pH gradients for drug loading, such as use a calcium acetate gradient, to improve amphiphilic weak acid loading in LB-MSNP, a strategy that has been utilized in liposomes (Avnir et al. (2008) *Arthritis Rheum.* 58: 119-129).

Conclusions

In summary, we have developed a MSNP delivery platform for irinotecan, which, in spite of its morphological resemblance to a liposome, provides biocompatibility and therapeutic efficacy superior to an equivalent liposomal formulation or free drug. The new carrier could be used to advance irinotecan delivery and drug combinations in the FOLFIRINOX regimen to first-line treatment status for PDAC.

Methods

Materials

Tetraethylorthosilicate (TEOS), triethanolamine, cetyltrimethylammonium chloride solution (CTAC, 25 wt % in water), triethylamine (TEA), Dowex 50WX8 resin, Sepharose CL-4B, and Sephadex G-25 were purchased from Sigma-Aldrich, USA. 1,2-Distearoyl-sn-glycero-3-phosphocholine (DSPC), 1,2-distearoyl-sn-glycero-3-phosphoethanolamine-N-[methoxy(polyethylene glycol)-2000] (ammonium salt) (DSPE-PEG2000), and cholesterol (Chol) were purchased from Avanti Polar Lipids, USA. Sucrose octasulfate (SOS) sodium salt was purchased from Toronto Research Chemicals, Inc., Canada. Irinotecan hydrochloride trihydrate was purchased from LC Laboratories, USA. Penicillin, streptomycin, and Dulbecco's modified Eagle medium (DMEM) were obtained from Invitrogen. Fetal bovine serum (FBS) was purchased from Gemini Bio Products. A rabbit mAb antibody (catalog #9664) that detects activated (cleaved) caspase-3 was purchased from Cell Signaling. Matrigel Matrix Basement Membrane was purchased from BD Bioscience. Centrifugal filter units (cutoff size: 10K and 30K) were purchased from EMD Millipore. All chemicals were directly used without further purification.

Preparation of Irinotecan-Loaded LB-MSNP Using a Trapping Reagent.

Synthesis of MSNP.

MSNP cores were synthesized by slight modification of our previous sol/gel procedure (Meng et al. (2015) *ACS Nano*, 9(4): 3540-3557). To synthesize a batch of ~500 mg of MSNP, 50 mL of CTAC was mixed with 150 mL of $H_2O$ in a 500 mL conical flask, followed by stirring at 350 rpm for 15 min at 85° C. This was followed by the addition of 8 mL of 10% triethanolamine for 30 min at the same temperature. Then, 7.5 mL of the silica precursor, TEOS, was added dropwise at a rate of 1 mL/min using a peristaltic pump. The solution was stirred at 350 rpm at 85° C. for 20 min, leading to the formation particles with a primary size of ~65 nm. The surfactant was removed by washing the particles with a mixture of methanol/HCl (500:19 v/v) at room temperature for 24 h. The particles were centrifuged at 10 000 rpm for 60 min and washed three times in methanol.

Synthesis of Trapping Agent TEA8SOS.

$TEA_8SOS$ was synthesized from a commercially available SOS sodium salt by ion-exchange chromatography (Drummond et al. (2006) *Cancer Res.*, 66(6): 3271-3277). Briefly, 500 mg of the salt was dissolved in 1 mL of deionized (DI) water, yielding an aqueous solution of 500 mg/mL. The solution was passed through an 8 cm×1.5 cm cationic ion-exchange resin (Dowex 50WX8) column, prepared in DI water. The SOS salt was added to the column and eluted with the water for conversion to sucrose octasulfonic (SOS) acid. The acidic SOS eluate was titrated immediately with neat triethylamine to reach a final pH of 5.8. This resulted in the formation of the TEA8SOS. The salt concentration was adjusted to ~80 mM and stored at 4° C. in a refrigerator before use.

TEA8SOS Loading and Entrapment by a LB in MSNP.

We used a novel method for entrapment of TEA8SOS in MSNP through the use of LB coating (Meng et al. (2015) *ACS Nano*, 9(4): 3540-3557). The synthesis commenced by soaking 100 mg of empty MSNPs in 4 mL of an aqueous 80 mM $TEA_8SOS$ by probe sonication for 5 min, with a 15/15 s on/off working cycle and a power output of 32.5 W. The particle suspension was added immediately to a coated lipid biofilm, obtained by adding a mixture of 110 mg of DSPC/Chol/DSPE-PEG2000 (molar ratio 3:2:0.15), suspended in chloroform at 10 mg/mL, to the bottom of a 6 cm round-bottom flask. This is equivalent to a particle:lipid ratio of 1.0:1.1. Following solvent evaporation in a rotary evaporator at room temperature, we obtained a biofilm with ~30 cm² surface area. Following the addition of the particle suspension to the biofilm, probe sonication was used for 30 min with a 15/15 s on/off working cycle at a power output of 32.5 W. Unentrapped $TEA_8SOS$ was removed by size-exclusion chromatography over a Sepharose CL-4B column (1.5×15 cm), using a HEPES-buffered dextrose solution (5 mM HEPES, 5% dextrose, pH 6.5) for elusion.

Use of TEA8SOS-Loaded LB-MSNP for Irinotecan Loading.

Irinotecan was dissolved in HEPES-buffered dextrose (5 mM HEPES, 5% dextrose, pH 6.5) at 10 mg/mL, which was mixed with the $TEA_8SOS$-loaded particles to achieve an irinotecan/MSNP ratio of 1:1 (w/w). The mixture was incubated at 65° C. in a water bath for 30 min and then quenched in ice water for 10 min. The drug-loaded particles were washed and purified three times by centrifugation at 15 000 rpm for 10 min. The washed particles were resuspended in water, saline, or PBS as indicated.

Preparation of a Comparative Liposomal Formulation for Irinotecan Delivery.

Irinotecan Encapsulation by LB-MSNP in the Absence of a Trapping Agent.

Empty MSNPs (40 mg) were added to 4 mL of a 10 mg/mL irinotecan solution (in water) with sonication, followed by stirring for 4 h at room temperature. The drug was then encapsulated by a LB, using sonication of lipid biofilm of similar composition as described above. After probe sonication, the particles were purified by centrifugation and washing and resuspended as described above.

Liposomal Encapsulation of Irinotecan Using TEA8SOS.

In order to develop an in-house analogue of the MM-398 formulation (Drummond et al. (2006) *Cancer Res.*, 66(6): 3271-3277; Ko et al. (2013) *Br. J. Cancer,* 109: 920-925), 212 mg of a lipid mixture containing DSPC/Chol/DSPE-PEG2000 (at a molar ratio of 3:2:0.015) was dissolved in 0.4 mL of ethanol at 65° C. Four milliliters of a $TEA_8SOS$ solution (80 mM) was mixed with the lipid ethanol solution at the same temperature, followed by sonication in a water bath for 2 min. The lipid suspension was extruded 15 times through a polycarbonate membrane with a 0.1 μm pore size at 65° C. Unentrapped $TEA_8SOS$ was removed by a size-exclusion chromatography column (Sepharose CL-4B), eluted with a HEPES-buffered dextrose solution (5 mM HEPES, 5% dextrose, pH 6.5). An irinotecan solution, prepared at 10 mg/mL in HEPES-buffered dextrose (5 mM HEPES, 5% dextrose, pH 6.5), was mixed with $TEA_8SOS$-loaded liposomal suspension (irinotecan/lipids=1:2.1 w/w) and incubated in a water bath at 65° C. for 30 min. The sample was immediately quenched in ice water for 10 min. The free drug was removed using a Sephadex G-25 column eluted with HEPES-buffered saline (5 mM HEPES, 145 mM NaCl, pH 6.5).

Synthesis of an Irinotecan Liposomal Carrier in the Absence of a Trapping Agent.

We also synthesized an irinotecan-delivering liposome that uses a passive encapsulation approach, instead of an entrapment agent. Briefly, a mixture of lipids (53 mg lipids, DSPC/Chol/DSPE-PEG2000 at molar ratio of 3:2:0.015) was dissolved in 0.1 mL of ethanol at 65° C. One milliliter of an irinotecan solution (10 mg/mL in water) was mixed with the lipid ethanol solution at 65° C., followed by sonication for 2 min. The lipid suspension was extruded 15 times through a polycarbonate membrane with a 0.1 μm pore size at 65° C. The drug-laden liposome was purified using the same method as described above.

Physicochemical Characterization.

All particles used in this example were extensively characterized for morphology, size, size distribution, shape, and surface charge. The uniformity of LB coating and its intactness were characterized by TEM (JEOL 1200-EX) and cryoEM (TF20 FEI Tecnai-G2). Particle size and ζ-potential were measured by a ZETAPALS instrument (Brookhaven Instruments Corporation). These measurements were performed with the nanoparticles suspended in water, PBS, and cell culture media plus 10% FBS at a particle concentration of 100 μg/mL.

The drug loading capacity of each carrier was determined by a subtraction method, as described previously (Meng et al. (2015) *ACS Nano,* 9(4): 3540-3557). Briefly, the amount of non-encapsulated irinotecan detected during purification ($m_1$) was determined by OD (360 nm) in a microplate reader (M5e, Molecular Device, USA) or through the use of HPLC (Raytest, Germany). Drug loading capacity was defined as DLC=[the total amount of irinotecan ($m_0$)–non-encapsulated irinotecan ($m_1$)]/[the total amount of particle (mMSNP or mlipid)]×100%. The drug retention stability was tested in 100% FBS at 37° C. for 24 h. Briefly, 40 μL of drug-loaded NPs (irinotecan: 10 mg/mL) was added to 1 mL of serum at 37° C., with continuous shaking. The mixture was centrifuged at set time intervals, using a centrifugal filter separation device (MW cutoff of 10K). The released irinotecan was quantified in a microplate reader or by HPLC. A serum filtrate without NPs was used as a control. The stability of both carriers was also tested through a lyophilization procedure. Briefly, Ir-MSNPs were suspended in 5% dextrose. The sample was lyophilized at −60° C. overnight and stored in a −80° C. freezer. The stored samples were resuspended in water by gentle vortexing, following which the suspended solutions were characterized for size, ζ-potential, and drug release as described previously.

Cell Culture.

An immortalized cell line derived from a spontaneously developed tumor in a transgenic KrasLSL-G12D/+, Trp53LSL-R172H/+, Pdx1-Cre mouse was kindly provided by Dr. Andrew Lowy at UC San Diego. PANC-1 cells were purchased from American Type Culture Collection (ATCC). Both cell types were cultured in DMEM, containing 10% FBS, 100 U/mL penicillin, 100 μg/mL streptomycin, and 2 mM L-glutamine. To allow bioluminescence tumor imaging in an IVIS system, both cells were permanently transfected with a luciferase-based lentiviral vector in the UCLA vector core facility, as previously described (Meng et al. (2015) *ACS Nano,* 9(4): 3540-3557). Following a limiting dilution protocol to select single cell clones, the KPC-luc and PANC-1-luc cell populations were used to develop PDAC models.

Assessment of Maximum Tolerated Dose.

The MTDs of free and encapsulated irinotecan formulations were determined using a protocol from the Toxicology and Pharmacology Branch (dtp.nci.nih.gov/branches/tpb/default.htm) at the National Cancer Institute (Drummond et al. (2006) *Cancer Res.,* 66(6): 3271-3277). Two healthy male BALB/c mice were IV injected with a 50 mg/kg (C1 dose) equivalent of free or encapsulated irinotecan. This was followed by a dose escalation factor of 1.8 to obtain the Cn dose, which results in animal death within 24 h after the last administration. The second round of dose-seeking began with the Cn-1 dose and utilized a 1.15 escalation factor (n=2) to find the MTD, which is defined as the absence of mortality or morbidity. The MTD was validated by injecting six mice, which were followed for 15 days to determine the absence of morbidity, mortality, or >15% weight loss.

Establishment of a KPC-Derived Orthotopic Tumor Model in Immunocompetent Mice.

Female B6/129 mice (~8 weeks) were purchased from The Jackson Laboratory and maintained under pathogen-free conditions. All animal experiments were performed with protocols approved by the UCLA Animal Research Committee. To grow orthotopic xenografts, the mice were anesthetized with isoflurane, followed by IP injection of 50 mg/kg ketamine and 10 mg/kg xylazine. The surgical site was shaved to leave a margin of 1 cm around the incision site and sterilized by scrubbing with betadine and 70% ethanol. The mice were positioned for surgery on a heating pad, and the incision site in the left flank was draped with sterile gauze. A surgical incision of 0.5-0.7 cm was made to expose the pancreatic injection site, followed by an injection of 50

μL of DMEM/Matrigel (1:1 v/v) containing 2×10⁶ KPC-luc cells into the pancreatic tail by a 27 gauge needle. The fascial layers were closed with absorbable sutures (PDS II, Ethicon) and the skin with nonabsorbable sutures (PROLENE, Ethicon). The mice were kept on the warming pads until full recovery from the anesthesia and then transferred to clean cages. The efficacy study was performed in tumor-bearing mice approximately 2 weeks after implantation, at which point the primary tumors had grown to ~0.5 cm, without evidence of macroscopic tumor metastasis. For the biodistribution experiments, the tumor-bearing mice were used 3 weeks after tumor implantation, at which point the primary tumors had grown to a size of ~0.8 cm.

Systemic and Intratumoral Biodistribution of IV Injected NIR-Labeled Nanoparticles.

An IVIS (Xenogen) in vivo imaging system was used to study the biodistribution of NIR-labeled MSNPs and liposomes in the KPC-derived orthotopic model (n=3 mice). NIR labeling was performed by incorporating 0.1% w/w Dylight 680-DMPE in the LB of both the liposomal and MSNP carriers without drug (Meng et al. (2015) *ACS Nano*, 9(4): 3540-3557). For bioluminescence imaging of the tumor site, mice were injected IP with 75 mg/kg D-Luciferin. Reference fluorescence images for the tumor-bearing mice were captured before particle injection. NIR images were obtained over 48 h in animals IV injected with 100 mg/kg NIR-labeled particles. Following animal sacrifice, ex vivo images were obtained of excised tumors and major organs to quantitatively assess particle biodistribution. A small section of the tumor tissue was cryo-embedded, using the OCT reagent, and used to prepare tumor sections. The intratumoral distribution of the NIR-labeled particles was studied by confocal microscopy (SP2-1P-FCS, Leica) using a NIR laser. Nuclear staining of the same sections was performed by using Hoechst 33342 dye (blue). In animals treated with LB-MSNP, the tumor tissue and major organs were also used to assess the Si content by ICP-OES. Particle biodistribution was expressed as the % total injected dose (% ID) that could be shown to distribute to individual organs. In order to measure the irinotecan content in the tumor or other normal tissues, animals were injected with 60 mg/kg free or encapsulated irinotecan (particle dose, 120 mg/kg for MSNPs and 150 mg/kg for liposomes), followed by sacrifice after 24 h. HPLC analysis was performed on harvested tumor tissue, liver, spleen, kidney, intestines, and blood to determine irinotecan content.

HPLC Analysis.

The harvested tumor and organ samples were weighed and homogenized on ice. Following the extraction of 0.1 mL of plasma or tissue homogenate with 0.4 mL of an acidic solution (0.1 mol/L phosphoric acid/methanol, 1:4 v/v), the extracts were vortexed twice for 10 s and centrifuged at 13 000 rpm for 10 min. The irinotecan-containing supernatants were filtrated through 0.22 μm filters for HPLC analysis in a system containing a Knauer Smartline pneumatic pump, C18 column, K-2600 spectrophotometer, and Gina data acquisition software. The mobile phase, delivered at a flow rate of 1.00 mL/min, comprised a 3% triethylammonium acetate aqueous buffer (pH 5.5) and acetonitrile (73:27 v/v) (Noble et al. (2006) *Cancer Res.*, 66(5): 2801-2806). Twenty microliters of irinotecan-containing sample was injected to measure the drug absorption at 254 nm, typically eluted in 4.4 min. An irinotecan standard curve was generated over the concentration range of 0.05-100 μg/mL. Irinotecan content was expressed as % of injected dose per gram of tissue (% ID/g).

Efficacy Assessment Using the KPC-Derived Orthotopic Model.

Tumor-bearing B6/129 mice were randomly assigned to four groups, including eight animals per group. The mice were IV injected with free or encapsulated irinotecan to receive a dose of 40 mg/kg (i.e., a liposomal dose of 100 or 80 mg/kg MSNP) every 4 days. A maximum of eight injections were administered over a 28 day observation period. Saline injections served as a negative control. Tumor burden was monitored by IVIS imaging every 8 days and quantitatively expressed as bioluminescence imaging intensity in the operator-defined ROI. The statistical analysis of the differences between the groups was performed using a t-test (Excel software, Microsoft). All surviving mice were sacrificed at day 47, at which point all animals in the saline and drug-free group had died. The tumor tissue and major organs (GI tract, liver, spleen, heart, lung, and kidneys) were harvested for quantification of ex vivo bioluminescence image intensity.

Comparison of the Toxicity Potential of Different Irinotecan Formulations.

Major tissues collected during the efficacy testing experiment (liver, kidney, spleen, stomach, and intestines) were fixed in 10% formalin, followed by paraffin embedding. Tissue sections were stained by H&E for histological analysis and also used for IHC analysis of the expression of activated (cleaved) caspase-3. The slides were read in a blinded fashion by an experienced veterinary pathologist. The second approach for assessing bone marrow toxicity used three IV administrations, 2 days apart, of free drug and carrier formulations at 40 mg/kg in healthy mice. The animals were sacrificed on day 7, and the sternum was used for fixation in 10% formalin, decalcification, paraffin embedding, and H&E staining. We also collected blood for differential white cell counting by the UCLA Division of Laboratory Animal Medicine (DLAM) diagnostic laboratory services. To understand the mechanism of differential liver toxicity by free drug and the carriers, mice receiving a single injection of the dose equivalent of 60 mg/kg irinotecan were sacrificed after 24 h. The liver tissues were cryo-embedded for immunofluorescence staining of KCs and the expression of activated caspase-3, using a FITC-labeled anti-F4/80 antibody or a RITC-conjugated secondary antibody to identify KC and cleaved caspase-3, respectively. Hoechst 33342 dye was used to localize the cellular nuclei in the same sections. The stained slides were examined under a confocal microscope (Observer D1, Zeiss).

Statistical Analysis.

Comparative analysis of the differences between groups was performed using the two-sided Student's t-test (Excel software, Microsoft). A statistically significant difference was determined at $p<0.05$. Values were expressed as mean±SD or SEM of multiple determinations, as stated in the figure legends.

Example 2

Pancreatic ductal adenocarcinoma (PDAC) is an incurable disease with a 5-year survival rate less than 5%. Currently, first line chemotherapy for PDAC includes treatment by gemcitabine (GEM) (single agent therapy) or use of a four-drug regimen, which includes leucovorin, 5-FU, oxaliplatin, and irinotecan, a.k.a. FOLFIRINOX. While FOLFIRINOX has an increased PDAC response rate compared to GEM, i.e. 31.6% versus 9.4%, this regimen is far more toxic and therefore restricted to a minority of advanced stage PDAC patients with good functional status (Conroy et al. (2011) *N Engl. J. Med.* 364: 1817-1825). Irinotecan contributes in a major way to FOLFIRINOX toxicity due to adverse effects on the bone marrow (e.g., ~60% incidence of neutropenia), as well as the G.I.T. (e.g., vomiting, diarrhea, nausea, anorexia in ~50% of patients) (Ueno et al. (2007) *Cancer Chemother. Pharmacol.* 59(4): 447-454). There is an unmet need to develop a FOLFIRINOX regimen that is less toxic, including the reducing the toxicity of irinotecan.

Use of nanoparticle carriers to deliver irinotecan provides a potential solution to reducing the toxicity of this drug, as illustrated by the delivery of irinotecan by liposomal (Messerer et al. (2004) *Clin. Cancer Res,* 10(19): 6638-6649; Drummond et al. (2006) *Cancer Res.,* 66(6): 3271-3277) or polymer-based nanocarriers (Onishi et al. (2003) *Biol. Pharmaceut. Bull.* 26(1): 116-119). At pre-clinical level, the benefits of using these nanocarriers include toxicity reduction, increased antitumor efficacy, and enhanced survival rates of various murine PDAC models. To date, only a few irinotecan carriers have been tested in clinical trials, including liposomal formulations that promote drug loading by an ionophore, A23187, (Irinophore C) or a protonating entrapment agent, triethylammonium sucrose octasulfate ($TEA_8SOS$). The therapeutic efficacy of MM-398 is dependent on the encapsulation and trapping of iriotecan in the liposome through the use of a multivalent anionic trapping agent, $TEA_8SOS$. $TEA_8SOS$ leads to the protonation of irinotecan diffusing across the lipid bilayer, converting it into a hydrophilic component that cannot exit the lipid bilayer. The drug is therefore trapped at concentrations that exceed the passive encapsulation by a liposome bilayer 10-fold (Drummond et al. (2006) *Cancer Res.,* 66(6): 3271-3277). MM-398, is currently in Phase 3 trials by Merrimack Pharmaceuticals(www.merrimackpharma.com) (Poster presentation by Hoff et al., Society for Medical Oncology, 2014). This poster can be viewed at //merrimackpharma.com/sites/default/files/documents/ESMOGI2014MM398.pdf). In the AACR 2012 meeting, the Merrimack company published an abstract, containing a statement that "MM-398 induces tumor regression in multiple mouse models of pancreatic cancer, including an orthotopic metastatic model." The subcutaneous models included BxPC3, AsPC-1, Panc-1 and MiaPaCa. The orthotopic implant in the pancreas was carried out with BxPC3. No detailed data were presented. IV administration of MM-398 has been shown to induce complete tumor regression in various PDAC tumor models in mice, including inhibition on metastatic tumor foci formation (Drummond et al. (2006) *Cancer Res.* 15(66): 3271-3277). Treatment of 417 patients in a Phase 3 PDAC trial with a combination of MM-398, 5-FU and leucovorin showed increased overall survival (6.1 months) compared to 1.9 months in people control receiving 5-FU and leucovorin (Hoff et al. ESMO Poster, www.merrimackpharma.com).

In this example, we describe a novel mesoporous silica nanoparticle (MSNP) platform, capable of achieving active loading, entrapment, and encapsulation of irinotecan by a nanocarrier that has superior capabilities compared to the liposomal equivalent. Synthesis of these particles was achieved by the rapid encapsulation of $TEA_8SOS$ in the porous interior of the particles by a supported lipid bilayer LB. Subsequent incubation of these particles in an irinotecan solution allowed active entrapment of irinotecan, which diffuses across the bilayer and is then protonated by $TEA_8SOS$. Comparative analysis was performed between irinotecan-loaded LB-MSNP versus an in-house synthesized liposomal equivalent of MM-398. This analysis demonstrates superior loading capacity, loading efficiency, and release profile by the MSNP carrier. We also showed a similar in vitro effectiveness and in vivo toxicity reduction compared to the in house MM-398 liposome. We are currently conducting animal efficacy studies to compare these carriers in subcutaneous and orthotopic human PDAC tumor models.

We believe the LB-MSNP mediated nano-encapsulation and targeted delivery of irinotecan will improve the clinical use of FOLFIRINOX by decreasing toxicity, including reduced toxicity of irinotecan in the bone marrow and GIT. This discovery permits an IV injectable, efficient, biocompatible, and commercially competitive irinotecan formulation capable of outperforming liposomal carriers because of loading capacity and sufficient cancer site drug release. In certain embodiments this invention could also be employed as an effective design principle for delivering other weak basic molecules (pKa >7.0) that can be used for cancer treatment as well as treatment of other diseases.

The following description illustrates certain embodiments of a carrier design for irinotecan loading as well as the comparative analysis of the LB-MSNP carrier with an in-house-synthesized liposomal formulation similar to MM-398.

Irinotecan Encapsulation by a LB-MSNP that Also Includes a Trapping Agent to Achieve Additional Active Loading In order to provide effective loading of irinotecan by LB-MSNP, we adapted our recently discovered biofilm procedure for drug loading by first encapsulating the trapping agent, $TEA_8SOS$, which is then responsible for irinotecan import and retention by protonating the drug diffusing across the supported LB to enter the pores. This leads to stable entrapment of irinotecan in the sealed MSNP pores, creating a gradient for further diffusion across the LB until equilibrium is reached. This actually allows the drug to accumulate at high concentration with the assistance of the large surface area of the porous interior and the trapping agent mediated drug retention. In certain embodiments the synthesis procedure is comprised of four parts, namely, MSNP core synthesis, synthesis of $TEA_8SOS$ loaded LB-MSNP, active loading of irinotecan into the particles through the action of $TEA_8SOS$, and finally purification of the carrier.

Chemicals:

Tetraethyl orthosicate (TEOS, ≥99.0%, Lot #BCBK9540V), triethanolamine (≥99.0%, Lot #BCBH9036V), cetyltrimethylammonium chloride solution (CTAC, 25 wt. % in water, Lot #STBC7888V), triethylamine (TEA, ≥99.0%, Lot #SHBD9006V) were purchased from Sigma-Aldrich, USA. Distearoylphosphatidylcholine (DSPC, >99.0% Lot #180PC-147), methoxypoly(ethylene) glycol (PEG2000)-derivatized distearoylphosphatidylethanolamine (DSPE-PEG2000, >99.0%, Lot #180PEG2PE-122), and cholesterol (Chol, >98.0%, Lot #CH-94) were purchased from Avanti Polar Lipids, USA. Sucrose octasulfate sodium salt (Lot #1-TMH-175-4) was purchased from Toronto Research Chemicals, Inc, Canada. Irinotecan hydrochloride trihydrate (IRIN, ≥99.0%, Lot #RCN-104) was purchased LC Laboratories, USA. All chemicals were directly used without further purification.

Sol-Gel Synthesis of MSNP and Template Removal

MSNP cores were synthesized by a minor modification of our sol/gel procedure. The reaction was carried out in a 500 mL conical flask. 50 mL CTAC (25%) was mixed with 150 mL $H_2O$, while stirring at 350 rpm for 15 min at 85° C. This was followed by the addition of 8 mL 10% triethanolamine at 85° C. for 30 min. The silica precursor, TEOS (7.5 mL), was added drop-wise to the mixture at a rate of 1 mL/min controlled by a peristaltic pump. To achieve the synthesis of particles with primary size of ~60 nm, the solution was stirred at 350 rpm at 85° C. for 20 min. To remove the surfactant, the particles were washed by menthol and HCl (500:19, v/v) at room temperature for 24 hours. The particles were centrifuged at 10,000 rpm for 60 min and washed 3 times in menthol. In order to obtain high quality MSNP cores, frequent quality checks were performed, including DLS measurements to monitor particle aggregation and contamination, TEM for visualizing particle morphology, and infrared spectroscopy & cytotoxicity assays to check whether the detergent was thoroughly removed.

Preparation of Irinotecan Loaded LB-MSNP Using $TEA_8SOS$ as Trapping Agent

Figure 5:
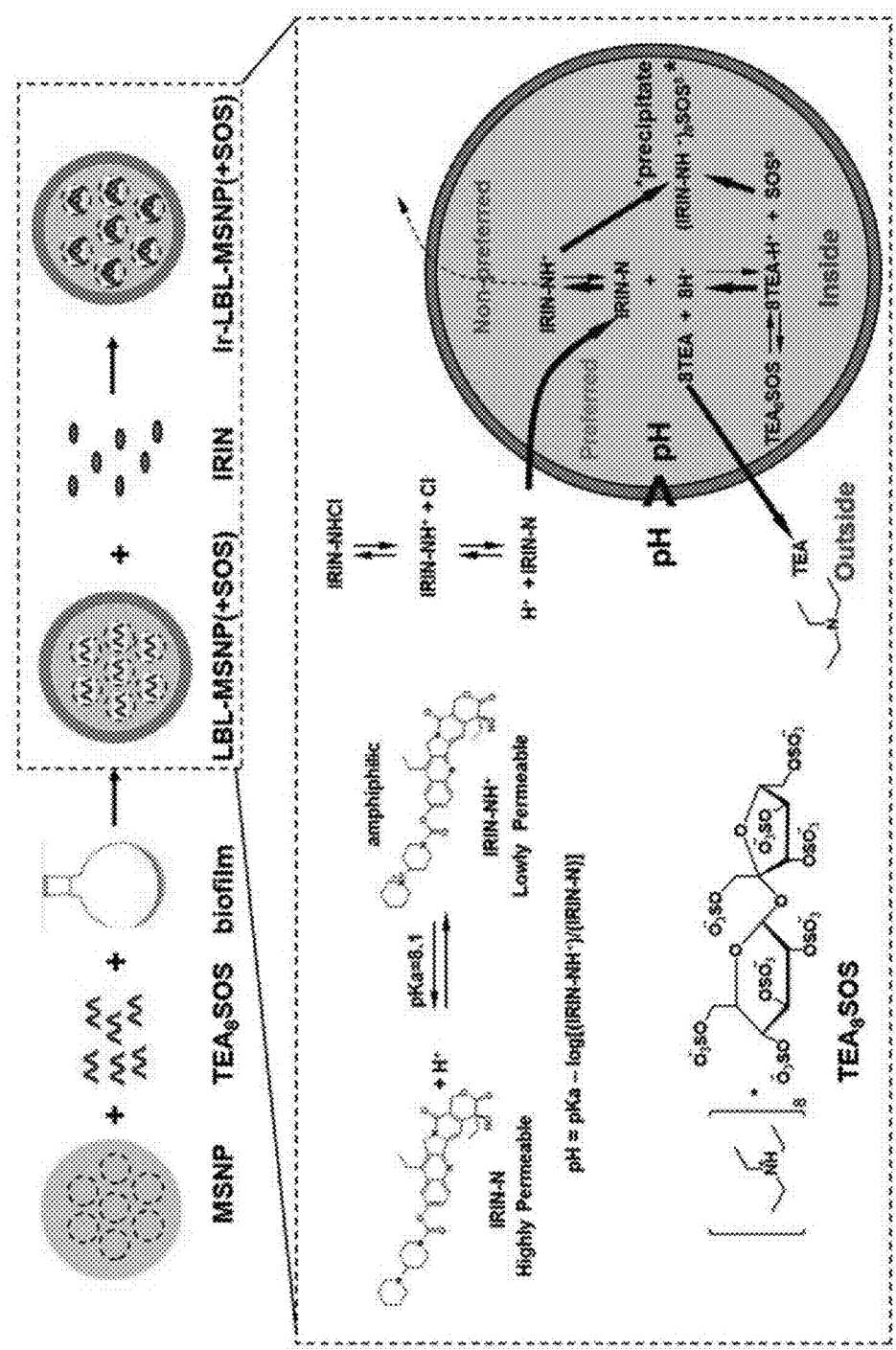
FIG. 5 illustrates a scheme depicting the synthesis procedure of a lipid bilayer coated mesoporous silica nanoparticle (LB-MSNP) and mechanism of $TEA_8SOS$ mediated irinotecan (IRIN) loading, in accordance with one or more embodiments of the invention. MSNP was synthesized using sol/gel chemistry. $TEA_8SOS$ (synthesized in-house) was first incubated with MSNP. This was followed by depositing a LB coat using our biofilm technique (Meng et al. (2015) *ACS Nano*, 9(4): 3540-3557). $TEA_8SOS$ soaked MSNPs were added to the dry lipid biofilm (e.g. DSPC/cholesterol/DSPE-PEG in a molar ratio of 3:2:0.15) followed by pore sealing upon sonication. After removal of the free trapping agent, $TEA_8SOS$ loaded LB-MSNP was incubated with irinotecan. This allows free, lipophilic irinotecan diffusing into the particle to be protonated and trapped in the pores. This reaction proceeds as follows: Due to the presence of the trapping agent inside the LB-MSNP, the equilibrium of "$TEA_8SOS \leftrightarrow 8\ TEA\text{-}H^+ + SOS^{8-}$" leads to efflux of the lipid permeable triethylamine (TEA) into the particle incubation medium. The $H^+$ release inside the particles creates a pH gradient that leads to the protonation of lipophilic irinotecan, which diffuses through the LB. The protonated IRIN, which is lipid impermeable, interacts with $SOS^{8-}$ to form a precipitate, thus leading an efficient IRIN entrapment in LB-MSNP.

In order to establish the optimal procedure for irinotecan loading by LB-MSNP, we developed a novel approach in which we trapped the protonating agent in the particles, using a biofilm procedure (previously disclosed), before incubating the particles in the irinotecan solution. This allows the lipophilic irinotecan to diffuse through the LB membrane with subsequent protonation in the pores, leading to drug entrapment against a concentration gradient (see FIG. 5). Considering the loading capacity and drug release behavior, we optimized the irinotecan loading procedure by systemically varying loading time, trapping agent concentration, LB-MSNP concentration, irinotecan concentration, and irinotecan/LB-MSNP ratio. This allowed us to achieve an irinotecan loading capacity of 85% (irinotecan/MSNP, w/w), which exceeds the drug loading capacity in the absence of the trapping reagent ~4-fold. This amounted to twice the loading capacity of in-parallel synthesized liposomal version of MM-398. For further discussion, we have designated the irinotecan-loaded LB-MSNP as "Ir-LB-MSNP(+SOS)".

Synthesis of $TEA_8SOS$ Loaded LB-MSNP

Preparation of Trapping Agent Triethylammonium Sucrose Octasulfate ($TEA_8SOS$) from Commercially Available Sucrose Octasulfate Sodium Salt.

We used an ion-exchange reaction to synthesize $TEA_8SOS$ from its precursor, the sodium salt of sucrose octasulfate. Briefly, 500 mg of the precursor salt was dissolved in 1 mL D.I. water, yielding an aqueous solution of 500 mg/mL. This solution was passed through a cationic Dowex 50WX8 resin ion-exchange column (15 mm in diameter and 8 cm in length, purchased from Sigma, Lot #MKBH8810V). Following the elution of the column with D.I. water, the sucrose sodium is converted to protonated octasulfate in the process. The collected sucrose octasulfonic acid was immediately titrated with trimethylamine (TEA) to a final pH of 5.5 to 6.0, resulting in the formation of $TEA_8SOS$. The $TEA_8SOS$ concentration was adjusted to ~80 mM, based on titration of the amount of TEA. The multivalent anionic $TEA_8SOS$ was stored in a 4° C. refrigerator before use.

Preparation of $TEA_8SOS$ Loaded LB-MSNP.

We adapted our previously disclosed biofilm technique for LB coating (PCT/US2014/020857 (UCLA disclosure 2013-534-2), which is incorporated by reference in its entirety) to encapsulate $TEA_8SOS$, before proceeding to irinotecan loading. Briefly, 100 mg empty MSNPs were soaked in 4 mL $TEA_8SOS$ aqueous solution (40 mM), using probe sonication for 30 minutes with 15/15 seconds on/off working cycle, at a power output of 32.5 W. The suspension was immediately added on top of the coated lipid biofilm, which occupied a ~30 cm² surface area at the bottom of a round-bottom flask (6 cm diameter). Following experimentation to achieve an optimal mix of lipid components (with the aim at stable coating without leaking), we decided on a mixture containing 228 mg DSPC/Chol/DSPE-PEG at molar ratio of 3:2:0.15. This mixture was dissolved in chloroform at 10 mg/mL. Biofilm formation was achieved by solvent evaporation over ~1 h, using a rotary evaporator connected to a vacuum system at room temperature. Following the addition of the 4 mL particle suspension to the biofilm, probe sonication was used for 30 minutes with 15/15 seconds on/off working cycle, at a power output of 32.5 W. Since the sonicated suspension contains coated particles, liposomes, and free $TEA_8SOS$, $TEA_8SOS$ LB-MSNP was purified using a chromatography procedure, in which a Sepharose CL-4B column (15 mm in diameter and 15 cm in length, purchased from Sigma, Lot #MKBP0885V) was eluted with a HEPES-buffer (5 mM HEPES, 5% dextrose, pH 6.5).

Use of $TEA_8SOS$-Loaded LB-MSNP for Active Irinotecan Loading.

Irinotecan was dissolved in a HEPES buffered solution (5 mM HEPES, 5% dextrose, pH 6.5) at concentration of 10 mg/mL. The drug solution was mixed with a $TEA_8SOS$ loaded LB-MSNP suspension at an irinotecan/particle ratio of 1:1 (w/w), and incubated in a water bath at 60° C. for 0.5 h. The reaction was terminated by placing the container in ice water for 10 min.

Particle Purification

The Ir-LB-MSNP(+SOS) was purified from the free liposomes and free irinotecan by particle centrifugation at 15,000 rpm for 10 minutes, followed by re-suspension in saline or 5% dextrose. The washing procedure was repeated 3 times.

Preparation of Control Formulations for Comparative Studies, Using the Ir-LB-MSNP (+SOS) Particles To conduct comparative analysis reflecting the unique properties of the Ir-LB-MSNP(+SOS) particles, we synthesized the LB-MSNP without the trapping agent, allowing the soaked irinotecan to be sealed off by the LB. We also prepared a liposomal equivalent of MM-398, prepared with the trapping agent, as well as a control liposome that encapsulates irinotecan, without the trapping agent.

Synthesis of Irinotecan LB-MSNP not Containing the Trapping Agent:

Empty MSNPs (40 mg) were placed in 4 mL irinotecan solution (in water, 10 mg/mL) with sonication for 5 min, and then stirred for another 4 h at room temperature. The irinotecan-soaked MSNP suspension was added to the dry lipid membrane (91 mg of a lipid mixture containing DSPC/Cholesterol/PE-PEG2000 at molar ratio of 3:2:0.15), followed by probe sonication for 30 minutes, using a 15/15 seconds on/off working cycle at a power output of 32.5 W. The particles were purified from free liposomes and free drug using centrifugation at 15,000 rpm for 10 minutes, followed by particle washing and re-suspension as described above. We refer to the particles without the trapping agent as "Ir-LB-MSNP (−SOS)".

In House Synthesis of a Liposomal Equivalent of the Commercially Developed Liposomal Preparation, MM-398.

The synthesis was carried out according to the published procedure for MM-398 by Drummond et al. (Cancer Res. 2006, 66, 3271-3277). Briefly, a mixture of lipids (212 mg lipid, DSPC/Chol/DSPE-PEG at a molar ratio of 3:2:0.015) was dissolved in 0.4 mL ethanol at 60-65° C. A 4 mL $TEA_8SOS$ solution (80 mM) was mixed with the lipid ethanol solution at the same temperature, followed by sonication in a water bath for 2 minutes. The lipid suspension was extruded 15 times through a polycarbonate membrane with 0.1 μm pore size at 60-65° C. Non-entrapped $TEA_8SOS$ was removed by chromatography over a Sepharose CL-4B column, eluted with a HEPES-buffer (5 mM HEPES, 5% dextrose, pH 6.5). The irinotecan solution (10 mg/mL aqueous solution containing HEPES-buffer, 5 mM HEPES, and 5% dextrose at pH 6.5) was mixed with the TEA$_8$SOS pre-loaded liposome suspension (irinotecan:lipid=1:2.1 w/w), and then incubated in a water bath at 65° C. for 0.5 h. The reaction was terminated by placing the mixture in ice water for 10 min. The irinotecan-loaded liposomes were then purified by removing the free irinotecan over a Sephadex G-25 column (15 mm in diameter and 15 cm in length, Sigma, Lot #019K1077), eluted by HEPES-buffered saline (5 mmol/L HEPES, 145 mmol/L NaCl, pH 6.5). We will refer to the in-house synthesized liposomal formulation as "Ir-Lipo(+SOS)".

Synthesis of Irinotecan-Encapsulated Liposomes, without the Use of a Trapping Agent.

We also synthesized a liposome that uses a passive encapsulation approach. Briefly, a mixture of lipids (53 mg lipid, DSPC/Chol/DSPE-PEG at molar ratio of 3:2:0.015) was dissolved in 0.1 mL ethanol at 60° C. to 65° C. 1 mL irinotecan solution (in water, 10 mg/mL) was mixed with the lipid ethanol solution at 60° C. to 65° C., followed by water bath sonication for 2 minutes. The lipid suspension was extruded 15 times through a polycarbonate membrane with 0.1 um pore size at 60° C. to 65° C. The drug-laden liposomes were purified by removing the free irinotecan using a Sephadex G-25 column, eluted with HEPES-buffered saline (5 mmol/L HEPES, 145 mmol/L NaCl, pH 6.5). We refer to this liposomal preparation as "Ir-Lipo(−SOS)".

Comparative Analysis of Ir-LB-MSNP(+SOS) with Control Irinotecan Formulations.

Physicochemical Characterization of Ir-LB-MSNP(+SOS) and Control Formulations.

Table 3 shows the hydrodynamic sizes, size distribution and surface charge of Ir-LB-MSNP(+SOS) compared to the control formulations. Ir-LB-MSNP(+SOS) has a hydrodynamic size of 110~130 nm with a polydispersity index (PDI) of ~0.1. This particle showed a negative zeta potential value in pure water, i.e. −24.7 mV. The zeta potential changed to −2.95 mV in PBS, and −3.27 mV in complete DMEM culture medium. These physicochemical parameters were similar to the control formulations, such as Ir-Lipo(−SOS), Ir-Lipo(+SOS), and Ir-LB-MSNP(−SOS), in different solutions.

Table 4 shows the loading capacity and loading efficiency of the LB-MSNP with and without the use of the trapping agent. The loading capacity=(Total irinotecan−irinotecan in supernatant)/(the mass of MSNP or liposome)×100%. The loading efficiency is defined as [(Total irinotecan−irinotecan in supernatant)/total irinotecan]×100%. For liposomes, the loading capacities were 4.12% w/w and 45.2% w/w in the absence or presence of 80 mM trapping reagent. The loading efficiencies of irinotecan in the liposome platform, increased from 8.71% to 95.5% as a result of the action of the trapping agent. This is in agreement with the published data (Cancer Res. 2006, 66, 3271) for synthesized MM-398 liposomes. Following experimentation to obtain the most stable particle formulation, we used 40 mM of trapping agent to synthesize the LB-MSNP. Following incubation with irinotecan, we achieved an Ir-LB-MSNP(+SOS) with loading capacity 83.5% w/w, compared to a loading capacity of 22.5% w/w for LB-MSNP without the trapping reagent. While the Ir-LB-MSNP used less trapping agent (40 mM), it actually resulted in 2× loading capacity when compared to the in house MM-398 liposome that contains 80 mM trapping agent.

TABLE 4

Loading capacity and efficiency of LB-MSNP vs liposomes in the absence and presence of the TEO$_8$SOS trapping agent

| NP | IRIN in feed (g/mol phospholipid) | Loading capacity IRIN/MSNP w/w | Loading capacity IRIN/lipid w/w | Encapsulation efficiency |
|---|---|---|---|---|
| Ir-Lipo(−SOS) | 500 | N/A | 4.12% | 8.71% |
| Ir-Lipo(+SOS) | 500 | N/A | 45.2% | 95.5% |
| IF-LBL-MSNP(−SOS) | 500 | 22.5% | N/A | 22.5% |
| Ir-LBL-MSNP(+SOS) | 500 | 83.5% | N/A | 83.5% |

Figure 6A:
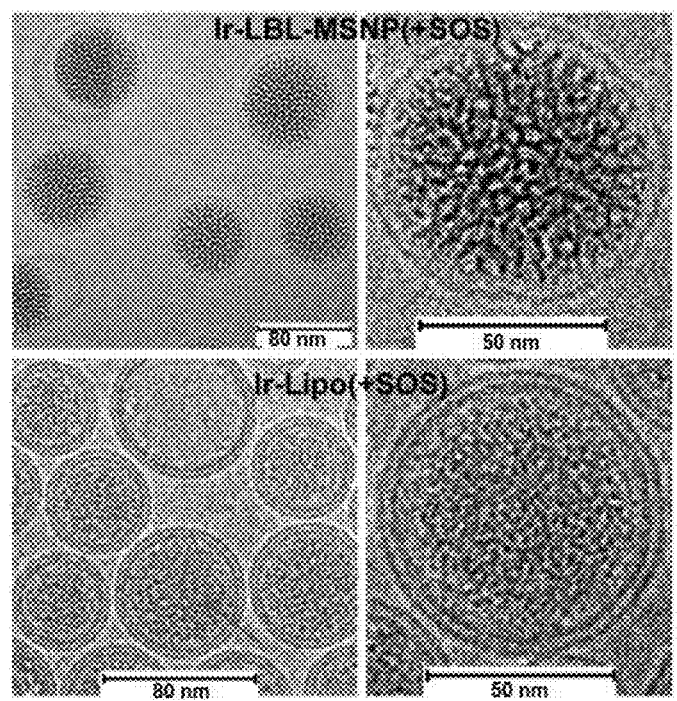
FIGS. 6A and 6B show morphology and drug release profiles of irinotecan loaded LB-MSNP containing the trapping reagent (Ir-LB-MSNP(+SOS)) and irinotecan loaded liposome using trapping reagent (Ir-Lipo(+SOS)), in accordance with one or more embodiments described herein.

We also performed cryoEM analysis to visualize the morphology of Ir-LB-MSNP(+SOS). This confirmed the uniform coating of the MSNP surface by a lipid bilayer (FIG. 6A, upper panel). High magnification cryoEM images demonstrated primary particle sizes of ~80 nm, with complete surface coating by a bilayer ~7.1 nm thick. The zoom-in image confirmed the presence of an intact lipid coat, while also demonstrating the presence of high density material in the pores; this material represents the irinotecan-

TABLE 3

Size and zeta potential of Ir-loaded particles in different incubation media.

| NP | DLS hydrodynamic size (nm) (PDI) | | | Zeta Potential | | |
|---|---|---|---|---|---|---|
| | Water | PBS | DMEM + 10% FBS | Water | PBS | DMEM + 10% FBS |
| Ir-Lipo(−SOS) | 101.7 (0.113) | 95.5 (0.014) | 76.5 (0.275) | −11.7 | −4.95 | −4.63 |
| Ir-Lipo(+SOS) | 102.0 (0.112) | 104.7 (0.067) | 98.6 (0.172) | −13.4 | −2.26 | −4.38 |
| IF-LBL-MSNP(−SOS) | 129.4 (0.140) | 116.1 (0.087) | 110.2 (0.17) | −22.4 | −5.87 | −3.57 |
| Ir-LBL-MSNP(+SOS) | 128.0 (0.107) | 125.7 (0.112) | 121.1 (0.200) | −24.7 | −2.95 | −3.27 |

Hydrodynamic size, size distribution and surface charge of different irinotecan-loaded particles. The particles were dispersed in water, PBS and DMEM media supplemented with 10% FBS at a MSNP or lipid concentrations of ~0.1 mg/mL. Size and zeta potential were measured by ZETAPALS particle sizer and zeta potential analyzer (Brookhaven instruments Corp.). The results represent the mean of three measurements TEA$_8$SOS complex. We observed occasional particles that were encapsulated by a slightly larger liposome that was not tightly adhered to the particle surface, however, the LB layer remains intact. The image of Ir-Lipo(+SOS) showed a liposome structure of ~75 nm with a unilaminar bilayer ~6.5 nm thick (FIG. 6A, lower panel). High magnification cryoEM provides sufficient resolution to see the high density IRIN-TEA$_8$SOS precipitates inside the liposome (red arrows).

Figure 6B:
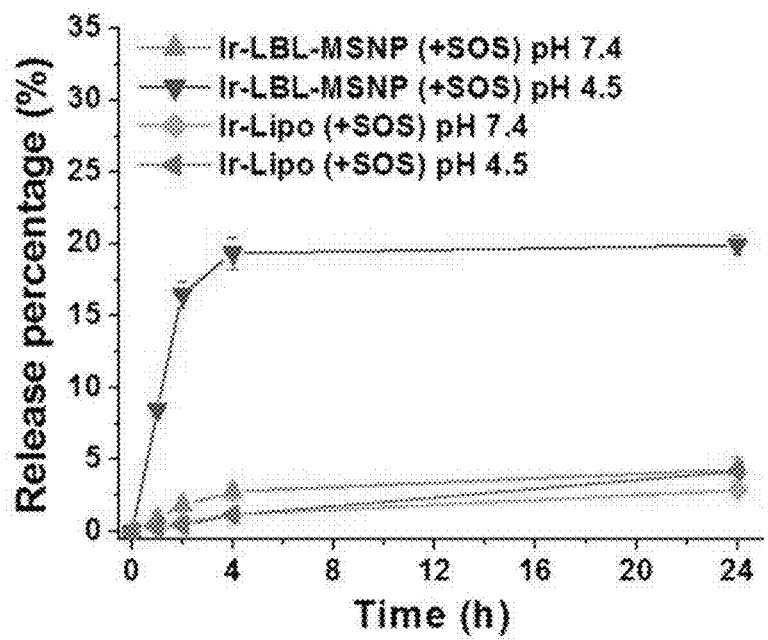

In order to assess the stability of each formulation, we compared the drug stability in PBS (pH=7.4) at 37° C. (FIG. 6B), with an intention to estimate the irinotecan stability in the blood stream. This demonstrated that Ir-LB-MSNP(+SOS) is very stable in PBS, resulting in <5% release over 24 hours. A comparable stability in PBS was found in the in house MM-398 liposome.

Due to the elevated glucose uptake, glycolysis, lactic acid production (Warburg effect), abnormal blood perfusion, and presence of a dense stroma, the pH value of PDAC is acidic (Wojtkowiak, et al. (2012) *Cancer Res.* 72(16): 3938-3947; Estrella et al. (2013) *Cancer Res.* 73(5):1524-1535). Thus, we also looked at the drug release profile in an acidic pH condition. The tumor pH classically drops to ~6.5, but can be as low as ~5.5 (Jähde et al. (1992) *Cancer Res.* 52: 6209-6215). The pH could further drop to <5 in lysosomal compartments when the particles were taken up by PDAC cells (Mindell et al. (2012) *Annu Rev Physiol.* 74: 69-86). Thus, we performed drug release experiment in the phagolysosomal simulant fluid (PSF, pH=4.5). In PSF, a rapid irinotecan release (i.e. 20% over 4 hours) could be seen in LB-MSNP. However, in the in house MM-398 formulation, we found a significantly slower drug release profile in PSF, i.e. only ~4% drug release in 24 hours.

Figure 7:
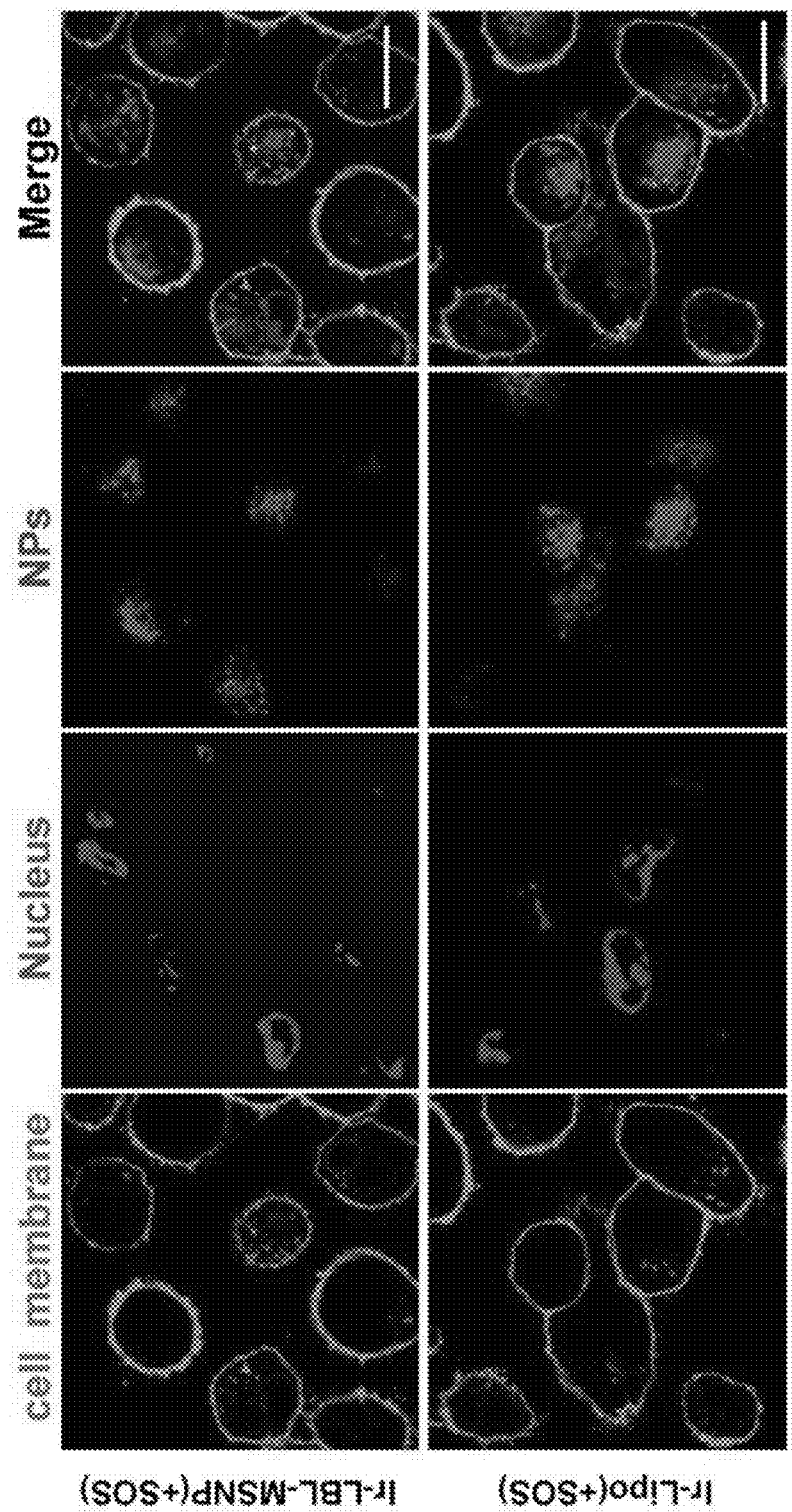
FIG. 7 illustrates cellular uptake and intracellular distribution of Ir-LB-MSNP(+SOS) and Ir-Lipo(+SOS) as determined by confocal microscope, in accordance with one or more embodiments described herein. LB-MSNPs and liposomes were fluorescently labeled by 0.1% w/w Texas red-DHPE in the lipid bilayer. Both particles were incubated with PANC-1 cells for 24 hours and then washed three times in PBS. After cell fixing and washing with PBS, cell membranes were stained with WGA 488 and nuclei with Hoechst dye. The slides were visualized using a confocal microscope.
Figure 8:
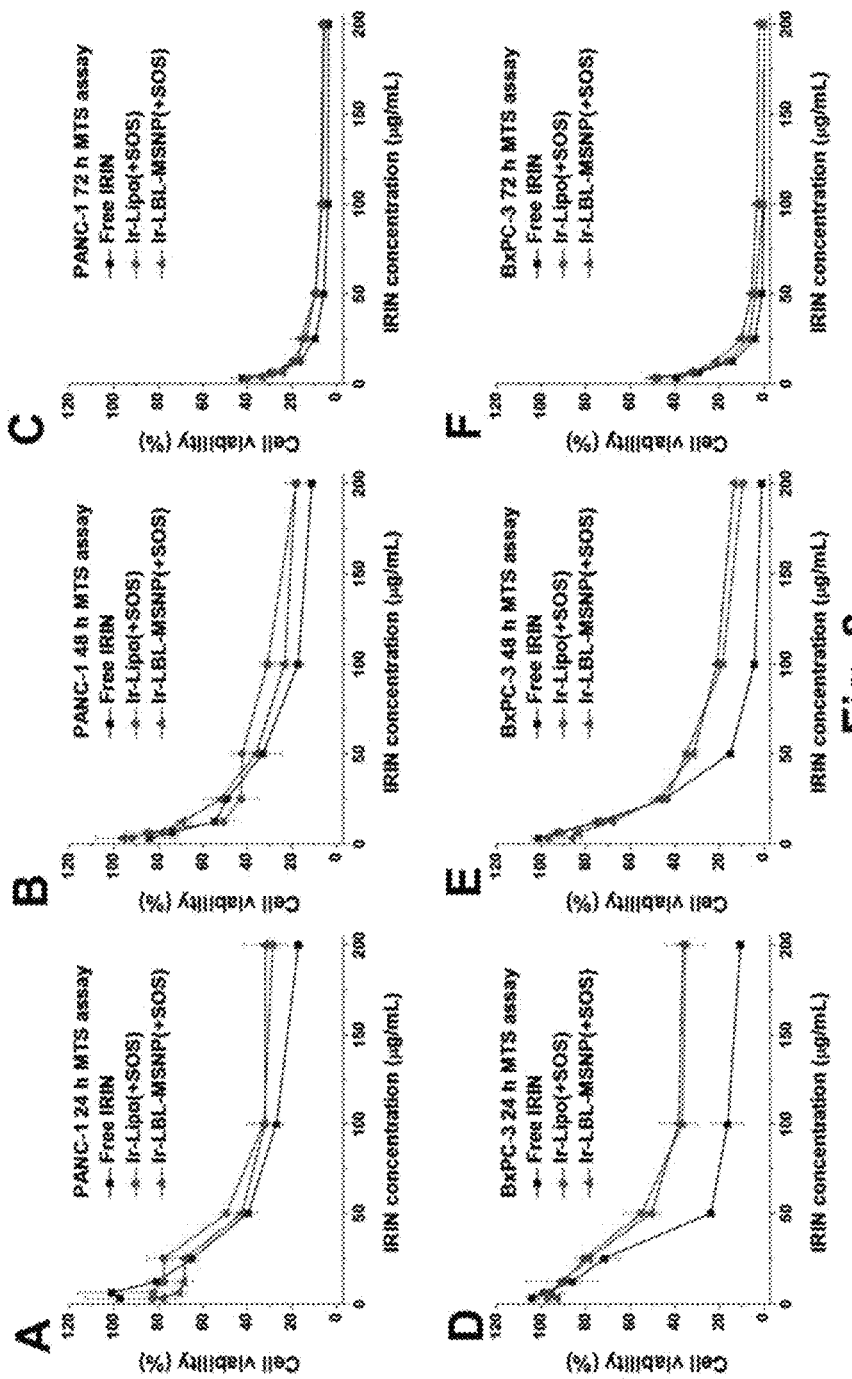
FIG. 8, panels A-F, illustrates comparative cytotoxicity analysis of Ir-LB-MSNP(+SOS) versus Ir-Lipo(+SOS) or free drug, in accordance with one or more embodiments of the invention.

Cellular Uptake and Killing Efficiency of Ir-LB-MSNP(+SOS) in Cultured PDAC Cells Confocal microscopy, utilizing Texas red-labeled LB-MSNP or liposomes, demonstrated abundant cellular uptake in a pen-nuclear distribution in PANC-1 cells (FIG. 7). We also employed a MTS cytotoxicity assay to determine the effect of Ir-LB-MSNP(+SOS) on PANC-1 and BxPC3 cells during treatment with incremental irinotean concentrations. We compared the effect of these particles with free drug and Ir-Lipo(+SOS) controls. While the free drug is more effective in killing over 24 hours, both Ir-LB-MSNP(+SOS) and the liposomes showed comparable killing at 72 hours in both cell types (FIG. 8). Empty nanoparticles do not induce toxicity at concentrations up to 500 µg/mL over 48 hours.

Comparative Analysis of the In Vivo Toxicological Effects of Ir-LB-MSNP(+SOS) vs Ir-Lipo(+SOS) in Mice.

Maximum Tolerated Dose (MTD).

We began the in vivo toxicity studies by determining the MTD of the various irinotecan formulations. This was accomplished using the NCI protocol from the Toxicology and Pharmacology Branch (dtp.nci.nih.gov/branches/tpb/default.htm). Two healthy male BALB/c mice were IV injected with 50 mg/kg ($C_1$ dose) free or encapsulated drug. We then used a dose escalation factor of 1.8 to determine the $C_n$ dose where both animals (n=2) died within 24 hours. After treatment with free or encapsulated irinotecan. The second round of dose-seeking began with $C_{n-1}$ dose, and utilized a 1.15 escalation factor (n=2) to find the MTD, where there was no mortality or serious morbidity. The MTD was further validated by injecting 5 mice, and following them for 15 days to ascertain that there was no morbidity, mortality or >20% weight loss. Our results demonstrated that the MTD dose values of Ir-LB-MSNP(+SOS), Ir-Lipo(+SOS), and free irinotecan were 295 mg/kg, 350 mg/kg, and 60 mg/kg, respectively. Compared to free drug, nano formulations showed approximately 5-fold higher MTD doses, clearly suggesting the ability of toxicity reduction in use of both LB-MSNP and liposomal formulations.

Histological Analysis.

Figure 9:
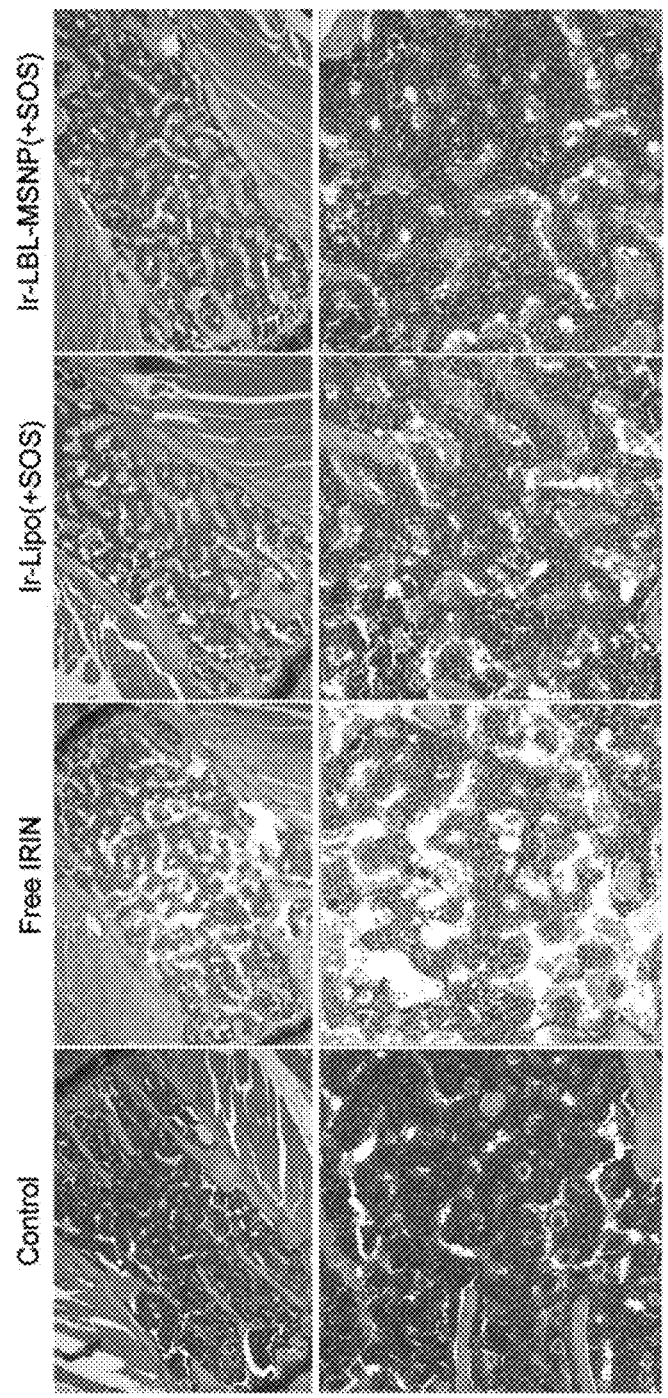
FIG. 9 shows a histological analysis of the bone marrow, in accordance with one or more embodiments described herein. Bone marrow histology after treatment with free IRIN, Ir-Lipo(+SOS) and Ir-LB-MSNP(+SOS). BALB/c male mice was IV injected with IRIN, Ir-Lipo(+SOS) or Ir-LB-MSNP(+SOS) at a drug dose of 60 mg/kg. After 24 hours, the mice were sacrificed and the sternum was collected and fixed in 10% formalin. The sections were stained with hematoxylin-eosin (H&E), and examined by light microscopy. The data indicate that both LB-MSNP and liposomal formulations lowered the bone marrow depletion induced by irinotecan. Severe bone marrow damage and apoptosis can be seen in free drug group.
Figure 10:
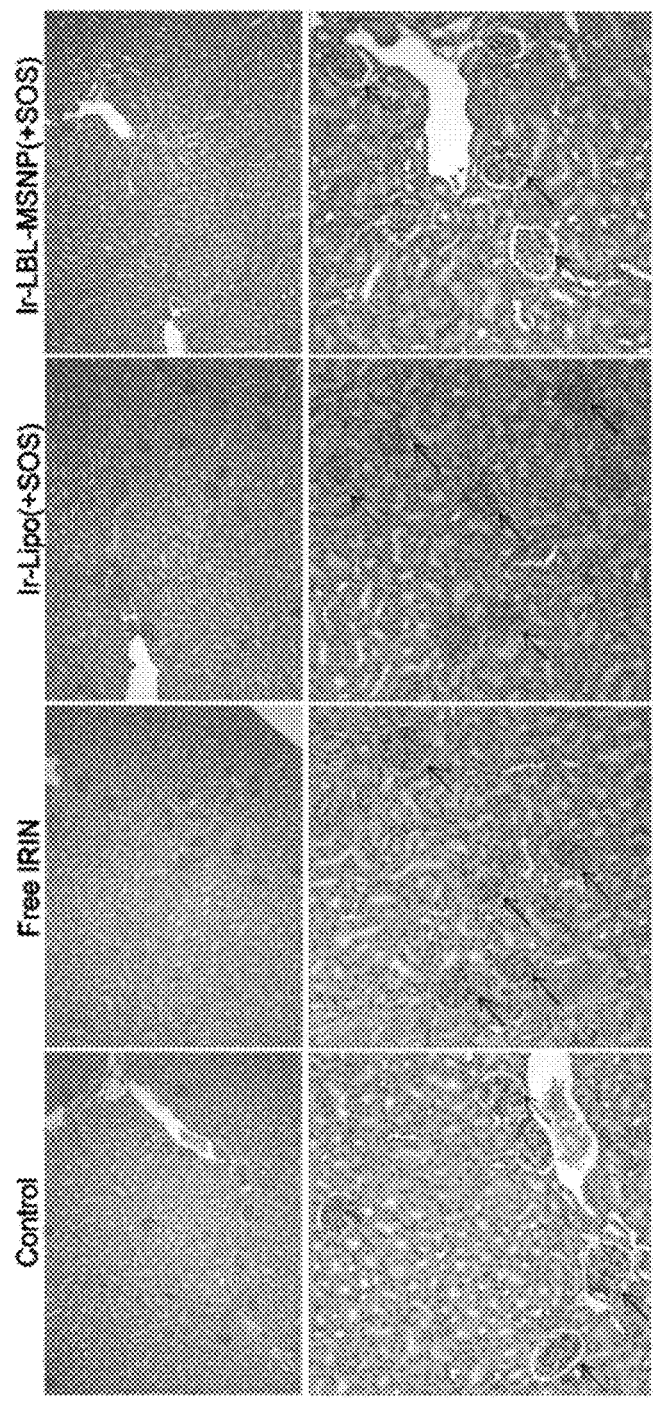
FIG. 10 shows a histological analysis of the kidney, in accordance with one or more embodiments described herein. Histological analysis of the kidney after treatment with free IRIN, Ir-Lipo(+SOS) and Ir-LB-MSNP(+SOS). BALB/c male mice was IV injected with IRIN, Ir-Lipo(+SOS) or Ir-LB-MSNP(+SOS) at a drug dose of 60 mg/kg. After 24 hours, the mice were sacrificed and the kidneys were collected and fixed in 10% formalin, followed by paraffin embedding. Tissue sections of 4 µm thickness were mounted on glass slides. The sections were stained with hematoxylin-eosin (H&E), and examined by light microscopy. Representative histological images showing swelling and edema of Bowman's space (arrows marked) were observed in free IRIN or Ir-Lipo(+SOS) treated animals. These lesions are indicative of acute glomerular inflammation. No significant renal abnormalities were found in the Ir-LB-MSNP(+SOS) group.

In a separate experiment, the healthy mice received single IV administration of Ir-LB-MSNP(+SOS), Ir-Lipo(+SOS), and free irinotecan at a drug dose of 60 mg/kg IV. 24 hours post-treatment, the mice were sacrificed for organ harvest. Appropriate size sections of the sternum, gastrointestinal (GI, stomach and intestine) tract, thymus, liver, kidney, spleen, and lung were fixed in 10% formalin and then embedded into paraffin. Tissue sections of 4 µm thickness were mounted on glass slides. The sections were stained with hematoxylin-eosin (H&E) and examined by light microscopy. The slides were read by an experienced veterinary pathologist. The results showed a much reduced bone marrow toxicity for Ir-LB-MSNP(+SOS) and Ir-Lipo(+SOS) than free IRIN (FIG. 9). We are performing more detailed studies on sternal bone marrow, using immunohistochemistry to assess whether there is differential toxicity on erithroid, megacariocyte or white blood cell precursors. Free irinotecan and the liposomal formulation resulted in nephrotoxicity, which manifested as glomerular swelling. No significant renal abnormalities were found in the mice treated by Ir-LB-MSNP(+SOS) particles (FIG. 10).

Conclusions

The goal of this project is to develop an IV injectable irinotecan nano delivery platform for effective PDAC killing and toxicity reduction. Through the use of high drug loading capacity, nanocarrier biocompatability, and efficient drug encapsulation, the LB-MSNP platform has shown promising results in PDAC cells and acute animal toxicity studies.

Example 3 iRGD-Mediated Transcytosis Enhances Irinotecan Delivery and Efficacy of a Silicasome Nanocarrier in Murine and Human Pancreatic Cancer Although pancreatic ductal adenocarcinoma (PDAC) is almost uniformly fatal, some improved overall survival has been achieved with the introduction of nanocarriers that deliver irinotecan or paclitaxel. We have further improved these results in animal orthotopic models, using an irinotecan silicasome carrier that is comprised of mesoporous silica nanoparticles (MSNPs) coated with a lipid bilayer. The silicasome carrier also provides major toxicity reduction compared to a liposomal carrier for irinotecan. Although it is generally assumed that nanocarriers rely principally on abnormal leaky vasculature (a.k.a. the enhanced permeability and retention effect) for tumor access, a transcytosis transport pathway that is regulated by the neuropilin-1 (NRP-1) receptor has recently been reported. This unique transport pathway can be triggered by the cyclical iRGD peptide, which binds to tumor-associated integrins, where the peptide is processed for subsequent binding to NRP-1. Co-administration of iRGD enhanced the uptake of irinotecan-silicasomes 3-4 fold in a robust Kras orthotopic PDAC model, leading to a survival benefit and significant decrease in metastasis. Silicasomes with imbedded gold-nanoparticle cores were used for ultrastructural viewing of the transcytosis pathway in vivo, demonstrating that iRGD co-administration induces a vesicular transport pathway that transports the electron-dense carriers from the blood vessel lumen to a perinuclear site in cancer cells. iRGD-mediated enhancement of silicasome uptake was also observed in patient-derived xenografts, commensurate with the level of NRP-1 expression on tumor blood vessels. These results demonstrate the utility of iRGD for a potential personalized approach to PDAC therapy, using the irinotecan-silicasome carrier.

In this example we describe the development of a lipid bilayer coated mesoporous silica nanocarrier (silicasome) for irinotecan delivery that outperforms liposomes in a robust pancreatic ductal adenocarcinoma (PDAC) animal model. We demonstrate that silicasome uptake at the orthotopic tumor site can be enhanced 3-4 fold by the co-administration of iRGD peptide, which triggers a novel transcytosis pathway through ligation of the neuropilin-1 receptor. iRGD also enhanced silicasome uptake in patient-derived xenografts that express the same vascular receptor. We provide ultrastructural evidence of the vesicle-based transcytosis pathway, which could complement the enhanced permeability and retention effect commonly used to explain nanocarrier uptake at tumor sites. The transcytosis pathway presents the possibility of enhancing the benefit of the irinotecan-silicasome carrier in PDAC patients.

Introduction

We have developed a multifunctional mesoporous silica nanoparticle (MSNP) platform, that has been adapted to provide high dose PDAC chemotherapy using a supported lipid bilayer (LB) for drug encapsulation (see, e.g., Example 1). This carrier has also been designated as a "silicasome" to distinguish it from morphologically similar liposomal carriers, which contain a non-supported LB. Compared to liposomes, including an in-house liposomal carrier for the irinotecan, silicasomes described herein have been shown to exhibit a significantly higher loading capacity for this drug, improved circulatory stability (as a result of the supported LB), and reduced drug leakage. These features allow for improved pharmacokinetics and treatment efficacy of silicasomes vs. liposomes in a stringent orthotopic Kras PDAC model (see, e.g., Example 1). In addition, silicasomes also provide major toxicity reduction in the gastrointestinal tract, liver, and bone marrow compared to the liposomal equivalent (Id.). Besides the success with irinotecan, the silicasome platform has also been adapted for synergistic delivery of paclitaxel and gemcitabine, allowing it to significantly (>10-fold) outperform the combination of free gemcitabine with Abraxane® in an orthotopic PDAC model. Noteworthy, above results with silicasome carriers could be achieved by "passive" delivery, without the need to resort to the use of targeting ligands.

Given this background, we were interested whether the efficacy of PDAC treatment by the irinotecan-loaded silicasome (Ir-silicasome) could be improved by transcytosis, and whether this is best accomplishable by iRGD conjugation to the carrier or its co-administration. In this Example, we demonstrate the feasibility of using the co-administration of free iRGD peptide to enhance carrier uptake and treatment efficacy in a Kras orthotopic model. Moreover, we provide ultrastructural evidence of a grouped vesicle system that allows transport of Au-labeled silicasomes from the blood vessel lumen to a perinuclear site in cancer cells. We also demonstrate in patient-derived PDAC xenografts that the relative abundance of NRP-1 expression on the tumor vasculature determines the response magnitude to silicasomes through the use of iRGD co-administration.

Results

Figure 21A:
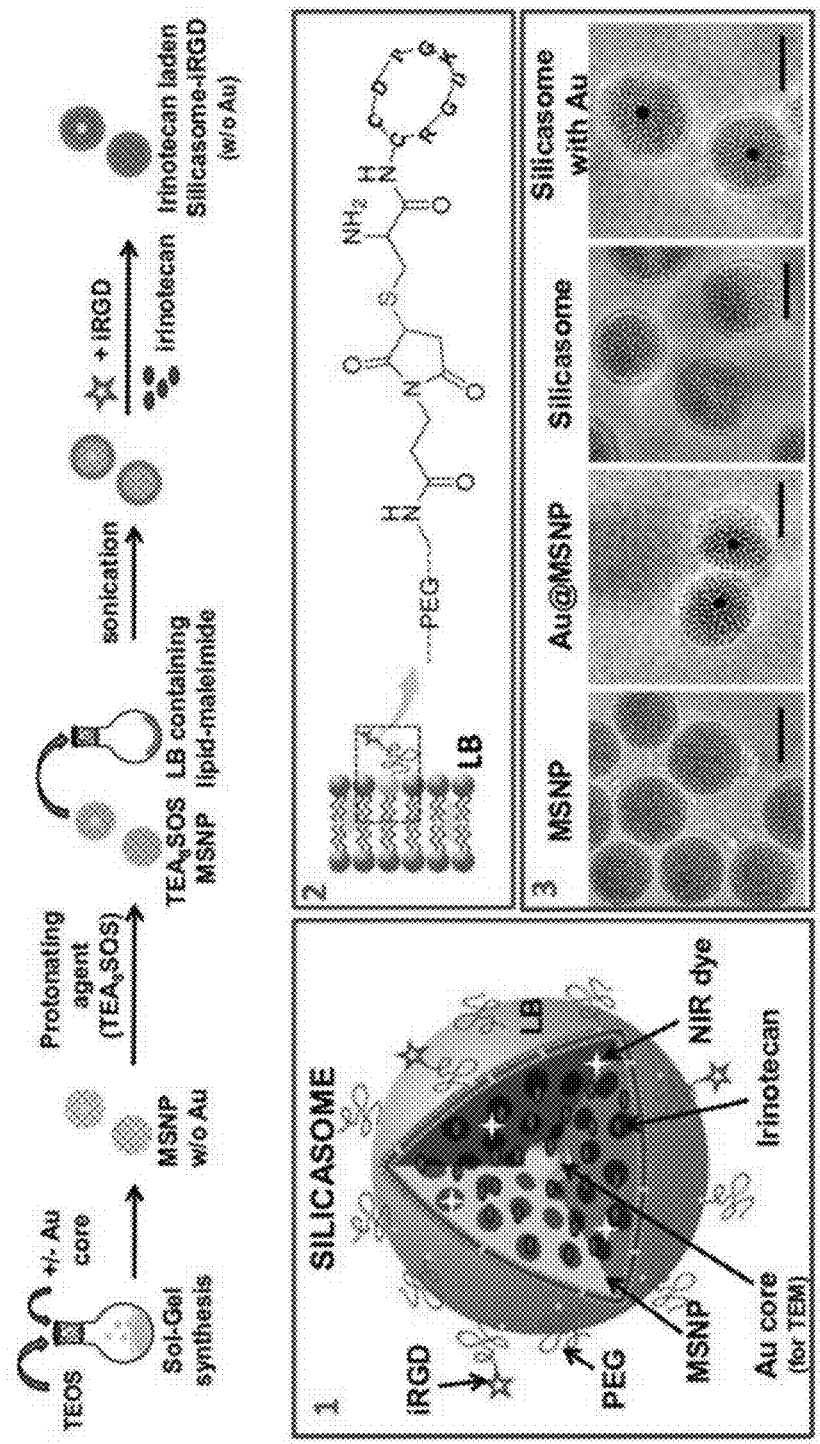
FIGS. 21A and 21B illustrate the synthesis and characterization of silicasomes for drug loading and visualization.
Figure 27:
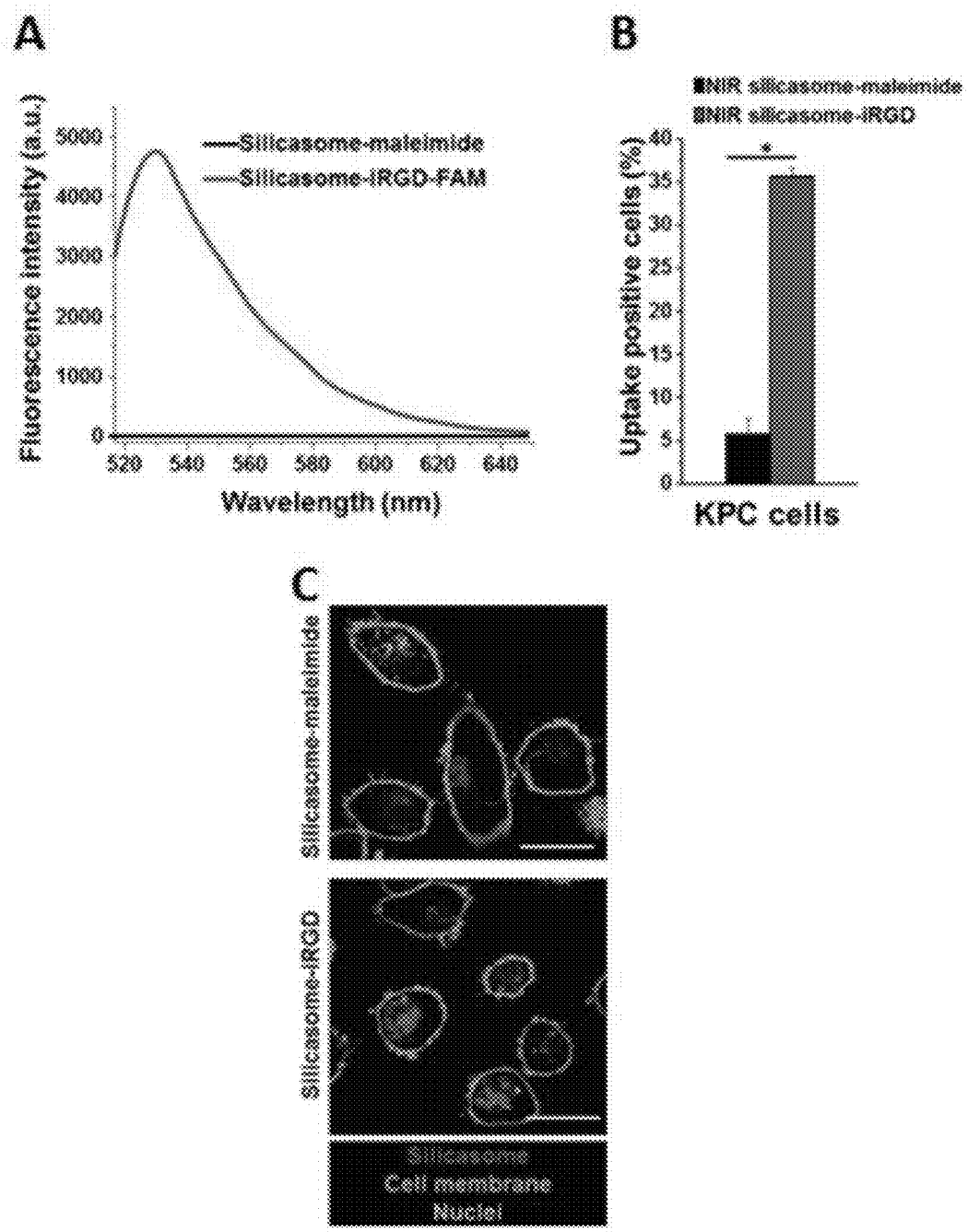
FIG. 27, panels A-C, illustrate the use of a thiol-maleimide reaction for successful covalent conjugation of iRGD to the lipid bilayer on silicasomes. To validate the success of covalent conjugation, a reactive fluorescein (FAM) labeled iRGD peptide, provided by Dr. Ruoslahti (Sugahara et al. (2009) *Cancer Cell,* 16: 510-520), was used for binding to DSPE-PEG-maleimide. The detailed method is described in Example 3 methods section. Panel A: Fluorescence spectra of pristine and FAM-iRGD-silicasomes, suspended at 100 μg/mL, were obtained in a microplate reader (Molecular Device M5e) at excitation wavelength of 488 nm, the significant retentions of the fluorescence signal on the washed and purified FAM-iRGD-silicasomes confirms a successful conjugation reaction (*Cancer Cell* 2009, 16:510). Panels B and C: The effect of iRGD conjugation to the silicasome was tested for its impact on cellular uptake. A batch of the silicasome-iRGD was synthesized with NIR-labeling (DyLight 680) of the MSNP framework, as described in the methods section. KPC cells were treated at a particle concentration of 100 µg/mL at 37° C. for 2 h and uptake was determined by flow cytometry (panel B), and confocal microscopy (panel C). An iRGD-free NIR-silicasome with similar labeling efficiency was used as control. Data represent mean±SD, *p<0.05. Confocal microscopy confirmed the results (cell membranes were green stained with wheat germ agglutinin and nuclei blue stained with Hoechst 33342). Bars=20 µm.

Synthesis and Characterization of Silicasomes for Drug Loading and Visualization in PDAC Tumors We have demonstrated high irinotecan loading by a LB-coated MSNP (a.k.a. a silicasome), using a remote loading technique that relies on a protonating agent (see, e.g., FIG. 21A, top panel, and Liu et al. (2016) ACS Nano. 10(2): 2702-2715). Irinotecan is a weak basic and amphipathic molecule that can diffuse across the LB into the MSNP interior packaging space, where proton release by prior entrapped triethylammonium sucrose octasulfate ($TEA_8SOS$) converts the drug into a hydrophilic derivative, incapable of back-diffusion across the LB (FIG. 21A, top panel). The remote loading procedure was used to synthesize an Ir-silicasome batch that achieved a drug loading capacity of 50 wt % (w/w, irinotecan/MSNP) (Id.). To determine whether conjugation of an iRGD peptide onto the silicasome surface can impact carrier biodistribution to the PDAC tumor site, we also synthesized a particle batch in which the $DSPE-PEG_{2000}$ component of the LB was used for conjugation to a cysteine residue in the peptide. This was accomplished by substituting $DSPE-PEG_{2000}$ with $DSPE-PEG_{2000}$-maleimide (see methods section), allowing thiol-maleimide coupling to the cysteine-modified peptide, Cys-c(CRGDKGPDC) (SEQ ID NO:11) (FIG. 21A, box 2). To confirm the success of the conjugation reaction, we also used a fluorescein-labeled version of the peptide (FAM-iRGD), developed by Ruoslahti et al., to perform fluorescence spectroscopy of conjugated silicasomes after extensive washing (FIG. 27, panel A) (Sugahara et al. (2009) Cancer Cell, 16(6): 510-520). This confirmed the stable association of the fluorescent peptide with the LB. The density of iRGD conjugation was limited to ~3 mol % (of all LB components) to prevent colloidal instability and interference in carrier uptake. The uptake of the intact silicasome-iRGD carrier was confirmed by flow cytometry and confocal microscopy in KPC cells (FIG. 27, panels B and C).

In order to perform TEM visualization of the transcytosis process in PDAC tumors, we also synthesized a batch of core-shell MSNPs that include ~10 nm electron-dense Au-nanoparticles (FIG. 1A, box 3). Similar to the bare particles, the core/shell particles could be effectively coated with a LB, as demonstrated by CryoEM (FIG. 21A, box 3). The detailed synthesis and characterization procedures for all the carriers used in this communication are discussed in the methods section of the Supporting Information. The main physicochemical characteristics of silicasomes are summarized below in Table 5.

TABLE 5

Illustrative silicasome physiochemical properties.

| Property | Value |
|---|---|
| MSNP surface area (BET) | ~850 m²/g |
| MSNP pore volume (BET) | ~0.75 cm³/g |
| MSNP pore size (BET, TEM) | ~3 nm |
| MSNP core size (TEM) | ~65 nm |
| LB thickness (cryo-EM) | ~7 nm |
| Silicasome size (cryl-EM) | ~80 nm |
| Hydrodynamic size (DLS) | ~130 nm |
| Zeta potential | ~−10 mV |
| Drug loading capacity (irinotecan) | ~50% (w/w, drug/MSNP) |

Figure 21B:
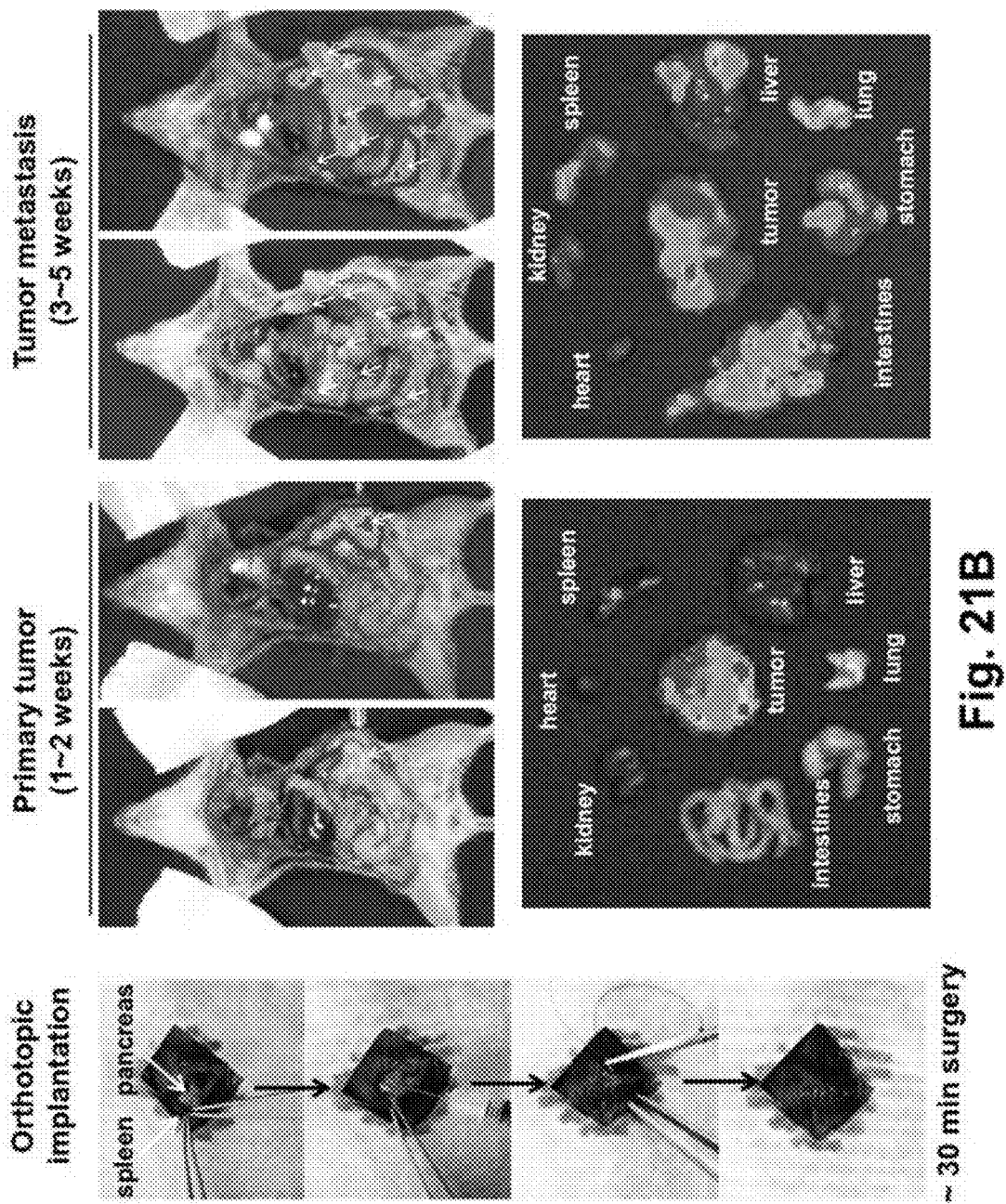
Figure 22A:
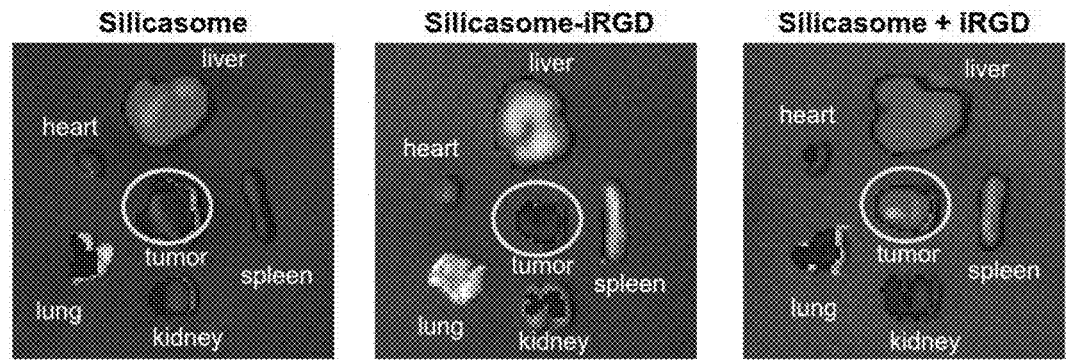
FIGS. 22A and 22B show that co-administrated iRGD enhanced the tumor biodistribution of IV-injected silicasomes in the KPC-derived orthotopic model.
Figure 22B:
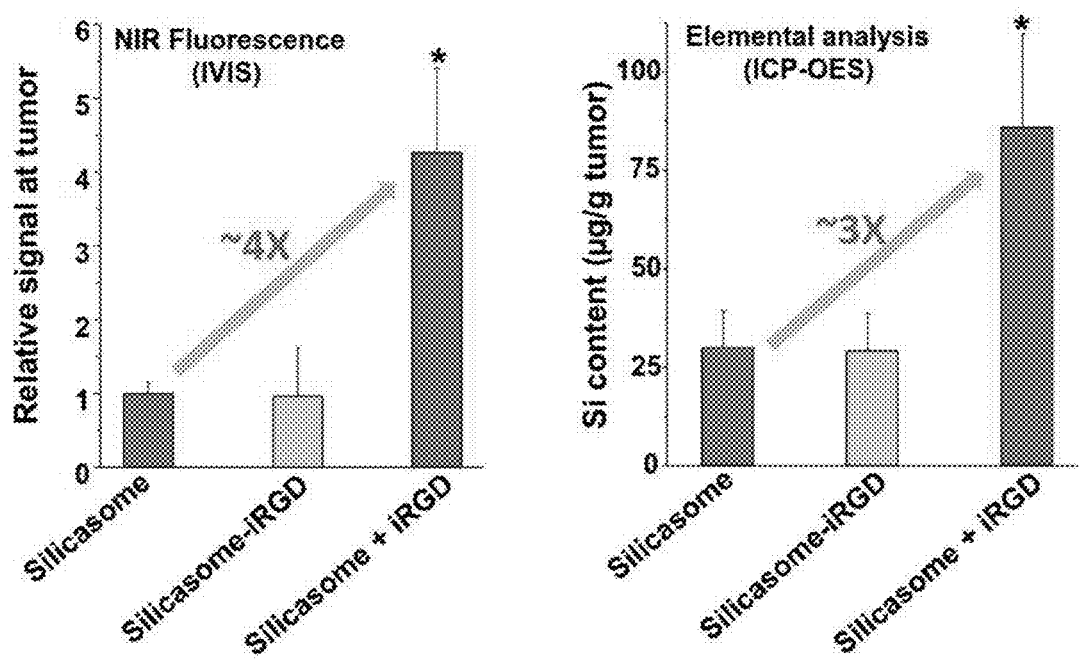
Figure 28:
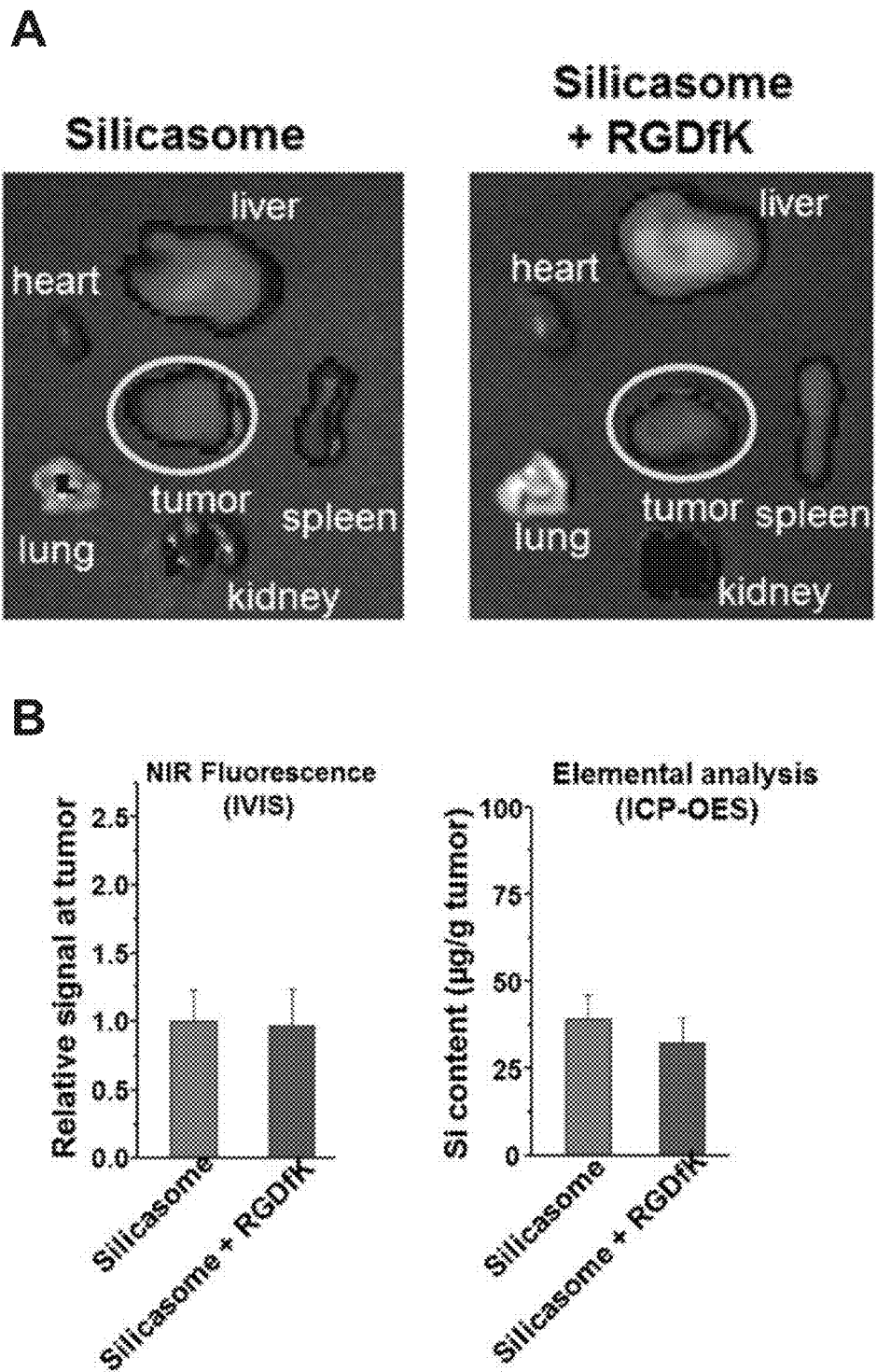
FIG. 28, panels A-B, illustrates assessment of the effect of a non-functional peptide (lacking the CendR motif) on IV silicasome biodistribution. Panel A: We used a non-CendR peptide, cyclo (RGDfK), to repeat the biodistribution experiment in orthotopic model shown in FIG. 22. Briefly, tumor-bearing animals received IV injection of 50 mg/kg NIR-labeled silicasome co-administered with PBS or 8 µmol/kg free cyclo (RGDfK), followed by animal sacrifice at 24 h (n=3). Representative ex vivo organ NIR fluorescence images were obtained to show nanoparticle biodistribution. Panel B: NIR fluorescence intensity analysis (by IVIS software) and determination of Si content (by ICP-OES) showed that the non-CendR peptide is incapable of improving silicasome uptake at the tumor site. Data represent mean±SD.

Comparison of the Effect of Conjugated Vs. Non-Conjugated iRGD Peptide on Silicasome Biodistribution in an Orthotopic PDAC Model Luciferase-expressing KPC cells, derived from a spontaneous PDAC tumor from a transgenic $Kras^{LSL-G12D/+}$; $Trp53^{LSL-R172H/+}$; Pdx-1-Cre animal were orthotopically implanted in the pancreas tails in immunocompetent B6/129 mice (see, e.g., FIG. 21B, left panel, and Liu et al. (2016) *ACS Nano.* 10(2): 2702-2715; Tseng et al. (2010) *Clin. Cancer Res.* 16(14): 3684-3695). This stringent PDAC tumor model mimics human PDAC for oncogene expression, growth characteristics, metastasis, histological features and development of a dysplastic stroma. FIG. 21B summarizes the details of the tumor growth characteristics and metastasis as seen during animal autopsy and IVIS imaging (FIG. 21B) (Tseng et al. (2010) *Clin. Cancer Res.* 16(14): 3684-3695; Tones et al. (2013) *PloS One* 8: e80580). Silicasome biodistribution to the orthotopic tumor site was assessed by a one-time intravenous (IV) injection of 50 mg/kg near-infrared (NIR) labeled (DyLight 680) particles that were either non-conjugated (i.e., "IRGD free" status) or peptide-conjugated ("silicasome-iRGD") (FIG. 22A). A third group of animals received co-administration of 8 μmol/kg free peptide plus non-conjugated particles ("silicasome+iRGD"). IVIS imaging of the explanted organs, performed 24 h after initial injection and animal sacrifice, demonstrated a prominent increase in the NIR signaling intensity at the tumor site for the "silicasome+iRGD" group compared to the signaling intensity in the silicasome-iRGD or silicasome only groups (FIG. 22A). Imaging intensity was quantified by IVIS Lumina Living Image software. In contrast to their lack of an in vivo effect, the peptide-conjugated silicasomes could be seen to enhance carrier uptake in KPC cells (FIG. 27, panels B and C). We interpret that as sufficient NRP-1 receptor density to initiate trans-membrane uptake, while the receptor abundance at the tumor vascular site may be limited in the number of conjugated particles that are allowed to go through, as previously reported for in vitro/in vivo comparisons by Ruoslahti et al. (Sugahara et al. (2009) *Cancer Cell*, 16(6): 510-520; Teesalu et al. (2009) *Proc. Natl. Acad. Sci. USA,* 106(38): 16157-16162; Hussain et al. (2014) *Sci Rep* 4: 5232). In order to show that the NIR intensity (FIG. 22B, left panel) reflects actual MSNP uptake, inductively coupled plasma optical emission spectrometry (ICP-OES) was used for quantification of the tumor silicon (Si) content (FIG. 22B, right panel). This demonstrated a significant (~3-fold) increase in Si content in the "silicasome+iRGD" group compared to the silicasome-iRGD or the silicasome only groups. We also demonstrated the importance of the C-terminal (CendR) motif for PDAC biodistribution by performing a separate experiment to show that silicasome co-administration with a control non-CendR peptide, cyclo (RGDfK) (Sugahara et al. (2010) *Science,* 328 (5981): 1031-1035) is incapable of enhancing silicasome uptake (FIG. 28). This result was also confirmed by ICP-OES (FIG. 28).

Figure 29:
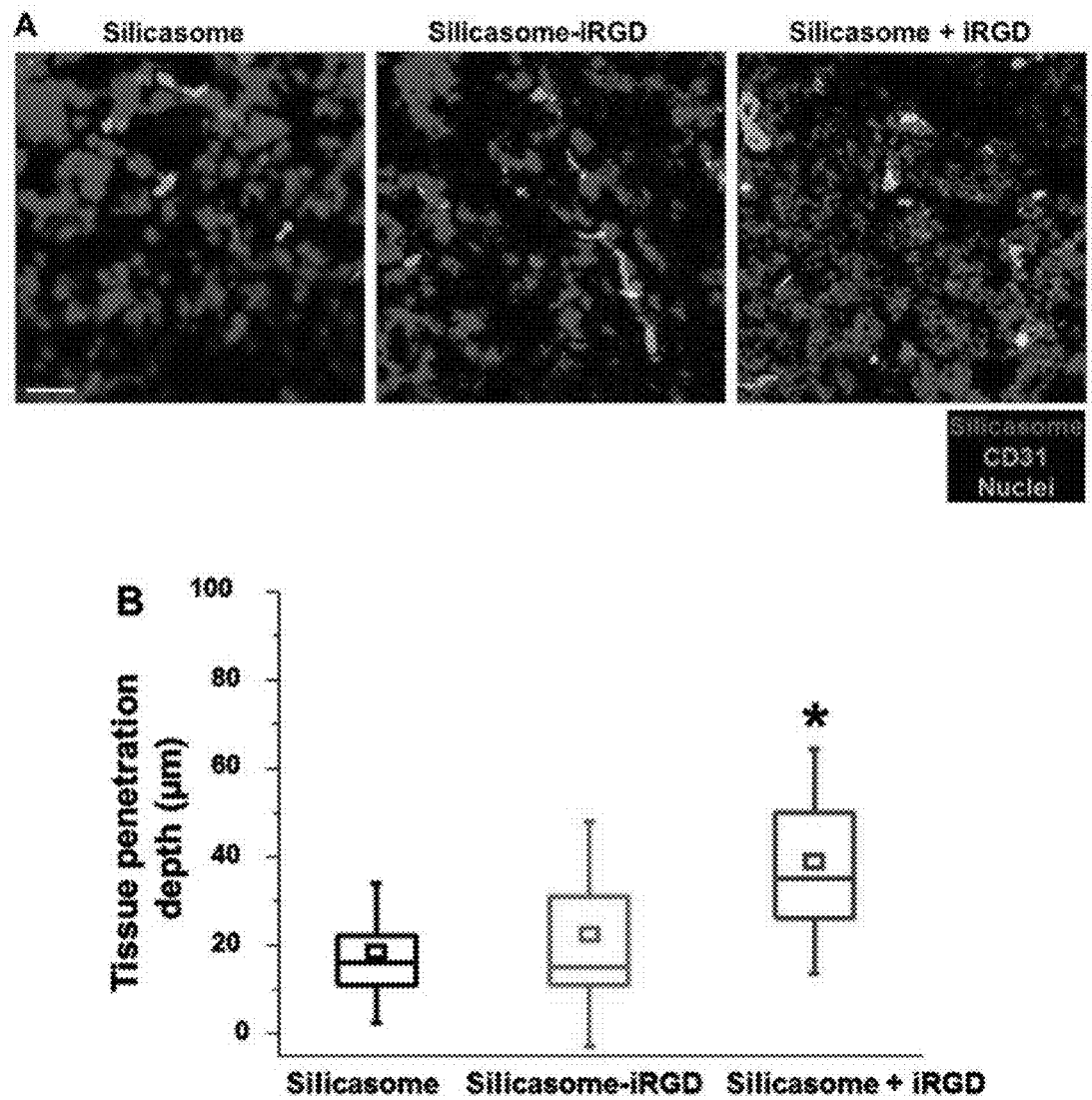
FIG. 29, panels A-B, illustrates assessment of silicasome transport in the tumor by confocal microscopy. Panel A: Tumor sections were obtained from experiment in FIG. 22. Representative confocal images were obtained to assess the intratumoral abundance of the NIR labeled silicasome abundance under a SP2-1P-FCS, Leica microscope, using a 633 nm laser. IHC staining of the same section to review the presence of blood vessels (CD31 in green) and the presence of nuclei (DAPI staining in blue), allowed us to determine the presence and migration of nanoparticles in the tumor tissue, using the methodology described by Sugahara et al. (2010) *Science*, 328: 1031-1035). Bar=20 µm. Panel B: Calculation of the penetration distance silicasomes from the closest tumor blood vessel was estimated for ~15 blood vessels, using Image J software. Box-and-whisker plots (Origin software) were developed to show median (horizontal line), $25^{th}$-$75^{th}$ percentiles (box), mean (open square) and SD (whiskers). *, p<0.05 compared with silicasome alone or silicasome-iRGD.

Tumor tissue sections were used to assess the relative abundance of intratumor biodistribution of NIR-labeled silicasomes and traveling distance from the tumor blood vessels, which were elucidated by anti-CD31 Alexa Fluor® 488-staining (FIG. 29). This analysis showed that iRGD co-administration was the most effective strategy to enhance silicasome uptake at orthotopic tumor sites. In contrast, the iRGD-conjugated carrier failed to exert a significant effect on the number of particles as well as the traveling distance in our KPC orthotopic model (FIG. 29). The above findings resulted in the use of free iRGD to perform subsequent efficacy studies.

Figure 23A:
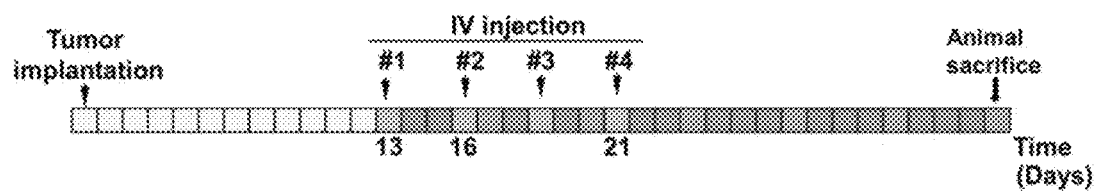
FIGS. 23A-23E show that iRGD co-administration enhances the uptake and efficacy of the Ir-silicasome in the KPC-derived orthotopic model.
Figure 23B:
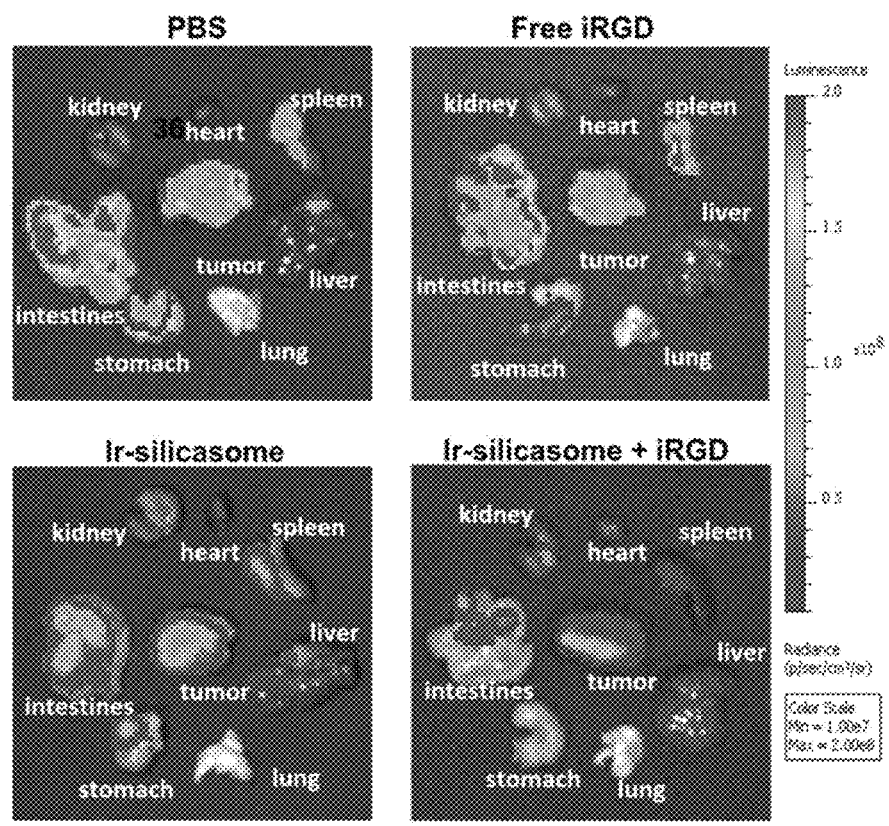
Figure 23C:
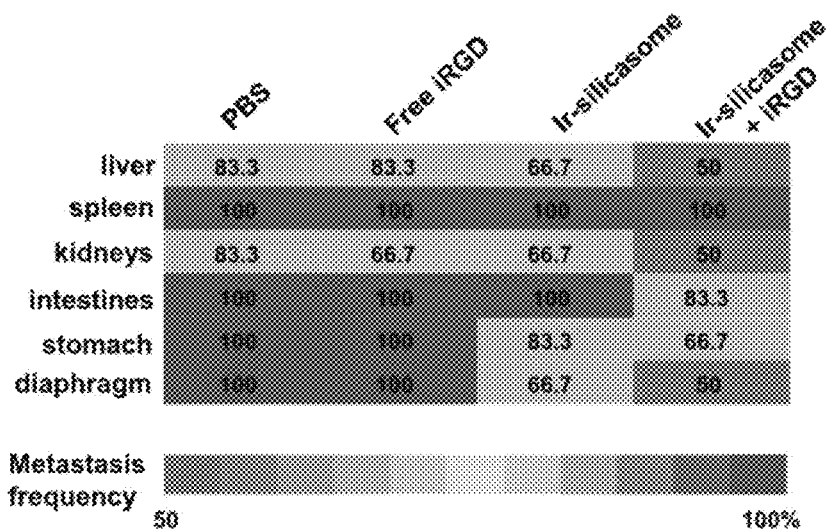
Figure 23D:
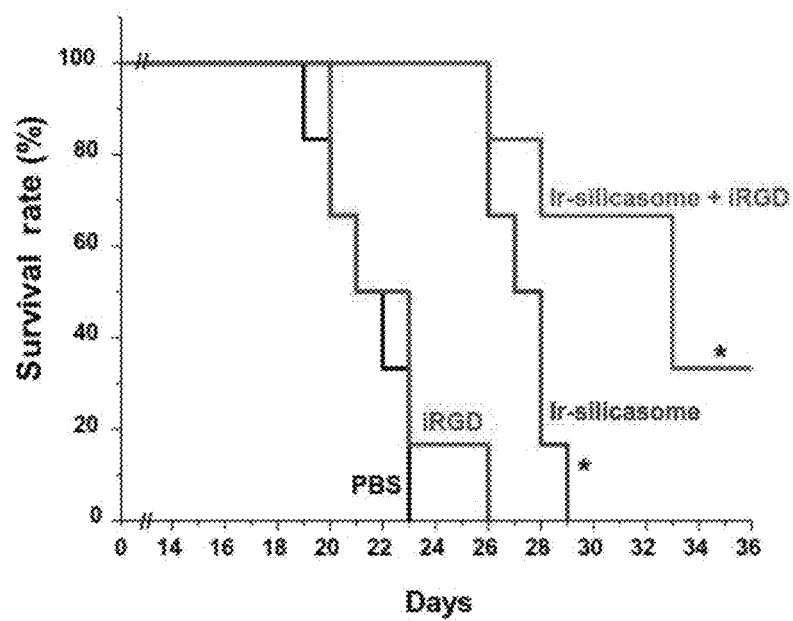
Figure 23E:
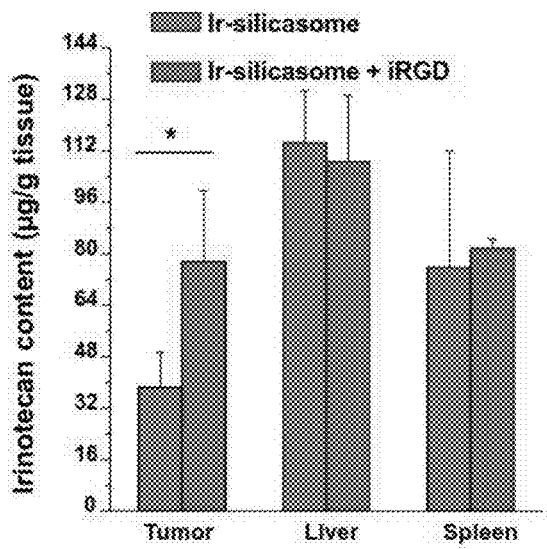
Figure 24A:
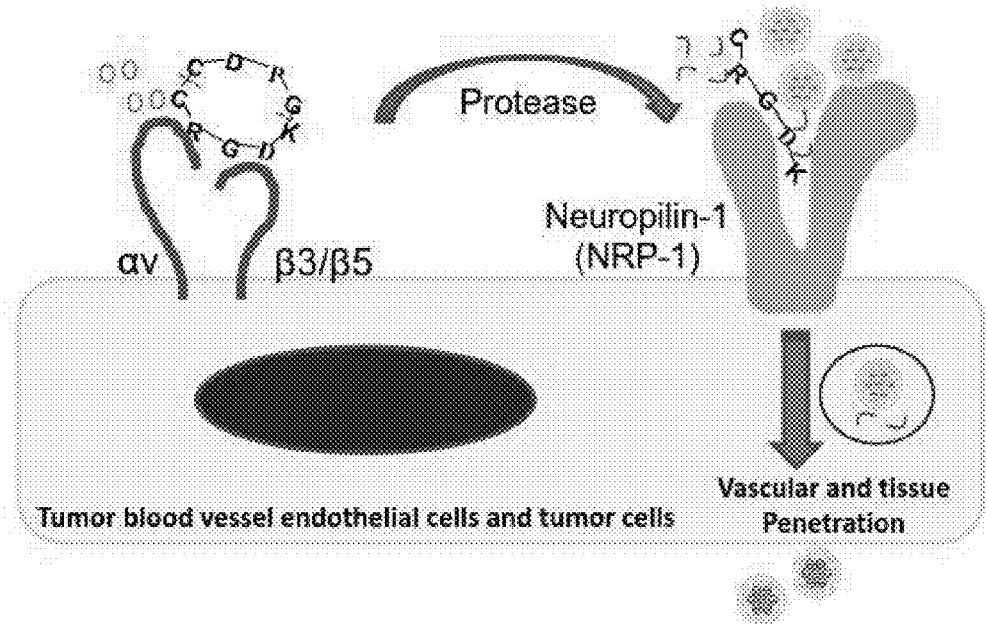
FIGS. 24A and 24C show that iRGD-mediated silicasome uptake requires NRP-1 expression on the tumor vasculature.
Figure 24B:
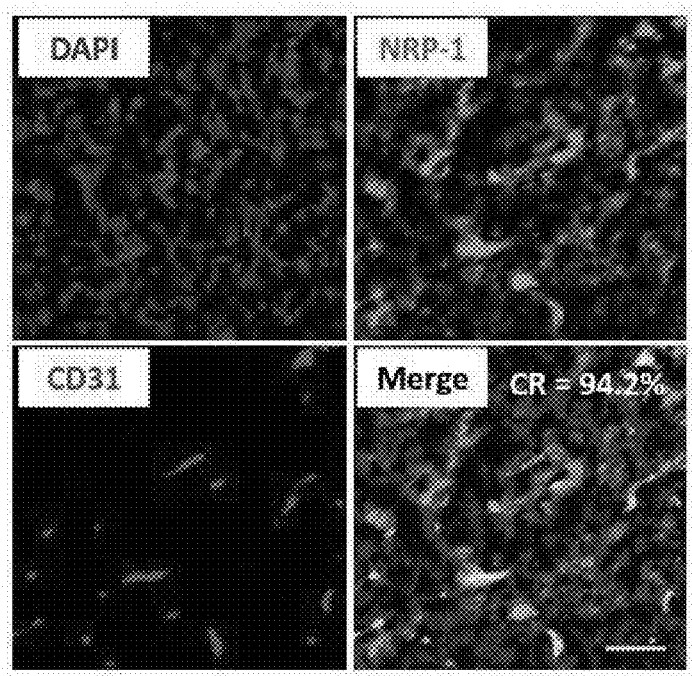
FIG. 24B: Multi-color IHC staining of NRP-1 (green) and CD31 (red), plus nuclear staining (blue) in a KPC-derived tumor section. The IHC staining methodology is described in the methods section. NRP-1 is expressed on both the tumor tissue as well the blood vessels. The merged image shows a high degree of co-localization (94.2%) of NRP-1 with CD31; the co-localization ratio (CR) was determined by Image J software. Bar=100 μm.
Figure 24C:
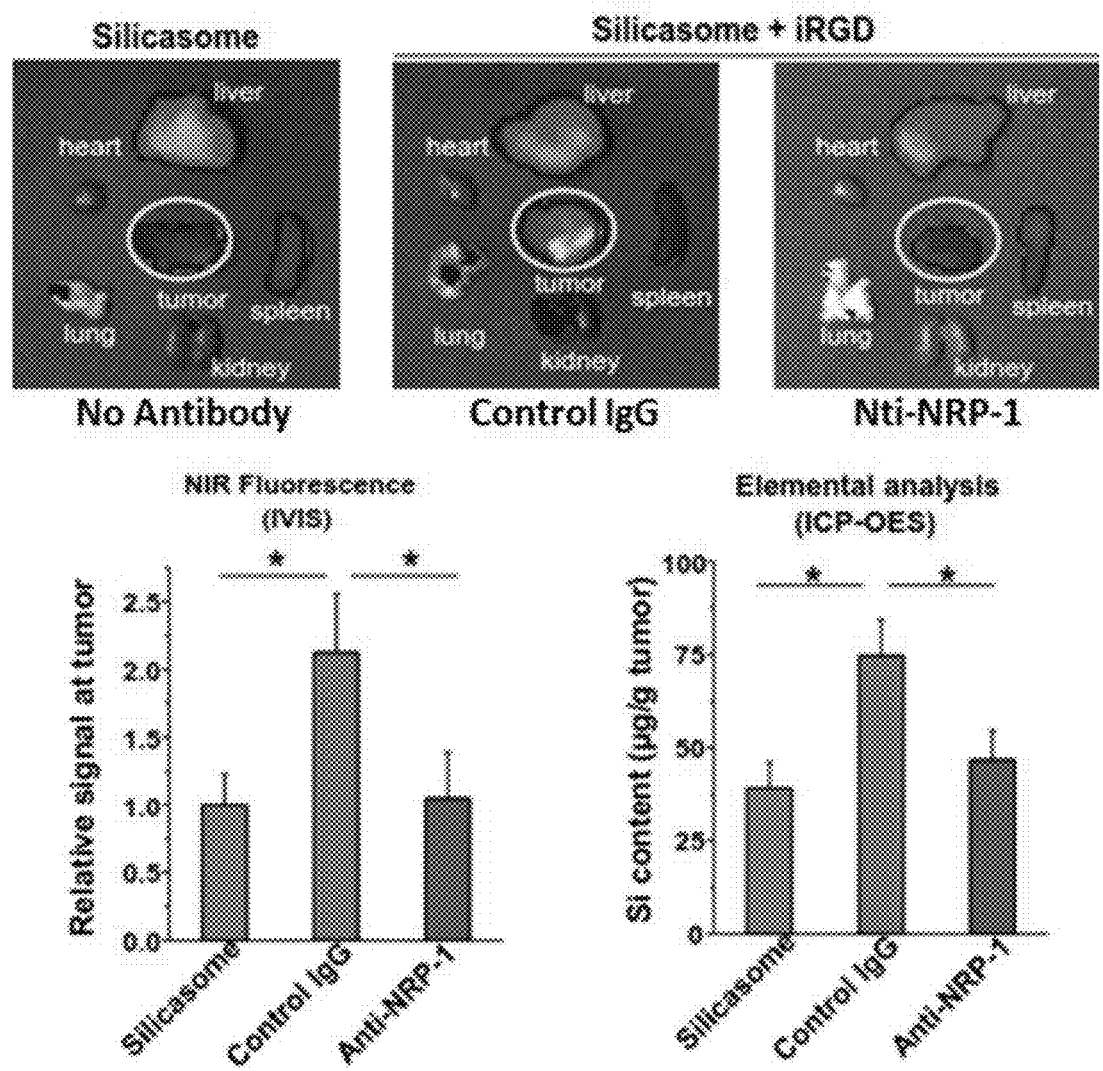
Figure 30:
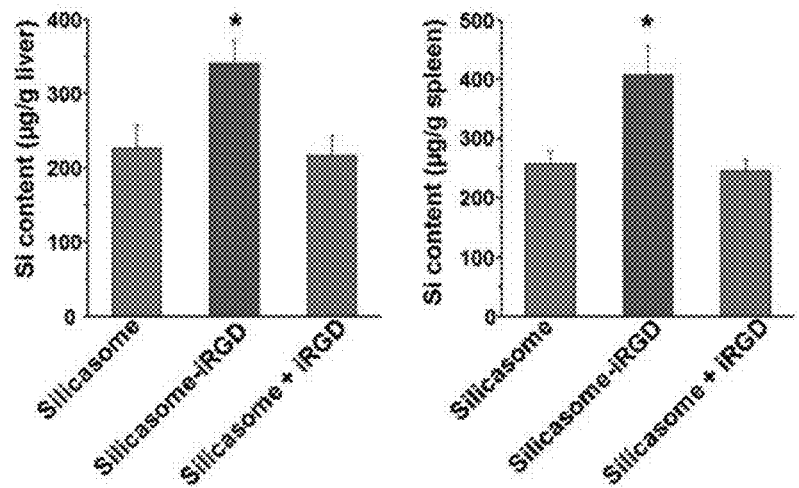
FIG. 30 shows Si contents in the liver (left) and spleen (right), using organs obtained from the animals used in FIG. 22, were determined by ICP-OES analysis. Data represent mean±SD, *p<0.05 compared with silicasome or "silicasome+iRGD" groups.

Because all nanocarriers are also taken up in the reticuloendothelial system (RES), it is important to comment on the observable silicasome uptake in the liver and spleen (with little appreciable effects on the lungs, hearts, and kidneys). Interestingly, IVIS imaging showed a possible increase in the biodistribution of the conjugated carrier to the RES organs (FIG. 22A). This was confirmed by an increased Si content in the liver and spleen during performance of ICP-OES (FIG. 30). While we lack an exact explanation for this observation, it is possible that peptide conjugation, directly or indirectly, leads to particle opsonization and increased uptake by scavenger receptors, independent of NRP-1 (Li and Huang (2008) *Mol. Pharm.* 5(4): 496-504).

iRGD Co-Administration Enhances the Efficacy of Irinotecan Delivery by the Silicasome To demonstrate the possible therapeutic benefits of iRGD co-administration in PDAC treatment with the Ir-silicasome, an efficacy experiment was performed in the same orthotopic tumor model. Animals received IV injection of the Ir-silicasomes at a drug dose of 40 mg/kg (equivalent to carrier dose of 80 mg/kg), with or without co-administration of 8 μmol/kg iRGD. Treatment commenced 13 days after orthotopic implementation of $2 \times 10^6$ KPC-luc cells (FIG. 23A), at which time the primary tumor size was ~3-5 mm in the absence of macro-metastasis (see above, and Liu et al. (2016) *ACS Nano.* 10(2): 2702-2715). Injections were repeated every 3 days, for a total of 4 administrations (FIG. 23A). The control groups consisted of animals receiving IV PBS, the Ir-silicasome alone (same dose), or free iRGD alone (same dose). Kaplan-Meier plots were used to express animal survival (Id.) and animal autopsy was used to assess the local tumor spread and the presence of metastasis. Numerous metastatic foci could be seen in the spleens, intestines, stomachs, livers, and kidneys of animals treated with saline or free iRGD peptide (FIG. 23B). While the Ir-silicasome significantly reduced the tumor burden and number of metastases, iRGD co-administration further enhanced the shrinking of the primary tumor as well as inhibiting the spread to the liver, stomach and intestines (FIG. 23B). The heat map in FIG. 23C provides a quantitative display of the impact of the co-administered peptide on metastatic disease. Log-rank testing (SPSS 19.0 software, IBM SPSS Statistics, USA) also demonstrated that, compared to the PBS group, treatment with the Ir-silicasome alone improved the survival by 28.6% as compared to 57.1% during co-administration of the iRGD peptide (FIG. 23D); this difference is statistically significant (p=0.027). We also confirmed that there is a significant (~2-fold) increase in the intratumoral content of irinotecan in animals receiving a one-time administration of iRGD (8 μmol/kg) IV together with Ir-silicasomes (40 mg/kg drug), as determined by high performance liquid chromatography (HPLC) at 24 h (FIG. 23E).

iRGD-Mediated Silicasome Uptake Requires NRP-1 Expression on the Tumor Vasculature The mechanism of action of iRGD in mediating drug uptake is dependent on homing to $\alpha_v\beta_3$ or $\alpha_v\beta_5$ integrins, which are preferentially expressed on cancer blood vessels (Ruoslahti and Pierschbacher (1987) *Science,* 238(4826): 491-497; Hanahan and Weinberg (2000) *Cell,* 100(1): 57-70). Binding of the cyclical peptide to the integrins is followed by cleavage and release of the C-terminal end of the peptide, which mediates the interaction with NRP-1 (this is also known as C-end rule). NRP-1 binding leads to the triggering of a system of vesicles that can assist drug and nanoparticle transport (Sugahara et al. (2009) *Cancer Cell*, 16(6): 510-520; Pang et al. (2014) *Nat. Commun.* 5: 4904). In order to determine the expression of NRP-1 at the KPC tumor site, IHC staining was performed by Alexa Fluor® 488-labeled anti-NRP-1, while endothelial cells and nuclei were localized by staining with Alexa Fluor® 594-labeled anti-CD31 and DAPI, respectively. Fluorescent microscopy and Image J analysis was performed to determine % overlap of NRP-1 with CD31; this demonstrated 94.2% co-localization (FIG. 24B). To verify the role of NRP-1 in silicasome uptake at the orthotopic tumor site, tumor-bearing mice were pre-injected with an antagonist antibody to the b1b2 domain of NRP-1 (Sugahara et al. (2009) *Cancer Cell*, 16(6): 510-520; Sugahara et al. (2010) *Science*, 328(5981): 1031-1035). Subsequent administration of iRGD plus NIR-labeled silicasomes demonstrated a definitive reduction in the carrier uptake compared to animals not treated with a blocking antibody (FIG. 24C). The same interference was not seen with the control IgG (FIG. 24C). These data confirm the role of NRP-1 in iRGD-mediated silicasome uptake.

Figure 25A:
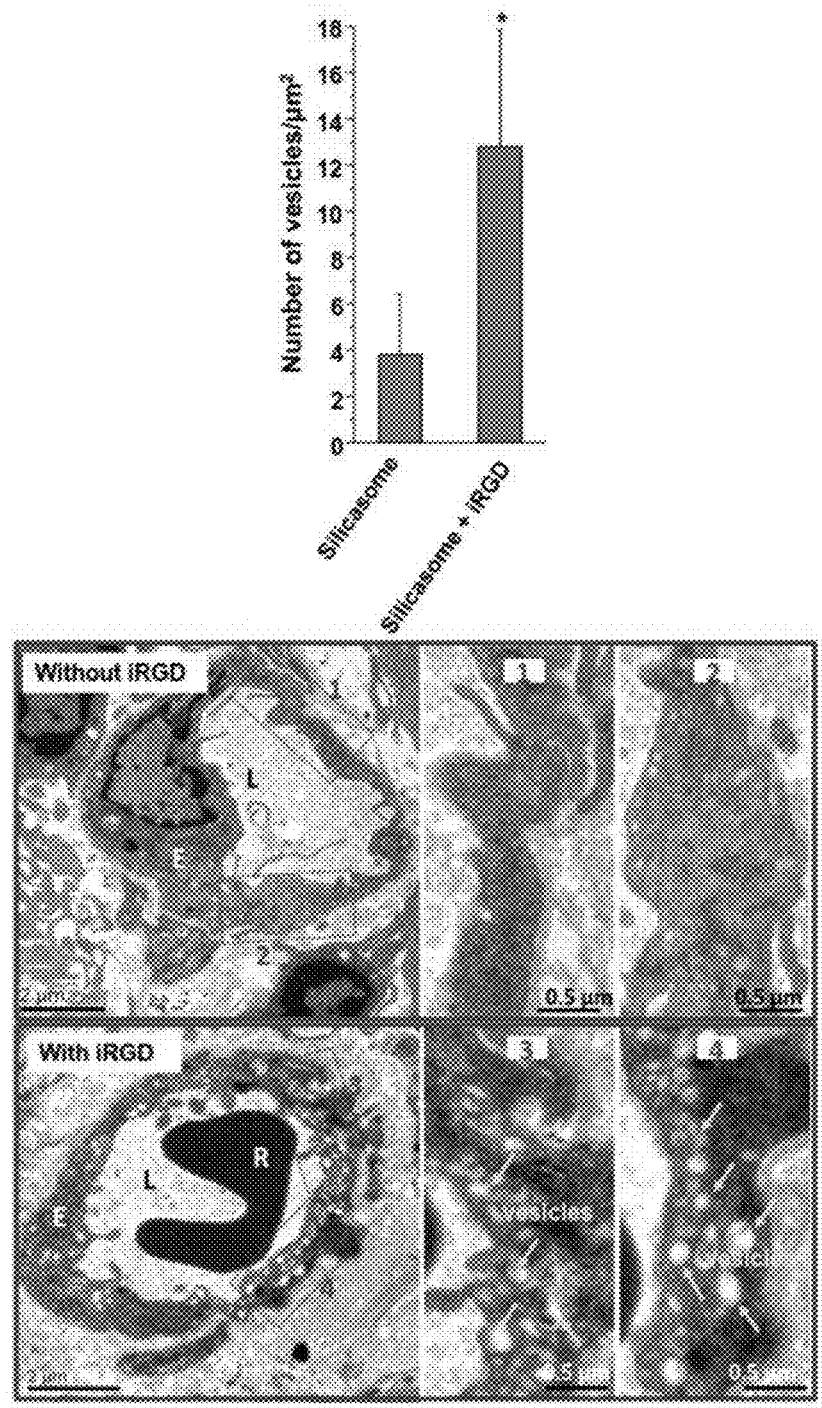
FIGS. 25A-25C provide ultrastructural viewing of the silicasome transport system initiated by iRGD co-administration.

Ultrastructural Demonstration of the Transport of Silicasomes by Transcytosis Vesicles at the KPC Cancer Site It has been demonstrated that binding of the C-terminal end of iRGD to NRP-1 can initiate a bulk transcytosis pathway that involves a novel vesicular transport mechanism of importance for nutrient delivery to cancer (Sugahara et al. (2009) *Cancer Cell*, 16(6): 510-520; Sugahara et al. (2010) *Science*, 328(5981): 1031-1035; Pang et al. (2014) *Nat. Commun.* 5: 4904). To the best of our knowledge, this transcytosis pathway has never been directly visualized during the transport a therapeutic nanocarrier to the site of a tumor. Electron microscopy (EM), which could provide visual enhancement demonstration, was used to attempt for ultrastructural analysis of the iRGD-mediated transport pathway in the KPC model. Initially, we compared TEM images taken of the harvested tumor site at different intervals after the IV injection of silicasomes, with or without iRGD co-administration (FIG. 25A). At 24 h, iRGD co-administration could clearly be seen to induce the formation of grape-like vesicles, 110–370 nm in diameter, that are spread across the endothelial cells, from the luminal to the abluminal side of the blood vessel (FIG. 25A, regions "3" and "4"). These features resemble the vesiculo-vacuolar organelle or VVO described by Dvorak et. al (Feng et al. (1996) *J. Exp. Med.* 183(5): 1981-1986). Semi-quantitative analysis of vesicle density, determined by counting the number of vesicles in at least 10 regions of interest (ROIs) and expressing the vesicle number per $\mu m^2$ of interior surface area in the cell, demonstrated that iRGD can increase the vesicle density ~3-fold compared to animals not receiving peptide co-administration (FIG. 25A, left panel).

Figure 25B:
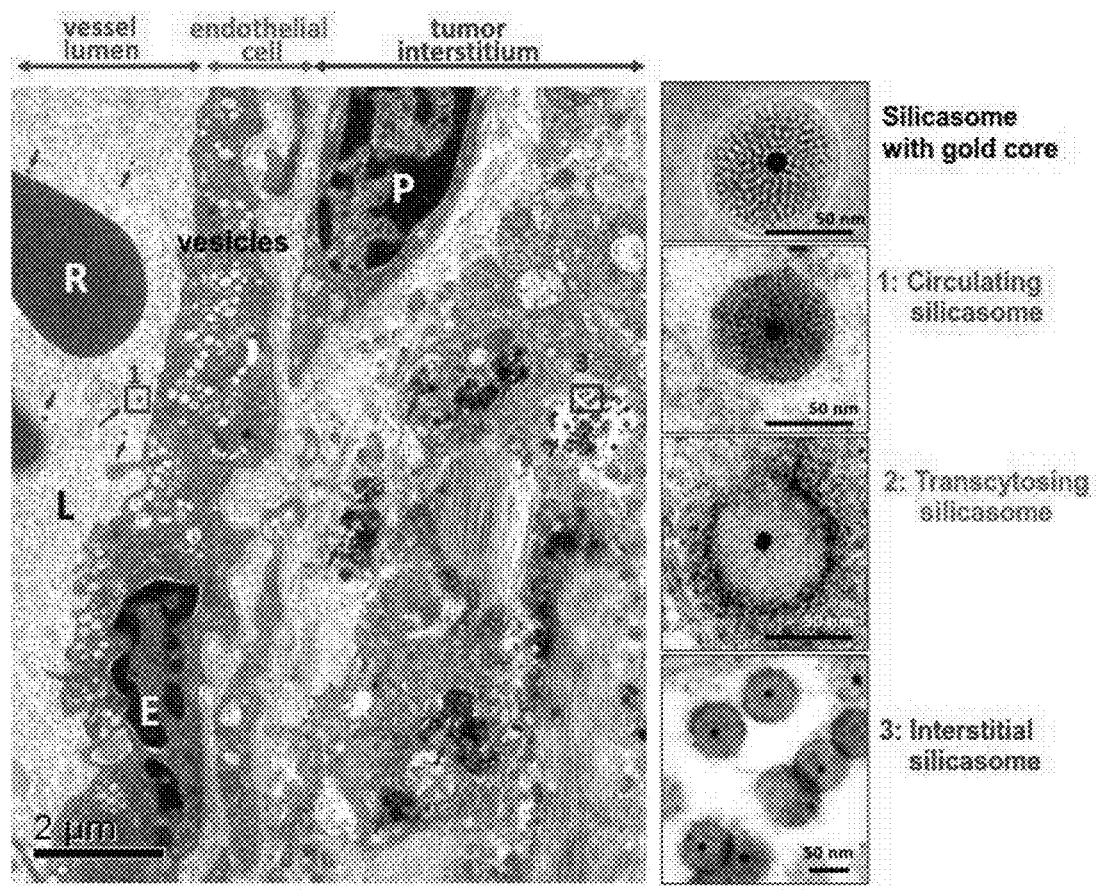
Figure 25C:
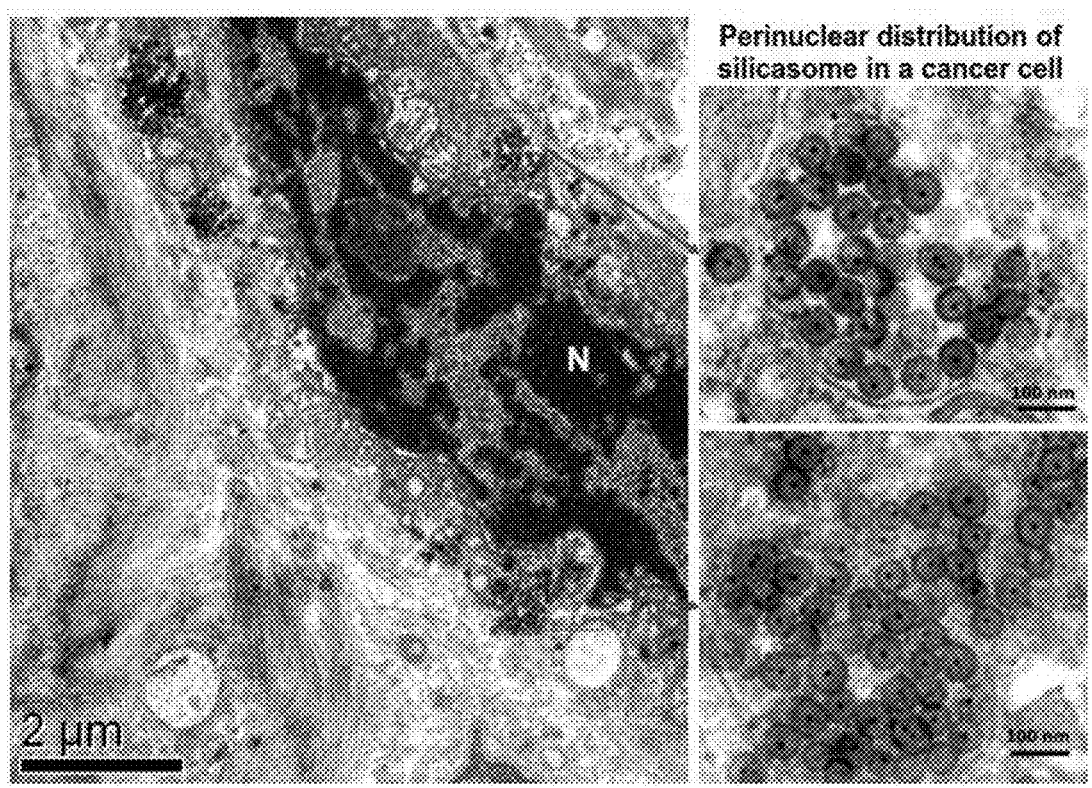
Figure 31:
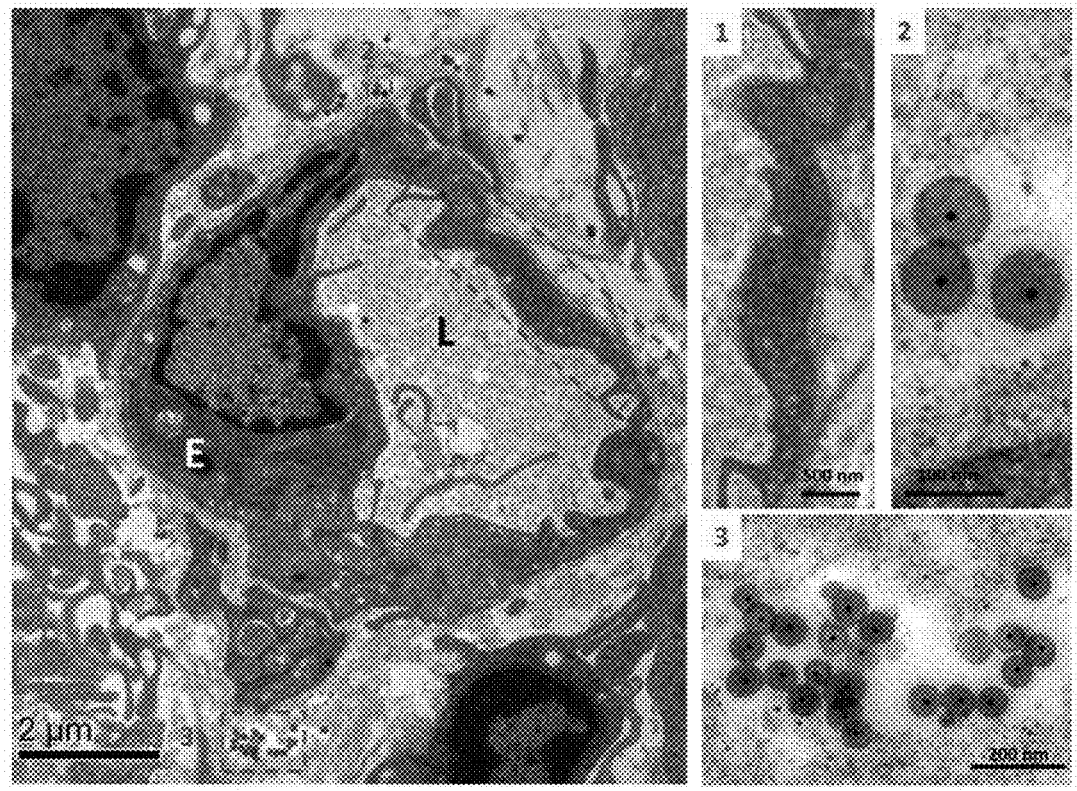
FIG. 31 shows representative TEM images of a KPC-derived tumor from an animal that was prior (24 h) injected with 50 mg/kg Au-embedded silicasomes without iRGD co-administration is shown. The image demonstrates the absence of transcytosis vesicles, with particle deposition on the adluminal side. E=endothelial cell, L=lumen.

When attempting to visualize silicasome transport by the vesicular system, the low electron-density of the MSNPs is difficult to resolve the presence of the carrier in the heterogeneous and complex PDAC microenvironment. To address this challenge, silicasomes were synthesized to include a ~10 nm Au-nanoparticle that can be readily visualized by TEM (FIG. 21A) (Liu et al. 92013) *ACS Nano.* 7(7): 6244-6257). Mice expressing orthotopic KPC tumors were IV injected with 50 mg/kg Au-silicasomes, in the absence or presence of 8 µmol/kg iRGD. Tumor tissue was harvested 24 h post-injection and fixed to perform TEM analysis. A representative electron micrograph displaying, in one image, (i) electron-dense silicasomes in the blood vessel lumen, (ii) vesicular transport in endothelial cells, and (iii) particle deposition in the tumor matrix of an animal receiving iRGD co-administration is shown in FIG. 25B. Higher magnifications of regions 1-3 of the image confirm the presence of Au-containing particles. It was also possible during iRGD co-administration to demonstrate the appearance of silicasomes in a perinuclear distribution in tumor cells undergoing apoptosis (FIG. 25C). This site is several hundred µm away from the nearest tumor blood vessel (FIG. 25C). While it was possible to observe lower particle density in the tumor matrix of animals not receiving iRGD treatment, we could not locate any silicasomes being carried by the vesicular transport system, nor could we identify and alternative mechanism for entry in the static images (FIG. 31).

Figure 26A:
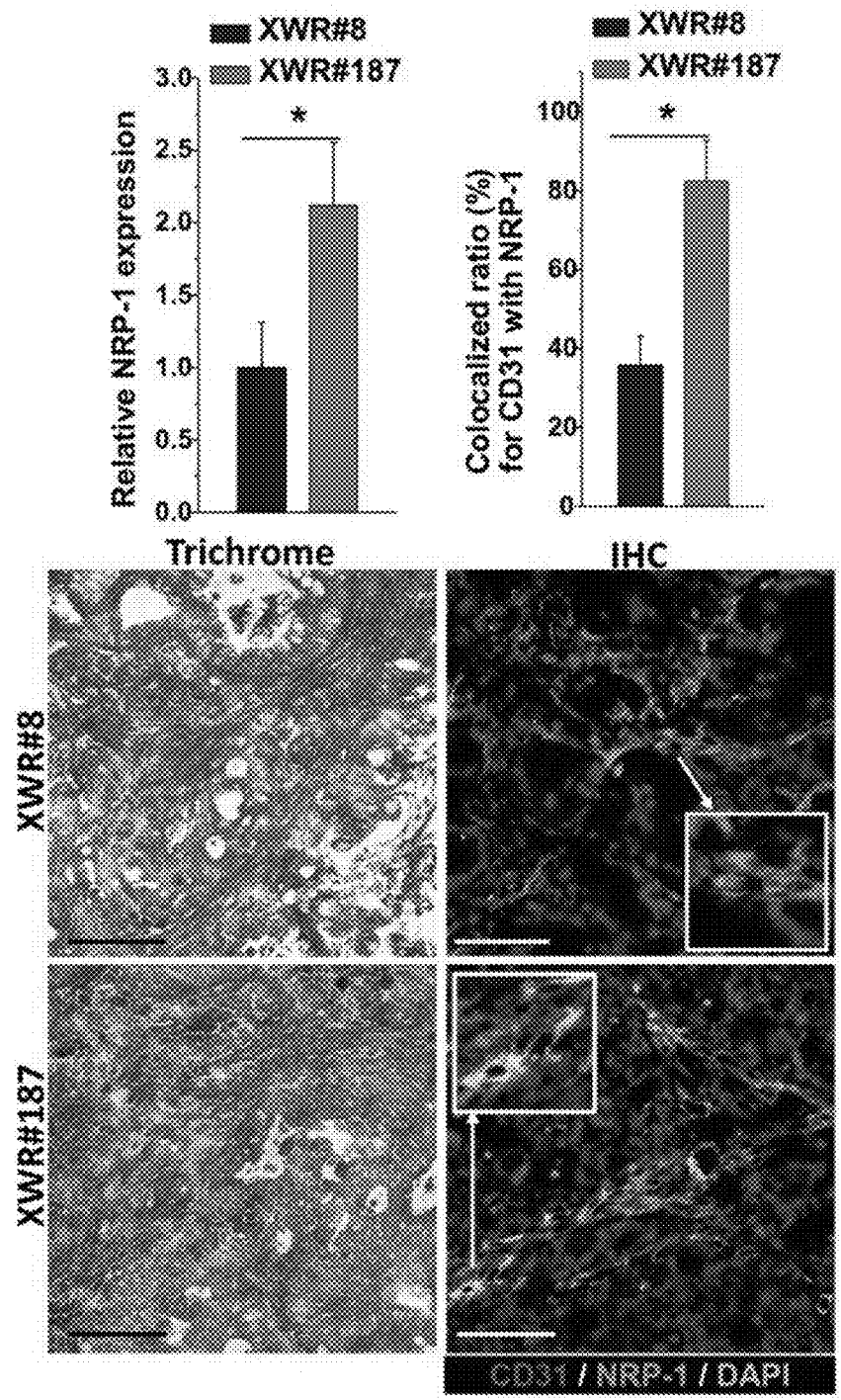
FIGS. 26A-26B illustrate iRGD-induced silicasome biodistribution in patient-derived xenografts in NSG mice.
Figure 26B:
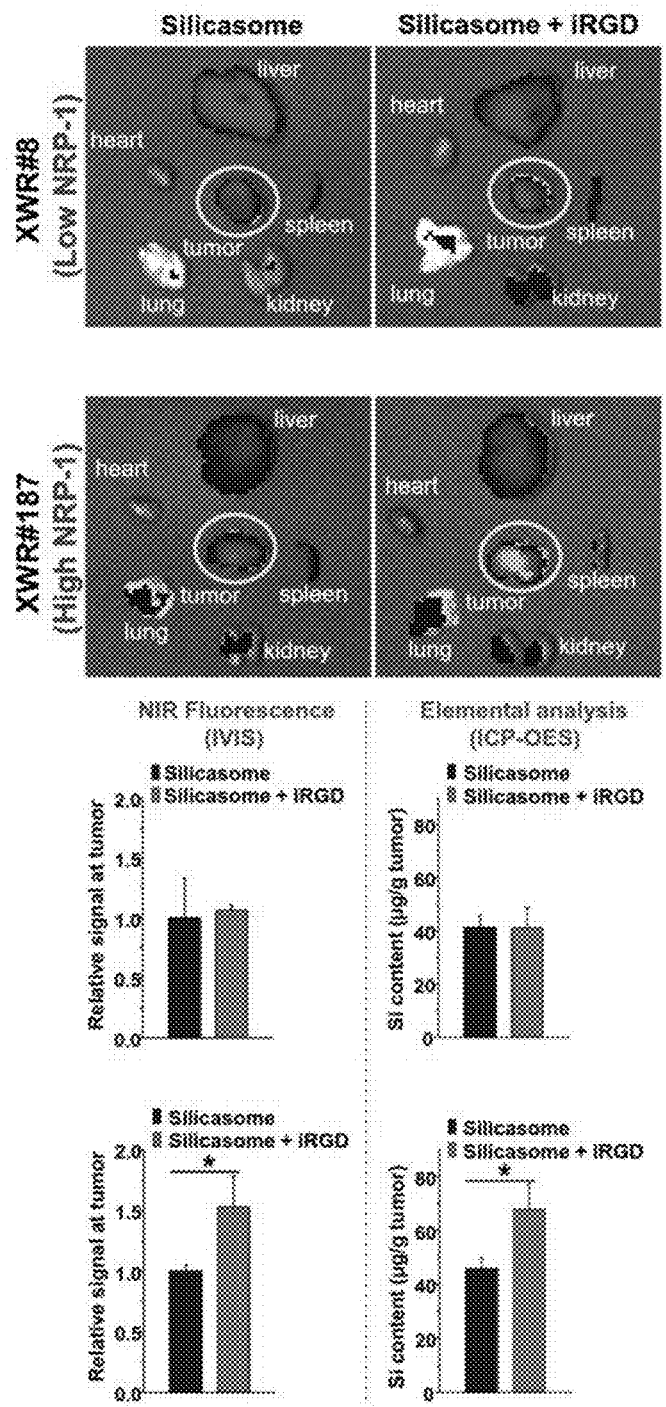

Differential Impact of iRGD Co-Administration on Silicasome Uptake in Patient-Derived PDAC Tumors, Phenotyped for NRP-1 Expression While it is clear that the NRP-1 pathway can be functionally engaged by iRGD in the KPC tumor model, we were interested to see if the peptide could affect silicasome uptake in patient-derived xenografts growing in NOD SCID IL2α knockout (NSG) mice (Rückert et al. (2012). *J. Surg. Res.* 172(1): 29-39). One of us (TD) has established a repository of 23 human PDAC tumors in NSG mice; these tumor samples were obtained from patients during Whipple's surgery. Transferred tumor tissues were phenotypically characterized for cancer features that are distinctive of the corresponding human PDAC tumors, including stromal abundance and the expression of oncogenes and signal pathway components that are characteristic of PDAC (Id.). We used the phenotyping information to select a pair of tumors with equivalent stromal abundance but differing in the density and distribution of NRP-1 expression, as determined by IHC staining. The staining was performed on tumor tissue harvested from NSG mice at the $3^{rd}$ or $4^{th}$ tumor passage, using image J software to compare the density of NRP-1 expression, as well as its co-localization with CD31 and the cellular nucleus (DAPI) (FIG. 26A). We were able to identify two patient tumor samples, designated XWR #8 and XWR #187, that showed similar collagen density (trichrome staining) but differing in NRP-1 expression (FIG. 26A). Thus, while XWR #8 was characterized by low NRP-1 abundance, XWR #187 had high NRP-1 expression levels (FIG. 26A). XWR #187 also exhibited more NRP-1 positive tumor blood vessels (~80%) compared to XWR #8 (~35%). Subcutaneous xenografts (n=3) were established on the flank of NSG mice before the animals were IV injected with NIR labeled silicasomes (50 mg/kg), with or without co-administration of the iRGD peptide (8 µmol/kg). Following animal sacrifice after 24 h, IVIS imaging of the explanted tissues showed a 50% increase of NIR intensity at the tumor site of XWR #187 mice receiving iRGD; similar enhancement was not seen in XWR #8 (FIG. 26B). These data were confirmed by assessing the elemental Si content of the tumor tissues using ICP-OES (FIG. 26B). All things considered, our data indicate that the density and distribution of NRP-1 expression determine the degree of silicasome biodistribution to human tumors in vivo.

Discussion

In this example we demonstrate that the efficacy of an irinotecan-silicasome carrier can be significantly improved by the co-administration of an unconjugated iRGD peptide that does not require to be attached to the carrier to enhance tumor uptake. Co-administration of the free iRGD peptide increased silicasome uptake at orthotopic KPC tumors sites 3-4 fold, leading to enhanced killing of the primary tumor as well as metastasis inhibition. Overall, this resulted in a significant improvement in animal survival over the Ir-silicasome alone. The iRGD effect is mediated by interacting with tumor-associated integrins initially, followed by peptide cleavage and the release of the C-terminal end that engages NRP-1. Although the physiological role of NRP-1 is to control transcytosis for nutritional purposes, the vesicular system can also be used for the transport of nanoparticles, as demonstrated by the reduction of particle transport after the injection of receptor-blocking antibodies. Moreover, EM imaging provided ultrastructural evidence that iRGD could induce the appearance of grouped vesicles in endothelial cells, with the ability to carry Au-labeled silicasomes from the blood vessel lumen to the tumor matrix. We also obtained evidence that NRP-1 regulates a transcytosis pathway in human pancreatic tumors, which have been implanted in NSG mice. The selection of a tumor pair with differential NRP-1 expression on the tumor vasculature demonstrated differences in carrier uptake and irinotecan delivery during iRGD treatment. All things considered, these data indicate that it is possible to use a personalized approach to PDAC chemotherapy to enhance the efficacy of the irinotecan silicasome carrier by iRGD co-administration.

The utility of a transcytosis pathway to enhance irinotecan delivery in PDAC is significant for a number of reasons. The first is the display of a dysplastic stroma, which contributes to drug resistance at the tumor site, in addition to augmenting tumor growth and metastasis (Feig et al. (2012) *Clin. Cancer Res.* 18(16): 4266-4276; Dimou et al. (2012) *Ther. Adv. Med. Oncol.* 1758834012446008). While it is often understood that abnormal vascular permeability is the reason for the nanoparticle extravasation, a concept referred to as the EPR effect, we know that the pancreatic cancer stroma actively interfere in vascular permeability (Meng et al. (2013) *ACS Nano.* 7(11): 10048-10065; Kano et al. (2007) *Proc. Natl. Acad. Sci. USA,* 104(9): 3460-3465; Cabral et al. (2011) *Nat. Nanotechnol.* 6(12): 815-823; Liu et al. (2012) *Proc. Natl. Acad. Sci. USA,* 109(41): 16618-16623). This includes the presence of pericytes that tightly adhere to vascular endothelial cells (Id.). Thus, while the EPR effect may contribute to the nanocarrier uptake in PDAC, it is important to consider the possibility that other vascular mechanisms may contribute to the nanoparticle uptake at the tumor site, including the possible contribution of nutritional transport pathways and vascular growth factors that regulate this transport, as well as vascular leakage (Jain and Stylianopoulos (2010) *Nat. Rev. Clin. Oncol.* 7(11): 653-664; Ruoslahti et al. (2010) *J. Cell. Biol.* 188(6): 759-768; Maeda et al. (2000) *J. Control. Release* 65(1): 271-284; Li and Huang (2008) *Mol. Pharm.* 5(4): 496-504; Feng et al. (1996) *J. Exp. Med.* 183(5): 1981-1986; Kobayashi et al. (2014) *Theranostics,* 4(1): 81-89). Ruoslahti et al. described an endocytic pathway, which plays a role in tumor nutrition, and can also be therapeutically engaged by tumor-penetrating iRGD peptides (Pang et al. (2014) *Nat. Commun.* 5: 4904). In addition, vascular growth factors, such as VEGF, VEGF-A, VEGF-A165, TGF-β and semaphorin 3A, display RGD motifs that allow binding to $\alpha_v\beta_3$ and $\alpha_v\beta_5$ integrins on the tumor vasculature (Sugahara et al. (2009) *Cancer Cell,* 16(6): 510-520; Sugahara et al. (2010) *Science,* 328(5981): 1031-1035; Pang et al. (2014) *Nat. Commun.* 5: 4904). Thus, proteolytic cleavage and release of the CendR motif could trigger NRP-1 mediated transcytosis (Pang et al. (2014) *Nat. Commun.* 5: 4904) in addition to the role of the signaling pathways and vascular permeability associated with growth factor receptors (Kolodkin et al. (1997) *Cell.* 90(4): 753-762; Ellis (2006) *Mol. Cancer Ther.* 5(5): 1099-1107; Glinka and Prud'homme (2008) *J. Leukoc. Biol.* 84(1): 302-310). Consequently, it is possible that the NRP-1 pathway may coexist with vascular leakage, including the EPR effect, but displaying different time kinetics. While the response to the CendR motif may commence within minutes, the EPR effect typically requires 6-8 hours to peak (Sugahara et al. (2009) *Cancer Cell,* 16(6): 510-520; Maeda et al. (2003) *Int. Immunopharmacol.* 3(3): 319-328).

Our data for silicasome transcytosis during iRGD co-administration supplement previous attempts to overcome the stromal-vascular barrier during PDAC treatment (Feig et al. (2012) *Clin. Cancer Res.* 18(16): 4266-4276; Dimou et al. (2012) *Ther. Adv. Med. Oncol.* 1758834012446008; Meng et al. (2013) *ACS Nano.* 7(11): 10048-10065; Meng et al. (2015) *ACS Nano.* 9(4): 3540-3557). Several angiogenic drugs have been introduced to improve the tumor access of nanocarriers (Dimou et al. (2012) *Ther. Adv. Med. Oncol.* 1758834012446008; Kobayashi et al. (2014) *Theranostics,* 4(1): 81-89). Among these, VEGF can provide a temporary increase in the perfusion and blood vessel leakiness at the PDAC site to augment nanoparticle uptake (Olive et al. (2009) *Science,* 324(5933): 1457-1461; Jacobetz et al. (2013) *Gut,* 62(1): 112-120). Other agents that promote vascular permeability at the tumor site include bradykinin, nitric oxide, angiotensin-converting enzyme inhibitors, tumor necrosis factor α, heme oxygenase-1, collagenase and hyaluronidase (Kobayashi et al. (2014) *Theranostics,* 4(1): 81-89; Eikenes et al. (2004) *Cancer Res.* 64(14): 4768-4773; Seynhaeve et al. (2007) *Cancer Res.* 67(19): 9455-9462; Fang et al. (2011) *Adv. Drug Deliv. Rev.* 63(3): 136-151; Fang et al. (2012) *Cancer Sci.* 103(3): 535-541; Maeda (2013) *Cancer Sci.* 104(7): 779-789; Eikenes et al. (2005) *Br. J. Cancer.* 93(1): 81-88). We have also demonstrated that the use of a nanocarrier that delivers a small molecule inhibitor of the transforming growth factor beta (TGF-β) pathway, LY364947, can rapidly (<2 h) reverse pericyte adherence to endothelial cells in vivo (Meng et al. (2013) *ACS Nano.* 7(11): 10048-10065). The accompanying multiple fold increase in vascular permeability was demonstrated to provide a dramatic increase in the egress of gemcitabine-delivering liposomes at the tumor site (19). Other approaches for enhancing blood vessel permeability by targeting of the TGF-β pathway have also been reported (Cabral et al. (2011) *Nat. Nanotechnol.* 6(12): 815-823; Liu et al. (2012) *Proc. Natl. Acad. Sci. USA,* 109(41): 16618-16623). Finally, it is worth mentioning that the silicasome carrier can achieve stromal reduction by co-delivery of paclitaxel with gemcitabine (Meng et al. (2015) *ACS Nano.* 9(4): 3540-3557), to the extent that our carrier could outperform the administration of Abraxane plus free gemcitabine during treatment of orthotopic PDAC tumors in mice (Frese et al. (2012) *Cancer Discov.* 2(3): 260-269).

Based on the demonstration that co-delivery of iRGD enhances the uptake of silicasomes at PDAC tumor sites (FIG. 22), it is important to stress that the co-administration approach overcomes a major limitation of the alternative delivery mechanism where the peptide is conjugated the nanocarrier. The explanation for this difference lies in the transport capacity of the carrier system, based on the available number of NRP-1 receptors (Sugahara et al. (2010) *Science,* 328(5981): 1031-1035; Ruoslahti (2012) *Adv. Mater.* 24(28): 3747-3756; Ruoslahti (2016) *Adv. Drug Deliv. Rev.* pii: S0169-409X(16)30094-1. doi: 10.1016/j.addr.2016.03.008). Thus, while the transport of the conjugated silicasome is limited by the relatively small and finite number of target receptors on the vasculature, separate injection of the unconjugated peptide triggers bulk transfer of bystander silicasomes (in greater number) at the tumor site. Moreover, free iRGD also harbors anti-metastatic activity through the regulation of integrin function, as demonstrated by interference in the attachment and migration of culture tumor cells on a fibronectin matrix (Sugahara et al. (2015) *Mol. Cancer Ther.* 14(1): 120-128). This could explain, in part, the peptide interference on tumor metastasis in our study (FIGS. 23B and 23C). The use of the free peptide is also more practical and affordable for clinical use, as compared to relying on a conjugation mechanism that increases the cost and the complexity of the carrier synthesis.

Materials and Methods

A more detailed description of Materials and Experimental Procedures appear in the Supplemental Materials and Methods below.
Silicasome Preparation
Synthesis of Irinotecan Loaded Silicasome:

The 65 nm MSNP core was synthesized using a sol-gel procedure as shown above (see also, Liu et al. (2016) *ACS Nano.* 10(2): 2702-2715). A lipid biofilm was used to produce the silicasomes as previously reported (Meng et al. (2015) *ACS Nano.* 9(4): 3540-3557; see Example 1 and Liu et al. (2016) *ACS Nano.* 10(2): 2702-2715). Briefly, 500 mg MSNPs were soaked in a 20 mL TEA$_8$SOS (80 mM solution, which was added on top of the lipid biofilm, comprised of a 550 mg mixture of DSPC/Chol/DSPE-PEG$_{2000}$ (molar ratio 3:2:0.15), coated at the bottom of a round bottom flask (see Example 1, and Liu et al. (2016) *ACS Nano.* 10(2): 2702-2715). After sonication to accomplish particle coating with a LB, free TEA$_8$SOS was removed by size exclusion chromatography over a Sepharose CL-4B column. The TEA$_8$SOS loaded silicasomes were incubated in a 10 mg/mL irinotecan solution for drug loading in a water bath at 65° C. The loading was stopped after 30 min by quenching in and ice water bath, following which the drug-loaded silicasomes were washed 3 times by centrifugation and re-suspended in PBS.
Synthesis of iRGD Conjugated Silicasome:

iRGD-conjugated silicasomes were synthesized by linking the peptide to a PEG chain included in the LB. This was accomplished by using commercially available DSPE-PEG$_{2000}$-maleimide in place of DSPE-PEG$_{2000}$, while maintaining the molar ratio of the lipids as described above. An excess (0.15 mL, 5 mg/mL) of the cysteine-modified iRGD peptide was conjugated to the DSPE-PEG$_{2000}$-maleimide, using a thiol-maleimide reaction, carried out at room temperature for 4 h (Sugahara et al. (2009) *Cancer Cell,* 16(6): 510-520). The particles were washed to remove the non-reacted iRGD. The success of the conjugation reaction was confirmed by also preparing a batch of particles conjugated to a fluorescein (FAM) labeled iRGD peptide, followed by extensive washing (Id.) (FIG. 27, panel A).
Synthesis of Silicasomes with a Told Core Marker:

10 nm Au nanoparticles were synthesized in a citrate containing solution (see Supplemental Materials and Materials below). To grow the MSNP shell on the Au nanoparticle core, 36 mL of the citrate-capped particles was rapidly injected into 12 mL CTAC solution (25 wt % in H$_2$O). The particles were washed and re-suspended in a CTAC solution (6.25 wt % in H$_2$O), with stirring at 350 rpm for 5 min at 85° C. To this mixture, we added 0.256 mL of 10% (w/v) triethanolamine for 10 min, followed by drop wise addition of 0.32 mL of the silica precursor, TEOS. The solution was stirred at 350 rpm for 20 min, leading to the creation of Au core/MSNP shell particles with an average size of ~65 nm. The particles were purified by sequential washing in 1% NaCl in methanol (w/v) and pure methanol. The Au-labeled MSNPs were then coated with a LB, as described before.
Biodistribution Study of IV Injected Silicasomes with or without iRGD Co-Administration IVIS (Xenogen) imaging was used to study the biodistribution of NIR-labeled silicasomes in the KPC-derived orthotopic model (n=3 mice/group) (see Example 1, and Liu et al. (2016) *ACS Nano.* 10(2): 2702-2715). Animals were IV injected with 50 mg/kg of the conjugated and non-conjugated silicasomes, with or without the co-administration of 8 μmol/kg iRGD. Animals were sacrificed after 24 h followed by ex vivo imaging of the excised tumors and major organs. Tumor biodistribution was also confirmed by assessing the Si content, using an ICP-OES protocol (Id.).
Assessment of Ir-Silicasome Efficacy by iRGD Co-Administration in the KPC-Derived Orthotopic Tumor Model Tumor-bearing B6/129 mice were randomly assigned into 4 groups, with 6 animals each. The first group was IV injected with silicasomes containing an irinotecan dose of 40 mg/kg (80 mg/kg MSNP) every 3 days, for a total of 4 administrations. The second group received the same dose of the Ir-silicasome plus co-administration of 8 μmol/kg iRGD. The third and fourth groups were treated with PBS or iRGD alone. The mice were monitored daily up to the point of spontaneous animal death or approaching moribund status (see Example 1 and Liu et al. (2016) *ACS Nano.* 10(2): 2702-2715; Olive et al. (2009) *Science,* 324(5933): 1457-1461). Bioluminescence imaging of the primary tumor and metastasis sites were performed by injecting the animals intraperitoneally with 75 mg/kg D-Luciferin, 10 min before sacrifice. The tumor tissue and major organs (GI tract, liver, spleen, heart, lung and kidneys) were harvested for quantitative assessment of the bioluminescence image intensity.
Ultrastructural Analysis of the Transcytosis Pathway Through TEM Viewing KPC orthotopic tumor mice were treated by IV injection of 50 mg/kg of the Au-encapsulated silicasomes, with or without the co-administration of 8 μmol/kg iRGD. Tumor biopsies were collected after 24 h, washed in PBS, and immediately fixed at 4° C. with 2.5% glutaraldehyde. Further sample preparation and sectioning were performed by the Electron Microscopy Services Center at UCLA. After fixation in 1% 0504, the samples were dehydrated in propylene oxide and embedded in resin. Tissue slices of 60-80 nm thick were placed on copper grids, and viewed under a JEOL 1200-EX electron microscope.
Silicasome Biodistribution in Patient-Derived PDAC Tumors A repository of 23 PDAC samples were collected, with institutional human subject approval, from patients undergoing Whipple's surgery, and used to establish xenografts in NSG mice in Dr. Timothy Donahue's laboratory. Utilizing phenotyping data and performance of IHC staining for NRP-1 expression, two patient samples (XWR #8 and #187) were collected for growing fresh subcutaneous xenografts in the flanks of 6 weeks old female NSG mice (Rückert et al. (2012). *J. Surg. Res.* 172(1): 29-39). When the tumor size grew to a diameter of ~0.8 cm, 3 animals in each group receiving silicasomes, with or without iRGD co-administration, were used to assess biodistribution to the tumor site, similar to the procedure described above. Animals were sacrificed after 24 h for the performance of ex vivo imaging to determine the uptake of NIR-labeled silicasomes. The imaging data were also confirmed by assessing the Si content at the tumor sites by ICP-OES.

Statistical Analysis

Comparative analysis of differences between groups was performed using the two-sided Student's t-test (Excel software, Microsoft). A statistically significant difference was determined at p<0.05. Values were expressed as mean±SD of multiple determinations, as stated in the figure legends. The survival data was processed by Log Rank test (Mantel-Cox) using SPSS software.

Supplemental Materials and Methods

Materials

Tetraethylorthosicate (TEOS). triethanolamine. cetyltrimethylammonium chloride solution (CTAC. 25 wt % in water). (3-aminopropyl)triethoxysilane (APTES). triethylamine (TEA). gold (III) chloride hydrate. trisodium citrate dehydrate. Dowex 50WX8 resin. and Sepharose CL-4B were purchased from Sigma-Aldrich. USA. 1. 2-Distearoyl-sn-glycero-3-phosphocholine (DSPC). 1. 2-distearoyl-sn-glycero-3-phosphoethanolamine-N-[methoxy(polyethylene glycol)-2000] (ammonium salt) (DSPE-PEG$_{2000}$). 1. 2-distearoyl-sn-glycero-3-phosphoethanolamine-N-[maleimide (polyethylene glycol)-2000] (ammonium salt) (DSPE-PEG$_{2000}$-maleimide) and cholesterol (Chol) were purchased from Avanti Polar Lipids. USA. Sucrose octasulfate (SOS) sodium salt was purchased from Toronto Research Chemicals. Canada. Irinotecan hydrochloride trihydrate was purchased from LC Laboratories. USA. Penicillin. streptomycin. and Dulbecco's modified Eagle medium (DMEM) were obtained from Invitrogen. Fetal bovine serum (FBS) was purchased from Gemini Bio Products. USA. iRGD (CRGDKGPDC, SEQ ID NO: 11) was purchased from Biomatik. USA. Reactive iRGD modified with cysteine residue and blocking anti-NPR-1 antibody (against recombinant b1b2 domain of NRP-1) were kindly provided by Dr. Ruoslahti. Cyclo (-RGDfK) (SEQ ID NO:12) was purchased from ApexBio Technology. USA. Anti-CD31 antibody (catalog #553708) was purchased from BD Pharmingen™. USA. Anti-NPR-1 antibody (ab81321) was purchased from Abcam. USA. Control normal goat IgG (sc-2028) was purchased from Santa Cruz Biotechnology. USA. Alexa Fluor® 488 conjugated goat anti-rabbit IgG (H+L) secondary antibody (A11008). Alexa Fluor® 594 conjugated goat anti-rat IgG (H+L) secondary antibody (A11007) and DyLight 680 NHS ester were purchased from Thermo Fisher Scientific Inc. USA. Matrigel™ Matrix Basement Membrane was purchased from BD Bioscience. USA. All chemicals were directly used without further purification.

NIR Labeling of MSNPs Using DyLight 680

The NIR fluorescent dye. DyLight 680 NHS ester was used for MSNP labeling. First. the MSNP surface was functionalized with NH$_2$ groups for conjugation of the NHS ester. Briefly. 10 mg MSNPs were suspended in 1 mL of ethanol and mixed with 1 μL, of APTES. The reaction took place under an inert N2 atmosphere. while stirring at 80° C. overnight. Subsequently. the mixture was centrifuged and washed 3 times with ethanol. The NH$_2$-conjugated MSNPs were suspended in 1 mL of DMF, mixed with 0.01 mg of DyLight 680 NHS ester and stirred at room temperature for 2 h. The labeled MSNPs were washed with ethanol and deionized water. NIR-labeled MSNPs were used to make the silicasomes.

Synthesis of ~10 nm Gold Nanoparticle

Gold nanoparticles of ~10 nm were made by adding 5 mL HAuCl$_4$ (10 mM) and 45 mL Milli-Q water to a 100 mL round-bottom flask equipped with a condenser. After reaching boiling temperature. while being stirred vigorously. 5.8 mL of sodium citrate (38.8 mM) was added into the boiling solution. This was accompanied by in a color change from pale yellow to burgundy. The boiling solution was stirred for 10 min at 160° C. and then stirred for an additional 15 min without heating. The gold particles were used as a core for synthesis of silicasomes. as described in the methods section of the manuscript.

Cell Line

An immortalized cell line was derived from a spontaneously tumor in a transgenic Kras$^{LSL-G12D/+}$; Trp53$^{LSL-R172H/+}$; Pdx-1-Cre mouse. To allow bioluminescence tumor imaging of the growing tumors after orthotopic implantation. the cells were permanently transfected with a luciferase-based lentiviral vector in the UCLA vector core facility. A representative cell clone was obtained after use of a limiting dilution protocol.

Preparation of Orthotopic Tumors in Immune Competent Mice, Using the KPC-Derived Cell Line All animal experiments were performed with protocols approved by the UCLA Animal Research Committee. Female B6/129 mice (~8 weeks) were purchased from The Jackson Laboratory. To grow orthotopic xenografts. the mice were anesthetized with isoflurane. followed by IP injection of 50 mg/kg ketamine and 10 mg/kg xylazine. The surgical site was shaved to leave a margin of 1 cm around the incision site and sterilized by scrubbing with betadine and 70% ethanol. The mice were positioned for surgery on a heating pad. and the incision site in the left flank was draped with sterile gauze. A surgical incision of ~0.7 cm was made to expose the injection site. followed by an injection of 50 μL of DMEM/Matrigel (1:1 v/v) containing 2×10$^6$ KPC-luc cells into the pancreatic tail through a 27 G needle. The fascial layers were closed with absorbable sutures (PDS II. Ethicon) and the skin with nonabsorbable sutures (PROLENE. Ethicon). The mice were kept on the warming pads until full recovery from the anesthesia. and then transferred to clean cages. Artificial tear ointment was used to protect the mouse eyes during the surgery.

Use of Anti-NRP-1 Blocking Antibody to Interfere in the iRGD Effect

50 μg of a blocking anti-NRP-1 antibody or a control IgG was injected 15 min before the KPC-derived orthotopic tumor-bearing mice received IV injection of 50 mg/kg NIR-labeled silicasome plus 8 μmol/kg free iRGD. Animals receiving the silicasome alone were used as controls. Animals were sacrificed at 24 h post-injection. and ex vivo NIR imaging was used to study the biodistribution of NIR labeled silicasomes. The ex vivo imaging data was quantified by NIR intensity analysis using IVIS software. followed by Si content analysis using ICP-OES.

HPLC Analysis

For HPLC analysis of irinotecan in tissues. the harvested tumor and organ samples were weighed and homogenized on ice. Following the extraction of 0.1 mL tissue homogenate with 0.4 mL of an acidic solution (0.1 mol/L phosphoric acid/methanol. 1:4 v/v). the extracts were vortexed twice for 10 s and centrifuged at 13,000 rpm for 10 min. The irinotecan-containing supernatants were filtered through 0.22 μm filters for HPLC analysis in a system containing a Knauer Smartline pneumatic pump. C18 column. K-2600 spectrophotometer. and Gina data acquisition software. The mobile phase, delivered at a flow rate of 1.0 mL/min, was comprised of a 3% triethylammonium acetate aqueous buffer (pH=5.5) and acetonitrile (73:27 v/v). Twenty microliters of an irinotecan-containing sample was injected to measure the drug absorption at 254 nm typically eluted in ~4.4 min. An irinotecan standard curve was generated over the concentration range 0.05-100 μg/mL.

Immunofluorescence Staining

Dual color immunofluorescence staining was used to determine the NPR-1 positive blood vessels in KPC tumor tissue. The tumor tissues were cryo-embedded. using the OCT reagent. and used to prepare tumor sections. The sections were first treated with anti-NRP1 monoclonal antibody (1:250) at 4° C. overnight. After removal of the primary antibody and washing in PBS 3 times. the Alexa Fluor® 488 secondary antibody (1:500) was added and incubated for 1 h at room temperature. The same sections were also stained with anti-CD31 antibody. followed by Alexa Fluor® 594-conjugated secondary antibody treatment to identify CD31 expression. DAPI was used to localize the cellular nuclei. The stained slides were examined under a fluorescence microscope (Observer D1. Zeiss). The colocalization ratio of NRP-1$^+$/CD31$^+$ blood vessels were determined by Imaging J software.

Example 4

Comparative Analysis of the Protocell to the Silicasome

One approach to the preparation of lipid bilayer coated nanoparticles involved the use of MSNPs synthesized by an aerosol-assisted self-assembly method. The MSNPs were coated by the use of electrostatically charged liposomes, which sequentially adhere, rupture and then fuse with the negatively charged MSNP surface (see, e.g., Liu et al. (2009) J. Am. chem. Soc. 131: 7567-7569). This product, developed by Dr. Brinker's group at Sandia and the University of New Mexico, is called a "Protocell", and received a US patent (U.S. Pat. No. 8,992,984 B1) with the title: "Protocells and their use for targeted delivery of multicomponent cargos to cancer cells". The patent teaches, inter alia, that the "protocell can be formed by mixing the cargo components and the porous particle with liposomes or lipids, followed by fusing the lipid bilayer on the porous particle and synergistically loading the cargo components into one or more pores of the porous particle to form the protocell compound". An example protocell shown in FIG. 1C of the 8,992,984 patent depicts "positively charged porous particles [that] can be fused with negatively charged lipid bilayers, such as a DOPS lipid bilayer, wherein the positively charged porous particles can absorb negatively charge cargo components (e.g., calcein or DNA or siRNA)".

In developing the methods and silicasomes described herein we actively avoided the procedures and ingredients used in the Protocell because we regarded this approach as unpredictable and non-enabling for a number of reasons. Not only did we fail to achieve uniform MSNP coating using the liposomal fusion method described in the 8,992,984 patent, but we could not accomplish significant drug loading in a large number of attempts. This prompted us to develop the biofilm technique, sonication procedure, and loading methods described herein to obtain a reproducible procedure for uniform particle coating with an LB of different lipid composition to the protocell.

Figure 32:
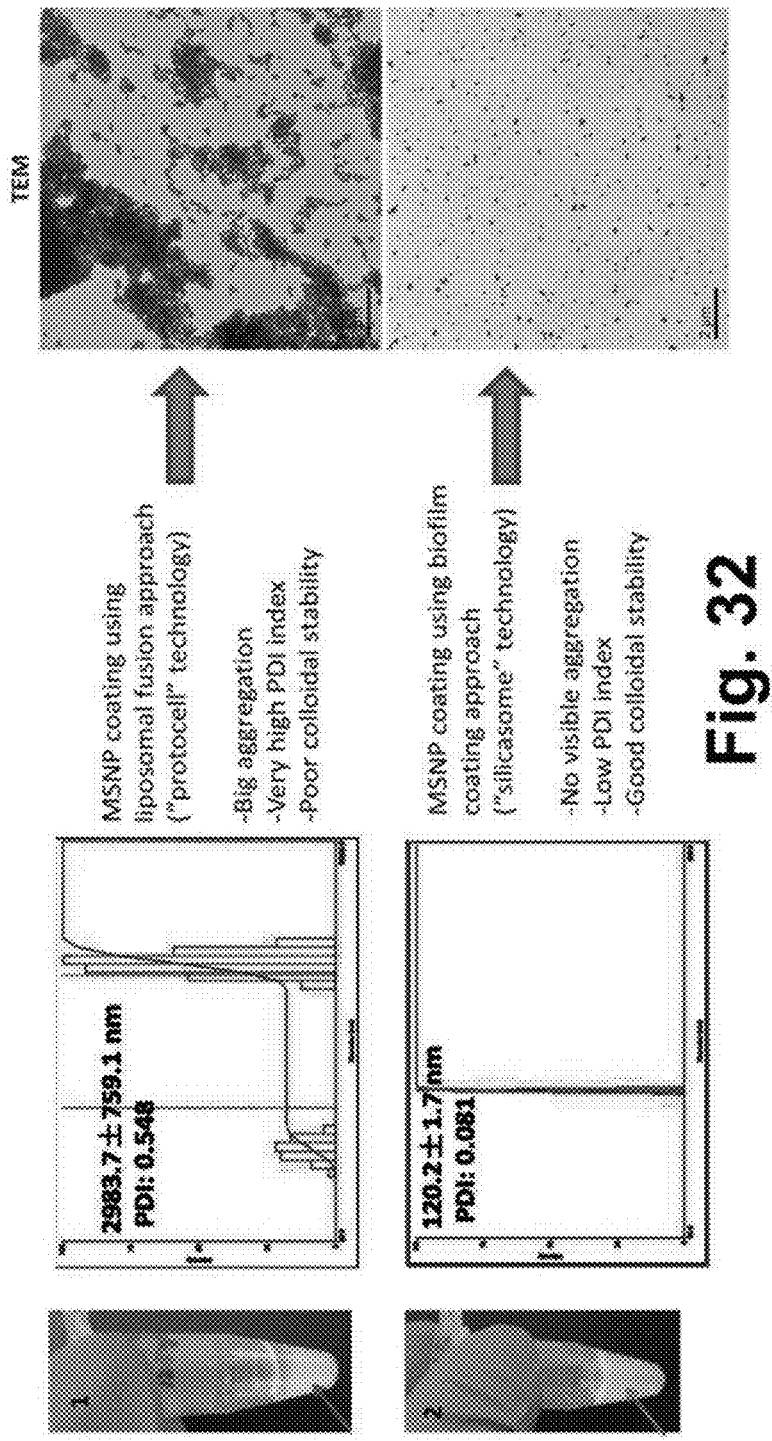
FIG. 32 illustrates the results of a comparison between protocell and silicasome technologies.

FIG. 32 depicts data generated during our attempt to produce a "Protocell" that is equivalent to the protocells described by Ashley et al. (2011) Nat. Mat., 10:389-397. Briefly, 100 μL 25 mg/mL MSNPs were added to 100 μL of a liposome at 2.5 mg/mL, followed by the sequence of steps described in the Ashley et al. publication (Id.). The final product is shown in the upper panel. This product was subjected to assessment of hydrodynamic size, size distribution and colloidal stability. The picture insert on the left shows a phase separation of the "coated" product and the DLS panel in the middle shows a small peak of uncoated particles plus a large speak of an agglomerated particle mass. The TEM image at the right confirms particle aggregation for the procells and colloidal stability for the silicasomes. The lack of colloidal stability of the protocells disqualifies the product for use by IV administration. In summary, unlike the protocell, the silicasome exhibits excellent colloidal stability, low PDI, and a narrow size distribution.

Table 6 illustrates various differences between the silicasome and protocell technologies.

TABLE 6

Comparison of certain features of the silicasome versus the protocell technologies.

| Composition, method, or outcome | Silicasome | Protocell |
|---|---|---|
| MSNP synthesis method | Sol-gel method, yielding uniform particle size distribution with characteristics shown in Examples 1-3 | Aerosol-assisted self-assembly, yielding particles with a heterogeneous size distribution and characteristics shown above |
| LB composition | The lipid composition of the biofilm of illustrative, but non-limiting silicasomes is: DPPC/Chol/DSPE-PEG (PTX/GEM co-delivery silicasome) DSPC/Chol/DSPE-PEG (irinotecan silicasome) | The actual lipid composition of the coated particles is unknown, but is made from liposomes with the following compositions: DOPC/Chol/DOTAP DOPC/Chol/DOPS DOPC/Chol/DSPE-PEG DPPC/Chol/DSPE-PEG DOPC/Chol/DOPE-PEG DSPC/Chol/DSPE-PEG |
| MSNP:lipid ratio (wt/wt) | 1:1.1 | 10:1 (changed in Ashley et al. supra to 1:2) |

TABLE 6-continued

Comparison of certain features of the silicasome versus the protocell technologies.

| Composition, method, or outcome | Silicasome | Protocell |
|---|---|---|
| Coating technique and efficiency | Single step approach, using sonication with high energy input and instantaneous encapsulation of ~100% of particles, with Cry EM proof in a population of particles | Multi-step approach, using vortexing of the particle/liposome mix, with low energy input, and lack of evidence for coating most particles in a population |
| Particle size, size distribution | In illustrative, but non-limiting embodiments, MSNP core size ranges from 60-70 nm. They are highly uniform with PDI <0.1. After LB coating, the silicasome exhibits a hydrodynamic size of 110-130 nm with a PDI of <0.1. CryoEM shows the primary silicasome size of ~80 nm. Our LB coating procedure is also effective in coating MSNPs with uniform and smaller or bigger MSNP core size, such as 50-300 nm. | The MSNP core is not made in a sol-gel procedure, therefore, the core particles are not uniform but a mixture of large and small particles. In the protocells, MSNP core size ranges between 50 to 300 nm. Therefore, the PDI of the sample is too heterogeneous to be calculated. |
| Pore distribution and size | Worm like size distribution, size ~3 nm | Worm like; 1.95-2.25 nm |
| Colloidal stability | High colloidal stability. Ongoing stability test shows good and unchanged stability from the moment of production through storage in PBS at 4° C. for more than 6 months. | Instantaneuos agglomeration, making further stability testing impossible |
| Synthesis Reproducibility | Highly reproducible, even by undergraduate students performing the technique for the 1$^{st}$ time | Non-reproducible in our hands as well as working side-by-side with the Brinker people |
| Drug loading methods | Remote loading by a proton gradient | Mostly soaking in and using electrostatic attachment to the pores before encapsulation |
| Active Pharmaceutical Ingredient (API) characteristics | Hydrophilic drugs, hydrophobic drugs, combination of hydrophilic and hydrophobic, remote loading of drugs with weak base characteristics described according to the following paradigm: The general characteristics of these cargo molecules include the following chemical properties: (i) organic molecular compounds that include primary, secondary, tertiary, or quaternary amine(s); (ii) a p$K_a$ <11 to allow protonation and entrapment behind the LB; (iii) a water solubility ranging from around 5 to 25 mg/mL and amphipathic characteristics that allow diffusion across the LB; (iv) an octanol/water partition coefficient or log P value of -3.0 to 3.0; (v) suitable molecular weight with a geometric size less than MSNP pore size (2-8 nm) to allow entry into the MSNP pores. | 8,992,984 patent recites a large number of payloads without clear definition on the structure of these APIs. Minimally, this includes about 360 payload structures, such as chemoagents, kinase inhibitors, antibodies and protein. The encapsulation of various DNAs and siRNAs is also claimed. While electrostatic interaction may play a role in certain cases, most of these APIs are encapsulated via a passive encapsulation process. |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of making a drug nanocarrier, comprising:

providing a nanocarrier comprising a silica body having a surface including a plurality of pores suitable to receive molecules therein, disposing a cargo trapping agent within the plurality of pores;

coating the plurality of pores of the nanocarrier with a phospholipid bilayer, wherein the phospholipid bilayer encapsulates said silica body and seals the plurality of pores; and introducing a cargo comprising a drug into the plurality of pores, so that a phospholipid bilayer coated drug nanocarrier is made, wherein the nanocarrier shows <5% drug leakage over 24 hours in a biological buffer with pH of 7.4 at 37° C.

2. The method of claim 1, wherein said silica body comprises a sol-gel synthesized, size-controlled and colloidally stable silica body.

3. The method of claim 1, wherein the cargo trapping agent is a protonating agent.

4. The method of claim 3, wherein the protonating agent comprises an ammonium salt, a trimethylammonium salt, a triethylammonium salt, or an ionophore combined with a metal salt.

5. The method of claim 3, wherein the protonating agent is triethylammonium sucrose octasulfate (TEA8SOS).

6. The method of claim 3, wherein the nanocarrier has a drug loading capacity of at least 20% w/w.

7. The method of claim 6, wherein the nanocarrier has colloidal stability in physiological fluids with pH 7.4 and remains monodisperse to allow systemic biodistribution and is capable of entering a disease site by vascular leakage or transcytosis.

8. The method of claim 1, wherein the phospholipid bilayer comprises cholesterol.

9. A method of making a nanocarrier, comprising:

providing an unloaded nanocarrier including a silica body having a surface and defining a plurality of pores that are suitable to receive molecules therein, and a phospholipid bilayer coating the surface; and encapsulating a cargo-trapping agent within the phospholipid bilayer.

10. The method of claim 9, further comprising exposing the nanocarrier to a cargo selected to interact with the cargo-trapping agent.

11. The method of claim 10, wherein the cargo is selected to have a pKa greater than 7 and less than 11 and capable of being protonated, and the cargo-trapping agent includes at least one anionic group.

12. The method of claim 10, wherein the cargo is irinotecan and the cargo-trapping agent is triethylammonium sucrose octasulfate (TEA8SOS).

13. The method of claim 10, wherein the cargo is a topoisomerase I inhibitor, topotecan; one or more antitumor anthracycline antibiotics, doxorubicin and mitoxantrone; one or more mitotic inhibitors, vinblastine and vinorelbine; or one or more tyrosine-kinase inhibitors imatinib, osimertinib, and sunitinib.

14. The method of claim 10, wherein the nanocarrier has a drug loading capacity of at least 30% w/w.

15. The method of claim 10, wherein the cargo comprises one or more drugs independently selected from the group consisting of a topoisomerase inhibitor, an antitumor anthracycline antibiotic, a mitotic inhibitor, an alkaloid, an alkaline alkylating agent, a purine or pyrimidine derivative, and a protein kinase inhibitor.

16. The method of claim 10, wherein the cargo-trapping agent converts the cargo into a hydrophilic derivative that is incapable of back diffusion across the lipid bilayer.

17. The method of claim 2, wherein the cargo is protonated by the cargo-trapping agent and trapped in the plurality of pores as a gel precipitate.

18. The method of claim 10, wherein the cargo-trapping agent before reaction with the cargo comprises an ammonium salt, a trimethylammonium salt, a triethylammonium salt, or an ionophore combined with a metal salt.

19. The method of claim 18, wherein the ammonium salt is selected from the group consisting of ammonium sulfate, ammonium sucrose octasulfate, ammonium α-cyclodextrin sulfate, ammonium β-cyclodextrin sulfate, ammonium γ-cyclodextrin sulfate, ammonium phosphate, ammonium α-cyclodextrin phosphate, ammonium β-cyclodextrin phosphate, ammonium γ-cyclodextrin phosphate, ammonium citrate, and ammonium acetate.

20. The method of claim 18, wherein the trimethylammonium salt is selected from the group consisting of trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, and trimethylammonium acetate.

21. The method of claim 18, wherein the triethylammonium salt is selected from the group consisting of triethylammonium sulfate, triethylammonium sucrose octasulfate, triethylammonium α-cyclodextrin sulfate, triethylammonium β-cyclodextrin sulfate, triethylammonium γ-cyclodextrin sulfate, triethylammonium phosphate, triethylammonium α-cyclodextrin phosphate, triethylammonium β-cyclodextrin phosphate, triethylammonium γ-cyclodextrin phosphate, triethylammonium citrate, and triethylammonium acetate.

22. The method of claim 9, wherein the method produces a plurality of nanocarriers having a median diameter of less than one micron.

\* \* \* \* \*

```
                         SEQUENCE LISTING

<160> NUMBER OF SEQ ID NOS: 12

<210> SEQ ID NO 1
<211> LENGTH: 23
<212> TYPE: PRT
<213> ORGANISM: Artificial
<220> FEATURE:
<223> OTHER INFORMATION: Synthetic fusogenic peptide.

<400> SEQUENCE: 1

Gly Leu Phe His Ala Ile Ala His Phe Ile His Gly Gly Trp His Gly
1               5                   10                  15

Leu Ile His Gly Trp Tyr Gly
            20

<210> SEQ ID NO 2
<211> LENGTH: 5
<212> TYPE: PRT
<213> ORGANISM: Artificial
<220> FEATURE:
<223> OTHER INFORMATION: Cyclized peptide
<220> FEATURE:
<221> NAME/KEY: misc_feature
<222> LOCATION: (4)..(4)
<223> OTHER INFORMATION: Xaa is D phenylalanine

<400> SEQUENCE: 2

Arg Gly Asp Xaa Lys
1               5

<210> SEQ ID NO 3
<211> LENGTH: 5
<212> TYPE: PRT
<213> ORGANISM: Artificial
<220> FEATURE:
<223> OTHER INFORMATION: Cyclized peptide
<220> FEATURE:
<221> NAME/KEY: misc_feature
<222> LOCATION: (4)..(4)
<223> OTHER INFORMATION: Xaa is D phenylalanine

<400> SEQUENCE: 3

Arg Gly Asp Xaa Cys
1               5

<210> SEQ ID NO 4
<211> LENGTH: 5
<212> TYPE: PRT
<213> ORGANISM: Artificial
<220> FEATURE:
<223> OTHER INFORMATION: Cyclized peptide
<220> FEATURE:
<221> NAME/KEY: misc_feature
<222> LOCATION: (4)..(4)
<223> OTHER INFORMATION: Xaa is D phenylalanine

<400> SEQUENCE: 4

Arg Gly Asp Xaa Cys
1               5

<210> SEQ ID NO 5
<211> LENGTH: 12
<212> TYPE: PRT
```

```
<213> ORGANISM: Artificial
<220> FEATURE:
<223> OTHER INFORMATION: Synthetic targeting peptide

<400> SEQUENCE: 5

Tyr His Trp Tyr Gly Tyr Thr Pro Gln Asn Val Ile
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic targeting peptide

<400> SEQUENCE: 6

Gly Ser Gly Lys Cys Cys Tyr Ser Leu
1               5

<210> SEQ ID NO 7
<211> LENGTH: 8
<212> TYPE: PRT
<213> ORGANISM: Artificial
<220> FEATURE:
<223> OTHER INFORMATION: Synthetic targeting peptide

<400> SEQUENCE: 7

Gln Trp Ala Val Gly His Met Leu
1               5

<210> SEQ ID NO 8
<211> LENGTH: 8
<212> TYPE: PRT
<213> ORGANISM: Artificial
<220> FEATURE:
<223> OTHER INFORMATION: Synthetic targeting peptide

<400> SEQUENCE: 8

Asp Tyr Met Gly Trp Met Asp Phe
1               5

<210> SEQ ID NO 9
<211> LENGTH: 6
<212> TYPE: PRT
<213> ORGANISM: Artificial
<220> FEATURE:
<223> OTHER INFORMATION: Synthetic targeting peptide

<400> SEQUENCE: 9

Arg Arg Pro Tyr Ile Leu
1               5

<210> SEQ ID NO 10
<211> LENGTH: 19
<212> TYPE: PRT
<213> ORGANISM: Artificial
<220> FEATURE:
<223> OTHER INFORMATION: Synthetic targeting peptide

<400> SEQUENCE: 10

Arg Arg Pro Tyr Ile Leu Gln Leu Tyr Glu Asn Lys Pro Arg Arg Pro
1               5                   10                  15

Tyr Ile Leu

<210> SEQ ID NO 11
<211> LENGTH: 10
```

-continued

```
<212> TYPE: PRT
<213> ORGANISM: Artificial
<220> FEATURE:
<223> OTHER INFORMATION: Cyclized peptide

<400> SEQUENCE: 11

Cys Cys Arg Gly Asp Lys Gly Pro Asp Cys
1               5                   10

<210> SEQ ID NO 12
<211> LENGTH: 5
<212> TYPE: PRT
<213> ORGANISM: Artificial
<220> FEATURE:
<223> OTHER INFORMATION: Cyclized peptide
<220> FEATURE:
<221> NAME/KEY: misc_feature
<222> LOCATION: (4)..(4)
<223> OTHER INFORMATION: Xaa is D phenylalanine

<400> SEQUENCE: 12

Arg Gly Asp Xaa Lys
1               5
```